(12) United States Patent
Chen et al.

(10) Patent No.: US 11,084,850 B2
(45) Date of Patent: Aug. 10, 2021

(54) RECOMBINANT PREFUSION RSV F PROTEINS AND USES THEREOF

(71) Applicants: INSTITUTE FOR RESEARCH IN BIOMEDICINE, Bellinzona (CH); THE PIRBRIGHT INSTITUTE, Surrey (GB); THE UNITED STATES OF AMERICA, AS REPRESENTED BY THE SECRETARY, DEPARTMENT OF HEALTH AND HUMAN SERVICES, Rockville, MD (US)

(72) Inventors: Lei Chen, Bethesda, MD (US); Baoshan Zhang, Bethesda, MD (US); Peter D. Kwong, Bethesda, MD (US); Davide Corti, Bellinzona (CH); Antonio Lanzavecchia, Porza (CH); Geraldine Taylor, Berkshire (GB)

(73) Assignees: THE PIRBRIGHT INSTITUTE, Surrey (GB); INSTITUTE FOR RESEARCH IN BIO-MEDICINE, Bellinzona (CH); THE UNITED STATES OF AMERICA, AS REPRESENTED BY THE SECRETARY, DEPARTMENT OF HEALTH AND HUMAN SERVICES, Rockville, MD (US)

( * ) Notice: Subject to any disclaimer, the term of this patent is extended or adjusted under 35 U.S.C. 154(b) by 0 days.

(21) Appl. No.: 16/468,174

(22) PCT Filed: Dec. 15, 2017

(86) PCT No.: PCT/EP2017/083180
§ 371 (c)(1),
(2) Date: Jun. 10, 2019

(87) PCT Pub. No.: WO2018/109220
PCT Pub. Date: Jun. 21, 2018

(65) Prior Publication Data
US 2019/0330277 A1  Oct. 31, 2019

Related U.S. Application Data

(60) Provisional application No. 62/435,275, filed on Dec. 16, 2016.

(51) Int. Cl.
| | | |
|---|---|---|
| C07K 14/135 | (2006.01) | |
| A61K 39/12 | (2006.01) | |
| A61K 39/155 | (2006.01) | |
| C07K 14/005 | (2006.01) | |
| A61P 31/14 | (2006.01) | |
| A61K 39/39 | (2006.01) | |
| A61K 45/06 | (2006.01) | |
| C07K 16/10 | (2006.01) | |
| G01N 33/536 | (2006.01) | |
| G01N 33/569 | (2006.01) | |
| A61K 39/00 | (2006.01) | |

(52) U.S. Cl.
CPC .......... *C07K 14/005* (2013.01); *A61K 39/155* (2013.01); *A61K 39/39* (2013.01); *A61K 45/06* (2013.01); *A61P 31/14* (2018.01); *C07K 16/1027* (2013.01); *G01N 33/536* (2013.01); *G01N 33/56983* (2013.01); *A61K 2039/5258* (2013.01); *A61K 2039/545* (2013.01); *A61K 2039/552* (2013.01); *A61K 2039/55505* (2013.01); *A61K 2039/55511* (2013.01); *A61K 2039/55516* (2013.01); *A61K 2039/55561* (2013.01); *A61K 2039/55577* (2013.01); *C07K 2317/76* (2013.01); *C07K 2319/03* (2013.01); *C07K 2319/21* (2013.01); *C07K 2319/22* (2013.01); *C07K 2319/50* (2013.01); *C12N 2760/18523* (2013.01); *C12N 2760/18534* (2013.01); *C12N 2760/18571* (2013.01)

(58) Field of Classification Search
None
See application file for complete search history.

(56) References Cited

U.S. PATENT DOCUMENTS

2014/0271699 A1* 9/2014 Kwong ............... C07K 14/005
424/187.1

FOREIGN PATENT DOCUMENTS

| WO | 2014160463 A1 | 10/2014 |
| WO | 2017172890 A1 | 10/2017 |

OTHER PUBLICATIONS

Joyce et al., "Iterative structure-based improvement of a fusion-glycoprotein vaccine against RSV", Nat. Struct. Mol. Biol., 23(9): 811-820, 2016.

(Continued)

*Primary Examiner* — Nianxiang Zou
(74) *Attorney, Agent, or Firm* — Harness, Dickey & Pierce, P.L.C.

(57) ABSTRACT

The present invention provides immunogens comprising a recombinant Respiratory Syncytial Virus (RSV) F protein stabilized in a prefusion conformation and nucleic acids encoding such immunogens. In particular the present invention provides polypeptides, polynucleotides, compositions, and uses thereof for eliciting an immune response to bovine respiratory syncytial virus (bRSV). Methods for generating an immune response in a subject are also disclosed. In some embodiments, the method is a method for treating or preventing a RSV infection in a subject by administering a therapeutically effective amount of the antigen to the subject.

18 Claims, 28 Drawing Sheets
Specification includes a Sequence Listing.

(56) References Cited

OTHER PUBLICATIONS

International Search Report from PCT Application No. PCT/EP2017/083180 dated Mar. 7, 2018.
Written Opinion from PCT Application No. PCT/EP2017/083180 dated Mar. 7, 2018.

\* cited by examiner

```
hRSV A2 gb|AAB86664.1      -----MELLILKANAITTILTAVTFCFASGQNITEEFYQSTCSAVSKGYLSALRTGWYTS
bRSV gb|AAA42804.1         MATTTMRMII-SIILISTYVP----HITLCQNITEEFYQSTCSAVSRGYLSALRTGWYTS
bRSV gb|ACL80037.1         -----MRMII-SIILISTYVP----HITLCQNITEEFYQSTCSAVSRGYLSALRTGWYTS
bRSV emb|CAN90052.1        MATTTMRMII-SIIIIFIYVQ----HITLCQNITEEFYQSTCSAVSRGYLSALRTGWYTS
bRSV dbj|BAA00798.1        MATTAMRMII-SIIFISTYVT----HITLCQNITEEFYQSTCSAVSRGYLSALRTGWYTS
bRSV gb|AAB28458.1         MGTTAMRMVI-SIIFISTYVT----HITLCQNITEEFYQSTCSAVSRGYLSALRTGWYTS
bRSV gb|AAA42808.1         MAATAMRMII-SIIFISTYMT----HITLCQNITEEFYQSTCSAVSRGYLSALRTGWYTS
bRSV ref|NP_048055.1       MATTAMRMII-SIIFISTYVT----HITLCQNITEEFYQSTCSAVSRGYLSALRTGWYTS
bRSV gb|AAL49399.1         MATTAMRMII-SIIFISTYVT----HITLCQNITEEFYQSTCSAVSRGYLSALRTGWYTS
bRSV emb|CAA76980.1        MATTAMTMII-SIIFISTYVT----HITLCQNITEEFYQSTCSAVSRGYLSALRTGWYTS
                                * ::* .    *    :        ::  ****************:********* hRSV A2 gb|AAB86664.1      VITIELSNIKENKCNGTDAKVKLIKQELDKYKNAVTELQLLMQSTPATNNRARRELPRFM
bRSV gb|AAA42804.1         VVTIELSKIQKNVCNGTDSKVKLIKQELERYNNAVAELQSLMQNEPTSSSRAKRGIPESI
bRSV gb|ACL80037.1         VVTIELSKIQKNVCNGTDSKVKLIKQELERYNNAVVELQSLMQNEPTSSSRAKRGIPESI
bRSV emb|CAN90052.1        VVTIELSKIQKNVCNSTDSNVKLIKQELERYNNAVVELQSLMQNEPASSSRAKRGIPELI
bRSV dbj|BAA00798.1        VVTIELSKIQKNVCNSTDSNVKLIKQELERYNNAVVELQSLMQNEPASSSRAKRGIPELI
bRSV gb|AAB28458.1         VVTIELSKIQKNVCKSTDSKVKLIKQELERYNNAVIELQSLMQNEPASFSRAKRGIPELI
bRSV gb|AAA42808.1         VVTIELSKIQKNVCKSTDSKVKLIKQELERYNNAVIELQSLMQNEPASFSRAKRGIPELI
bRSV ref|NP_048055.1       VVTIELSKIQKNVCKSTDSKVKLIKQELERYNNAVVELQSLMQNEPASFSRAKRGIPELI
bRSV gb|AAL49399.1         VVTIELSKIQKNVCNSTDSKVKLIKQELERYNNAVVELQSLMQNEPASFSRAKRGIPELI
bRSV emb|CAA76980.1        VVTIELSKIQKNVCKSTDSKVKLIKQELERYNNAVVELQSLMQNEPASFSRAKRSIPELI
                           *:*****:*::* *:.**::*******::*:*** *** ***. *:: .**:* :*. :

hRSV A2 gb|AAB86664.1      NYTLNNAKKTNVTLSKKRKRRFLGFLLGVGSAIASGVAVSKVLHLEGEVNKIKSALLSTN
bRSV gb|AAA42804.1         HYTRNSTKKFYGLMGKKRKRRFLGFLLGIGSAIASGVAVSKVLHLEGEVNKIKNALLSTN
bRSV gb|ACL80037.1         HYTRNSTKKFYGLMGKKRKRRFLGFLLGIGSAIASGVAVSKVLHLEGEVNKIKNALLSTN
bRSV emb|CAN90052.1        HYKRNSTKKFYGLMGKKRKRRFLGFLLGIGSAIASGVAVSKVLHLEGEVNKIKNALLSTN
bRSV dbj|BAA00798.1        HYKRNSTKKFYGLMGKKRKRRFLGFLLGIGSAIASGVAVSKVLHLEGEVNKIKNALLSTN
bRSV gb|AAB28458.1         HYPRNSTKRFYGLMGKKRKRRFLGFLLGIGSAIASGVAVSKVLHLEGEVNKIKNALLSTN
bRSV gb|AAA42808.1         HYTRNSTKRFYGLMGKKRKRRFLGFLLGIGSAIASGVAVSKVLHLEGEVNKIKNALLSTN
bRSV ref|NP_048055.1       HYTRNSTKKFYGLMGKKRKRRFLGFLLGIGSAVASGVAVSKVLHLEGEVNKIKNALLSTN
bRSV gb|AAL49399.1         HYTRNSTKKFYGLMGKKRKRRFLGFLLGIGSAIASGVAVSKVLHLEGEVNKIKNALLSTN
bRSV emb|CAA76980.1        HYTRNSTKKFYGLMGKKRKRRFLGFLLGIGSAIASGVAVSKVLHLEGEVNKIKNALLSTN
                           .*  *:.*:      :.**********:*.**********************.**** hRSV A2 gb|AAB86664.1      KAVVSLSNGVSVLTSKVLDLKNYIDKQLLPIVNKQSCSISNIATVIEFQQKNNRLLEITR
bRSV gb|AAA42804.1         KAVVSLSNGVSVLTSKVLDLKNYIDKELLPKVNNHDCRISNIATVIEFQQKNNRLLEIAR
bRSV gb|ACL80037.1         KAVVSLSNGVSVLTSKVLDLKNYIDKKLLPKVNNHDCRISNIETVIEFQQKNNRLLEIAR
bRSV emb|CAN90052.1        KAVVSLSNGVSVLTSKVLDLKNYIDKELLPKVNNHDCQISNIATVIEFQQKNNRLLEIAR
bRSV dbj|BAA00798.1        KAVVSLSNGVSVLTSKVLDLKNYIDKELLPKVNNHDCKISNIATVIEFQQKNNRLLEIAR
bRSV gb|AAB28458.1         KAVVSLSNGVSVLTSKVLDLKNYIDKELLPKVNNHDCRISNIGTVIEFQQKNNRLLEIAR
bRSV gb|AAA42808.1         KAVVSLSNGVSVLTSKVLDLKNYIDKELLPKVNNHDCRISNIETVIEFQQKNNRLLEIAR
bRSV ref|NP_048055.1       KAVVSLSNGVSVLTSKVLDLKNYIDKELLPQVNNHDCRISNIETVIEFQQKNNRLLEIAR
bRSV gb|AAL49399.1         KAVVSLSNGVSVLTSKVLDLKNYIDKELLPKVNNHDCRISKIETVIEFQQKNNRLLEIAR
bRSV emb|CAA76980.1        KAVVSLSNGVSVLTSKVLDLKNYIDKELLPKVNNHDCRISNIATVIEFQQKNNRLLEIAR
                           ************************:* **::.* **:*  **************:* hRSV A2 gb|AAB86664.1      EFSVNAGVTTPVSTYMLTNSELLSLINDMPITNDQKKLMSNNVQIVRQQSYSIMSIIKEE
bRSV gb|AAA42804.1         EFSVNAGITTPLSTYMLTNSELLSIINDMPITNDQKKLMS-VCQIVRQQSYSIMSVLR-E
bRSV gb|ACL80037.1         EFSVNAGITTPLSTYMLTNSELLSLINDMPITNDQKKLMSSNVQIVRQQSYSIMSVVKEE
bRSV emb|CAN90052.1        EFSVNAGITTPLSTYMLTNSELLSLINDMPITNDQKKLMSSNVQIVRQQSYSIMSVVKEE
bRSV dbj|BAA00798.1        EFSVNAGITTPLSTYMLTNSELLSLINDMPITNDQKKLMSSNVQIVRQQSYSIMSVVKEE
bRSV gb|AAB28458.1         EFSVNAGITTPLSTYMLTNSELLSLINDMPITNDQKKLMSSNVQIVRQQSYSIMSVVKEE
bRSV gb|AAA42808.1         EFSVNAGITTPLSTYMLTNSELLSLINDMPITNDQKKLMSSNVQIVRQQSYSIMSVVKEE
bRSV ref|NP_048055.1       EFSVNAGITTPLSTYMLTNSELLSLINDMPITNDQKKLMSSNVQIVRQQSYSIMSVVKEE
bRSV gb|AAL49399.1         EFSVNAGITTPLSTYMLTNSELLSLINDMPITNDQKKLMSSNVQIVRQQSYSIMSVVKEE
bRSV emb|CAA76980.1        EFSVNAGITTPLSTYMLTNSELLSLINDMPITNDQKKLMSSNVQIVRQQSYSIMSVVKEE
                           *******:***:*********:*************     *************:::  *
```

Figure 1

```
hRSV A2 gb|AAB86664.1      VLAYVVQLPLYGVIDTPCWKLHTSPLCTTNTKEGSNICLTRTDRGWYCDNAGSVSFFPQA
bRSV gb|AAA42804.1         VIAYVVQLPLYGVIDTPCWKLHTSPLCTTDNKEGSNICLTRTDRGWYCDNAGSVSFFPQA
bRSV gb|ACL80037.1         VIAYVVQLPIYGVIDTPCWKVHTSPLCTTDNKEGSNICLTRTDRGWYCDNAGSVSFFPQA
bRSV emb|CAN90052.1        VMAYVVQLPIYGVIDTPCWKLHTSPLCTTDNKEGSNICLTRTDRGWYCDNAGSVSFFPQA
bRSV dbj|BAA00798.1        VMAYVVQLPIYGVIDTPCWKLHTSPLCTTDNKEGSNICLTRTDRGWYCDNAGSVSFFPQA
bRSV gb|AAB28458.1         VIAYEVQLPIYGVIDTPCWKIHTSPLCTTDNKEGSNICLTRTDRGWYCDNAGSVSFFPQA
bRSV gb|AAA42808.1         VIAYVVQLPIYGVIDTPCWKLHTSPLCTTDNKEGSNICLTRTDRGWYCDNAGSVSFFPQA
bRSV ref|NP_048055.1       VIAYVVQLPIYGVIDTPCWKLHTSPLCTTDNKEGSNICLTRTDRGWYCDNAGSVSFFPQT
bRSV gb|AAL49399.1         VIAYVVQLPIYGVIDTPCWKLHTSPLCTTDNKEGSNICLTRTDRGWYCDNAGSVSFFPQT
bRSV emb|CAA76980.1        VIAYVVQLPIYGVIDTPCWKLHTSPLCTTDNKEGSNICLTRTDRGWYCDNAGSVSFFPQA
                           *:** ****:**********:*******..***************************:

hRSV A2 gb|AAB86664.1      ETCKVQSNRVFCDTMNSLTLPSEVNLCNVDIFNPKYDCKIMTSKTDVSSSVITSLGAIVS
bRSV gb|AAA42804.1         ETCKVQSNRVFCDTMNSLTLPTDVNLCNTDIFNSKYDCKIMTSKTDISSSVITSIGAIVS
bRSV gb|ACL80037.1         ETCKVQSNRVFCDTMNSLTLPTDVNLCNTDIFNTKYDCKIMTSKTDISSSVITSIGAIVS
bRSV emb|CAN90052.1        ETCKVQSNRVFCDTMNSLTLPTDVNLCNTDIFNAKYDCKIMTSKTDISSSVITSIGAIVS
bRSV dbj|BAA00798.1        ETCKVQSNRVFCDTMNSLTLPTDVNLCNTDIFNAKYDCKIMTSKTDISSSVITSIGAIVS
bRSV gb|AAB28458.1         ETCKVQSNRVFCDTMNSLTLPTDVNLCNTDIFNTKYDCKIMTSKTDISSSVITSIGAIVS
bRSV gb|AAA42808.1         ETCKVQSNRVFCDTMNSLTLPTDVNLCNTDIFNTKYDCKIMTSKTDISSSVITSIGAIVS
bRSV ref|NP_048055.1       ETCKVQSNRVFCDTMNSLTLPTDVNLCNTDIFNTKYDCKIMTSKTDISSSVITSIGAIVS
bRSV gb|AAL49399.1         ETCKVQSNRVFCDTMNSLTLPTDVNLCNTDIFNTKYDCKIMTSKTDISSSVITSIGAIVS
bRSV emb|CAA76980.1        ETCKVQSNRVFCDTMNSLTLPTDVNLCNTDIFNTKYDCKIMTSKTDISSSVITSIGAIVS
                           *******************:.. ********:**:*** hRSV A2 gb|AAB86664.1      CYGKTKCTASNKNRGIIKTFSNGCDYVSNKGVDTVSVGNTLYYVNKQEGKSLYVKGEPII
bRSV gb|AAA42804.1         CYGKTKCTASNKNRGIIKTFSNGCDYVSNKGVDTVSVGNTLYYVNKLEGKALYIKGEPII
bRSV gb|ACL80037.1         CYGKTKCTASNKNRGIIKTFSNGCDYVSNKGVDTVSVGNTLYYVNKLEGKALYIKGEPII
bRSV emb|CAN90052.1        CYGKTKCTASNKNRGIIKTFSNGCDYVSNRGVDTVSVGNTLYYVNKLEGKALYIKGEPII
bRSV dbj|BAA00798.1        CYGKTKCTASNKNRGIIKTFSNGCDYVSNRGVDTVSVGNTLYYVNKLEGKALYIKGEPII
bRSV gb|AAB28458.1         CYGKTKCTASNKNRGIIKTFPIGCDYVSNKGVDTVSVGNTLYYVNKLEGKALYIKGEPII
bRSV gb|AAA42808.1         CYGKTKCTASNKNRGIIKTFSNGCDYVSNKGVDTVSVGNTLYYVNKLEGKALYIKGEPII
bRSV ref|NP_048055.1       CYGKTKCTASNKNRGIIKTFSNGCDYVSNKGVDTVSVGNTLYYVNKLEGKALYIKGEPII
bRSV gb|AAL49399.1         CYGKTKCTASNKNRGIIKTFSNGCDYVSNKGVDTVSVGNTLYYVNKLEGKALYIKGEPII
bRSV emb|CAA76980.1        CYGKTKCTASNKNRGIIKTFSNGCDYVSNKGVDTVSVGNTLYYVNKLEGKALYIKGEPII
                           ******************  **:************* *::**** hRSV A2 gb|AAB86664.1      NFYDPLVFPSDEFDASISQVNEKINQSLAFIRKSDELLHNVNAGKSTINIMITTIIIVII
bRSV gb|AAA42804.1         NYYNPLVFPSDEFDASIAQVNAKINQSLAFIRRSDELLHSVDVGKSTTNVVITTIIIVIV
bRSV gb|ACL80037.1         NYYNPLVFGTYEFDASIAQVNAK-------------------------------------
bRSV emb|CAN90052.1        NYYDPLVFPSDEFDASIAQVNAKINQSLAFIRRSDELLHSVDVGKSTTNVVITTIIIVIV
bRSV dbj|BAA00798.1        NYYDPLVFPSDEFDASIAQVNAKINQSLAFIRRSDELLHSVDVGKSTTNVVITTIIIVIV
bRSV gb|AAB28458.1         NYYDPLVFPSDEFDASIAQVNAKINQSLAFIRRSDELLHSVDVGKSTTNVVITTIIIVIV
bRSV gb|AAA42808.1         NYYDPLVFPSDEFDASIAQVNAKINQSLAFIRRSDELLHSVDVGKSTTNVVITTIIIVIV
bRSV ref|NP_048055.1       NYYDPLVFPSDEFDASIAQVNAKINQSLAFIRRSDELLHSVDVGKSTTNVVITTIIIVIV
bRSV gb|AAL49399.1         NYYDPLVFPSDEFDASIAQVNAKINQSLAFIRRSDELLHSVDVGKSTTNVVITTIIIVIV
bRSV emb|CAA76980.1        NYYDPLVFPSDEFDASIAQVNAKINQSLAFIRRSDELLHSVDVGKSTTNVVITTIIIVIV
                           *:*:**  : **:* * hRSV A2 gb|AAB86664.1      VILLSLIAVGLLLYCKARSTPVTLSKDQLSGINNIAFSN
bRSV gb|AAA42804.1         VVILMLITVGLLFYCKTRSTPIMLGKDQLSSINNLSFSK
bRSV gb|ACL80037.1         ---------------------------------------
bRSV emb|CAN90052.1        VVILMLIAVGLLFYSKTRSTPIMLGKDQLSGINNLSFSK
bRSV dbj|BAA00798.1        VVILMLIAVGLLFYSKTRSTPIMLGKDQLSGINNLSFSK
bRSV gb|AAB28458.1         VVILMLIAVGLLFYCKTRSTPIMLGKDQLSGINNLSFSK
bRSV gb|AAA42808.1         VVILMLIAVGLLFYCKTRSTPIMLGKDQLSGINNLSFSK
bRSV ref|NP_048055.1       VVILMLIAVGLLFYCKTKSTPIMLGKDQLSGINNLSFSK
bRSV gb|AAL49399.1         VVILMLIAVGLLFYCKTKSTPIMLGKDQLSGINNLSFSK
```

Figure 1 (continued)

|  | Strain or isolate | GenBank accession number of RSV F protein |
|---|---|---|
| Human RSV | A/A2 | AAB86664.1 |
|  | A/Long | ACO83302.1 |
|  | A/9830 | AGL96787.1 |
|  | A/9846 | AFP99057.1 |
|  | B/18537 | BAA00240.1 |
|  | B/9717 | AFP99062.1 |
|  | B/9320 | AAR14266.1 |
| Bovine RSV | ATue51908 | NP_048055.1 |
|  | RB94 | CAN90052.1 |
|  | A/375 | ACL80037.1 |
|  | A51908 | AAA42804.1 |
|  | Snook | CAA76980.1 |
|  | 391-2 (also known as Copenhagen) | AAA42808.1 |
|  | RB94 F-11 | BAA00798.1 |
|  | FS1 | AAB28458.1 |
|  | ATCC 51908 | AAL49399.1 |

Figure 2

| Name | Yield (mg/L) | Antibody Binding | | |
|---|---|---|---|---|
| | | D25 | MPE8 | Mota |
| RB94 DS-Cav1 | 0.76 | + | + | + |
| ATue51908 DS-Cav1 | 2.98 | + | + | + |
| 391-2 DS-Cav1 | 3.66 | + | + | + |
| A/375 DS-Cav1 | 0.12 | ND | ND | ND |
| FS1 DS-Cav1 | 0.06 | ND | ND | ND |
| ATCC 51908 DS-Cav1 | 0.05 | ND | ND | ND |
| A51908 DS-Cav1 | 0.12 | ND | ND | ND |

+ Recognized by respective monoclonal antibody at a response level > 0.5 nm in an biolayer interferometry Octet binding analysis.
ND, not determined due to low yield.

Figure 4

| Variant Number | bRSV F variants | D25 | Mota | MPE8 | MPE8+D25* |
|---|---|---|---|---|---|
| sc-v1 | sc9-10_DS-CAV1_bRSV(RB94)_Fd_hp2_fp2_ig1 | 2.3744 | 2.4157 | 2.2996 | 4.674 |
| sc-v2 | sc9-10_DS-CAV1_bRSV(RB94)_Fd_hp1_ig1 | 2.4359 | 2.4177 | 2.1813 | 4.6172 |
| sc-v3 | sc9-10_DS-CAV1_bRSV(RB94)_Fd_hp2_ig1 | 2.4348 | 2.5178 | 2.2052 | 4.64 |
| sc-v4 | 391-2-site 0 hRSV bovSurf DS-Cav1-BZGJ9 Long | 2.2973 | 2.271 | 2.1879 | 4.4852 |
| sc-v5 | sc9-10_DS-CAV1_bRSV(RB94)_Fd_hp2_fp1_ig1 | 2.169 | 2.1809 | 2.2468 | 4.4158 |
| sc-v6 | RB94 site 0 hRSV DS-Cav1-BZGJ9 Long FdPL | 2.1649 | 2.2615 | 2.1954 | 4.3603 |
| sc-v7 | RB94 site 0 hRSV bovSurf DS-Cav1-BZGJ9 Long FdPL | 2.2051 | 2.2136 | 2.1372 | 4.3423 |
| sc-v8 | sc9-10_DS-CAV1_bRSV(RB94)_Fd_hp1_fp1_ig1 | 2.1659 | 2.2182 | 2.1565 | 4.3224 |
| sc-v9 | 391-2-site 0 hRSV DSCav1-BZGJ9 Long | 2.0159 | 2.0817 | 2.0785 | 4.0944 |
| sc-v10 | 391-2-DS-Cav1-BZGJ9_gyc5 | 1.9306 | 2.0434 | 1.8007 | 3.7313 |
| sc-v11 | sc9-10_DS-CAV1_bRSV(RB94)_Fd_pm1_ig1 | 1.8577 | 2.2202 | 1.8691 | 3.7268 |
| sc-v12 | 391-2-DS-Cav1-BZGJ9 Long K226L | 1.9187 | 1.9386 | 1.7829 | 3.7016 |
| sc-v13 | sc9-10_DS-CAV1_bRSV(RB94)_Fd_hp1_fp2_ig1 | 1.8766 | 1.8026 | 1.8053 | 3.6819 |
| sc-v14 | RB94 site 0 hRSV bovSurf DS-Cav1 Long FdPL | 1.6989 | 1.8559 | 1.8441 | 3.543 |
| sc-v15 | sc9-10_DS-CAV1_bRSV(RB94)_Fd_pm1_fp1_ig1 | 1.6714 | 1.8148 | 1.7303 | 3.4017 |
| sc-v16 | 391-2-DS-Cav1-BZGJ9_gyc1 | 1.399 | 2.1194 | 1.5463 | 2.9453 |
| sc-v17 | 391-2-DS-Cav1-BZGJ9 Long | 1.3021 | 1.5521 | 1.4491 | 2.7512 |
| sc-v18 | 391-2 hu/bov-DS-Cav1-BZGJ9 Long | 1.394 | 1.6985 | 1.3246 | 2.7186 |
| sc-v19 | 391-2-DS-Cav1-IP-5 | 1.2846 | 1.8271 | 1.4142 | 2.6988 |
| sc-v20 | RB94 hu/bov DS-Cav1 Long FdPL | 1.2526 | 1.4433 | 1.3831 | 2.6357 |
| sc-v21 | 391-2_DS-Cav1-tzsc7 | 0.9968 | 1.9888 | 1.5045 | 2.5013 |
| sc-v22 | RB94 site 0 hRSV DS-Cav1 Long FdPL | 1.0215 | 1.7457 | 1.3938 | 2.4153 |
| sc-v23 | 391-2-DS-Cav1-BZGJ9 Long S190V | 1.128 | 1.3054 | 1.193 | 2.321 |
| sc-v24 | sc9-10_DS-CAV1_bRSV(RB94)_Fd_pm1_fp2_ig1 | 1.0061 | 1.3201 | 0.9732 | 1.9793 |
| sc-v25 | 391-2_DS-Cav1-tzsc5 | 0.6616 | 1.5748 | 1.2161 | 1.8777 |
| sc-v26 | 391-2wt-F_SC_11R | 0.7394 | 1.7935 | 0.8867 | 1.6261 |
| sc-v27 | 391-2-DS-Cav1-BZGJ9_gyc7 | 0.7315 | 0.9771 | 0.8206 | 1.5521 |
| sc-v28 | 391-2wt_F-SC_12R core | 0.7091 | 0.821 | 0.6464 | 1.3555 |
| sc-v29 | KXint1 | 0.4162 | 0.5949 | 0.5989 | 1.0151 |
| sc-v30 | KXlinker1 | 0.3988 | 0.8314 | 0.5441 | 0.9429 |
| sc-v31 | RB94 DS-Cav1 Long FdPL | 0.3921 | 0.841 | 0.4889 | 0.881 |
| sc-v32 | 391-2-DS-Cav1-IP-4 | 0.3332 | 0.9326 | 0.5406 | 0.8738 |
| sc-v33 | 391-2_DS-Cav1-tzsc3 | 0.3834 | 0.7847 | 0.433 | 0.8164 |
| sc-v34 | sc9-10_DS-CAV1_bRSV(RB94)_Fd_fp2_ig1 | 0.2993 | 0.7481 | 0.4638 | 0.7631 |
| sc-v35 | KXlinker2 | 0.3211 | 0.7483 | 0.3606 | 0.6817 |
| sc-v36 | 391-2-DSCav1- F-SC_7R | 0.2247 | 0.6495 | 0.3116 | 0.5363 |

Figure 5

| Variant Number | bRSV F variants | D25 | Mota | MPE8 | MPE8+D25* |
|---|---|---|---|---|---|
| sc-v37 | 391-2_DS-CAV1 | 0.2439 | 0.3872 | 0.2888 | 0.5327 |
| sc-v38 | RB94_sc9-10 DS-CAV1 L373R | 0.2696 | 0.6889 | 0.258 | 0.5276 |
| sc-v39 | 391-2_DS-Cav1-tzsc4 | 0.2191 | 0.6387 | 0.2627 | 0.4818 |
| sc-v40 | 391-2-DS-Cav1-IP-2 | 0.1972 | 0.556 | 0.2175 | 0.4147 |
| sc-v41 | RB94 DS-CAV1 N70K S104F K117T | 0.1702 | 0.2705 | 0.2008 | 0.371 |
| sc-v42 | RB94_DS-CAV1 | 0.1454 | 0.3714 | 0.199 | 0.3444 |
| sc-v43 | sc9-10_DS-CAV1_bRSV(RB94)_Fd_(hRSV-leader)_ig1 | 0.1967 | 0.5376 | 0.1051 | 0.3018 |
| sc-v44 | sc9-10_DS-CAV1_bRSV(RB94)_Fd_fp1_ig1 | 0.191 | 0.5449 | 0.0965 | 0.2875 |
| sc-v45 | 391-2-DS-Cav1-BZGJ9_gyc3 | 0.1638 | 0.5992 | 0.1226 | 0.2864 |
| sc-v46 | 391-2-DS-Cav1-IP-7 | 0.2013 | 0.5461 | 0.0761 | 0.2774 |
| sc-v47 | 391-2-DS-Cav1-BZGJ9 | 0.1834 | 0.5 | 0.0926 | 0.276 |
| sc-v48 | 391-2-DS-Cav1-BZGJ9_gyc2 | 0.1444 | 1.5821 | 0.1198 | 0.2642 |
| sc-v49 | 391-2-DS-Cav1-SC-IP-1 | 0.0985 | 1.1035 | 0.1552 | 0.2537 |
| sc-v50 | KXds2 | 0.1091 | 0.3645 | 0.1426 | 0.2517 |
| sc-v51 | 391-2_DS-Cav1-tzsc4 | 0.138 | 0.5048 | 0.096 | 0.234 |
| sc-v52 | 391-2_DS-Cav1-tzsc9 | 0.1315 | 1.5872 | 0.1004 | 0.2319 |
| sc-v53 | 391-2-DS-Cav1-BZGJ9_gyc4 | 0.1382 | 0.4864 | 0.0901 | 0.2283 |
| sc-v54 | 391-2-DS-Cav1- F-SC_11R | 0.1606 | 0.5379 | 0.0668 | 0.2274 |
| sc-v55 | 391-2-DS-Cav1-BZGJ9_gyc6 | 0.1346 | 1.0546 | 0.0866 | 0.2212 |
| sc-v56 | KXsb2 | 0.1321 | 0.4832 | 0.0752 | 0.2073 |
|  | Medium control | 0.1271 | 0.5517 | 0.074 | 0.2011 |
| sc-v57 | 391-2_DS-Cav1-tzsc2 | 0.0883 | 0.3662 | 0.1092 | 0.1975 |
| sc-v58 | 391-2_DS-Cav1-tzsc6 | 0.1379 | 0.5268 | 0.0583 | 0.1962 |
| sc-v59 | 391-2-DS-Cav1-BZGJ9deleteFS | 0.1193 | 0.1522 | 0.0675 | 0.1868 |
| sc-v60 | 391-2-DS-Cav1-BZGJ9_gyc10 | 0.1363 | 0.4606 | 0.0498 | 0.1861 |

* Immunogens are ranked according to combined D25 and MPE8 ELISA binding values.

Figure 5 (continued)

| Variant Number | bRSV F variants | D25 | Mota | MPE8 | MPE8+D25* |
|---|---|---|---|---|---|
| DS2-v1 | 391-2 sc9 DS-Cav1 Q98C-Q361C | 0.5993 | 0.764 | 0.6675 | 1.2668 |
| DS2-v2 | 391-2 sc9 DS-Cav1 98C-362C | 0.4334 | 0.7505 | 0.4798 | 0.9132 |
| DS2-v3 | RB94 sc9 DS-CAV1 N183GC-N428C | 0.3712 | 1.0925 | 0.5232 | 0.8944 |
| DS2-v4 | 391-2-DS-Cav1-sc9deleteFS 98C-362C | 0.3618 | 0.5891 | 0.4481 | 0.8099 |
| DS2-v5 | RB94 sc9 DS-CAV1 A149C-Y458C | 0.3177 | 1.8511 | 0.4248 | 0.7425 |
| DS2-v6 | 391-2-DS-Cav1-sc9 100C-362C | 0.274 | 0.6028 | 0.1308 | 0.4048 |
| DS2-v7 | RB94 hu/bov DS-CAV1 A149C-Y458C Long | 0.2737 | 0.7898 | 0.2904 | 0.5641 |
| DS2-v8 | 391-2-DS-Cav1-sc9deleteFS 98C-361C | 0.2705 | 0.8987 | 0.4296 | 0.7001 |
| DS2-v9 | RB94 sc9 DS-CAV1 N183GC-N428C L373R Long | 0.2597 | 0.4883 | 0.3354 | 0.5951 |
| DS2-v10 | 391-2-DS-Cav1-sc9 99C-362C | 0.2486 | 0.3926 | 0.3111 | 0.5597 |
| DS2-v11 | 391-2-DS-Cav1-sc9 99C-361C | 0.2246 | 1.6809 | 0.1977 | 0.4223 |
| DS2-v12 | RB94 sc9 DS-CAV1 N183GC-N428C L373R Long K226L | 0.2061 | 0.633 | 0.2935 | 0.4996 |
| DS2-v13 | RB94 sc9 DS-CAV1 N183GC-N428C L373R Long S190V | 0.2059 | 0.6165 | 0.1554 | 0.3613 |
| DS2-v14 | 391-2-DS-Cav1_sc9_I28C-G464C | 0.202 | 0.5692 | 0.2034 | 0.4054 |
| DS2-v15 | 391-2-DS-Cav1-sc9deleteFS 99C-361C | 0.1979 | 0.6056 | 0.2289 | 0.4268 |
| DS2-v16 | 391-2-DS-Cav1-sc9deleteFS 99C-362C | 0.1967 | 0.612 | 0.1999 | 0.3966 |
| DS2-v17 | RB94 sc9 DS-CAV1 N183GC-N428C L373R | 0.1872 | 1.0436 | 0.3216 | 0.5088 |
| DS2-v18 | RB94 dscav1T369C-T455C Long S190V | 0.182 | 0.511 | 0.3713 | 0.5533 |
| DS2-v19 | 391-2-DS-Cav1-sc9 100C-361C | 0.1815 | 1.6326 | 0.1729 | 0.3544 |
| DS2-v20 | RB94 sc9 DS-CAV1 A149C-Y458C L373R | 0.1752 | 0.5639 | 0.1539 | 0.3291 |
| DS2-v21 | 391-2-DS-Cav1-sc9deleteFS 100C-362C | 0.1597 | 0.5032 | 0.0757 | 0.2354 |
| DS2-v22 | RB94 sc9 DS-CAV1 A149C-Y458C L373R Long | 0.1583 | 0.5122 | 0.0692 | 0.2275 |
| DS2-v23 | 391-2-DS-Cav1_sc9_S398C-S485C | 0.1444 | 0.4868 | 0.0849 | 0.2293 |
| DS2-v24 | RB94 sc9 DS-CAV1 A149C-Y458C L373R Long K226L | 0.1437 | 0.4863 | 0.0872 | 0.2309 |
| DS2-v25 | 391-2-DS-Cav1_S398C-S485C | 0.1409 | 0.5454 | 0.0824 | 0.2233 |
| DS2-v26 | 391-2-DS-Cav1_I28C-G464C | 0.1386 | 1.2097 | 0.0815 | 0.2201 |
| DS2-v27 | 391-2-DS-Cav1_sc9_I395C-A490C | 0.1362 | 0.8906 | 0.0919 | 0.2281 |
| DS2-v28 | 391-2-DS-Cav1_sc9_S485C-A490C | 0.1356 | 0.5945 | 0.0579 | 0.1935 |
| DS2-v29 | 391-2-DS-Cav1-sc9deleteFS 100C-361C | 0.1332 | 0.4766 | 0.0592 | 0.1924 |
| DS2-v30 | RB94 sc9 DS-CAV1 A149C-Y458C L373R Long S190V | 0.1332 | 0.537 | 0.0477 | 0.1809 |
| DS2-v31 | 391-2-DS-Cav1_sc9_T449C-V459C | 0.1325 | 0.4905 | 0.1002 | 0.2327 |
| DS2-v32 | RB94 DS-CAV1 T369C-T455C Long | 0.1294 | 0.4477 | 0.0667 | 0.1961 |

* Immunogens are ranked according to combined D25 and MPE8 ELISA binding values.

Figure 6

|  | Variant Number | bRSV F variant | Yield (mg/L) |
|---|---|---|---|
| Single chain with interprotomer disulfide bond alterations | DS2-v1 | 391-2 sc9 DS-Cav1 Q98C-Q361C | 2.80 |
|  | DS2-v3 | RB94 sc9 DS-CAV1 N183GC-N428C | 0.03 |
|  | DS2-v5 | RB94 sc9 DS-Cav1 A149C-Y458C | 0.06 |
|  | DS2-v33 | 391-2 sc9-10 DS-Cav1 Q98C-Q361C | 2.44 |
|  | DS2-v34 | 391-2 sc9 DS-Cav1 A149C-Y458C | 0.05 |
|  | DS2-v35 | ATue51908 sc9-10 DS-Cav1 A149C-Y458C | 0.24 |
|  | DS2-v36 | ATue51908 sc9-10 DS-Cav1 N183GC-N428C | 0.03 |
| Single chain | sc-v1 | sc9-10_DS-CAV1_bRSV(RB94)_Fd_hp2_fp2_ig1 | 21.50 |
|  | sc-v7 | 391-2-site 0 hRSV bovSurf DS-Cav1-BZGJ9 Long | 18.60 |

Figure 7

| bRSV F variant | Oligomeric state[*] | Yield (mg/L)[†] | Antibody affinity $K_D$ (nM)[‡] | | | | Physical stability (Fractional antibody reactivity[§]) | | | | | | |
|---|---|---|---|---|---|---|---|---|---|---|---|---|---|
| | | | | QP[ǁ] | | | Temp (°C) | | pH | | Osmolarity (mM) | | Freeze-thaw |
| | | | Site Ø D25 | Site III MPE8 | Site V AM14 | Site II Mz[¶] | 50 | 70 | 3.5 | 10.0 | 10 | 3,000 | 10[**] |
| 391-2 sc9 DS-Cav1 Q98C Q361C | trimer | 2.80 | 24.3 | 0.4 | 8.6 | 0.8 | 0.9 | 0.8 | 1.2 | 1.0 | 1.0 | 0.9 | 1.0 |
| 391-2 sc9-10 DS-Cav1 Q98C Q361C | trimer | 2.44 | 57.5 | 0.8 | 12.8 | 1.2 | 1.0 | 1.0 | 0.9 | 0.9 | 0.8 | 0.8 | 1.0 |
| 391-2 DS-Cav1 | trimer | 3.66 | 0.4 | 0.2 | 1.8 | 0.8 | 0.7 | 0.1 | 0.9 | 1.2 | 0.9 | 0.6 | 1.0 |
| 391-2 post-F | trimer | 4.10 | >1,000 | >1,000 | >1,000 | 0.6 | 1.0 | 1.0 | 0.8 | 1.1 | 0.9 | 0.6 | 1.0 |
| ATue51908 DS-Cav1 | trimer | 2.98 | 10.8 | 0.2 | 4.8 | 0.8 | 0.9 | 0.1 | 0.9 | 1.1 | 0.7 | 0.4 | 1.0 |
| ATue51908 sc9-10 DS-Cav1 A149C Y458C | trimer | 0.24 | 420 | 0.5 | 12.8 | 1.2 | 0.9 | 0.9 | 1.0 | 0.9 | 0.7 | 0.8 | 1.0 |
| ATue51908 post-F | trimer | 3.80 | >1,000 | >1,000 | >1,000 | 0.5 | 1.0 | 1.0 | 0.9 | 1.1 | 1.0 | 0.8 | 1.0 |
| RB94 DS-Cav1 | trimer | 0.76 | 24.3 | 0.2 | 4.9 | 0.9 | 0.6 | 0.1 | 1.2 | 1.3 | 0.8 | 0.5 | 1.0 |
| RB94 post-F | trimer | 4.78 | >1,000 | >1,000 | >1,000 | 0.4 | 1.0 | 1.0 | 0.9 | 1.1 | 1.0 | 1.0 | 1.0 |

[*] Variants were often observed to exist in a mixture of oligomeric states on size chromatography. If a measureable trimeric fraction was observed, then this is indicated by the label "Trimer", and the various properties of the trimer fraction are listed.

[†] Yield shown is for the specified oligomeric state.

[‡] When no binding was observed for 1 uM Fab, the $K_D$ is shown as >1,000 .

[§] D25 was used for pre-F proteins and Mz was used for post-F proteins.

[ǁ] QP: quaternary-specific antibody sites.

[¶] Motavizumab (Mz).

[**] Ten cycles of freeze-thaw in the presence of 10% glycerol.

|  | ATue51980 DS-Cav1 | 391-2 sc9 DS-Cav1 Q98C Q361C |
|---|---|---|
| PDB ID | 5TDG | 5TDL |
| Data collection | | |
| Space group | $P12_11$ | $P4_132$ |
| Cell constants | | |
| $a, b, c$ (Å) | 73.1, 127.0, 92.4 | 172.1, 172.1, 172.1 |
| $\alpha, \beta, \gamma$ (°) | 90, 93.9, 90 | 90, 90, 90 |
| Resolution (Å) | 43.3-2.65 (2.74-2.65) | 47.7-3.5 (3.59-3.50) |
| $R_{merge}$ (%) | 10.8 (76.1) | 13.3 (105.7) |
| $I/\sigma(I)$ | 16.5 (2.1) | 9.6 (2.0) |
| Completeness (%) | 97.0 (98.5) | 99.5 (100.0) |
| Redundancy | 3.4 (2.9) | 10.4 (11.1) |
| Wilson B | 66.2 | 158.9 |
| Refinement | | |
| Resolution (Å) | 43.3-2.65 | 40.6-3.5 |
| No. reflections | 47,383 | 11,449 |
| $R_{work} / R_{free}$ (%) | 18.5/23.9 | 25.6/27.2 |
| No. atoms | | |
| Protein | 11,204 | 3,484 |
| Carbohydrate | 42 | 14 |
| Water | 30 | 0 |
| *B*-factors | | |
| Protein | 81.2 | 162.0 |
| Carbohydrate | 133.5 | 188.3 |
| Water | 73.0 | NA |
| R.m.s. deviations | | |
| Bond lengths (Å) | 0.003 | 0.002 |
| Bond angles (°) | 0.579 | 0.490 |

A single crystal was used for each structure. Values in parentheses are for the highest resolution shell. NA, non-applicable.

| Immuni-zation group | 391-2 sc9 DS-Cav1 98C Q361C | 391-2 sc9-10 DS-Cav1 98C Q361C | 391-2 DS-Cav1 | 391-2 post-F | ATue 51908 DS-Cav1 | ATue 51908 sc9-149C-458C | ATue 51908 post-F | RB94 DS-Cav1 | RB94 post-F |
|---|---|---|---|---|---|---|---|---|---|
| | 1,909 | 17,183 | 1,909 | 100 | 4,243 | 5,728 | 178 | 4,243 | 141 |
| | 57,276 | 17,183 | 6,815 | 100 | 12,728 | 5,728 | 212 | 11,339 | 141 |
| | 5,728 | 6,815 | 1,909 | 100 | 12,728 | 5,728 | 212 | 27,000 | 141 |
| | 6,815 | 5,728 | 2,272 | 100 | 27,000 | 5,728 | 150 | 4,243 | 141 |
| | 17,183 | 68,148 | 6,8148 | 100 | 4,243 | 17,183 | 150 | 12,728 | 1273 |
| | 14,453 | 2,272 | 4,818 | 100 | 12,728 | 14,453 | 178 | 11,339 | 100 |
| | 5,728 | 25,747 | 4,818 | 100 | 38,184 | 14,453 | 212 | 3,000 | 141 |
| | 17,183 | 17,183 | 20,444 | 100 | 5,072 | 14,453 | 212 | 4,243 | 100 |
| | 14,453 | 2,272 | 5,728 | 100 | 4,243 | 17,183 | 636 | 11,339 | 100 |
| | 25,747 | 1,909 | 22,716 | 100 | 4,243 | 5,728 | 178 | 12,728 | 141 |
| Geometric mean | 11,453 | 8,984 | 6,880 | 100 | 9,002 | 9,419 | 210 | 8,250 | 158 |

Undetectable levels of neutralization were assigned a value of 100.

Figure 13

| Immunization group | Calf no. | DoB* | Sex | Breed† | Age at study onset (days) | Age at study onset (weeks) |
|---|---|---|---|---|---|---|
| Pre-F<br>391-2 sc9 DS-Cav1 98C 361C | 603941 | 9/23/15 | M | HF | 42 | 6 |
| | 103943 | 9/28/15 | M | HF | 37 | 5 |
| | 303567 | 2/29/15 | M | HF | 36 | 5 |
| | 703571 | 10/8/15 | M | HF | 27 | 4 |
| | 303574 | 10/13/15 | M | NRX | 22 | 3 |
| Post-F<br>391-2 post-F | 703942 | 9/24/15 | M | HF | 41 | 6 |
| | 203566 | 9/27/15 | M | HF | 38 | 6 |
| | 503569 | 9/30/15 | M | AA | 35 | 5 |
| | 403946 | 10/9/15 | M | AAX | 26 | 4 |
| | 103572 | 10/13/15 | M | HF | 22 | 3 |
| Placebo<br>PBS | 703564 | 9/24/15 | M | HF | 41 | 6 |
| | 103565 | 9/26/15 | M | HF | 39 | 6 |
| | 403568 | 9/29/15 | M | HF | 36 | 5 |
| | 603570 | 10/2/15 | M | HF | 33 | 5 |
| | 203573‡ | 10/13/15 | M | HF | 22 | 3 |

\* DoB, date of birth.
† Breeds: HF, Holstein Friesians; NRX, Norwegian Red Cross; AA, Aberdeen Angus; AAX, Aberdeen Angus Cross.
‡ Calf 203573 was lost at 15 days post prime immunization due to a joint infection.

Figure 15

| Immunization | Calf no. | Week post immunization | | | | |
|---|---|---|---|---|---|---|
| | | 0 | 2 | 4 | 6 | 8 |
| Pre-F 391-2 sc9 DS-Cav1 Q98C Q361C | 603941 | 100 | 357 | 1,273 | 28,905 | 11,455 |
| | 103943 | 100 | 357 | 3,212 | 96,351 | 13,630 |
| | 303567 | 100 | 141 | 424 | 38,184 | 17,165 |
| | 703571 | 100 | 424 | 1,273 | 136,296 | 136,296 |
| | 303574 | 100 | 119 | 424 | 38,184 | 13,630 |
| | Geometric Mean | 100 | 246 | 987 | 56,055 | 21,849 |
| Post-F 391-2 post-F | 703942 | 100 | 100 | 100 | 424 | 213 |
| | 203566 | 100 | 100 | 100 | 100 | 119 |
| | 503569 | 100 | 100 | 100 | 100 | 141 |
| | 403946 | 100 | 100 | 100 | 168 | 424 |
| | 103572 | 100 | 100 | 100 | 168 | 100 |
| | Geometric Mean | 100 | 100 | 100 | 164 | 172 |
| Placebo PBS | 703564 | 100 | 100 | 100 | 100 | 100 |
| | 103565 | 141 | 141 | 100 | 100 | 100 |
| | 403568 | 424 | 505 | 424 | 505 | 141 |
| | 603570 | 100 | 100 | 100 | 100 | 100 |
| | Geometric Mean | 156 | 163 | 144 | 150 | 109 |

Undetectable levels of neutralization were assigned a value of 100.

Figure 16

| | | Viral titers ($\log_{10}$ pfu/ml)* | | | | | | |
|---|---|---|---|---|---|---|---|---|
| Immunization | Calf no. | Days post inoculation | | | | | | |
| | | 0 | 1 | 2 | 3 | 4 | 5 | 6 |
| Pre-F | 603941 | 0.6 | 0.6 | 0.6 | 0.6 | 0.6 | 0.6 | 0.6 |
| 391-2 sc9 DS-Cav1 | 103943 | 0.6 | 0.6 | 0.6 | 0.6 | 0.6 | 0.6 | 0.6 |
| Q98C Q361C | 303567 | 0.6 | 0.6 | 0.6 | 0.6 | 0.6 | 0.6 | 0.6 |
| | 703571 | 0.6 | 0.6 | 0.6 | 0.6 | 0.6 | 0.6 | 0.6 |
| | 303574 | 0.6 | 0.6 | 0.6 | 0.6 | 0.6 | 0.6 | 0.6 |
| | Mean | 0.6 | 0.6 | 0.6 | 0.6 | 0.6 | 0.6 | 0.6 |
| | sd | 0.0 | 0.0 | 0.0 | 0.0 | 0.0 | 0.0 | 0.0 |
| Post-F | 703942 | 0.6 | 0.6 | 0.6 | 0.6 | 0.6 | 1 | 0.6 |
| 391-2 post-f | 203568 | 0.6 | 0.6 | 0.6 | 0.6 | 0.6 | 0.6 | 0.6 |
| | 503569 | 0.6 | 0.6 | 0.6 | 0.6 | 2.95 | 0.6 | 0.7 |
| | 403946 | 0.6 | 0.6 | 0.6 | 0.6 | 2.65 | 2.52 | 2.5 |
| | 103572 | 0.6 | 0.6 | 0.6 | 0.6 | 2.11 | 3.23 | 2.7 |
| | Mean | 0.6 | 0.6 | 0.6 | 0.60 | 1.78 | 1.59 | 1.42 |
| | sd | 0.0 | 0.0 | 0.0 | 0.0 | 1.1 | 1.2 | 1.1 |
| Placebo | 703564 | 0.6 | 0.6 | 0.6 | 0.6 | 0.6 | 2.6 | 0.6 |
| PBS | 103565 | 0.6 | 0.6 | 0.6 | 1.5 | 0.6 | 2.87 | 1.81 |
| | 403568 | 0.6 | 0.6 | 0.6 | 0.6 | 0.6 | 0.6 | 1.3 |
| | 603570 | 0.6 | 0.6 | 0.6 | 0.6 | 1.18 | 0.6 | 0.6 |
| | Mean | 0.6 | 0.6 | 0.6 | 0.8 | 0.7 | 1.7 | 1.1 |
| | sd | 0.0 | 0.0 | 0.0 | 0.5 | 0.3 | 1.2 | 0.5 |

| Mean | 0 | 1 | 2 | 3 | 4 | 5 | 6 |
|---|---|---|---|---|---|---|---|
| Pre-F | 0.6 | 0.6 | 0.6 | 0.6 | 0.6 | 0.6 | 0.6 |
| Post-F | 0.6 | 0.6 | 0.6 | 0.6 | 1.782 | 1.59 | 1.42 |
| Placebo | 0.6 | 0.6 | 0.6 | 0.825 | 0.745 | 1.6675 | 1.0775 |

* Undetectable levels of virus were assigned a value of 0.6.

| Immunization | Calf no. | Viral titers ($Log_{10}$ pfu/ml)* Respiratory tract samples† | | | | |
|---|---|---|---|---|---|---|
| | | TSc | LWC | RA | RC | LC |
| Pre-F | 603941 | 0.6 | 0.6 | 0.6 | 0.6 | 0.6 |
| 391-2 sc9 DS-Cav1 | 103943 | 0.6 | 0.6 | 0.6 | 0.6 | 0.6 |
| Q98C Q361C | 303567 | 0.6 | 0.6 | 0.6 | 0.6 | 0.6 |
| | 703571 | 0.6 | 0.6 | 0.6 | 0.6 | 0.6 |
| | 303574 | 0.6 | 0.6 | 0.6 | 0.6 | 0.6 |
| | Mean | 0.60 | 0.60 | 0.60 | 0.60 | 0.60 |
| | sd | 0.00 | 0.00 | 0.00 | 0.00 | 0.00 |
| Post-F | 703942 | 0.6 | 1.65 | 0.6 | 0.6 | 0.6 |
| 391-2 post-F | 203566 | 1.18 | 1.18 | 0.6 | 1.48 | 0.6 |
| | 503569 | 3.2 | 3.08 | 0.6 | 0.6 | 0.6 |
| | 403946 | 0.6 | 2.95 | 0.6 | 0.6 | 0.6 |
| | 103572 | 2.81 | 2 | 0.6 | 0.6 | 0.6 |
| | Mean | 1.68 | 2.17 | 0.60 | 0.78 | 0.60 |
| | sd | 1.24 | 0.82 | 0.00 | 0.39 | 0.00 |
| Placebo | 703564 | 2.54 | 1.3 | 2.54 | 1.3 | 2 |
| PBS | 103565 | 2.81 | 2.93 | 2.7 | 2.88 | 2.3 |
| | 403568 | 3.2 | 3.65 | 3.58 | 2.4 | 0.6 |
| | 603570 | 0.6 | 0.6 | 2 | 2.11 | 2.11 |
| | Mean | 2.29 | 2.12 | 2.71 | 2.17 | 1.75 |
| | sd | 1.16 | 1.41 | 0.66 | 0.66 | 0.78 |

| Mean | TSc | LWC | RA | RC | LC |
|---|---|---|---|---|---|
| Pre-F | 0.6 | 0.6 | 0.6 | 0.6 | 0.6 |
| Post-F | 1.68 | 2.17 | 0.60 | 0.78 | 0.60 |
| Placebo | 2.29 | 2.12 | 2.71 | 2.17 | 1.75 |

* Undetectable levels of virus were assigned a value of 0.6.
† TrSc, tracheal epithelium; LWC, lung wash cells; RA, right apical lobe of the lung; RC, right cardiac lobe of the lung; LC, left cardiac lobe of the lung.

Figure 21

| Clinical scores | | Days post inoculation | | | | | | | |
|---|---|---|---|---|---|---|---|---|---|
| | | -1 | 0 | 1 | 2 | 3 | 4 | 5 | 6 |
| Pre-F 391-2 sc9 DS-Cav1 Q98C Q361C | 603941 | 0 | 0 | 1 | 0 | 0 | 1 | 3 | 2 |
| | 103943 | 0 | 0 | 0 | 1 | 0 | 0 | 0 | 0 |
| | 303567 | 0 | 0 | 0 | 1 | 0 | 0 | 0 | 1 |
| | 703571 | 0 | 0 | 9 | 0 | 0 | 1 | 0 | 1 |
| | 303574 | 0 | 0 | 0 | 0 | 0 | 0 | 1 | 1 |
| | Mean | 0 | 0 | 2 | 0.4 | 0.0 | 0.4 | 0.8 | 1.0 |
| | sd | 0.0 | 0.0 | 3.9 | 0.5 | 0.0 | 0.5 | 1.3 | 0.7 |
| Post-F 391-2 post-F | 703942 | 0 | 0 | 0 | 1 | 0 | 0 | 0 | 0 |
| | 203566 | 1 | 2 | 1 | 3 | 1 | 1 | 1 | 1 |
| | 503569 | 1 | 0 | 1 | 5 | 3 | 2 | 3 | 3 |
| | 403946 | 0 | 0 | 0 | 1 | 0 | 0 | 1 | 2 |
| | 103572 | 0 | 1 | 1 | 0 | 0 | 0 | 1 | 0 |
| | Mean | 0.4 | 0.6 | 0.6 | 2 | 0.8 | 0.6 | 1.2 | 1.2 |
| | sd | 0.5 | 0.9 | 0.5 | 2.0 | 1.3 | 0.9 | 1.1 | 1.3 |
| Placebo PBS | 703564 | 0 | 1 | 0 | 5 | 0 | 1 | 0 | 1 |
| | 103565 | 0 | 0 | 0 | 0 | 0 | 0 | 0 | 3 |
| | 403568 | 0 | 0 | 0 | 1 | 0 | 0 | 3 | 5 |
| | 603570 | 0 | 0 | 0 | 0 | 0 | 0 | 3 | 5 |
| | Mean | 0 | 0.3 | 0.0 | 1.5 | 0.0 | 0.3 | 1.5 | 3.5 |
| | sd | 0.0 | 0.5 | 0.0 | 2.4 | 0.0 | 0.5 | 1.7 | 1.9 |
| Respiratory rate | | | | | | | | | |
| | | -1 | 0 | 1 | 2 | 3 | 4 | 5 | 6 |
| Pre-F 391-2 sc9 DS-Cav1 Q98C Q361C | 603941 | 28 | 32 | 36 | 24 | 32 | 42 | 38 | 38 |
| | 103943 | 20 | 24 | 28 | 40 | 28 | 32 | 26 | 30 |
| | 303567 | 24 | 28 | 32 | 38 | 28 | 32 | 26 | 36 |
| | 703571 | 32 | 32 | 40 | 32 | 32 | 36 | 30 | 38 |
| | 303574 | 32 | 28 | 32 | 34 | 26 | 28 | 40 | 42 |
| | Mean | 27.2 | 28.8 | 33.6 | 33.6 | 29.2 | 34.0 | 32.0 | 36.8 |
| | sd | 5.2 | 3.3 | 4.6 | 6.2 | 2.7 | 5.3 | 6.6 | 4.4 |
| Post-F 391-2 post-F | 703942 | 28 | 24 | 32 | 40 | 28 | 28 | 34 | 32 |
| | 203566 | 40 | 40 | 44 | 50 | 38 | 40 | 38 | 42 |
| | 503569 | 40 | 32 | 40 | 48 | 40 | 36 | 38 | 32 |
| | 403946 | 28 | 24 | 28 | 40 | 26 | 34 | 36 | 40 |
| | 103572 | 32 | 36 | 36 | 30 | 30 | 28 | 36 | 32 |
| | Mean | 33.6 | 31.2 | 36 | 41.6 | 32.4 | 33.2 | 36.4 | 35.6 |
| | sd | 6.1 | 7.2 | 6.3 | 7.9 | 6.2 | 5.2 | 1.7 | 5.0 |
| Placebo PBS | 703564 | 28 | 24 | 28 | 42 | 30 | 36 | 28 | 40 |
| | 103565 | 24 | 28 | 32 | 32 | 30 | 30 | 30 | 40 |
| | 403568 | 28 | 24 | 32 | 32 | 28 | 30 | 40 | 50 |
| | 603570 | 32 | 28 | 32 | 28 | 26 | 32 | 36 | 52 |
| | Mean | 28 | 26.0 | 31.0 | 33.5 | 28.5 | 32.0 | 33.5 | 45.5 |
| | sd | 3.3 | 2.3 | 2.0 | 6.0 | 1.9 | 2.8 | 5.5 | 6.4 |

Figure 22

| Temperatures | | \multicolumn{8}{c}{Days post inoculation} | | | | | | | |
|---|---|---|---|---|---|---|---|---|---|
| | | -1 | 0 | 1 | 2 | 3 | 4 | 5 | 6 |
| Pre-F | 603941 | 37.9 | 38.6 | 38.5 | 38.4 | 37.8 | 38.3 | 38.3 | 37.6 |
| 391-2 sc9 DS-Cav1 Q98C Q361C | 103943 | 37.9 | 37.4 | 38.3 | 38.2 | 38.3 | 38.3 | 38.4 | 37.6 |
| | 303567 | 37.3 | 38.6 | 37.9 | 38.7 | 38.2 | 38 | 38 | 37.6 |
| | 703571 | 38 | 38.6 | 40.1 | 37.9 | 38.7 | 38.2 | 38.1 | 38.2 |
| | 303574 | 38 | 37.8 | 38.2 | 38 | 38 | 38.2 | 38.4 | 39.3 |
| | Mean | 37.82 | 38.2 | 38.6 | 38.2 | 38.2 | 38.2 | 38.2 | 38.1 |
| | sd | 0.3 | 0.6 | 0.9 | 0.3 | 0.3 | 0.1 | 0.2 | 0.7 |
| Post-F 391-2 post-F | 703942 | 38.6 | 37.9 | 38.1 | 38.4 | 38.2 | 38.6 | 38.4 | 37.5 |
| | 203566 | 38.5 | 38.6 | 38.5 | 38.4 | 38.7 | 38 | 38.6 | 38.7 |
| | 503569 | 38.4 | 38.4 | 38.7 | 38.2 | 39 | 38.5 | 38.6 | 38.9 |
| | 403946 | 38.1 | 38.1 | 38 | 37.6 | 38.6 | 38.8 | 38.5 | 38.4 |
| | 103572 | 38.1 | 38.4 | 38.3 | 38 | 37.9 | 38.1 | 38.2 | 38.4 |
| | Mean | 38.34 | 38.28 | 38.32 | 38.12 | 38.48 | 38.4 | 38.46 | 38.38 |
| | sd | 0.2 | 0.3 | 0.3 | 0.3 | 0.4 | 0.3 | 0.2 | 0.5 |
| Placebo PBS | 703564 | 38 | 38.4 | 38.2 | 38.4 | 38.2 | 38.8 | 38.8 | 39.1 |
| | 103565 | 38.1 | 38.2 | 37.9 | 38.4 | 37.6 | 37.8 | 38.6 | 39.5 |
| | 403568 | 38.4 | 38.5 | 38.5 | 38.3 | 38.1 | 38.5 | 38.8 | 39.5 |
| | 603570 | 37.9 | 38.3 | 37.9 | 38.4 | 38.5 | 38.5 | 38.3 | 39.4 |
| | Mean | 38.1 | 38.4 | 38.1 | 38.4 | 38.1 | 38.4 | 38.6 | 39.4 |
| | sd | 0.2 | 0.1 | 0.3 | 0.1 | 0.4 | 0.4 | 0.2 | 0.2 |

Figure 22 (continued)

| Clinical signs | Score | | | | | |
|---|---|---|---|---|---|---|
| | 0 | 1 | 2 | 3 | 5 | 10 |
| Temperature | For each 0.1°C > 39.3°C add a score of 1 | | | | | |
| Nasal signs | None | Slight discharge | Moderate discharge | Copious discharge | NA | NA |
| Ocular signs | None | Slight discharge | Moderate discharge | Copious discharge | NA | NA |
| Cough | None | Occurs during handling | Spontaneous, infrequent | | NA | Persistent loud cough |
| Respiratory rate (RR) | <35 breaths/min | 35-45 breaths/min | NA | 45-55 breaths/min | 55-65 breaths/min | >75 breaths/min |
| Dyspnoea | Normal | Slight | Moderate | NA | NA | Severe (stretched neck & open mouth breathing) |
| Feeding | Normal | NA | NA | NA | NA | Reluctant to feed |
| Behavior | Normal | Slight apathy (ears back, avoids handling) | Moderate apathy (head down, reluctant to move) | NA | NA | Sever apathy (unable to move, lying down) |

NA, Not applicable.

Figure 23

| Immunization | Calf no. | x10^6 cells/ml | %PMN* | No. bacterial colonies in 100 µl of BAL | %Lung lesions |
|---|---|---|---|---|---|
| Pre-F 391-2 sc9 DS-Cav1 Q98C Q361C | 603941 | 2.1 | 21.9 | 2 | 0 |
| | 103943 | 1.3 | 3.8 | TNTC† | 0 |
| | 303567 | 2.2 | 5.6 | 0 | 0 |
| | 703571 | 1.8 | 2.0 | 33 | 0.3 |
| | 303574 | 2.0 | 65.2 | 0 | 16 |
| | Mean | 1.9 | 19.7 | | |
| | sd | 0.4 | 26.7 | | |
| Post-F 391-2 post-F | 703942 | 2.5 | 44.3 | 0 | 0 |
| | 203566 | 2.1 | 66.1 | 0 | 4 |
| | 503569 | 4.9 | 60.9 | 0 | 7 |
| | 403946 | 1.3 | 20.0 | 0 | 1 |
| | 103572 | 8.8 | 70.1 | TNTC | 6 |
| | Mean | 3.9 | 52.3 | | |
| | sd | 3.0 | 20.1 | | |
| Placebo PBS | 703564 | 26.0 | 66.8 | 0 | 11 |
| | 103565 | 8.7 | 80.7 | 0 | 21 |
| | 403568 | 8.1 | 69.6 | 0 | 19 |
| | 603570 | 11.0 | 77.7 | 0 | 33 |
| | Mean | 13.5 | 73.7 | | |
| | sd | 8.5 | 6.6 | | |

* %PMN, percentage polymorph nuclear neutrophils in BAL.
† TNTC, Too numerous to count.

Figure 24

RECOMBINANT PREFUSION RSV F PROTEINS AND USES THEREOF

This application is a national stage application under 35 U.S.C. § 371 of PCT International Application No. PCT/EP2017/083180, which has an international filing date of 15 Dec. 2017 and claims priority to U.S. Provisional Application No. 62/435,275 filed on 16 Dec. 2016. The contents of each application recited above are incorporated herein by reference in their entirety.

The present invention relates to the field of vaccination against bovine respiratory syncytial virus (bRSV), in particular the present invention relates to polypeptides, polynucleotides, compositions, and uses thereof for eliciting an immune response to bovine respiratory syncytial virus (bRSV).

Respiratory syncytial virus (RSV) is an enveloped non-segmented negative-strand RNA virus in the family Paramyxoviridae, genus *Pneumovirus*. RSVs encode three envelope glycoproteins, a small hydrophobic (SH) protein of unknown function, a glycoprotein (G) known as attachment protein, and a fusion (F) glycoprotein (also referred to herein as "RSV F protein" or "RSV F"). The RSV F protein is structurally similar to F proteins from other Paramyxoviridae with respect to the location of hydrophobic domains, heptad repeats, and cysteine residues, as well as to proteolytic activation resulting in the exposition of a hydrophobic fusion peptide. The RSV F protein is responsible for virus entry and membrane fusion. In nature, the RSV F protein is initially expressed as a single polypeptide precursor, designated F0. The inactive precursor F0 trimerizes in the endoplasmic reticulum and is cleaved by a cellular furin-like protease at two conserved sites into an N-terminal F2 subunit and a C-terminal, membrane-anchored F1 subunit carrying the fusion peptide. A peculiarity of RSV F is cleavage at two neighboring multibasic cleavage motifs, resulting in release of a peptide, pep27. The Pep27 polypeptide is excised and does not form part of the mature F protein. The F2 polypeptide originates from the N-terminal portion of the F0 precursor and links to the F1 polypeptide via two disulfide bonds. The F1 polypeptide originates from the C-terminal portion of the F0 precursor and anchors the mature F protein in the membrane via a transmembrane domain, which is linked to an –24 amino acid cytoplasmic tail. Three protomers of the F2-F1 heterodimer assemble to form a mature F protein, which adopts a metastable prefusion (pre-F) conformation that is triggered to undergo a conformational change that fuses the viral and target-cell membranes. Due to its obligatory role in RSV entry, the RSV F protein is the target of neutralizing antibodies and the subject of vaccine development. In contrast to the pre-F form of RSV F, which is metastable and spontaneously undergoes structural rearrangements to the post-fusion (post-F) form, the post-F form of RSV F no longer presents epitopes for many potently neutralizing antibodies. Accordingly, most potently neutralizing RSV antibodies identified thus far target the pre-fusion (pre-F) form of the RSV fusion (F) glycoprotein (Ngwuta, J. O., et al. Prefusion F-specific antibodies determine the magnitude of RSV neutralizing activity in human sera. *Sci Transl Med* 7, 309ra162 (2015); Magro, M., et al. Neutralizing antibodies against the preactive form of respiratory syncytial virus fusion protein offer unique possibilities for clinical intervention. *Proceedings of the National Academy of Sciences of the United States of America* 109, 3089-3094 (2012)).

hRSV is the most common cause of bronchiolitis and pneumonia among children in their first year of life. RSV also causes repeated infections including severe lower respiratory tract disease, which may occur at any age, especially among the elderly or those with compromised cardiac, pulmonary, or immune systems. hRSV is responsible for over 3 million hospitalizations for severe respiratory illness in young children and the elderly each year (Borchers, A. T., Chang, C., Gershwin, M. E. & Gershwin, L. J. Respiratory Syncytial Virus-A Comprehensive Review. *Clin Rev Allerg Immu* 45, 331-379 (2013); Nair, H., et al. Global burden of acute lower respiratory infections due to respiratory syncytial virus in young children: a systematic review and meta-analysis. *Lancet* 375, 1545-1555 (2010); Falsey, A. R., Hennessey, P. A., Formica, M. A., Cox, C. & Walsh, E. E. Respiratory syncytial virus infection in elderly and high-risk adults. *New Engl J Med* 352, 1749-1759 (2005)).

Currently, no licensed vaccine is available for hRSV. The infection cannot be avoided, because RSV is ubiquitous in all parts of the world. In order to prevent severe illness caused by RSV infection in infants with prematurity, bronchopulmonary dysplasia, or congenital heart disease currently passive immunization by the monoclonal antibody Palivizumab (SYNAGIS®; Medimmune, Inc.) is used. Palivizumab is moderately effective and binds to a 24-20 amino acid epitope on the RSV fusion (F) protein (RSV F). Accordingly, the interest in developing a vaccine is high, in particular as the annual medical burden relating to hRSV has remained high, equal to Influenza and Pneumococcus. However, despite continued interest in this highly sought after vaccine, at present no vaccine is approved by the authorities. In August 2015, Novavax announced positive Top-Line data from Phase 2 HRSV F-Protein Vaccine Clinical Trial in Older Adults. This was the first successful HRSV immunization Phase 2 trial for any population. However, in a Pivotal Phase 3 Trial of the HRSV F Vaccine in Older Adults Top Line results released in 2016 failed to prove that the vaccine was effective in preventing HRSV in older adults.

Recently, structure-based design was employed to engineer thermostable versions of the pre-F hRSV F glycoprotein (McLellan, J. S., et al. Structure-based design of a fusion glycoprotein vaccine for respiratory syncytial virus. *Science* 342, 592-598 (2013); Joyce, M. G., et al. Iterative structure-based improvement of a respiratory syncytial virus fusion glycoprotein vaccine. *Nature structural biology* 23, 811-820 (2016)), which preserve the pre-F conformation and the associated target epitopes for highly potent neutralizing monoclonal antibodies (mAbs) such as AM14 and D25 (Gilman, M. S. A., et al. Characterization of a Prefusion-Specific Antibody That Recognizes a Quaternary, Cleavage-Dependent Epitope on the RSV Fusion Glycoprotein. *PLoS pathogens* 11, e1005035 (2015); McLellan, J. S., et al. Structure of RSV fusion glycoprotein trimer bound to a prefusion-specific neutralizing antibody. *Science* 340, 1113-1117 (2013)). These immunogens were subsequently observed to elicit high levels of neutralizing antibodies in immunized mice and non-human primates (McLellan, J. S., et al. Structure-based design of a fusion glycoprotein vaccine for respiratory syncytial virus. *Science* 342, 592-598 (2013); Joyce, M. G., et al. Iterative structure-based improvement of a respiratory syncytial virus fusion glycoprotein vaccine. *Nature structural biology* 23, 811-820 (2016)).

Although promising hRSV-vaccine candidates have been evaluated in mouse, cotton rat, and non-human primate (NHP) animal models, hRSV is only semipermissive in these animals and thus does not authentically represent natural infection. Therefore, the absence of a relevant animal model for hRSV has complicated assessment of promising hRSV-vaccine candidates. However, human respiratory syncytial virus (hRSV) and bovine respiratory syncytial virus (bRSV) are genetically and antigenically closely related (Taylor, G. Bovine Model of Respiratory Syncytial Virus Infection. *Curr Top Microbiol* 372, 327-345 (2013)) and cause lower respiratory tract disease in humans and cattle, respectively. As clinical features after infection are very similar for both viruses, the natural disease caused by bRSV is an important animal model for all aspects of hRSV infection (Collins, P. L., K. Mcintosh, and R. M. Chanock. 1996. Respiratory syncytial virus, p. 1313-1352. In B. N. Fields, D. M. Knipe, P. M. Howley, R. M. Chanock, J. L. Melnik, T. P. Monath, and S. E. Straus (ed.), Fields virology. Lippincott-Raven, Philadelphia, Pa.). Accordingly, bRSV infection in calves provides an opportunity to monitor RSV pathogenesis and RSV vaccine effectiveness in a natural host (Graham, B. S. Biological challenges and technological opportunities for respiratory syncytial virus vaccine development. *Immunol Rev* 239, 149-166 (2011)).

Like infants, young calves are particularly vulnerable to bRSV, even in the presence of moderate levels of maternal antibodies (Kimman, T. G., Zimmer, G. M., Westenbrink, F., Mars, J. & Vanleeuwen, E. Epidemiological-Study of Bovine Respiratory Syncytial Virus-Infections in Calves—Influence of Maternal Antibodies on the Outcome of Disease. *Vet Rec* 123, 104-109 (1988)), with prevalence rates of up to 70% in the first year of life (Sacco, R. E., McGill, J. L., Pillatzki, A. E., Palmer, M. V. & Ackermann, M. R. Respiratory Syncytial Virus Infection in Cattle. *Vet Pathol* 51, 427-436 (2014)).

Bovine respiratory syncytial virus (bRSV) is responsible for the majority of respiratory disease in cattle annually, resulting in considerable morbidity and mortality and losses of approaching $1 billion per year (Valarcher, J. F. & Taylor, G. Bovine respiratory syncytial virus infection. *Vet Res* 38, 153-180 (2007); Taylor, G. Bovine Model of Respiratory Syncytial Virus Infection. *Curr Top Microbiol* 372, 327-345 (2013); Sacco, R. E., McGill, J. L., Pillatzki, A. E., Palmer, M. V. & Ackermann, M. R. Respiratory Syncytial Virus Infection in Cattle. *Vet Pathol* 51, 427-436 (2014)).

Although several licensed vaccines are available for bRSV, low levels of maternal antibodies against bRSV can mitigate vaccine response in calves (Kimman, T. G., Zimmer, G. M., Westenbrink, F., Mars, J. & Vanleeuwen, E. Epidemiological-Study of Bovine Respiratory Syncytial Virus-Infections in Calves—Influence of Maternal Antibodies on the Outcome of Disease. *Vet Rec* 123, 104-109 (1988); Kimman, T. G., Westenbrink, F. & Straver, P. J. Priming for Local and Systemic Antibody Memory Responses to Bovine Respiratory Syncytial Virus—Effect of Amount of Virus, Virus-Replication, Route of Administration and Maternal Antibodies. *Vet Immunol Immunop* 22, 145-160 (1989)). Inactivated bRSV vaccines may enhance disease (Schreiber, P., et al. High mortality rate associated with bovine respiratory syncytial virus (BRSV) infection in Belgian White Blue calves previously vaccinated with an inactivated BRSV vaccine. *J Vet Med B* 47, 535-550 (2000); Antonis, A. F. G., et at Vaccine-induced immunopathology during bovine respiratory syncytial virus infection: Exploring the parameters of pathogenesis. *Journal of virology* 77, 12067-12073 (2003)), live-attenuated vaccines pose risks of reversion to virulence, and attenuation is generally associated with reduced immunogenicity. Furthermore, live vaccines have the potential to exacerbate bRSV disease if administered intramuscularly in the presence of a concurrent bRSV infection (Kimman, T. G., Sol, J., Westenbrink, F. & Straver, P. J. A Severe Outbreak of Respiratory-Tract Disease Associated with Bovine Respiratory Syncytial Virus Probably Enhanced by Vaccination with Modified Live Vaccine. *Vet Quart* 11, 250-253 (1989)).

In view of the above, it was an object of the present invention to overcome the drawbacks of current vaccines for bRSV outlined above and to provide an improved vaccine against bRSV. Such a vaccine preferably induces high-titer neutralizing responses and protection from viral replication, lung inflammation and clinical signs of disease. Moreover, such a vaccine preferably avoids vaccine-associated disease enhancement. The inventive vaccine may be used in order to prevent and/or treat bRSV infection in cattle. In addition, it is also an object of the present invention to provide an improved animal model of hRSV infection, which authentically represents natural infection and vaccine responses. Moreover, it is also an object of the present invention to provide a tool for diagnosis of bRSV.

This object is achieved by means of the subject-matter set out below and in the appended claims.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a subject or patient is intended to include prevention, prophylaxis, attenuation, amelioration and therapy. The terms "subject" or "patient" are used interchangeably herein to mean all mammals including humans. Examples of subjects include humans, cows (cattle), dogs, cats, horses, goats, sheep, pigs, and rabbits. Preferably, the subject is a cow (cattle).

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein.

Doses are often expressed in relation to the bodyweight. Thus, a dose which is expressed as [g, mg, or other unit]/kg (or g, mg etc.) usually refers to [g, mg, or other unit] "per kg (or g, mg etc.) bodyweight", even if the term "bodyweight" is not explicitly mentioned.

The term "specifically binding" and similar reference does not encompass non-specific sticking.

The term "vaccine" as used herein is typically understood to be a prophylactic or therapeutic material providing at least one antigen, preferably an immunogen. The antigen or immunogen may be derived from any material that is suitable for vaccination. The antigen or immunogen typically stimulates the body's adaptive immune system to provide an adaptive immune response. In particular, an "antigen" or an "immunogen" refers typically to a substance which may be recognized by the immune system, preferably by the adaptive immune system, and which is capable of triggering an antigen/immunogen-specific immune response, e.g. by formation of antibodies and/or antigen-specific T cells as part of an adaptive immune response. Typically, an antigen may be or may comprise a peptide or protein which may be presented by the MHC to T-cells. Preferably, a vaccine is a pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents.

As used herein, "sequence variant" (also referred to as "variant") refers to any alteration in a reference sequence, whereby a reference sequence may be any of the sequences listed in the "Tables of Sequences and SEQ ID Numbers" (sequence listing), i.e. SEQ ID NO: 1 to SEQ ID NO: 65.

Thus, the term "sequence variant" includes nucleotide sequence variants and amino acid sequence variants. Of note, the sequence variants referred to herein are in particular functional sequence variants, i.e. sequence variants maintaining the biological function of, for example, the immunogen. In the context of the present invention such a maintained biological function is preferably the binding of the immunogen to an RSV F prefusion-specific antibody and/or the ability of the vaccine to elicit an immune response in the subject, e.g. by inducing antibodies against prefusion F RSV protein. Preferred sequence variants are thus functional sequence variants having at least 70%, at least 75%, at least 80%, at least 85%, at least 88%, at least 90%, at least 92%, at least 95%, at least 96%, at least 97%, at least 98% or at least 99% sequence identity to a reference sequence. The phrase "functional sequence variant thereof having at least 70%, at least 75%, at least 80%, at least 85%, at least 88%, at least 90%, at least 92%, at least 95%, at least 96%, at least 97%, at least 98% or at least 99% sequence identity", as used herein, means (i) that the sequence variant is functional as described herein and (ii) the higher the % sequence identity, the more preferred the sequence variant. In other words, the phrase "functional sequence variant thereof having at least 70%, at least 75%, at least 80%, at least 85%, at least 88%, at least 90%, at least 92%, at least 95%, at least 96%, at least 97%, at least 98% or at least 99% sequence identity", means in particular that the functional sequence variant has at least 70% sequence identity, preferably at least 75% sequence identity, preferably at least 80% sequence identity, more preferably at least 85% sequence identity, more preferably at least 88% sequence identity, even more preferably at least 90% sequence identity, even more preferably at least 92% sequence identity, still more preferably at least 95% sequence identity, still more preferably at least 96% sequence identity, particularly preferably at least 97% sequence identity, particularly preferably at least 98% sequence identity and most preferably at least 99% sequence identity to the respective reference sequence. Alternatively, it is also preferred that a (functional) sequence variant has at least 50%, preferably at least 60%, preferably at least 70%, preferably at least 75%, more preferably at least 80%, more preferably at least 82%, even more preferably at least 85%, even more preferably at least 87%, most preferably at least 90% or particularly preferably at least 95% sequence identity to a reference sequence. The term "sequence variant" includes in particular such variants that comprise mutations and/or substitutions in comparison to the respective reference sequence.

Sequence identity is usually calculated with regard to the full length of the reference sequence (i.e. the sequence recited in the application). In particular, sequence alignments are performed such that the highest percentage of sequence identity is obtained. Percentage identity, as referred to herein, can be determined, for example, using BLAST using the default parameters specified by the NCBI (the National Center for Biotechnology Information; http://www.ncbi.nlm.nih.gov/) [Blosum 62 matrix; gap open penalty=11 and gap extension penalty=1].

As used herein, a "nucleotide sequence variant" has an altered sequence in which one or more of the nucleotides in the reference sequence is deleted, or substituted, or one or more nucleotides are inserted into the sequence of the reference nucleotide sequence. Nucleotides are referred to herein by the standard one-letter designation (A, C, G, or T). Due to the degeneracy of the genetic code, a "nucleotide sequence variant" can either result in a change in the respective reference amino acid sequence, i.e. in an "amino acid sequence variant" or not. Preferred sequence variants are such nucleotide sequence variants, which do not result in amino acid sequence variants (silent mutations), but other non-silent mutations are within the scope as well, in particular mutant nucleotide sequences, which result in an amino acid sequence, which is at least 80%, preferably at least 90%, more preferably at least 95% sequence identical to the reference sequence.

An "amino acid sequence variant" has an altered sequence in which one or more of the amino acids in the reference sequence is deleted or substituted, or one or more amino acids are inserted into the sequence of the reference amino acid sequence. As a result of the alterations, the amino acid sequence variant has an amino acid sequence which is at least 80% identical to the reference sequence, preferably, at least 90% identical, more preferably at least 95% identical, most preferably at least 99% identical to the reference sequence. Variant sequences which are at least 90% identical have no more than 10 alterations, i.e. any combination of deletions, insertions or substitutions, per 100 amino acids of the reference sequence.

While it is possible to have non-conservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydoxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include the fusion to the N- or C-terminus of an amino acid sequence to a reporter molecule or an enzyme.

Importantly, the alterations in the sequence variants do not abolish the functionality of the respective reference sequence, in the present case, e.g., the functionality of a sequence of an immunogen, or of a fragment thereof, to bind to the same antibody and/or to elicit an immune response. Guidance in determining which nucleotides and amino acid residues, respectively, may be substituted, inserted or deleted without abolishing such functionality are found by using computer programs well known in the art.

As used herein, a nucleic acid sequence or an amino acid sequence "derived from" a designated nucleic acid, peptide, polypeptide or protein refers to the origin of the nucleic acid, peptide, polypeptide or protein. Preferably, the nucleic acid sequence or amino acid sequence which is derived from a particular sequence has an amino acid sequence that is essentially identical to that sequence or a portion thereof, from which it is derived, whereby "essentially identical" includes sequence variants as defined above. Preferably, the nucleic acid sequence or amino acid sequence which is derived from a particular peptide or protein, is derived from the corresponding domain in the particular peptide or protein. Thereby, "corresponding" refers in particular to the same functionality. For example, an "extracellular domain" corresponds to another "extracellular domain" (of another protein), or a "transmembrane domain" corresponds to another "transmembrane domain" (of another protein). "Corresponding" parts of peptides, proteins and nucleic acids are thus easily identifiable to one of ordinary skill in the art. Likewise, sequences "derived from" other sequence are usually easily identifiable to one of ordinary skill in the art as having its origin in the sequence.

Preferably, a nucleic acid sequence or an amino acid sequence derived from another nucleic acid, peptide, polypeptide or protein may be identical to the starting nucleic acid, peptide, polypeptide or protein (from which it is derived). However, a nucleic acid sequence or an amino acid sequence derived from another nucleic acid, peptide, polypeptide or protein may also have one or more mutations relative to the starting nucleic acid, peptide, polypeptide or protein (from which it is derived), in particular a nucleic acid sequence or an amino acid sequence derived from another nucleic acid, peptide, polypeptide or protein may be a functional sequence variant as described above of the starting nucleic acid, peptide, polypeptide or protein (from which it is derived). For example, in a peptide/protein one or more amino acid residues may be substituted with other amino acid residues or one or more amino acid residue insertions or deletions may occur.

As used herein, the term "mutation" relates to a change in the nucleic acid sequence and/or in the amino acid sequence in comparison to a reference sequence, e.g. a corresponding genomic sequence. A mutation, e.g. in comparison to a genomic sequence, may be, for example, a (naturally occurring) somatic mutation, a spontaneous mutation, an induced mutation, e.g. induced by enzymes, chemicals or radiation, or a mutation obtained by site-directed mutagenesis (molecular biology methods for making specific and intentional changes in the nucleic acid sequence and/or in the amino acid sequence). Thus, the terms "mutation" or "mutating" shall be understood to also include physically making a mutation, e.g. in a nucleic acid sequence or in an amino acid sequence. A mutation includes substitution, deletion and insertion of one or more nucleotides or amino acids as well as inversion of several successive nucleotides or amino acids. To achieve a mutation in an amino acid sequence, preferably a mutation may be introduced into the nucleotide sequence encoding said amino acid sequence in order to express a (recombinant) mutated polypeptide. A mutation may be achieved e.g., by altering, e.g., by site-directed mutagenesis, a codon of a nucleic acid molecule encoding one amino acid to result in a codon encoding a different amino acid, or by synthesizing a sequence variant, e.g., by knowing the nucleotide sequence of a nucleic acid molecule encoding a polypeptide and by designing the synthesis of a nucleic acid molecule comprising a nucleotide sequence encoding a variant of the polypeptide without the need for mutating one or more nucleotides of a nucleic acid molecule.

Immunogen

In a first aspect the present invention provides an immunogen comprising a recombinant RSV F protein or a fragment thereof specifically binding to an RSV F prefusion-specific antibody, wherein the recombinant RSV F protein or the fragment thereof comprises an F1 polypeptide and an F2 polypeptide of any RSV F protein characterized by the following substitutions at amino acid positions corresponding to the following amino acid positions in SEQ ID NO: 1 as a reference sequence:

(i) S155C and S290C substitutions, which form a non-natural disulfide bond;
(ii) a substitution at one or both of positions S190 and V207 by amino acids selected from the group consisting of F, L, W, Y, H, and M; and
(iii) a pair of substitutions forming a non-natural disulfide bond selected from the group consisting of the following substitution pairs: Q98C and Q361C, A149C and Y458C, N183GC and N428C, N88C and N254C, E92C and N254C, and S238C and Q279C;

and wherein the recombinant RSV F protein or the fragment thereof does not comprise a pep27 polypeptide.

In other words, the present invention provides an immunogen comprising an RSV F protein antigen that is stabilized or "locked" in a prefusion conformation (also termed "PreF antigens" or "PreF immunogens"). Using structure-guided design, positions of the RSV F1 and F2 polypeptides are targeted for modification (e.g., amino acid substitution) to hinder or prevent transition of the RSV F protein from a pre- to a postfusion conformation. Such antigens/immunogens have utility, for example, as immunogens to induce a neutralizing response to RSV F protein. The immunogen according to the present invention may be the recombinant RSV F protein or the fragment thereof itself (i.e., without any additional components), or it may comprise the recombinant RSV F protein or the fragment thereof and further components. Such further components are preferably covalently linked to recombinant RSV F protein or the fragment thereof. More preferably, such further components are of (poly)peptidic nature and form a fusion construct (fusion protein) with the recombinant RSV F protein or the fragment thereof. Examples of such further components include, e.g., purification tags, cleavage site and other components as described below.

As used herein (peptide and protein) "modifications" refer in particular to peptides, such as the disclosed recombinant RSV F proteins stabilized in a prefusion conformation, which is modified, for example by the amino acid substitutions outlined above as compared to a native RSV protein sequence, and/or by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide. Hydroxyl groups of the peptide side chains can be converted to $C_1$-$C_{16}$ alkoxy or to a $C_1$-$C_{16}$ ester using well recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Accordingly, as used herein, an "immunogen" is typically able to elicit an immune response. As used herein an "immunogen" is in particular a protein or a portion thereof that is capable of inducing an immune response in a mammal (such as humans and cattle, preferably cattle), such as a mammal infected or at risk of infection with a pathogen (such as hRSV or bRSV, preferably bRSV). Administration of an immunogen can for example lead to protective immunity and/or proactive immunity against a pathogen of interest.

The term "immune response" as used herein typically refers to a response of a cell of the immune system, such as a B cell, T cell, or monocyte, to a stimulus. Preferably, the response may be specific for a particular antigen (an "antigen-specific response"). An immune response is preferably a T cell response, such as a CD4+ response or a CD8+ response. It is also preferred that the immune response is a B cell response, and results in the production of specific antibodies. A "Th1" immune response is in particular characterized by the presence of CD4+T helper cells that produce IL-2 and IFN-γ, and thus, by the secretion or presence of IL-2 and IFN-γ. In contrast, a "Th2" immune response is in particular characterized by a preponderance of CD4+ helper cells that produce IL-4, IL-5, and IL-13.

The immunogens as disclosed herein comprises a recombinant RSV F protein or fragment thereof.

In general, an RSV Fusion (F) protein (also referred to as "RSV F protein" or "RSV F") is an RSV envelope glycoprotein that facilitates fusion of viral and cellular membranes. In nature, the RSV F protein is initially synthesized as a single polypeptide precursor approximately 574 amino acids in length, designated F0. Examples of F0 proteins are known from many different RSV subgroups, such as bRSV and hRSV. Amino acid sequences of referred exemplary bRSV F0 proteins are depicted in SEQ ID NO: 1-9.

bRSV 391-2 F0 (GenBank Acc. No: AAA42808.1):

[SEQ ID NO: 1]

```
maatamrmiisiifistymthiticqniteefyqstcsavsrgylsalrtgwytsvvtielskiqknvck stdskvklikqelerynnavielqslmqnepasfsrakrgipelihytrnstkrfyglmgkkrkrrflgf llgigsaiasgvavskvlhlegevnkiknallstnkavvslsngvsvltskvldlknyidkellpkvnnh dcrisnietviefqqknnrlleiarefsvnagittplstymltnsellslindmpitndqkklmssnyqi vrqqsysimsvvkeeviayvvqlpiygvidtpcwklhtsplcttdnkegsnicltrtdrgwycdnagsvs ffpqaetckvqsnrvfcdtmnsltlptdvnlcntdifntkydckimtsktdisssvitsigaivscygkt kctasnknrgiiktfsngcdyvsnkgvdtvsvgntlyyvnklegkalyikgepiinyydplvfpsdefda siaqvnakinqslafirrsdellhsvdvgksttnvvittiiivivvvilmliavgllfycktrstpimlg
```

-continued kdqlsginnlsfsk bRSV ATue51908 F0 (NCBI Reference Sequence: NP_048055.1)
[SEQ ID NO: 2]
mattamrmiisiifistyvthitlcqniteefyqstcsavsrgylsalrtgwytsvvtielskiqknvck
stdskvklikqelerynnavvelqslmqnepasfsrakrgipelihytrnstkkfyglmgkkrkrrflgf
llgigsavasgvavskvlhlegevnkiknallstnkavvslsngvsvltskvldlknyidkellpqvnnh
dcrisnietviefqqknnrlleiarefsvnagittplstymltnsellslindmpitndqkklmssnyqi
vrqqsysimsvvkeeviayvvqlpiygvidtpcwklhtsplcttdnkegsnicltrtdrgwycdnagsvs
ffpqtetckvqsnrvfcdtmnsltlptdvnlcntdifntkydckimtsktdisssvitsigaivscygkt
kctasnknrgiiktfsngcdyvsnkgvdtvsygntlyyvnklegkalyikgepiinyydplvfpsdefda
siaqvnakinqslafirrsdellhsvdvgksttnvvittiiivivvvilmliavgllfycktkstpimlg
kdqlsginnlsfsk bRSV RB94 F0 (GenBank Acc. No: CAN90052.1)
[SEQ ID NO: 3]
matttmrmiisiiiifiyvqhitlcqniteefyqstcsavsrgylsalrtgwytsvvtielskiqknvcn
stdsnvklikqelerynnavvelqslmqnepasssrakrgipelihykrnstkkfyglmgkkrkrrflgf
llgigsaiasgvavskvlhlegevnkiknallstnkavvslsngvsvltskvldlknyidkellpkvnnh
dcqisniatviefqqknnrlleiarefsvnagittplstymltnsellslindmpitndqkklmssnvqi
vrqqsysimsvvkeevmayvvqlpiygvidtpcwklhtsplcttdnkegsnicltrtdrgwycdnagsvs
ffpqaetckvqsnrvfcdtmnsltlptdvnlcntdifnakydckimtsktdisssvitsigaivscygkt
kctasnknrgiiktfsngcdyvsnrgvdtvsvgntlyyvnklegkalyikgepiinyydplvfpsdefda
siaqvnakinqslafirrsdellhsvdvgksttnvvittiiivivvvilmliavgllfysktrstpimlg
kdqlsginnlsfsk bRSV RB94 F-11 F0 (GenBank Acc. No: BAA00798.1)
[SEQ ID NO: 4]
mattamrmiisiifistyvthitlcqniteefyqstcsaysrgylsalrtgwytsvvtielskiqknvcn
stdsnvklikqelerynnavvelqslmqnepasssrakrgipelihykrnstkkfyglmgkkrkrrflgf
llgigsaiasgvavskvlhlegevnkiknallstnkavvslsngvsvltskvldlknyidkellpkvnnh
dckisniatviefqqknnrlleiarefsvnagittplstymltnsellslindmpitndqkklmssnvqi
vrqqsysimsvvkeevmayvvqlpiygvidtpcwklhtsplcttdkegsnicltrtdrgwycdnagsvsf
fpqaetckvqsnrvfcdtmnsltlptdvnlcntdifnakydckimtsktdisssvitsigaivscygktk
ctasnknrgiiktfsngcdyvsnrgvdtvsvgntlyyvnklegkalyikgepiinyydplvfpsdefdas
iaqvnakinqslafirrsdellhsvdvgksttnvvittiiivivvvilmliavgllfysktrstpimlgk
dqlsginnlsfsk bRSV A51908 F0 (GenBank Acc. No: AAA42804.1)
[SEQ ID NO: 5]
matttmrmiisiilistyvphitlcqniteefyqstcsavsrgylsalrtgwytsvvtielskiqknvcn
gtdskvklikqelerynnavaelqslmqneptsssrakrgipesihytrnstkkfyglmgkkrkrrflgf
llgigsaiasgvavskvlhlegevnkiknallstnkavvslsngvsvltskvldlknyidkellpkvnnh
dcrisniatviefqqknnrlleiarefsvnagittplstymltnsellsiindmpitndqkklmsvcqiv
rqqsysimsvlreviayvvqlplygvidtpcwklhtsplcttdnkegsnicltrtdrgwycdnagsvsff
pqaetckvqsnrvfcdtmnsltlptdvnlcntdifnskydckimtsktdisssvitsigaivscygktkc
tasnknrgiiktfsngcdyvsnkgvdtvsvgntlyyvnklegkalyikgepiinyynplvfpsdefdasi
aqvnakinqslafirrsdellhsvdvgksttnvvittiiivivvvilmlitvgllfycktrstpimlgkd qlssinnlsfsk bRSV A375 F0 (GenBank Acc. No: ACL80037.1)

[SEQ ID NO: 6]

mrmiisiilistyvphitlcqniteefyqstcsavsrgylsalrtgwytsvvtielskiqknvcngtdsk vklikqeleryrnnavvelqslmqneptsssrakrgipesihytrnstkkfyglmgkkrkrrflgfllgig saiasgvavskvlhlegevnkiknallstnkavvslsngvsvltskvldlknyidkkllpkvnnhdcris nietviefqqknnrlleiarefsvnagittplstymltnsellslindmpitndqkklmssnvqivrqqs ysimsvvkeeviayvvqlpiygvidtpcwkvhtsplcttdnkegsnicltrtdrgwycdnagsvsffpqa etckvqsnrvfcdtmnsltlptdvnlcntdifntkydckimtsktdisssvitsigaivscygktkctas nknrgiiktfsngcdyvsnkgvdtvsvgntlyyvnklegkalyikgepiinyynplvfgtyefdasiaqv nak bRSV FS1 F0 (GenBank Acc. No: AAB28458.1)

[SEQ ID NO: 7]

mgttamrmvisiifistyvthitlcqniteefyqstcsavsrgylsalrtgwytsvvtielskiqknvck stdskvklikqeleryrnnavielqslmqnepasfsrakrgipelihyprnstkrfyglmgkkrkrrflgf llgigsaiasgvavskvlhlegevnkiknallstnkavvslsngvsvltskvldlknyidkellpkvnnh dcrisnigtviefqqknnrlleiarefsvnagittplstymltnsellslindmpitndqkklmssnvqi vrqqsysimsvvkeeviayevqlpiygvidtpcwkihtsplcttdnkegsnicltrtdrgwycdnagsvs ffpqaetckvqsnrvfcdtmnsltlptdvnlcntdifntkydckimtsktdisssvitsigaivscygkt kctasnknrgiiktfpigcdyvsnkgvdtvsvgntlyyvnklegkalyikgepiinyydplvfpsdefda siaqvnakinqslafirrsdellhsvdvgksttnvvittiiivivvvilmliavgllfycktrstpimlg kdqlsginnlsfsk bRSV Snook F0 (GenBank Acc. No: CAA76980.1)

[SEQ ID NO: 8]

mattamtmiisiifistyvthitlcqniteefyqstcsavsrgylsalrtgwytsvvtielskiqknvck stdskvklikqeleryrnnavvelqslmqnepasfsrakrsipelihytrnstkkfyglmgkkrkrrflgf llgigsaiasgvavskvlhlegevnkiknallstnkavvslsngvsvltskvldlknyidkellpkvnnh dcrisniatviefqqknnrlleiarefsvnagittplstymltnsellslindmpitndqkklmssnvqi vrqqsysimsvvkeeviayvvqlpiygvidtpcwklhtsplcttdnkegsnicltrtdrgwycdnagsvs ffpqaetckvqsnrvfcdtmnsltlptdvnlcntdifntkydckimtsktdisssvitsigaivscygkt kctasnknrgiiktfsngcdyvsnkgvdtvsvgntlyyvnklegkalyikgepiinyydplvfpsdefda siaqvnakinqslafirrsdellhsvdvgksttnvvittiiivivvvilmliavgllfycktrstpimlg kdqlsginnlsfsk bRSV ATCC51908 F0 (GenBank Acc. No: AAL49399.1)

[SEQ ID NO: 9]

mattamrmiisiifistyvthitlcqniteefyqstcsavsrgylsalrtgwytsvvtielskiqknvcn stdskvklikqeleryrnnavvelqslmqnepasfsrakrgipelihytrnstkkfyglmgkkrkrrflgf llgigsaiasgvavskvlhlegevnkiknallstnkavvslsngvsvltskvldlknyidkellpkvnnh dcriskietviefqqknnrlleiarefsvnagittplstymltnsellslindmpitndqkklmssnvqi vrqqsysimsvvkeeviayvvqlpiygvidtpcwklhtsplcttdnkegsnicltrtdrgwycdnagsvs ffpqtetckvqsnrvfcdtmnsltlptdvnlcntdifntkydckimtsktdisssvitsigaivscygkt

```
kctasnknrgiiktfsngcdyvsnkgvdtvsvgntlyyvnklegkalyikgepiinyydplvfpsdefda siaqvnakinqslafirrsdellhsvdvgksttnvvittiiivivvvilmliavgllfycktkstpimlg kdqlsginnlsfsk
```

F0 includes an N-terminal signal peptide that directs localization to the endoplasmic reticulum, where the signal peptide (approximately the first 25 residues of F0) is proteolytically cleaved. The remaining F0 residues oligomerize to form a trimer which is again proteolytically processed by a cellular protease at two conserved furin consensus cleavage sequences to generate two disulfide-linked fragments, F1 and F2. The smaller of these fragments, F2, originates from the N-terminal portion of the F0 precursor and includes approximately residues 26-109 of F0. The larger of these fragments, F1, includes the C-terminal portion of the F0 precursor (approximately residues 137-574) including an extracellular/lumenal region (residues 137-524), a transmembrane domain (residues 525-550), and a cytoplasmic domain (-residues 551-574) at the C-terminus. Three F2-F1 protomers oligomerize in the mature F protein, which adopts a metastable "prefusion" conformation that is triggered to undergo a conformational change (to a "postfusion" conformation) upon contact with a target cell membrane. This conformational change exposes a hydrophobic sequence, known as the fusion peptide, which is located at the N-terminus of the F1 polypeptide, and which associates with the host cell membrane and promotes fusion of the membrane of the virus, or an infected cell, with the target cell membrane.

A "recombinant RSV F protein" may be any RSV F protein, which does not occur in nature. Accordingly, a "recombinant RSV F protein" typically has been modified from a native form, for example in order to increase immunogenicity. For example, the "recombinant RSV F protein" may be modified from the native RSV F protein to be stabilized in a prefusion conformation. Specific modifications according to the present invention are described herein, however, the "recombinant RSV F protein" may also differ in further aspects (not described herein) from the native RSV F protein. Accordingly, the modifications in which a "recombinant RSV F protein" differs from a native RSV F protein are not limited as long as the "recombinant RSV F protein" is still capable of specifically binding to an RSV F prefusion-specific antibody (and thus in particular of eliciting an immune response to prefusion RSV F).

A fragment of a recombinant RSV F protein refers to any fragment of the recombinant RSV F protein comprising at least 10 (consecutive) amino acids of the recombinant RSV F protein. Preferably, the fragment comprises at least 20 (consecutive) amino acids, preferably at least 30 (consecutive) amino acids, more preferably at least 40 (consecutive) amino acids, even more preferably at least 50 (consecutive) amino acids, and most preferably at least 60 (consecutive) amino acids of the recombinant RSV F protein.

Typically, RSV F prefusion-specific antibodies specifically bind to ("recognize") an antigenic site in the RSV F protein, which is only present in prefusion RSV F proteins, but not in postfusion RSV F proteins. As used herein, in particular in the context of the formation of an antibody: antigen protein complex, "specifically binding" refers to a binding reaction which determines the presence of a target protein, peptide, or polysaccharide (for example a glycoprotein), in the presence of a heterogeneous population of proteins and other biologics. Thus, under designated conditions, an antibody binds preferentially to a particular target protein, peptide or polysaccharide (such as an antigen present on the surface of a pathogen, for example RSV F) and does not bind in a significant amount to other proteins or polysaccharides present in the sample or subject. An antibody that specifically binds to the prefusion conformation of RSV F protein (e.g., antibodies specifically binding to antigenic site Ø, the epitope recognized by antibody MPE8 or the epitope recognized by antibody AM14) does typically not specifically bind to the postfusion conformation of RSV F protein. Specific binding can be determined by methods known in the art. With reference to an antibody:antigen or Fab:antigen complex, specific binding of the antigen and antibody has in particular a $K_d$ (or apparent $K_d$) of less than about $10^{-6}$ Molar, preferably less than about $10^{-7}$ Molar, more preferably less than about 10 Molar, even more preferably less than about $10^{-9}$, and most preferably less than about $10^{-10}$ Molar.

As used herein, "RSV F protein prefusion conformation" (also referred to as "prefusion RSV F protein" or "prefusion RSV F") refers to structural conformation adopted by the RSV F protein prior to triggering of the fusogenic event that leads to transition of RSV F to the postfusion conformation and following processing into a mature RSV F protein in the secretory system. The three-dimensional structure of an exemplary RSV F protein in a prefusion conformation is shown for example in FIGS. 3 *a-c* and 11 and described in Example 4. In the prefusion state, the RSV F protein includes an antigenic site at the membrane distal apex ("antigenic site Ø", see Example 4), that includes RSV F residues 62-69 and 196-209, and also includes the epitopes of the D25 and AM22 antibodies. However, the greatest structural differences between hRSV and bRSV prefusion F proteins are observed in the residues 206-215 at the apical loop between α4 and α5 near antigenic site Ø (FIG. 11 *a, b*, left panels), which is also the region of highest sequence divergence (only approx. 50% identity) between hRSV and bRSV. Therefore, antigenic-site-Ø recognizing antibodies raised against hRSV prefusion F protein (such as D25) may show a lower binding affinity to bRSV prefusion F protein than to hRSV prefusion F protein. However, such antibodies still specifically bind to bRSV prefusion F protein, even though their binding affinity may not be as high for bRSV prefusion F protein as for hRSV prefusion F protein. Such species differences may be avoided by antibodies binding to prefusion RSV F epitopes, which are more conserved, for example, the epitopes recognized by antibodies MPE8 and AM14, respectively.

As used herein, a recombinant RSV F protein stabilized in a prefusion conformation can be specifically bound by an antibody that is specific for the prefusion conformation of the RSV F protein, such as an antibody that specifically binds to an epitope within antigenic site Ø, for example the D25 antibody, an antibody that specifically binds to an MPE8 epitope, for example, the MPE8 antibody, and/or an antibody that specifically binds to an AM14 epitope, for example, the AM14 antibody.

Preferably, the RSV F prefusion-specific antibody is selected from D25, AM14 and MPE8. More preferably, the RSV F prefusion-specific antibody is AM14 and/or MPE8. In order to determine whether the recombinant RSV F protein or the fragment thereof binds to an RSV F prefusion-specific antibody, one or more of the above antibodies may be used.

MPE8 is a neutralizing monoclonal antibody that specifically binds to the prefusion conformation of the RSV F protein, but not to the postfusion conformation of RSV F protein. MPE8 is described in Corti et al. (Nature, 501(7467) 439-443, 2013, incorporated by reference herein in its entirety). MPE8 potently cross-neutralizes hRSV and hMPV as well as two animal paramyxoviruses: bovine RSV (bRSV) and pneumonia virus of mice (PVM). The core epitope of MPE8 was mapped on two highly conserved anti-parallel β-strands on the pre-fusion viral F protein, which are rearranged in the post-fusion F protein conformation. Accordingly, the MPE8 antibody binds to an epitope found on the pre- but not postfusion conformations of the RSV F protein. The MPE8 epitope is not part of antigenic site Ø. The heavy and light chain variable region sequences of the MPE8 antibody are set forth as SEQ ID NOs: 50 and 51, respectively.

MPE8 Heavy Chain Variable region:
[SEQ ID NO: 50]
EVQLVESGGGLVKPGGSLRLSCAASGFTFSSYSMNWVRQAPGKGLEWVSS

ISASSSYSDYADSAKGRFTISRDNAKTSLFLQMNSLRAEDTAIYFCARAR

ATGYSSITPYFDIWGQGTLVTVSS

MPE8 Light Chain Variable region:
[SEQ ID NO: 51]
QSVVTQTPSVSGAPGQRVTISCTGSSSNIGAGYDVHWYQQLPGTAPKLLI

YDNNNRPSGVPDRFSASKSGTSASLAITGLQAEDEADYYCQSYDRNLSGV

FGTGTKVTVL

AM14 is also a neutralizing monoclonal antibody that specifically binds to the prefusion conformation of the RSV F protein, but not to the postfusion conformation of RSV F protein. MPE8 is described in Gilman, M. S. A., et al. (PLoS pathogens 11, e1005035, 2015, incorporated by reference herein in its entirety). In contrast to other RSV F prefusion-specific antibodies, which typically recognize epitopes present on monomers, AM14 recognizes a quaternary epitope that spans two protomers and includes a region that undergoes extensive conformational changes in the pre- to post-fusion F transition. AM14 specifically recognizes trimeric furin-cleaved prefusion F. The epitope recognized by AM14 is located midway between the membrane-proximal region and the apex of the prefusion F trimer. The epitope is evenly distributed across two protomers. Thus, AM14 is trimer-specific and cleavage-dependent. The heavy and light chain variable region sequences of the AM14 antibody are set forth as SEQ ID NOs: 52 and 53, respectively.

AM14 Light Chain Variable region:
[SEQ ID NO: 52]
DIQMTQSPSSLSASVGDRVTITCQASQDIKKYLNWYHQKPGKVPELLMHD

ASNLETGVPSRFSGRGSGTDFTLTISSLQPEDIGTYYCQQYDNLPPLTFG

GGTKVEIKR

AM14 Heavy Chain Variable region:
[SEQ ID NO: 53]
EVQLVESGGGVVQPGRSLRLSCAASGFSFSHYAMHWVRQAPGKGLEWVAV

ISYDGENTYYADSVKGRFSISRDNSKNTVSLQMNSLRPEDTALYYCARDR

IVDDYYYGMDVWGQGATVTVSS

D25 is a neutralizing monoclonal antibody that specifically binds to the prefusion conformation of the RSV F protein, but not the post fusion conformation of RSV F protein. D25 protein and nucleic acid sequences are known, for example, the heavy and light chain amino acid sequences of the D25 antibody are set forth in U.S. Pat. App. Pub. No. 2010/0239593, which is incorporated herein in its entirety; see also, Kwakkenbos et al., Nat. Med., 40 16: 123-128, 2009). D25 specifically binds to a quaternary epitope (included on antigenic site Ø) found on the RSV F protein in its prefusion conformation, but not the post fusion conformation. This epitope is included within RSV F positions 62-69 and 196-209, and located at the membrane distal apex of the RSV F protein in the prefusion conformation. The heavy and light chain variable region sequences of the D25 antibody are set forth as SEQ ID NOs: 54 and 55, respectively.

D25 Light Chain Variable region:
[SEQ ID NO: 54]
DIQMTQSPSSLSAAVGDRVTITCQASQDIVNYLNWYQQKPGKAPKLLIYV

ASNLETGVPSRFSGSGSGTDFSLTISSLQPEDVATYYCQQYDNLPLTFGG

GTKVEIK

D25 Heavy Chain Variable region:
[SEQ ID NO: 55]
QVQLVQSGAEVKKPGSSVMVSCQASGGPLRNYIINWLRQAPGQGPEWMGG

IIPVLGTVHYAPKFQGRVTITADESTDTAYIHLISLRSEDTAMYYCATET

ALVVSTTYLPHYFDNWGQGTLVTVSS

Preferably, the RSV F prefusion-specific antibody, to which the immunogen specifically binds to, is D25, MPE8 and/or AM14. More preferably, the RSV F prefusion-specific antibody, to which the immunogen specifically binds to, is MPE8 and/or AM14.

The recombinant RSV F protein or the fragment thereof comprises an F1 polypeptide and an F2 polypeptide of any RSV F protein.

In general, the F1 polypeptide and the F2 polypeptide of the recombinant RSV F protein are typically (functional) sequence variants of the F1 polypeptide and the F2 polypeptide, respectively, of a native (naturally occurring) RSV F protein. Accordingly, the amino acid sequence of the F1 polypeptide of the recombinant RSV F protein typically has at least 50%, preferably at least 60%, preferably at least 70%, preferably at least 75%, more preferably at least 80%, more preferably at least 82%, even more preferably at least 85%, even more preferably at least 87%, most preferably at least 90% or particularly preferably at least 95% sequence identity to the amino acid sequence of the F1 polypeptide of a native (naturally occurring) RSV F protein. Moreover, the amino acid sequence of the F2 polypeptide of the recombinant RSV F protein typically has at least 70%, preferably at least 75%, preferably at least 80%, more preferably at least 85%, more preferably at least 88%, even more preferably at least 90%, even more preferably at least 92%, still more preferably at least 95% sequence identity and most preferably at least 98% sequence identity to the amino acid sequence of the F2 polypeptide of a native (naturally occurring) RSV F protein. However, the amino acid sequences of the F1 polypeptide and the F2 polypeptide of the recombinant RSV F protein differ at least in the specific mutations as described herein from the amino acid sequences of the F1 polypeptide and the F2 polypeptide of a native (naturally occurring) RSV F protein. F1 polypeptides and the F2 polypeptides of a native (naturally occurring) RSV F protein are well known in the art. They may be readily identified, for example based on the amino acid sequence of a native (naturally occurring) RSV F0 protein (see, for example, SEQ ID NOs: 1-9).

In general, an RSV F1 polypeptide (F1) is a peptide chain of the RSV F protein. As used herein, "F1 polypeptide" refers to both native F1 polypeptides and F1 polypeptides including modifications (e.g., amino acid substitutions, insertions, or deletion) from the native sequence, for example, modifications designed to stabilize a recombinant F protein (including the modified F1 polypeptide) in a RSV F protein prefusion conformation. Typically, native F1 includes approximately residues 137-574 of the RSV F0 precursor, and includes (from N- to C-terminus) an extracellular/lumenal region (residues 137-524), a transmembrane domain (residues 525-550), and a cytoplasmic domain (residues 551-574). Typically, the F1 polypeptide of a recombinant RSV F protein is modified from a native F1 sequence, for example an F1 polypeptide that lacks the transmembrane and cytosolic domain, and/or includes one or more amino acid substitutions that stabilize a recombinant F protein (containing the F1 polypeptide) in a prefusion conformation. For example, a preferred recombinant RSV F protein may include a F1 polypeptide with cysteine substitutions at positions 155, 290, and 361, a phenylalanine or a leucine substitution at position S190 and a leucine substitution at position V207. Such a F1 polypeptide of a preferred recombinant RSV F protein may further include a deletion of the transmembrane and/or cytosolic domains. In addition, such a F1 polypeptide of a preferred recombinant RSV F protein may also include a C-terminal linkage to a trimerization domain as described herein. For example, another preferred recombinant RSV F protein may include a F1 polypeptide with cysteine substitutions at positions 149, 155, and 458 a phenylalanine or a leucine substitution at position S190 and a leucine substitution at position V207. Such a F1 polypeptide of a preferred recombinant RSV F protein may further include a deletion of the transmembrane and/or cytosolic domains. In addition, such a F1 polypeptide of a preferred recombinant RSV F protein may also include a C-terminal linkage to a trimerization domain as described herein. For example, another preferred recombinant RSV F protein may include a F1 polypeptide with cysteine substitutions at positions 155, 183 and 428 a phenylalanine or a leucine substitution at position S190 and a leucine substitution at position V207. Such a F1 polypeptide of a preferred recombinant RSV F protein may further include a deletion of the transmembrane and/or cytosolic domains. In addition, such a F1 polypeptide of a preferred recombinant RSV F protein may also include a C-terminal linkage to a trimerization domain as described herein. Many examples of native F1 sequences are known which are provided herein as approximately positions 137-574 of SEQ ID NOs: 1-9.

RSV F2 polypeptide (F2) is typically a polypeptide chain of the RSV F protein. As used herein, "F2 polypeptide" refers to both native F2 polypeptides and F2 polypeptides including modifications (e.g., amino acid substitutions) from the native sequence, for example, modifications designed to stabilize a recombinant F protein (including the modified F2 polypeptide) in a RSV F protein prefusion conformation. Native F2 includes approximately residues 26-109 of the RSV F0 precursor. In native RSV F protein, the F2 polypeptide is linked to the F1 polypeptide by two disulfide bonds. Preferably, the F2 polypeptide of a recombinant RSV F protein is modified from a native F1 sequence, for example an F1 polypeptide that includes one or more amino acid substitutions that stabilize a recombinant F protein (containing the F2 polypeptide) in a prefusion conformation. For example, a preferred recombinant RSV F protein may include a F2 polypeptide with a cysteine substitution at position 98. Many examples of native F2 sequences are known which are provided herein as approximately positions 26-109 of SEQ ID NOs: 1-9.

In general, the F1 polypeptide and the F2 polypeptide of the recombinant RSV F protein comprise at least the following substitutions (in comparison to native RSV F0 proteins):

(i) a first pair of cysteines, which forms a non-natural disulfide bond, and which substitutes an amino acid pair corresponding to S155 and S290 in SEQ ID NO: 1;

(ii) one or two amino acids selected from the group consisting of F, L, W, Y, H, and M, which substitute one or both amino acids corresponding to S190 and/or V207 in SEQ ID NO: 1; and (iii) a second pair of cysteines, which forms a non-natural disulfide bond, and which substitutes an amino acid pair corresponding to one of the following amino acid pairs of SEQ ID NO: 1: Q98 and Q361, A149 and Y458, N183 and N428, N88 and N254, E92 and N254, and S238 and Q279.

Thereby, the (single) amino acid corresponding to N183 in SEQ ID NO: 1 is preferably substituted by the two amino acids GC (also referred to herein as "N183GC").

Many examples of native F0 sequences are known. Preferred examples thereof are provided herein as SEQ ID NOs: 1-9.

In general, the amino acid positions "S155", "S290", "S190", "V207", "Q98", "Q361", "A149", "Y458", "N183", "N428", "N88", "N254", "E92", "N254", "S238", "Q279" and the like (or the amino acid positions in the terms "S155C", "S290C", "S190X", "V207X", "Q98C", "Q361C", "149C", "458C", "183GC", "428C", "A149C", "Y458C", "N183GC", "N428C", "N88C", "N254C", "E92C", "N254C", "S238C", "Q279C" and the like) refer to the amino acid sequence of bRSV strain 391-2 F0 (SEQ ID NO: 1), which served herein as reference sequence. In other words, the amino acid positions "S155", "S290", "S190", "V207", "Q98", "Q361", "A149", "Y458", "N183", "N428", "N88", "N254", "E92", "N254", "S238", "Q279" and the like (or the amino acid positions in the terms "S155C", "S290C", "S190X", "V207X", "Q98C", "Q361C", "149C", "458C", "183GC", "428C", "A149C", "Y458C", "N183GC", "N428C", "N88C", "N254C", "E92C", "N254C", "S238C", "Q279C" and the like) refer to the exact positions in the amino acid sequence of bRSV 391-2 F0 (SEQ ID NO: 1). However, the mutations/substitutions outlined above (and described throughout the present application) may be introduced into any F1 and/or F2 polypeptide at positions corresponding to the specifically mentioned positions in the reference sequence (SEQ ID NO: 1). The respective corresponding positions in other native RSV F0 proteins (or in other F1 and/or F2 polypeptides) may be easily identified by (i) aligning a query amino acid sequence (of a native RSV F0 protein (or of any F1/F2 polypeptide) of interest) to the amino acid sequence of bRSV 391-2 F0 (SEQ ID NO: 1) and (ii) determining which amino acid position in the native RSV F0 protein of interest (or in any F1/F2 polypeptide of interest) corresponds according to said alignment to the position of interest in bRSV 391-2 F0 (SEQ ID NO: 1). Thereby, sequence alignments are in particular performed such that the highest percentage of sequence identity can be obtained.

In particular, the amino acid positions "S155", "S290", "S190", "V207", "Q98", "Q361", "A149", "Y458", "N183", "N428", "N88", "N254", "E92", "N254", "S238", "Q279" and the like (or the terms "S155C", "S290C", "S190X", "V207X", "Q98C", "Q361C", "149C", "458C", "183GC", "428C", "A149C", "Y458C", "N183GC", "N428C", "N88C", "N254C", "E92C", "N254C", "S238C", "Q279C" and the like) refer (i) to the outlined position in SEQ ID NO: 1 and (ii) also to the corresponding amino acid position in other RSV F0 proteins (or other F1/F2 polypeptides).

The recombinant RSV F protein or the fragment thereof comprises at least two non-natural disulfide bonds, namely (i) a first pair of cysteines, which forms a non-natural disulfide bond, and which substitutes an amino acid pair corresponding to S155 and S290 in SEQ ID NO: 1; and (ii) a second pair of cysteines, which forms a non-natural disulfide bond, and which substitutes an amino acid pair corresponding to one of the following amino acid pairs of SEQ ID NO: 1: Q98 and Q361, A149 and Y458, N183 and N428, N88 and N254, E92 and N254, S238 and Q279. Or, in other words, the recombinant RSV F protein or the fragment thereof comprises at least two non-natural disulfide bonds, namely (i) a non-natural disulfide bond formed by the cysteine pair introduced by S155C and S290C substitutions and (ii) a non-natural disulfide bond formed by the cysteine pair introduced by Q98C and Q361C substitutions, a non-natural disulfide bond formed by the cysteine pair introduced by 149C and 458C substitutions (in particular by A149C and Y458C substitutions), a non-natural disulfide bond formed by the cysteine pair introduced by 183GC and 428C substitutions (in particular by N183GC and N428C substitutions), a non-natural disulfide bond formed by the cysteine pair introduced by N88C and N254C substitutions, a non-natural disulfide bond formed by the cysteine pair introduced by E92C and N254C substitutions, and/or a non-natural disulfide bond formed by the cysteine pair introduced by S238C and Q279C substitutions. In particular, (i) the non-natural disulfide bond formed by the cysteine pair introduced by S155C and S290C substitutions represents an intra-protomer disulfide bond; and (ii) the non-natural disulfide bond formed by any of the cysteine pairs introduced by Q98C and Q361C substitutions, A149C and Y458C substitutions, N183GC and N428C substitutions, N88C and N254C substitutions, E92C and N254C substitutions, or S238C and Q279C substitutions represents an inter-protomer disulfide bond.

Preferably, the recombinant RSV F protein or the fragment thereof according to the present invention comprises at least two non-natural disulfide bonds, namely (i) a non-natural disulfide bond formed by the cysteine pair introduced by S155C and S290C substitutions (i.e. S155C and S290C substitutions, which form a non-natural disulfide bond) and (ii) a non-natural disulfide bond formed by the cysteine pair introduced by N88C and N254C substitutions (i.e. N88C and N254C substitutions, which form a non-natural disulfide bond).

Preferably, the recombinant RSV F protein or the fragment thereof according to the present invention comprises at least two non-natural disulfide bonds, namely (i) a non-natural disulfide bond formed by the cysteine pair introduced by S155C and S290C substitutions (i.e. S155C and S290C substitutions, which form a non-natural disulfide bond) and (ii) a non-natural disulfide bond formed by the cysteine pair introduced by E92C and N254C substitutions (i.e. E92C and N254C substitutions, which form a non-natural disulfide bond).

Preferably, the recombinant RSV F protein or the fragment thereof according to the present invention comprises at least two non-natural disulfide bonds, namely (i) a non-natural disulfide bond formed by the cysteine pair introduced by S155C and S290C substitutions (i.e. S155C and S290C substitutions, which form a non-natural disulfide bond) and (ii) a non-natural disulfide bond formed by the cysteine pair introduced by S238C and Q279C substitutions (i.e. S238C and Q279C substitutions, which form a non-natural disulfide bond).

More preferably, the recombinant RSV F protein or the fragment thereof according to the present invention comprises at least two non-natural disulfide bonds, namely (i) a non-natural disulfide bond formed by the cysteine pair introduced by S155C and S290C substitutions (i.e. S155C and S290C substitutions, which form a non-natural disulfide bond) and (ii) a non-natural disulfide bond formed by the cysteine pair introduced by N183GC and N428C substitutions (i.e. N183GC and N428C substitutions, which form a non-natural disulfide bond).

Even more preferably, the recombinant RSV F protein or the fragment thereof according to the present invention comprises at least two non-natural disulfide bonds, namely (i) a non-natural disulfide bond formed by the cysteine pair introduced by S155C and S290C substitutions (i.e. S155C and S290C substitutions, which form a non-natural disulfide bond) and (ii) a non-natural disulfide bond formed by the cysteine pair introduced by A149C and Y458C substitutions (i.e. A149C and Y458C substitutions, which form a non-natural disulfide bond).

Most preferably, the recombinant RSV F protein or the fragment thereof according to the present invention comprises at least two non-natural disulfide bonds, namely (i) a non-natural disulfide bond formed by the cysteine pair introduced by S155C and S290C substitutions (i.e. S155C and S290C substitutions, which form a non-natural disulfide bond) and (ii) a non-natural disulfide bond formed by the cysteine pair introduced by Q98C and Q361C substitutions (i.e. Q98C and Q361C substitutions, which form a non-natural disulfide bond).

Thus, the immunogen according to the present invention includes a recombinant RSV F protein stabilized in a prefusion conformation by (at least) two non-natural disulfide bonds formed by two pairs of cross-linked cysteine residues as described above. A non-natural disulfide bond is one that does not occur in a native RSV F protein, and is introduced by protein engineering (e.g., by including one or more substituted cysteine residues that form the non-natural disulfide bond). For example, in some embodiments, any of the disclosed recombinant RSV F protein is stabilized in a prefusion conformation by any one of 2, 3, 4, 5, 6, 7, 8, 9, or 10 disulfide bonds, each disulfide bond including a pair of cross-linked cysteine residues.

Preferably, the recombinant RSV F protein is stabilized in a prefusion conformation by (exactly) two pairs of non-natural cross-linked cysteine residues. For example, the recombinant RSV F protein comprises preferably (exactly) two pairs of non-natural cross-linked cysteine residues, namely (i) a non-natural disulfide bond formed by the cysteine pair introduced by S155C and S290C substitutions and (ii) a non-natural disulfide bond formed by the cysteine pair introduced by 183GC and 428C substitutions (in particular by N183GC and N428C substitutions). Alternatively, the recombinant RSV F protein comprises preferably (exactly) two pairs of non-natural cross-linked cysteine residues, namely (i) a non-natural disulfide bond formed by the cysteine pair introduced by S155C and S290C substitutions and (ii) a non-natural disulfide bond formed by the cysteine pair introduced by 149C and 458C substitutions (in particular by A149C and Y458C substitutions). Alternatively, the recombinant RSV F protein comprises preferably (exactly) two pairs of non-natural cross-linked cysteine residues, namely (i) a non-natural disulfide bond formed by the cysteine pair introduced by S155C and S290C substitutions and (ii) a non-natural disulfide bond formed by the cysteine pair introduced by N88C and N254C substitutions. Alternatively, the recombinant RSV F protein comprises preferably (exactly) two pairs of non-natural cross-linked cysteine residues, namely (i) a non-natural disulfide bond formed by the cysteine pair introduced by S155C and S290C substitutions and (ii) a non-natural disulfide bond formed by the cysteine pair introduced by E92C and N254C substitutions. Alternatively, the recombinant RSV F protein comprises preferably (exactly) two pairs of non-natural cross-linked cysteine residues, namely (i) a non-natural disulfide bond formed by the cysteine pair introduced by S155C and S290C substitutions and (ii) a non-natural disulfide bond formed by the cysteine pair introduced by S238C and Q279C substitutions. Most preferably, the recombinant RSV F protein comprises (exactly) two pairs of non-natural cross-linked cysteine residues, namely (i) a non-natural disulfide bond formed by the cysteine pair introduced by S155C and S290C substitutions and (ii) a non-natural disulfide bond formed by the cysteine pair introduced by Q98C and Q361C substitutions.

It is also preferred that the recombinant RSV F protein is stabilized in a prefusion conformation by (exactly) three pairs of non-natural cross-linked cysteine residues. For example, the recombinant RSV F protein comprises preferably (exactly) three pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by 183GC and 428C substitutions (in particular by N183GC and N428C substitutions). Alternatively, the recombinant RSV F protein comprises preferably (exactly) three pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by 149C and 458C substitutions (in particular by A149C and Y458C substitutions). Alternatively, the recombinant RSV F protein comprises preferably (exactly) three pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by N88C and N254C substitutions. Alternatively, the recombinant RSV F protein comprises preferably (exactly) three pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by E92C and N254C substitutions. Alternatively, the recombinant RSV F protein comprises preferably (exactly) three pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by S238C and Q279C substitutions. Most preferably, the recombinant RSV F protein comprises (exactly) three pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by Q98C and Q361C substitutions. For example, the recombinant RSV F protein comprises (exactly) three pairs of non-natural cross-linked cysteine residues, namely (i) a non-natural disulfide bond formed by the cysteine pair introduced by S155C and S290C substitutions, (ii) a non-natural disulfide bond formed by the cysteine pair introduced by 183GC and 428C substitutions (in particular by N183GC and N428C substitutions), and (iii) a non-natural disulfide bond formed by the cysteine pair introduced by 149C and 458C substitutions (in particular by A149C and Y458C substitutions). Alternatively, the recombinant RSV F protein comprises (exactly) three pairs of non-natural cross-linked cysteine residues, namely (i) a non-natural disulfide bond formed by the cysteine pair introduced by S155C and S290C substitutions, (ii) a non-natural disulfide bond formed by the cysteine pair introduced by 183GC and 428C substitutions (in particular by N183GC and N428C substitutions), and (iii) a non-natural disulfide bond formed by the cysteine pair introduced by Q98C and Q361C substitutions. Preferably, the recombinant RSV F protein comprises (exactly) three pairs of non-natural cross-linked cysteine residues, namely (i) a non-natural disulfide bond formed by the cysteine pair introduced by S155C and S290C substitutions, (ii) a non-natural disulfide bond formed by the cysteine pair introduced by 149C and 458C substitutions (in particular by A149C and Y458C substitutions), and (iii) a non-natural disulfide bond formed by the cysteine pair introduced by Q98C and Q361C substitutions.

It is also preferred that the recombinant RSV F protein is stabilized in a prefusion conformation by (exactly) four pairs of non-natural cross-linked cysteine residues. For example, the recombinant RSV F protein comprises preferably (exactly) four pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by 183GC and 428C substitutions (in particular by N183GC and N428C substitutions). Alternatively, the recombinant RSV F protein comprises preferably (exactly) four pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by 149C and 458C substitutions (in particular by A149C and Y458C substitutions). Alternatively, the recombinant RSV F protein comprises preferably (exactly) four pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by N88C and N254C substitutions. Alternatively, the recombinant RSV F protein comprises preferably (exactly) four pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by E92C and N254C substitutions. Alternatively, the recombinant RSV F protein comprises preferably (exactly) four pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by S238C and Q279C substitutions. Most preferably, the recombinant RSV F protein comprises (exactly) four pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by Q98C and Q361C substitutions. For example, the recombinant RSV F protein comprises (exactly) four pairs of non-natural cross-linked cysteine residues, namely (i) a non-natural disulfide bond formed by the cysteine pair introduced by S155C and S290C substitutions, (ii) a non-natural disulfide bond formed by the cysteine pair introduced by 183GC and 428C substitutions (in particular by N183GC and N428C substitutions), (iii) a non-natural disulfide bond formed by the cysteine pair introduced by 149C and 458C substitutions (in particular by A149C and Y458C substitutions), and (iv) a non-natural disulfide bond formed by the cysteine pair introduced by Q98C and Q361C substitutions.

It is also preferred that the recombinant RSV F protein is stabilized in a prefusion conformation by (exactly) five pairs of non-natural cross-linked cysteine residues. For example, the recombinant RSV F protein comprises preferably (exactly) five pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by 183GC and 428C substitutions (in particular by N183GC and N428C substitutions). Alternatively, the recombinant RSV F protein comprises preferably (exactly) five pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by 149C and 458C substitutions (in particular by A149C and Y458C substitutions). Alternatively, the recombinant RSV F protein comprises preferably (exactly) five pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by N88C and N254C substitutions. Alternatively, the recombinant RSV F protein comprises preferably (exactly) five pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by E92C and N254C substitutions. Alternatively, the recombinant RSV F protein comprises preferably (exactly) five pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by S238C and Q279C substitutions. Most preferably, the recombinant RSV F protein comprises (exactly) five pairs of non-natural cross-linked cysteine residues, namely at least (i) a non-natural disulfide bond formed by the cysteine pair introduced by S155C and S290C substitutions and (ii) a non-natural disulfide bond formed by the cysteine pair introduced by Q98C and Q361C substitutions.

It is also preferred that the recombinant RSV F protein is stabilized in a prefusion conformation by (exactly) six pairs of non-natural cross-linked cysteine residues. For example, the recombinant RSV F protein comprises preferably (exactly) four pairs of non-natural cross-linked cysteine residues, namely (i) a non-natural disulfide bond formed by the cysteine pair introduced by S155C and S290C substitutions, (ii) a non-natural disulfide bond formed by the cysteine pair introduced by 149C and 458C substitutions (in particular by A149C and Y458C substitutions), (iii) a non-natural disulfide bond formed by the cysteine pair introduced by Q98C and Q361C substitutions, (iv) a non-natural disulfide bond formed by the cysteine pair introduced by N88C and N254C substitutions, (v) a non-natural disulfide bond formed by the cysteine pair introduced by E92C and N254C substitutions, and (vi) a non-natural disulfide bond formed by the cysteine pair introduced by S238C and Q279C substitutions. For example, the recombinant RSV F protein comprises preferably (exactly) four pairs of non-natural cross-linked cysteine residues, namely (i) a non-natural disulfide bond formed by the cysteine pair introduced by S155C and S290C substitutions, (ii) a non-natural disulfide bond formed by the cysteine pair introduced by 183GC and 428C substitutions (in particular by N183GC and N428C substitutions), (iii) a non-natural disulfide bond formed by the cysteine pair introduced by Q98C and Q361C substitutions, (iv) a non-natural disulfide bond formed by the cysteine pair introduced by N88C and N254C substitutions, (v) a non-natural disulfide bond formed by the cysteine pair introduced by E92C and N254C substitutions, and (vi) a non-natural disulfide bond formed by the cysteine pair introduced by S238C and Q279C substitutions. For example, the recombinant RSV F protein comprises preferably (exactly) four pairs of non-natural cross-linked cysteine residues, namely (i) a non-natural disulfide bond formed by the cysteine pair introduced by S155C and S290C substitutions, (ii) a non-natural disulfide bond formed by the cysteine pair introduced by 183GC and 428C substitutions (in particular by N183GC and N428C substitutions), (iii) a non-natural disulfide bond formed by the cysteine pair introduced by 149C and 458C substitutions (in particular by A149C and Y458C substitutions), (iv) a non-natural disulfide bond formed by the cysteine pair introduced by N88C and N254C substitutions, (v) a non-natural disulfide bond formed by the cysteine pair introduced by E92C and N254C substitutions, and (vi) a non-natural disulfide bond formed by the cysteine pair introduced by S238C and Q279C substitutions. For example, the recombinant RSV F protein comprises preferably (exactly) four pairs of non-natural cross-linked cysteine residues, namely (i) a non-natural disulfide bond formed by the cysteine pair introduced by S155C and S290C substitutions, (ii) a non-natural disulfide bond formed by the cysteine pair introduced by 183GC and 428C substitutions (in particular by N183GC and N428C substitutions), (iii) a non-natural disulfide bond formed by the cysteine pair introduced by 149C and 458C substitutions (in particular by A149C and Y458C substitutions), (iv) a non-natural disulfide bond formed by the cysteine pair introduced by Q98C and Q361C substitutions, (v) a non-natural disulfide bond formed by the cysteine pair introduced by E92C and N254C substitutions, and (vi) a non-natural disulfide bond formed by the cysteine pair introduced by S238C and Q279C substitutions. For example, the recombinant RSV F protein comprises preferably (exactly) four pairs of non-natural cross-linked cysteine residues, namely (i) a non-natural disulfide bond formed by the cysteine pair introduced by S155C and S290C substitutions, (ii) a non-natural disulfide bond formed by the cysteine pair introduced by 183GC and 428C substitutions (in particular by N183GC and N428C substitutions), (iii) a non-natural disulfide bond formed by the cysteine pair introduced by 149C and 458C substitutions (in particular by A149C and Y458C substitutions), (iv) a non-natural disulfide bond formed by the cysteine pair introduced by Q98C and Q361C substitutions, (v) a non-natural disulfide bond formed by the cysteine pair introduced by N88C and N254C substitutions, and (vi) a non-natural disulfide bond formed by the cysteine pair introduced by S238C and Q279C substitutions. For example, the recombinant RSV F protein comprises preferably (exactly) four pairs of non-natural cross-linked cysteine residues, namely (i) a non-natural disulfide bond formed by the cysteine pair introduced by S155C and S290C substitutions, (ii) a non-natural disulfide bond formed by the cysteine pair introduced by 183GC and 428C substitutions (in particular by N183GC and N428C substitutions), (iii) a non-natural disulfide bond formed by the cysteine pair introduced by 149C and 458C substitutions (in particular by A149C and Y458C substitutions), (iv) a non-natural disulfide bond formed by the cysteine pair introduced by Q98C and Q361C substitutions, (v) a non-natural disulfide bond formed by the cysteine pair introduced by N88C and N254C substitutions, and (vi) a non-natural disulfide bond formed by the cysteine pair introduced by E92C and N254C substitutions.

It is also preferred that the recombinant RSV F protein is stabilized in a prefusion conformation by (exactly) seven pairs of non-natural cross-linked cysteine residues. For example, the recombinant RSV F protein comprises preferably (exactly) four pairs of non-natural cross-linked cysteine residues, namely (i) a non-natural disulfide bond formed by the cysteine pair introduced by S155C and S290C substitutions, (ii) a non-natural disulfide bond formed by the cysteine pair introduced by 183GC and 428C substitutions (in particular by N183GC and N428C substitutions), (iii) a non-natural disulfide bond formed by the cysteine pair introduced by 149C and 458C substitutions (in particular by A149C and Y458C substitutions), (iv) a non-natural disulfide bond formed by the cysteine pair introduced by Q98C and Q361C substitutions, (v) a non-natural disulfide bond formed by the cysteine pair introduced by N88C and N254C substitutions, (vi) a non-natural disulfide bond formed by the cysteine pair introduced by E92C and N254C substitutions, and (vii) a non-natural disulfide bond formed by the cysteine pair introduced by S238C and Q279C substitutions.

Preferably, the immunogen according to the present invention comprises a recombinant RSV F protein or a fragment thereof comprising (i) Q98C and Q361C substitutions, (ii) 149C and 458C substitutions (in particular by A149C and Y458C substitutions), and/or (iii) 183GC and 428C substitutions (in particular by N183GC and N428C substitutions).

More preferably, the immunogen according to the present invention comprises a recombinant RSV F protein or a fragment thereof comprising (i) Q98C and Q361C substitutions and/or (ii) 149C and 458C substitutions (in particular by A149C and Y458C substitutions).

Most preferably, the immunogen according to the present invention comprises a recombinant RSV F protein or a fragment thereof comprising Q98C and Q361C substitutions.

The cysteine residues that form the disulfide bond can be introduced into native RSV F protein sequence by one or more amino acid substitutions. Preferably, two cysteine residues are introduced into a native RSV sequence to form the disulfide bond.

In addition to the specific non-natural disulfide bonds described above, the recombinant RSV F protein may optionally comprise one or more further non-natural disulfide bonds, for example one or more further non-natural disulfide bonds as described in WO 2014/160463 A1, which is incorporated by reference herein in its entirety. Alternatively it is also preferred that the recombinant RSV F protein does not comprise any further non-natural disulfide bonds in addition to the seven above described non-natural disulfide bonds (i.e., (i) a non-natural disulfide bond formed by the cysteine pair introduced by S155C and S290C substitutions, (ii) a non-natural disulfide bond formed by the cysteine pair introduced by 183GC and 428C substitutions (in particular by N183GC and N428C substitutions), (iii) a non-natural disulfide bond formed by the cysteine pair introduced by 149C and 458C substitutions (in particular by A149C and Y458C substitutions), (iv) a non-natural disulfide bond formed by the cysteine pair introduced by Q98C and Q361C substitutions, (v) a non-natural disulfide bond formed by the cysteine pair introduced by N88C and N254C substitutions, (vi) a non-natural disulfide bond formed by the cysteine pair introduced by E92C and N254C substitutions, and (vii) a non-natural disulfide bond formed by the cysteine pair introduced by S238C and Q279C substitutions).

In addition, the recombinant RSV F protein or the fragment thereof comprises one or two amino acids selected from the group consisting of F, L, W, Y, H, and M, which substitute one or both amino acids corresponding to S190 and/or V207 in SEQ ID NO: 1. In other words, the recombinant RSV F protein or the fragment thereof comprises a F, L, W, Y, H, and/or M substitution at position S190, position V207, or positions S190 and V207.

In general, a F, L, W, Y, H, and/or M substitution at position S190, position V207, or positions S190 and V207 is a "cavity filling amino acid substitution".

Comparison of the structure of the prefusion conformation of the RSV F protein (e.g., in complex with an RSV F prefusion-specific antibody, such as D25, MPE8 or AM14) to the structure of the postfusion RSV F protein identifies several internal cavities or pockets in the prefusion conformation that must collapse for F to transition to the postfusion conformation. These cavities include Ser190 and Val207.

Thus, the immunogen according to the present invention comprises a recombinant RSV F protein or a fragment thereof, which comprises a cavity filling mutation filling the cavities of Ser190 and/or Val207. Accordingly, the recombinant RSV F protein or the fragment thereof is stabilized in a prefusion conformation by such amino acid substitutions that introduce an amino acid that reduces the volume of an internal cavity that collapses in the postfusion conformation of RSV F protein, in particular the introduced amino acid reduces the volume of the Ser190 and/or Val207 internal cavities. For example, the cavities may be filled by substituting amino acids with large side chains for those with small side chains. One particularly preferred example of a RSV F cavity filling amino acid substitution to stabilize the RSV protein in its prefusion conformation are the S190F and V207L substitutions. It is also preferred that the cavity filling amino acid substitution comprised by the recombinant RSV F protein or the fragment thereof includes a S190F, S190L, S190W, S190H, S190M, or S190Y substitution. In general, amino acid substitutions for reducing the volume of the Ser190 cavity include S190F, S190L, S190W, S190H, S190M, or S190Y. Amino acid substitutions for reducing the volume of the Val207 cavity include V207L and 220L. Amino acid substitutions for reducing the volume of both, the Ser190 cavity and the Val207 cavity, include for example S190F and V207L and 83W and 260W. Preferably, the recombinant RSV F protein or the fragment thereof comprised by the immunogen according to the present invention comprises a V207L substitution. Preferably, the recombinant RSV F protein or the fragment thereof comprised by the immunogen according to the present invention comprises a S190F substitution. Preferably, the recombinant RSV F protein or the fragment thereof comprised by the immunogen according to the present invention comprises a S190L substitution. Preferably, the recombinant RSV F protein or the fragment thereof comprised by the immunogen according to the present invention comprises a S190W substitution. Preferably, the recombinant RSV F protein or the fragment thereof comprised by the immunogen according to the present invention comprises a S190H substitution. Preferably, the recombinant RSV F protein or the fragment thereof comprised by the immunogen according to the present invention comprises a S190M substitution. Preferably, the recombinant RSV F protein or the fragment thereof comprised by the immunogen according to the present invention comprises a S190Y substitution.

More preferably, the recombinant RSV F protein or the fragment thereof comprised by the immunogen according to the present invention comprises a S190F substitution and a V207L substitution. More preferably, the recombinant RSV F protein or the fragment thereof comprised by the immunogen according to the present invention comprises a S190L substitution and a V207L substitution. More preferably, the recombinant RSV F protein or the fragment thereof comprised by the immunogen according to the present invention comprises a S190W substitution and a V207L substitution. More preferably, the recombinant RSV F protein or the fragment thereof comprised by the immunogen according to the present invention comprises a S190H substitution and a V207L substitution. More preferably, the recombinant RSV F protein or the fragment thereof comprised by the immunogen according to the present invention comprises a S190M substitution and a V207L substitution. More preferably, the recombinant RSV F protein or the fragment thereof comprised by the immunogen according to the present invention comprises a S190Y substitution and a V207L substitution.

The indicated cavities are referred to by a small residue abutting the cavity that can be mutated to a larger residue to fill the cavity. It will be understood that other residues (besides the one the cavity is named after) could also be mutated to fill the same cavity.

Preferably, the immunogen according to the present invention comprises a recombinant RSV F protein or the fragment thereof comprising one or more cavity-filling amino acid substitution selected from the group consisting of: S190F; S190L; S190W; S190Y; S190H; S190M; S190F and V207L; S190F and V207F; S190F and V207W; S190L and V207L; S190L and V207F; S190L and V207W; S190W and V207L; S190W and V207F; S190W and V207W; S190Y and V207L; S190Y and V207F; S190Y and V207W; S190H and V207L; S190H and V207F; S190H and V207W; S190M and V207L; S190M and V207F; and S190M and V207W.

Most preferably, the immunogen according to the present invention comprises a recombinant RSV F protein or a fragment thereof comprising S190F and/or V207L substitutions compared to the native bovine RSV F protein (e.g., SEQ ID NO: 1).

Furthermore the recombinant RSV F protein or the fragment thereof comprised by the immunogen according to the present invention does not comprise a pep27 polypeptide.

The RSV pep27 polypeptide (also referred to as "pep27") is a 27 amino acid polypeptide that is excised from the F0 precursor during maturation of the RSV F protein. pep27 is flanked by two furin cleavage sites that are cleaved by a cellular protease during F protein maturation to generate the F1 and F2 polypeptide. Examples of native pep27 sequences are known which are provided herein as positions 110-136 of SEQ ID NOs: SEQ ID NOs: 1-9.

Accordingly, it is preferred that the immunogen according to the present invention comprises a recombinant RSV F protein or a fragment thereof, wherein the recombinant RSV F protein or the fragment thereof does not comprise amino acids 106-144 or 104-144 of the native bovine RSV F protein. More preferably, the immunogen according to the present invention comprises a recombinant RSV F protein or a fragment thereof, wherein the recombinant RSV F protein or the fragment thereof does not comprise amino acids 106-144 or 104-144 of SEQ ID NO: 1.

More preferably, the recombinant RSV F protein or the fragment thereof comprised by the immunogen according to the present invention does not comprise a fusion peptide or a fragment thereof.

The RSV fusion peptide (also referred to as "fusion peptide") is a peptide of approx. 16 amino acids, which is located directly C-terminally of the pep27 polypeptide in a native RSV F0 protein. Examples of native fusion peptide sequences are known which are provided herein as positions 137-152 of SEQ ID NOs: SEQ ID NOs: 1-9.

A fragment of the fusion peptide comprises at least three (consecutive) amino acids of the fusion peptide. Preferably, the recombinant RSV F protein or the fragment thereof comprised by the immunogen according to the present invention does not comprise an N-terminal fragment of the fusion peptide, such the N-terminal 3 amino acids of the fusion peptide (i.e., those three amino acids, which directly follow the C-terminus of pep27 in the F0 protein; e.g., amino acids 137-139 of bRSV 391-2 F0 (SEQ ID NO: 1)). Preferably, the recombinant RSV F protein or the fragment thereof comprised by the immunogen according to the present invention does not comprise the N-terminal 4 amino acids of the fusion peptide (i.e., those four amino acids, which directly follow the C-terminus of pep27 in the F0 protein; e.g., amino acids 137-140 of bRSV 391-2 F0 (SEQ ID NO: 1)). More preferably, the recombinant RSV F protein or the fragment thereof comprised by the immunogen according to the present invention does not comprise the N-terminal 5 amino acids of the fusion peptide (i.e., those five amino acids, which directly follow the C-terminus of pep27 in the F0 protein; e.g., amino acids 137-141 of bRSV 391-2 F0 (SEQ ID NO: 1)). More preferably, the recombinant RSV F protein or the fragment thereof comprised by the immunogen according to the present invention does not comprise the N-terminal 6 amino acids of the fusion peptide (i.e., those six amino acids, which directly follow the C-terminus of pep27 in the F0 protein; e.g., amino acids 137-142 of bRSV 391-2 F0 (SEQ ID NO: 1)). Even more preferably, the recombinant RSV F protein or the fragment thereof comprised by the immunogen according to the present invention does not comprise the N-terminal 7 amino acids of the fusion peptide (i.e., those seven amino acids, which directly follow the C-terminus of pep27 in the F0 protein; e.g., amino acids 137-143 of bRSV 391-2 F0 (SEQ ID NO: 1)). Most preferably, the recombinant RSV F protein or the fragment thereof comprised by the immunogen according to the present invention does not comprise the N-terminal 8 amino acids of the fusion peptide (i.e., those eight amino acids, which directly follow the C-terminus of pep27 in the F0 protein; e.g., amino acids 137-144 of bRSV 391-2 F0 (SEQ ID NO: 1)).

As shown in the present examples, evaluation of the immunogenicity of immunogens according to the present invention comprising a recombinant RSV F protein or a fragment thereof specifically binding to an RSV F prefusion-specific antibody, wherein the recombinant RSV F protein or the fragment thereof comprises an F1 polypeptide and an F2 polypeptide of any RSV F protein characterized by the following substitutions at amino acid positions corresponding to the following amino acid positions in SEQ ID NO: 1 as a reference sequence:

(i) S155C and S290C substitutions, which form a non-natural disulfide bond;

(ii) a substitution at one or both of positions S190 and V207 by amino acids selected from the group consisting of F, L, W, Y, H, and M; and (iii) a pair of substitutions forming a non-natural disulfide bond selected from the group consisting of the following substitution pairs: Q98C and Q361C, A149C and Y458C, N183GC and N428C, N88C and N254C, E92C and N254C, and S238C and Q279C;

and wherein the recombinant RSV F protein or the fragment thereof does not comprise a pep27 polypeptide, in both mice and calves resulted in high-titer neutralizing responses, with heterologous bRSV challenge in calves revealing protection from viral replication, lung inflammation and clinical signs of disease and no evidence of vaccine-associated disease enhancement—an important milestone in the development of an effective bRSV subunit vaccine.

Preferably, the recombinant RSV F protein or the fragment thereof comprised by the immunogen according to the present invention is a single chain RSV F protein or a single chain RSV F protein fragment.

As used herein, a "single chain" RSV F protein refers to a recombinant RSV F protein that is expressed as a single polypeptide chain including the RSV F1 polypeptide and the RSV F2 polypeptide as described herein. Typically, the single chain RSV F protein trimerizes to form an RSV F protein ectodomain. A single chain RSV F protein does in particular not include the furin cleavage sites flanking the pep27 polypeptide of RSV F protein; therefore, when produced in cells, the F0 polypeptide is not cleaved into separate F1 and F2 polypeptides. Preferably, a single chain RSV F protein includes deletion of the two furin cleavage sites, the pep27 polypeptide, and the fusion peptide. More preferably, position 103 or 105 (i.e. the C-terminal amino acid of the F2 polypeptide) is linked to position 145 (i.e. the N-terminal amino acid of the F1 polypeptide) of the RSV protein to generate the single chain construction. For example, the remaining portions of the F1 and F2 polypeptides may be joined directly or by a linker, such as a peptide linker.

Accordingly, in the recombinant RSV F protein or the fragment thereof comprised by the immunogen according to the present invention it is preferred that the F2 polypeptide and the F1 polypeptide are linked by a heterologous peptide linker or are directly linked.

Preferably, the heterologous peptide linker comprises any of the following amino acid sequences (as shown in Table 1):

TABLE 1

Exemplary peptide linker sequences:

| SEQ ID NO. | Amino acid sequence |
|---|---|
| 10 | GSGNVGLGG |
| 11 | GSGNWGLGG |
| 12 | GSGNIGLGG |
| 13 | GSGGNGIGLGG |
| 14 | GSGGSGGSGG |
| 15 | GSGNVLGG |
| 16 | GGSG |
| 17 | GGSGGS |
| 18 | GGSGGSG |
| 19 | GGSGSGG |
| 20 | GGSGGGSGGSG |
| 21 | GGSGG |
| 22 | GGSGSGSG |
| 23 | GSGGGSG |
| 24 | GGPGG |
| 25 | GGGSGGGSGGSGGG |
| 26 | GGGSGGGSGGG |

It is also preferred that the heterologous peptide linker is a G, S, GG, GS, SG, GGG, or GSG linker. Accordingly, the heterologous peptide linker preferably comprises an amino acid sequence as set forth in any of SEQ ID NOs: 10-26, or is a G, S, GG, GS, SG, GGG, or GSG linker.

Most preferably, the linker is a GS-linker, i.e. the F2 polypeptide and the F1 polypeptide are linked by a GS-linker.

Accordingly, it is particularly preferred that position 103 or 105 of the F2 polypeptide is linked to position 1 of the F1 polypeptide by a Gly-Ser linker. Thereby, position 103 or 105 of the F2 polypeptide is the C-terminal amino acid of the F2 polypeptide and position 1 of the F1 polypeptide is the N-terminal amino acid of the F1 polypeptide.

Preferably, the immunogen according to the present invention comprises a multimer of the recombinant RSV F protein or of the fragment thereof. Accordingly, it is preferred that the recombinant RSV F protein or the fragment thereof forms a trimer in phosphate buffered saline at a physiological pH. To this end, the recombinant RSV F protein comprised by the immunogen according to the present invention is preferably linked to a trimerization domain.

The F1 polypeptide of the recombinant RSV F protein or of the fragment thereof maybe directly or indirectly linked to the trimerization domain. Thereby, "direct" linking means that the N-terminus of the trimerization domain follows directly upon the C-terminus of F1 polypeptide, i.e. without any amino acids in between. Accordingly, "indirect" linking refers to any (peptide) linkers present between the C-terminus of F1 polypeptide and the N-terminus of the trimerization domain, such as for example the peptide linkers as described above (cf. Table 1 and below).

Preferably, the immunogen comprises a recombinant RSV F protein including an F1 polypeptide with a trimerization domain directly or indirectly linked to its C-terminus. In particular, the trimerization domain promotes trimerization of the three F1/F2 monomers in the recombinant RSV F protein. Several exogenous multimerization domains promote stable trimers of soluble recombinant proteins: the GCN4 leucine zipper (Harbury et al. 1993 *Science* 262: 1401-1407), the trimerization motif from the lung surfactant protein (Hoppe et al. 1994 *FEES Lett* 344: 191-195), collagen (McAlinden et al. 2003 *J Biol Chem* 278:42200-42207), and the phage T4 fibritin Foldon (Miroshnikov et al. 1998 *Protein Eng* 11:329-414), any of which can be linked to the F1 polypeptide in the immunogen according to the present invention to promote trimerization of the recombinant F protein, as long as the immunogen can still be specifically recognized by a prefusion-specific antibody (e.g., D25, MPE8 or AM14 antibody), and/or includes an RSV F prefusion specific conformation (such as antigenic site Ø).

Preferably, the trimerization domain is a GCN4 leucine zipper domain, for example the immunogen can include a recombinant RSV F protein including an F1 polypeptide with a GCN4 leucine zipper domain linked to its C-terminus. More preferably the trimerization domain is a Foldon domain, for example, the immunogen can include a recombinant RSV F protein including an F1 polypeptide with a Foldon domain linked to its C-terminus. Most preferably, the Foldon domain is a T4 fibritin Foldon domain such as the amino acid sequence According to any of SEQ ID NOs: 27-29 described below, which adopts a B-propeller conformation, and can fold and trimerize in an autonomous way (Tao et al. 1997 Structure 5:789-798).

Typically, the heterologous multimerization motif is positioned C-terminal to the F1 domain. Optionally, the multimerization domain is connected to the F1 polypeptide via a linker, such as an amino acid linker, such as the sequence GG. The linker can also be a longer linker (for example, including the sequence GG, such as the amino acid sequences as described above (cf. Table 1 and below). Numerous conformationally neutral linkers are known in the art that can be used in this context without disrupting the conformation of the PreF antigen.

Preferably, the trimerization domain is a foldon domain. A trimerization domain, or a foldon domain, is an amino acid sequence that naturally forms a trimeric structure. A trimerization domain can be included in the amino acid sequence of a disclosed RSV F protein immunogen stabilized in a prefusion conformation so that the immunogen will form a trimer. Preferably, the foldon domain is the T4 Foldon domain set forth as (SEQ ID NO: 27)
GYIPEAPRDGQAYVRKDGEWVLLSTF.

More preferably, the trimerization domain comprises an amino acid according to SEQ ID NO 28:

(SEQ ID NO: 28)
SAIGGYIPEAPRDGQAYVRKDGEWVLLSTF.

Even more preferably, the trimerization domain comprises an amino acid according to SEQ ID NO 29:

(SEQ ID NO: 29)
SAIGGYIPEAPRDGQAYVRKDGEWVLLSTFLGGLVPRGSH.

Preferably, the trimerization domain can be cleaved from a purified protein, for example by incorporation of a thrombin cleavage site adjacent to the Foldon domain that can be used for cleavage purposes, i.e. for removing the Foldon domain from the F1 polypeptide. Accordingly, it is preferred that the immunogen according to the present invention comprises a protease cleavage site between the F1 polypeptide and the trimerization domain. For example, the cleavage site is a thrombin cleavage site, for example according to SEQ ID NO: 30:

(SEQ ID NO: 30)
LVPRGS.

Preferably, the immunogen according to the present invention comprises a transmembrane domain between the F1 polypeptide and the trimerization domain. More preferably, the immunogen according to the present invention comprises a transmembrane domain and a protease cleavage site between the F1 polypeptide and the trimerization domain, in particular a transmembrane domain between the protease cleavage site and the trimerization domain.

In general, a transmembrane domain is in particular an amino acid sequence that inserts into a lipid bilayer, such as the lipid bilayer of a cell or virus or virus-like particle. A transmembrane domain can be used to anchor an antigen to a membrane. Preferably, the transmembrane domain is a RSV F protein transmembrane domain. Exemplary RSV F transmembrane domains are familiar to the person of ordinary skill in the art, and provided herein. For example, the amino acid sequences of exemplary RSV F transmembrane domains are provided as approximately positions 525-550 of native RSV F0 proteins (SEQ ID NOs: 1-9).

Preferably, the recombinant RSV F protein includes a transmembrane domain linked to the F1 polypeptide, for example, for an application including a membrane anchored immunogen). For example, the presence of the transmembrane sequences is useful for expression as a transmembrane protein for membrane vesicle preparation. The transmembrane domain can be linked to a F1 protein containing any of the stabilizing mutations provided herein, for example, those described above, such as a F1 protein with a S 155C/S290C cysteine substitution. Additionally, the transmembrane domain can be further linked to a RSV F1 cytosolic tail.

Furthermore, it is preferred that the immunogen according to the present invention comprises a purification tag, preferably a His-tag and/or a Strep-tag. In general, protein are peptide sequences genetically grafted onto a recombinant protein. Such tags can optionally be removable by chemical agents or by enzymatic means, such as proteolysis. Purification tags are appended to proteins so that they can be purified from their crude biological source using, for example, an affinity technique. These include chitin binding protein (CBP), maltose binding protein (MBP), glutathione-S-transferase (GST), the poly(His) tag, which is a widely used protein tag binding to metal matrices and Strep tags. The "His tag" or "poly(His) tag" consists of at least six histidine (His) residues (see SEQ ID NO: 34 for an exemplary His tag). The Strep-tag is a synthetic peptide consisting of eight amino acids (WSHPQFEK; SEQ ID NO: 35). This peptide sequence exhibits intrinsic affinity towards Strep-Tactin, a specifically engineered streptavidin. By exploiting the highly specific interaction, Strep-tagged proteins can be isolated in one step from crude cell lysates. Because the Strep-tag elutes under gentle, physiological conditions it is especially suited for generation of functional proteins. Accordingly, it is preferred that the immunogen according to the present invention comprises a His-tag and/or a Strep-tag.

Preferably, the immunogen according to the present invention comprises a recombinant RSV F protein or a fragment thereof, wherein the F1 polypeptide and the F2 polypeptide of the recombinant RSV F protein or of the fragment thereof share at least 80%, preferably at least 85%, more preferably at least 90%, even more preferably at least 95% and most preferably at least 98% sequence identity with the F1 polypeptide and the F2 polypeptide, respectively, of a native bovine RSV F protein. Examples of native bovine RSV F proteins are provided as SEQ ID NOs: 1-9. Accordingly, it is preferred that said native bovine RSV F protein comprises an amino acid sequence according to any of SEQ ID NOs 1-9. In other words, the immunogen according to the present invention comprises a recombinant RSV F protein or a fragment thereof, wherein the F1 polypeptide and the F2 polypeptide of the recombinant RSV F protein or of the fragment thereof preferably share at least 80%, preferably at least 85%, more preferably at least 90%, even more preferably at least 95% and most preferably at least 98% sequence identity with an amino acid sequence selected from any of SEQ ID NOs: 1-9.

Preferably, said native bovine RSV F protein consists of an amino acid sequence according to SEQ ID NO: 1. SEQ ID NO: 1 depicts the amino acid sequence of the native 391-2 bRSV F0 protein. Accordingly, it is preferred that the immunogen according to the present invention comprises a recombinant RSV F protein or a fragment thereof, wherein the F1 polypeptide and the F2 polypeptide of the recombinant RSV F protein or of the fragment thereof preferably share at least 80%, preferably at least 85%, more preferably at least 90%, even more preferably at least 95% and most preferably at least 98% sequence identity with an amino acid according to SEQ ID NO: 1.

More preferably, the immunogen according to the present invention comprises a recombinant RSV F protein or a fragment thereof, wherein the recombinant RSV F protein or the fragment thereof comprises or consists of an F2 polypeptide and an F1 polypeptide comprising amino acid sequences at least 80%, preferably at least 85%, more preferably at least 90%, even more preferably at least 95% and most preferably at least 98% identical to amino acids 26-103 and 145-310, respectively, of SEQ ID NO: 1. Even more preferably, the immunogen according to the present invention comprises a recombinant RSV F protein or a fragment thereof, wherein the recombinant RSV F protein or the fragment thereof comprises or consists of an F2 polypeptide and an F1 polypeptide comprising amino acid sequences at least 80%, preferably at least 85%, more preferably at least 90%, even more preferably at least 95% and most preferably at least 98% identical to amino acids 26-103 and 145-513, respectively, of SEQ ID NO: 1. Amino acids 26-103 form the F2 polypeptide region of the native 391-2 bRSV F0 protein (SEQ ID NO: 1). Amino acids 145-513 form the F1 polypeptide region of the native 391-2 bRSV F0 protein (SEQ ID NO: 1).

It is also preferred that the immunogen according to the present invention comprises a recombinant RSV F protein or a fragment thereof, wherein the recombinant RSV F protein or the fragment thereof comprises or consists of an F2 polypeptide and an F1 polypeptide comprising amino acid sequences at least 80%, preferably at least 85%, more preferably at least 90%, even more preferably at least 95% and most preferably at least 98% identical to amino acids 26-103 and 145-529, respectively, of SEQ ID NO: 1. More preferably, the immunogen according to the present invention comprises a recombinant RSV F protein or a fragment thereof, wherein the recombinant RSV F protein or the fragment thereof comprises or consists of an F2 polypeptide and an F1 polypeptide comprising amino acid sequences at least 80%, preferably at least 85%, more preferably at least 90%, even more preferably at least 95% and most preferably at least 98% identical to amino acids 26-103 and 145-551, respectively, of SEQ ID NO: 1.

Preferably, the immunogen according to the present invention comprises a recombinant RSV F protein or a fragment thereof, wherein (i) the F2 polypeptide comprises or consists of 8-79 residues of bovine RSV F positions 26-105 and (ii) the F1 polypeptides comprises or consists of 14-365 residues of bovine RSV F positions 145-513; and wherein the bovine RSV F positions preferably correspond to the amino acid sequence of a reference F0 polypeptide according to SEQ ID NO: 1.

It is also preferred that the immunogen according to the present invention comprises a recombinant RSV F protein or a fragment thereof, wherein (the prefusion conformation of) the recombinant RSV F protein, or the fragment thereof, comprises an antigenic site Ø that specifically binds to a RSV F prefusion-specific antibody. More preferably, the immunogen according to the present invention comprises a recombinant RSV F protein or a fragment thereof, wherein (the prefusion conformation of) the recombinant RSV F protein, or the fragment thereof, comprises an antigenic site Ø that specifically binds to a RSV F prefusion-specific antibody and wherein the antigenic site Ø comprises residues 62-69 and 196-209 of a native bovine RSV F protein sequence set forth in any one of SEQ ID NOs: 1-9. Accordingly, it is preferred that the immunogen according to the present invention comprises a recombinant RSV F protein or a fragment thereof, wherein the F2 and F1 polypeptides comprise RSV F positions 62-69 and 196-209, preferably positions 62-69 and 196-209 of any of SEQ ID NOs 1-9, more preferably positions 62-69 and 196-209 of SEQ ID NO: 1.

In addition or alternatively, (the prefusion conformation of) the recombinant RSV F protein, or of the fragment thereof, preferably comprises an epitope recognized by MPE8 antibody and/or an epitope recognized by AM14 antibody. It is thus preferred that the immunogen according to the present invention comprises a recombinant RSV F protein or a fragment thereof, wherein (the prefusion conformation of) the recombinant RSV F protein, or the fragment thereof, comprises an epitope recognized by MPE8 antibody and/or an epitope recognized by AM14 antibody. Crystal structure and monoclonal antibody-resistant mutants revealed that AM14 recognizes a quaternary epitope that spans two protomers and includes a region that undergoes extensive comformational changes in the pre- to post-fusion F transition (Characterization of a Prefusion-Specific Antibody That Recognizes a Quaternary, Cleavage-Dependent Epitope on the RSV Fusion Glycoprotein. Gilman, M. S., Moin et al., Plos Pathog (2015). 11: e1005035-e1005035). AM14 makes a substantial interaction with the residues L160, N183, N426, R429, H514 and H515 on pre-fusion RSV F protein. Accordingly, it is preferred that the immunogen according to the present invention comprises a recombinant RSV F protein or a fragment thereof, wherein (the prefusion conformation of) the recombinant RSV F protein, or the fragment thereof, comprises an epitope recognized by AM14 antibody and wherein the epitope recognized by AM14 antibody comprises at least residues L160, N183, N426 and R429 of a native bovine RSV F protein sequence set forth in any one of SEQ ID NOs: 1-9, more preferably the epitope recognized by AM14 antibody comprises at least residues L160, N183, N426, R429, H514 and H515 of a native bovine RSV F protein sequence set forth in any one of SEQ ID NOs: 1-9.

The core epitope of MPE8 was mapped on two highly conserved anti-parallel b-strains on the pre-fusion viral F protein, which are rearranged in the post-fusion F conformation including residues T50, D310, L305, G307, and I309 (Cross-neutralization of four paramyxoviruses by a human monoclonal antibody Davide Corti1 et al., NATURE (2013) 501: 439-445). Accordingly, it is preferred that the immunogen according to the present invention comprises a recombinant RSV F protein or a fragment thereof, wherein (the prefusion conformation of) the recombinant RSV F protein, or the fragment thereof, comprises an epitope recognized by MPE8 antibody and wherein the epitope recognized by MPE8 antibody comprises at least residues T50, D310, L305, G307, and I309 of a native bovine RSV F protein sequence set forth in any one of SEQ ID NOs: 1-9.

More preferably, the immunogen according to the present invention thus comprises a recombinant RSV F protein, or a fragment thereof, which comprises:

(i) an antigenic site Ø that specifically binds to the RSV F prefusion-specific antibody, wherein the antigenic site Ø comprises residues 62-69 and 196-209 of a native bovine RSV F protein sequence set forth in any one of SEQ ID NOs: 1-9;

(ii) an epitope recognized by AM14 antibody, wherein the epitope recognized by AM14 antibody comprises at least residues L160, N183, N426, R429, H514 and H515 of a native bovine RSV F protein sequence set forth in any one of SEQ ID NOs: 1-9; and/or (iii) an epitope recognized by MPE8 antibody, wherein the epitope recognized by MPE8 antibody comprises at least residues T50, D310, L305, G307, and I309 of a native bovine RSV F protein sequence set forth in any one of SEQ ID NOs: 1-9.

As shown in the present Examples, three exemplary recombinant bRSV F proteins were identified, which provide (i) excellent stability (physical properties) and (ii) high immunogenicity:

1. bRSV 391-2sc9-10DS-Cav1Q98C Q361C (SEQ ID NO: 31)
MAATAMRMIISIIFISTYMTHITLCQNITEEFYQSTCSAVSRGYLSALRT

GWYTSVVTIELSKIQKNVCKSTDSKVKLIKQELERYNNAVIELQSLMCNE

PASgsGSAIASGVAVCKVLHLEGEVNKIKNALLSTNKAVVSLSNGVSVLI

TKVLDLKNYIDKELLPKLNNHDCRISNIETVIEFQQKNNRLLEIAREFSV

NAGITTPLSTYMLTNSELLSLINDMPITNDQKKLMSSNVQIVRQQSYSIM

CVVKEEVIAYVVQLPIYGVIDTPCWKLHTSPLCTTDNKEGSNICLTRTDR

GWYCDNAGSVSFFPQAETCKVCSNRVFCDTMNSLTLPTDVNLCNTDIFNT

KYDCKIMTSKTDISSSVITSIGAIVSCYGKTKCTASNKNRGIIKTFSNGC

DYVSNKGVDTVSVGNTLYYVNKLEGKALYIKGEPIINYYDPLVFPSDEFD

ASIAQVNAKINQSLAFIRRSDELLSaiggyipeaprdgqayvrkdgewvl lstflgglvprgshhhhhhsawshpqfek 2. bRSV 391-2sc9DS-Cav1Q98C Q361C (SEQ ID NO: 32)
MAATAMRMIISIIFISTYMTHITLCQNITEEFYQSTCSAVSRGYLSALRT

GWYTSVVTIELSKIQKNVCKSTDSKVKLIKQELERYNNAVIELQSLMCNE

PASFSgsGSAIASGVAVCKVLHLEGEVNKIKNALLSTNKAVVSLSNGVSV

LITKVLDLKNYIDKELLPKLNNHDCRISNIETVIEFQQKNNRLLEIAREF

SVNAGITTPLSTYMLTNSELLSLINDMPITNDQKKLMSSNVQIVRQQSYS

IMCVVKEEVIAYVVQLPIYGVIDTPCWKLHTSPLCTTDNKEGSNICLTRT

DRGWYCDNAGSVSFFPQAETCKVCSNRVFCDTMNSLTLPTDVNLCNTDIF

NTKYDCKIMTSKTDISSSVITSIGAIVSCYGKTKCTASNKNRGIIKTFSN

GCDYVSNKGVDTVSVGNTLYYVNKLEGKALYIKGEPIINYYDPLVFPSDE

FDASIAQVNAKINQSLAFIRRSDELLSaiggyipeaprdgqayvrkdgew vllstflgglvprgshhhhhhsawshpqfek 3. bRSV ATue51908sc9-10DS-Cav1 A149C-Y458C (SEQ ID NO: 33)
MDSKGSSQKGSRLLLLLVVSNLLLPQGVVGQNITEEFYQSTCSAVSRGYL

SALRTGWYTSVVTIELSKIQKNVCKSTDSKVKLIKQELERYNNAVVELQS

LMQNEPASgsGSAVcSGVAVCKVLHLEGEVNKIKNALLSTNKAVVSLSNG

VSVLTFKVLDLKNYIDKELLPQLNNHDCRISNIETVIEFQQKNNRLLEIA

REFSVNAGITTPLSTYMLTNSELLSLINDMPITNDQKKLMSSNVQIVRQQ

SYSIMCVVKEEVIAYVVQLPIYGVIDTPCWKLHTSPLCTIDNKEGSNICL

TRTDRGWYCDNAGSVSFFPQTETCKVQSNRVFCDTMNSLTLPTDVNLCNT

DIFNTKYDCKIMTSKTDISSSVITSIGAIVSCYGKTKCTASNKNRGIIKT

FSNGCDYVSNKGVDTVSVGNTLYcVNKLEGKALYIKGEPIINYYDPLVFP

SDEFDASIAQVNAKINQSLAFIRRSDELLSAIGGYIPEAPRDGQAYVRKD

GEWVLLSTFLGGLVPRGSHHHHHHSAWSHPQFEK

In addition, the following further preferred exemplary recombinant bRSV F proteins were identified:

4. 391-2 sc9 DS-Cav1 N88C N254C (SEQ ID NO: 63)
MAATAMRMIISIIFISTYMTHITLCQNITEEFYQSTCSAVSRGYLSALRT

GWYTSVVTIELSKIQKNVCKSTDSKVKLIKQELERYNcAVIELQSLMQNE

PASFSgsGSAIASGVAVCKVLHLEGEVNKIKNALLSTNKAVVSLSNGVSV

LTFKVLDLKNYIDKELLPKLNNHDCRISNIETVIEFQQKNNRLLEIAREF

SVNAGITTPLSTYMLTcSELLSLINDMPITNDQKKLMSSNVQIVRQQSYS

IMCVVKEEVIAYVVQLPIYGVIDTPCWKLHTSPLCTTDNKEGSNICLTRT

DRGWYCDNAGSVSFFPQAETCKVQSNRVFCDTMNSLTLPTDVNLCNTDIF

NTKYDCKIMTSKTDISSSVITSIGAIVSCYGKTKCTASNKNRGIIKTFSN

GCDYVSNKGVDTVSVGNTLYYVNKLEGKALYIKGEPIINYYDPLVFPSDE

FDASIAQVNAKINQSLAFIRRSDELLSAIGGYIPEAPRDGQAYVRKDGEW

VLLSTFLGGLVPRGSHHHHHHSAWSHPQFEK

-continued 5. 391-2 sc9 DS-Cav1 sc9 E92C N254C
(SEQ ID NO: 64)
MAATAMRMIISIIFISTYMTHITLCQNITEEFYQSTCSAVSRGYLSALRT GWYTSVVTIELSKIQKNVCKSTDSKVKLIKQELERYNNAVIcLQSLMQNE PASFSgsGSAIASGVAVCKVLHLEGEVNKIKNALLSTNKAVVSLSNGVSV

LTFKVLDLKNYIDKELLPKLNNHDCRISNIETVIEFQQKNNRLLEIAREF

SVNAGITTPLSTYMLTcSELLSLINDMPITNDQKKLMSSNVQIVRQQSYS

IMCVVKEEVIAYVVQLPIYGVIDTPCWKLHTSPLCTTDNKEGSNICLTRT

DRGWYCDNAGSVSFFPQAETCKVQSNRVFCDTMNSLTLPTDVNLCNTDIF

NTKYDCKIMTSKTDISSSVITSIGAIVSCYGKTKCTASNKNRGIIKTFSN

GCDYVSNKGVDTVSVGNTLYYVNKLEGKALYIKGEPIINYYDPLVFPSDE

FDASIAQVNAKINQSLAFIRRSDELLSAIGGYIPEAPRDGQAYVRKDGEW

VLLSTFLGGLVPRGSHHHHHHSAWSHPQFEK 6. 391-2 sc9 DS-Cav1 sc9 S238C Q279C
(SEQ ID NO: 65)
MAATAMRMIISIIFISTYMTHITLCQNITEEFYQSTCSAVSRGYLSALRT

GWYTSVVTIELSKIQKNVCKSTDSKVKLIKQELERYNNAVIELQSLMQNE

PASFSgsGSAIASGVAVCKVLHLEGEVNKIKNALLSTNKAVVSLSNGVSV

LTFKVLDLKNYIDKELLPKLNNHDCRISNIETVIEFQQKNNRLLEIAREF cVNAGITTPLSTYMLTNSELLSLINDMPITNDQKKLMSSNVcIVRQQSYS

IMCVVKEEVIAYVVQLPIYGVIDTPCWKLHTSPLCTTDNKEGSNICLTRT

DRGWYCDNAGSVSFFPQAETCKVQSNRVECDTMNSLTLPTDVNLCNTDIE

NTKYDCKIMTSKTDISSSVITSIGAIVSCYGKTKCTASNKNRGIIKTFSN

GCDYVSNKGVDTVSVGNTLYYVNKLEGKALYIKGEPIINYYDPLVFPSDE

FDASIAQVNAKINQSLAFIRRSDELLSAIGGYIPEAPRDGQAYVRKDGEW

VLLSTFLGGLVPRGSHHHHHHSAWSHPQFEK

Of those six exemplary recombinant bRSV F proteins bRSV 391-2sc9-10DS-Cav1Q98C-Q361C (SEQ ID NO: 31), bRSV 391-2sc9DS-Cav1Q98C-Q361C (SEQ ID NO: 32) and bRSV ATue51908sc9-10DS-Cav1 A149C-Y458C are more preferred. bRSV 391-2sc9-10DS-Cav1Q98C-Q361C (SEQ ID NO: 31) and bRSV 391-2sc9DS-Cav1Q98C-Q361C (SEQ ID NO: 32) are even more preferred. Those two exemplary recombinant bRSV F proteins achieved the highest yields (see FIG. 7). bRSV 391-2sc9DS-Cav1Q98C-Q361C (SEQ ID NO: 32) is most preferred.

Accordingly, it is preferred that the immunogen according to the present invention comprises a recombinant RSV F protein or a fragment thereof, wherein the recombinant RSV F protein or the fragment thereof comprises or consists of
(i) an F2 polypeptide comprising or consisting of amino acids 26-103 of SEQ ID NO: 31; and
(ii) an F1 polypeptide comprising or consisting of amino acids 106-474 of SEQ ID NO: 31.

It is also preferred that the immunogen according to the present invention comprises a recombinant RSV F protein or a fragment thereof, wherein the recombinant RSV F protein or the fragment thereof comprises or consists of
(i) an F2 polypeptide comprising or consisting of amino acids 31-108 of SEQ ID NO: 33; and
(ii) an F1 polypeptide comprising or consisting of amino acids 111-479 of SEQ ID NO: 33.

It is also preferred that the immunogen according to the present invention comprises a recombinant RSV F protein or a fragment thereof, wherein the recombinant RSV F protein or the fragment thereof comprises or consists of
(i) an F2 polypeptide comprising or consisting of amino acids 26-105 of SEQ ID NO: 63; and
(ii) an F1 polypeptide comprising or consisting of amino acids 108-476 of SEQ ID NO: 63.

It is also preferred that the immunogen according to the present invention comprises a recombinant RSV F protein or a fragment thereof, wherein the recombinant RSV F protein or the fragment thereof comprises or consists of
(i) an F2 polypeptide comprising or consisting of amino acids 26-105 of SEQ ID NO: 64; and
(ii) an F1 polypeptide comprising or consisting of amino acids 108-476 of SEQ ID NO: 64.

It is also preferred that the immunogen according to the present invention comprises a recombinant RSV F protein or a fragment thereof, wherein the recombinant RSV F protein or the fragment thereof comprises or consists of
(i) an F2 polypeptide comprising or consisting of amino acids 26-105 of SEQ ID NO: 65; and
(ii) an F1 polypeptide comprising or consisting of amino acids 108-476 of SEQ ID NO: 65.

Most preferably, the immunogen according to the present invention comprises a recombinant RSV F protein or a fragment thereof, wherein the recombinant RSV F protein or the fragment thereof comprises or consists of
(i) an F2 polypeptide comprising or consisting of amino acids 26-105 of SEQ ID NO: 32; and
(ii) an F1 polypeptide comprising or consisting of amino acids 108-476 of SEQ ID NO: 32.

Moreover, it is preferred that the immunogen according to the present invention comprises a recombinant RSV F protein or a fragment thereof, wherein the recombinant RSV F protein or the fragment thereof comprises or consists of
(i) an F2 polypeptide comprising or consisting of amino acids 26-103 of SEQ ID NO: 31;
(ii) an F1 polypeptide comprising or consisting of amino acids 106-474 of SEQ ID NO: 31; and
(iii) a foldon domain comprising or consisting of amino acids 475-513 of SEQ ID NO: 31, which is preferably directly linked to the C-terminus of the F1 polypeptide.

Furthermore, it is preferred that the immunogen according to the present invention comprises a recombinant RSV F protein or a fragment thereof, wherein the recombinant RSV F protein or the fragment thereof comprises or consists of
(i) an F2 polypeptide comprising or consisting of amino acids 31-108 of SEQ ID NO: 33;
(ii) an F1 polypeptide comprising or consisting of amino acids 111-479 of SEQ ID NO: 33; and
(iii) a foldon domain comprising or consisting of amino acids 480-518 of SEQ ID NO: 33, which is preferably directly linked to the C-terminus of the F1 polypeptide.

It is also preferred that the immunogen according to the present invention comprises a recombinant RSV F protein or a fragment thereof, wherein the recombinant RSV F protein or the fragment thereof comprises or consists of
(i) an F2 polypeptide comprising or consisting of amino acids 26-105 of SEQ ID NO: 63;
(ii) an F1 polypeptide comprising or consisting of amino acids 108-476 of SEQ ID NO: 63; and
(iii) a foldon domain comprising or consisting of amino acids 477-515 of SEQ ID NO: 63, which is preferably directly linked to the C-terminus of the F1 polypeptide.

It is also preferred that the immunogen according to the present invention comprises a recombinant RSV F protein or a fragment thereof, wherein the recombinant RSV F protein or the fragment thereof comprises or consists of
(i) an F2 polypeptide comprising or consisting of amino acids 26-105 of SEQ ID NO: 64;
(ii) an F1 polypeptide comprising or consisting of amino acids 108-476 of SEQ ID NO: 64; and
(iii) a foldon domain comprising or consisting of amino acids 477-515 of SEQ ID NO: 64, which is preferably directly linked to the C-terminus of the F1 polypeptide.

It is also preferred that the immunogen according to the present invention comprises a recombinant RSV F protein or a fragment thereof, wherein the recombinant RSV F protein or the fragment thereof comprises or consists of
(i) an F2 polypeptide comprising or consisting of amino acids 26-105 of SEQ ID NO: 65;
(ii) an F1 polypeptide comprising or consisting of amino acids 108-476 of SEQ ID NO: 65; and
(iii) a foldon domain comprising or consisting of amino acids 477-515 of SEQ ID NO: 65, which is preferably directly linked to the C-terminus of the F1 polypeptide.

Most preferably, the immunogen according to the present invention comprises a recombinant RSV F protein or a fragment thereof, wherein the recombinant RSV F protein or the fragment thereof comprises or consists of
(i) an F2 polypeptide comprising or consisting of amino acids 26-105 of SEQ ID NO: 32;
(ii) an F1 polypeptide comprising or consisting of amino acids 108-476 of SEQ ID NO: 32; and
(iii) a foldon domain comprising or consisting of amino acids 477-515 of SEQ ID NO: 32, which is preferably directly linked to the C-terminus of the F1 polypeptide.

Preferably, the immunogen according to the present invention comprises a recombinant RSV F protein or a fragment thereof, wherein the recombinant RSV F protein or the fragment thereof comprises or consists of amino acids 26-474 of SEQ ID NO: 31. More preferably, the immunogen according to the present invention comprises a recombinant RSV F protein or a fragment thereof, wherein the recombinant RSV F protein or the fragment thereof comprises or consists of amino acids 26-513 of SEQ ID NO: 31. Even more preferably, the immunogen according to the present invention comprises a recombinant RSV F protein or a fragment thereof, wherein the recombinant RSV F protein or the fragment thereof comprises or consists of amino acids 1-474 of SEQ ID NO: 31. Still more preferably, the immunogen according to the present invention comprises a recombinant RSV F protein or a fragment thereof, wherein the recombinant RSV F protein or the fragment thereof comprises or consists of amino acids 1-513 of SEQ ID NO: 31. Most preferably, the immunogen according to the present invention comprises a recombinant RSV F protein or a fragment thereof, wherein the recombinant RSV F protein or the fragment thereof comprises or consists of an amino acid sequence according to SEQ ID NO: 31.

It is also preferred that the immunogen according to the present invention comprises a recombinant RSV F protein or a fragment thereof, wherein the recombinant RSV F protein or the fragment thereof comprises or consists of amino acids 31-479 of SEQ ID NO: 33. More preferably, the immunogen according to the present invention comprises a recombinant RSV F protein or a fragment thereof, wherein the recombinant RSV F protein or the fragment thereof comprises or consists of amino acids 31-518 of SEQ ID NO: 33. Even more preferably, the immunogen according to the present invention comprises a recombinant RSV F protein or a fragment thereof, wherein the recombinant RSV F protein or the fragment thereof comprises or consists of amino acids 1-479 of SEQ ID NO: 33. Still more preferably, the immunogen according to the present invention comprises a recombinant RSV F protein or a fragment thereof, wherein the recombinant RSV F protein or the fragment thereof comprises or consists of amino acids 1-518 of SEQ ID NO: 33. Most preferably, the immunogen according to the present invention comprises a recombinant RSV F protein or a fragment thereof, wherein the recombinant RSV F protein or the fragment thereof comprises or consists of an amino acid sequence according to SEQ ID NO: 33.

It is also preferred that the immunogen according to the present invention comprises a recombinant RSV F protein or a fragment thereof, wherein the recombinant RSV F protein or the fragment thereof comprises or consists of amino acids 26-476 of SEQ ID NO: 63. More preferably, the immunogen according to the present invention comprises a recombinant RSV F protein or a fragment thereof, wherein the recombinant RSV F protein or the fragment thereof comprises or consists of amino acids 26-515 of SEQ ID NO: 63. Even more preferably, the immunogen according to the present invention comprises a recombinant RSV F protein or a fragment thereof, wherein the recombinant RSV F protein or the fragment thereof comprises or consists of amino acids 1-476 of SEQ ID NO: 63. Still more preferably, the immunogen according to the present invention comprises a recombinant RSV F protein or a fragment thereof, wherein the recombinant RSV F protein or the fragment thereof comprises or consists of amino acids 1-515 of SEQ ID NO: 63. Most preferably, the immunogen according to the present invention comprises a recombinant RSV F protein or a fragment thereof, wherein the recombinant RSV F protein or the fragment thereof comprises or consists of an amino acid sequence according to SEQ ID NO: 63.

It is also preferred that the immunogen according to the present invention comprises a recombinant RSV F protein or a fragment thereof, wherein the recombinant RSV F protein or the fragment thereof comprises or consists of amino acids 26-476 of SEQ ID NO: 64. More preferably, the immunogen according to the present invention comprises a recombinant RSV F protein or a fragment thereof, wherein the recombinant RSV F protein or the fragment thereof comprises or consists of amino acids 26-515 of SEQ ID NO: 64. Even more preferably, the immunogen according to the present invention comprises a recombinant RSV F protein or a fragment thereof, wherein the recombinant RSV F protein or the fragment thereof comprises or consists of amino acids 1-476 of SEQ ID NO: 64. Still more preferably, the immunogen according to the present invention comprises a recombinant RSV F protein or a fragment thereof, wherein the recombinant RSV F protein or the fragment thereof comprises or consists of amino acids 1-515 of SEQ ID NO: 64. Most preferably, the immunogen according to the present invention comprises a recombinant RSV F protein or a fragment thereof, wherein the recombinant RSV F protein or the fragment thereof comprises or consists of an amino acid sequence according to SEQ ID NO: 64.

It is also preferred that the immunogen according to the present invention comprises a recombinant RSV F protein or a fragment thereof, wherein the recombinant RSV F protein or the fragment thereof comprises or consists of amino acids 26-476 of SEQ ID NO: 65. More preferably, the immunogen according to the present invention comprises a recombinant RSV F protein or a fragment thereof, wherein the recombinant RSV F protein or the fragment thereof comprises or consists of amino acids 26-515 of SEQ ID NO: 65. Even more preferably, the immunogen according to the present invention comprises a recombinant RSV F protein or a fragment thereof, wherein the recombinant RSV F protein or the fragment thereof comprises or consists of amino acids 1-476 of SEQ ID NO: 65. Still more preferably, the immunogen according to the present invention comprises a recombinant RSV F protein or a fragment thereof, wherein the recombinant RSV F protein or the fragment thereof comprises or consists of amino acids 1-515 of SEQ ID NO: 65. Most preferably, the immunogen according to the present invention comprises a recombinant RSV F protein or a fragment thereof, wherein the recombinant RSV F protein or the fragment thereof comprises or consists of an amino acid sequence according to SEQ ID NO: 65.

Most preferably, the immunogen according to the present invention comprises a recombinant RSV F protein or a fragment thereof, wherein the recombinant RSV F protein or the fragment thereof comprises or consists of amino acids 26-476 of SEQ ID NO: 32. More preferably, the immunogen according to the present invention comprises a recombinant RSV F protein or a fragment thereof, wherein the recombinant RSV F protein or the fragment thereof comprises or consists of amino acids 26-515 of SEQ ID NO: 32. Even more preferably, the immunogen according to the present invention comprises a recombinant RSV F protein or a fragment thereof, wherein the recombinant RSV F protein or the fragment thereof comprises or consists of amino acids 1-476 of SEQ ID NO: 32. Still more preferably, the immunogen according to the present invention comprises a recombinant RSV F protein or a fragment thereof, wherein the recombinant RSV F protein or the fragment thereof comprises or consists of amino acids 1-515 of SEQ ID NO: 32. Most preferably, the immunogen according to the present invention comprises a recombinant RSV F protein or a fragment thereof, wherein the recombinant RSV F protein or the fragment thereof comprises or consists of an amino acid sequence according to SEQ ID NO: 32.

It is also preferred that the immunogen according to the present invention as described above, the virus-like particle according to the present invention as described below, or the protein nanoparticle according to the present invention as described below specifically bind to the antibodies D25, MPE8 and/or AM14, preferably with a $K_d$ of 1 μM or less.

As used herein, "$K_d$" refers to the dissociation constant for a given interaction, such as a polypeptide-ligand interaction or an antibody-antigen interaction. For example, for the bimolecular interaction of an antibody (such as D25, MPE8 or AM14) and an antigen (such as the immunogen according to the present invention, in particular the recombinant RSV F protein or the fragment thereof), it is the concentration of the individual components of the bimolecular interaction divided by the concentration of the complex. Methods of determining the $K_d$ of an antibody:antigen interaction are familiar to the person of ordinary skill in the art.

Virus-Like Particle and Protein Nanoparticle

In a further aspect the present invention also provides a virus-like particle comprising the immunogen according to the present invention as described herein.

As used herein, a "Virus-like particle" (also "VLP") refers in particular to a non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) *Biophys. J.* 60: 1445-1456; and Hagensee et al (1994) *J. Viral.* 68:4503-4505; Vincente, *J Invertebr Pathol.*, 2011; Schneider-Ohrum and Ross, *Curr. Top. Microbial. Immunol.*, 354: 53073, 2012).

A virus-like particle comprising the immunogen according to the present invention as described herein is thus in particular a virus-like particle (VLP) that includes a recombinant RSV F protein stabilized in a prefusion conformation as disclosed herein. Accordingly, the virus like particle includes a recombinant RSV F protein or a fragment thereof including an F2 polypeptide and an F1 polypeptide (such as an F1 polypeptide linked to a transmembrane domain); a disulfide bond between a pair of cysteines at positions 155 and 290; a cavity-filling amino acid substitution at position 5190 and a cavity-filling amino acid substitution at position V207; a disulfide bond between a pair of cysteines at positions Q98C and Q361 C, at positions A149C and Y458C, at positions N183GC and N428C, at positions N88C and N254C, at positions E92C and N254C, and/or at positions S238C and Q279C; wherein the recombinant RSV F protein or the fragment thereof does not comprise a pep27 polypeptide. Preferred embodiments of the VLP comprising the immunogen according to the present invention correspond to preferred embodiments of the immunogen according to the present invention.

VLPs lack the viral components that are required for virus replication and thus represent a highly attenuated form of a virus. The VLP can display a polypeptide (e.g., a recombinant RSV F protein stabilized in a prefusion conformation) that is capable of eliciting an immune response to RSV when administered to a subject. Virus like particles and methods of their production are known and familiar to the person of ordinary skill in the art, and viral proteins from several viruses are known to form VLPs, including human papillomavirus, HIV (Kang et al., Biol. Chem. 380: 353-64 (1999)), Semliki-Forest virus (Notka et al., Biol. Chem. 380: 341-52 (1999)), human polyomavirus (Goldmann et al., J. Virol. 73: 4465-9 (1999)), rota virus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Viral. 70: 5422-9 (1996)), hepatitis E virus (Li et al., J. Viral. 71: 35 7207-13 (1997)), and Newcastle disease virus. For example, a chimeric VLP containing a RSV antigen and can be a Newcastle disease virus-based VLP. Newcastle disease based VLPs have previously been shown to elicit a neutralizing immune response to RSV in mice. The formation of such VLPs can be detected by any suitable technique. Examples of suitable techniques known in the art for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

In a further aspect the present invention also provides a protein nanoparticle comprising the immunogen according to the present invention as described herein.

As used herein, a "protein nanoparticle" refers in particular to a multi-subunit, protein-based polyhedron shaped structure. The subunits are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, Y. *Int. J. Mol. Sci.*, 12:5406-5421, 2011, incorporated by reference herein), encapsulin nanoparticles (see, e.g., Sutter et al., Nature Struct. and Mol. Biol., 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nan op articles (see, e.g., Zhang et al., *J. Mol. Biol.*, 306: 1099-1114, 2001) or pyruvate dehydrogenase nan op articles (see, e.g., Izard et al., PNAS 96: 1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. Preferably, ferritin, encapsulin, SOR, lumazine synthase, or pyruvate dehydrogenase monomers are linked to an immunogen according to the present invention as disclosed herein (for example, a recombinant RSV F protein stabilized in a prefusion conformation as described herein) and self-assembled into a protein nanoparticle presenting the disclosed antigens on its surface, which can be administered to a subject to stimulate an immune response to the immunogen.

A protein nanoparticle particle comprising the immunogen according to the present invention as described herein is thus in particular a protein nanoparticle that includes a recombinant RSV F protein stabilized in a prefusion conformation as disclosed herein. Accordingly, the protein nanoparticle includes a recombinant RSV F protein or a fragment thereof including an F2 polypeptide and an F1 polypeptide (such as an F1 polypeptide linked to a transmembrane domain); a disulfide bond between a pair of cysteines at positions 155 and 290; a cavity-filling amino acid substitution at position S190 and a cavity-filling amino acid substitution at position V207; a disulfide bond between a pair of cysteines at positions Q98C and Q361 C, at positions A149C and Y458C, at positions N183GC and N428C, at positions N88C and N254C, at positions E92C and N254C, and/or at positions S238C and Q279C; wherein the recombinant RSV F protein or the fragment thereof does not comprise a pep27 polypeptide. Preferred embodiments of the protein nanoparticle comprising the immunogen according to the present invention correspond to preferred embodiments of the immunogen according to the present invention.

For example, the protein nanoparticle may include one or more of any of the disclosed immunogens, in particular recombinant RSV F protein stabilized in a prefusion conformation, wherein the protein nanoparticle is specifically bound by a prefusion-specific antibody (e.g., D25, MPE8 or AM14 antibody), and/or includes a RSV F prefusion specific conformation (such as antigenic site Ø).

Non-limiting example of nanoparticles include ferritin nanoparticles, encapsulin nanoparticles and Sulfur Oxygenase Reductase (SOR) nanoparticles, which are comprised of an assembly of monomeric subunits including ferritin proteins, encapsulin proteins and SOR proteins, respectively. To construct protein nanoparticles including the disclosed recombinant RSV F protein stabilized in a prefusion conformation, the antigen/immunogen (in particular the recombinant RSV F protein or the fragment thereof) is usually linked to a subunit of the protein nanoparticle (such as a ferritin protein, an encapsulin protein or a SOR protein). The fusion protein self-assembles into a nanoparticle under appropriate conditions.

Preferably, the protein nanoparticle is thus a ferritin nanoparticle, an encapsulin nanoparticle, a Sulfur Oxygenase Reductase (SOR) nanoparticle, a lumazine synthase nanoparticle or a pyruvate dehydrogenase nanoparticle. More preferably, the protein nanoparticle is a ferritin nanoparticle.

Ferritin nanoparticles and their use for immunization purposes (e.g., for immunization against influenza antigens) has been disclosed in the art (see, e.g., Kanekiyo et al., Nature, 499: 102-106, 2013, incorporated by reference herein in its entirety). Accordingly, a preferred protein nanoparticle is a ferritin nanoparticle. For example, any of the disclosed immunogens (in particular the recombinant RSV F proteins or the fragments thereof) may be linked to a ferritin polypeptide or hybrid of different ferritin polypeptides to construct a ferritin protein nanoparticle. Thereby the ferritin nanoparticle is preferably specifically bound by a prefusion-specific antibody (e.g., D25, MPE8 or AM14 antibody), and/or includes a RSV F prefusion specific conformation (such as antigenic site Ø).

Ferritin is a globular protein that is found in all animals, bacteria, and plants, and which acts primarily to control the rate and location of polynuclear $Fe(III)_2O_3$ formation through the transportation of hydrated iron ions and protons to and from a mineralized core. The globular form of ferritin is made up of monomeric subunits, which are polypeptides having a molecule weight of approximately 17-20 kDa. An example of the sequence of one such monomeric subunit is represented by SEQ ID NO: 48:

```
ferritin polypeptide:
                                      [SEQ ID NO: 48]
MLSKDIIKLLNEQVNKEMNSSNLYMSMSSWCYTHSLDGAGLFLFDHAAEE

YEHAKKLIVFLNENNVPVQLTSISAPEHKFEGLTQIFQKAYEHEQHISES

INNIVDHAIKGKDHATFNFLQWYVAEQHEEEVLFKDILDKIELIGNENHG

LYLADQYVKGIAKSRKS.
```

Each monomeric subunit has the topology of a helix bundle which includes a four antiparallel helix motifs, with a fifth shorter helix (the c-terminal helix) lying roughly perpendicular to the long axis of the 4 helix bundle. According to convention, the helices are labeled 'A, B, C, D & E' from the N-terminus respectively. The N-terminal sequence lies adjacent to the capsid three-fold axis and extends to the surface, while the E helices pack together at the four-fold axis with the C-terminus extending into the capsid core. The consequence of this packing creates two pores on the capsid surface. It is expected that one or both of these pores represent the point by which the hydrated iron diffuses into and out of the capsid. Following production, these monomeric subunit proteins self-assemble into the globular ferritin protein. Thus, the globular form of ferritin comprises 24 monomeric, subunit proteins, and has a capsid-like structure having 432 symmetry. Methods of constructing ferritin nanoparticles are known to the person of ordinary skill in the art and are further described herein (see, e.g., Zhang, *Int. J. Mol. Sci.*, 12:5406-5421, 2011, which is incorporated herein by reference in its entirety).

For example, the ferritin polypeptide is *E. coli* ferritin, *Helicobacter pylori* ferritin, human light chain ferritin, bullfrog ferritin or a hybrid thereof, such as *E. coli*-human hybrid ferritin, *E. coli*-bullfrog hybrid ferritin, or human-bullfrog hybrid ferritin. Exemplary amino acid sequences of ferritin polypeptides and nucleic acid sequences encoding ferritin polypeptides to be combined with the immunogen according to the present invention (in particular the recombinant RSV F protein or the fragment thereof) can be found in GENBANK®, for example at accession numbers ZP 03085328, ZP 06990637, EJB64322. I, AAA35832, NP 000137 AAA49532, AAA49525, AAA49524 and AAA49523, which are specifically incorporated by reference herein in their entirety as available Feb. 28, 2013. In one embodiment, any of the disclosed recombinant RSV F proteins stabilized in a prefusion conformation is linked to a ferritin protein including an amino acid sequence at least 80% (such as at least 85%, at least 90%, at least 95%, or at least 97%) identical to amino acid sequence set forth as SEQ ID NO: 48.

Preferably, the ferritin polypeptide is a *Helicobacter pylori* ferritin (such as a ferritin polypeptide set forth as SEQ ID NO: 48) and includes a substitution of the cysteine residue at position 31, such as a C31 S, C31A or C31V substitution. Any of the immunogens according to the present invention (in particular the recombinant RSV F proteins or the fragments thereof) can be linked to a *Helicobacter pylori* ferritin (such as a ferritin polypeptide set forth as SEQ ID NO: 48) that preferably further includes a substitution of the cysteine residue at position 31 of the ferritin polypeptide, such as a C31S, C31A or C31V substitution.

Preferably, the ferritin protein nanoparticle includes an immunogen according to the present invention comprising a recombinant RSV F protein or a fragment thereof including an F2 polypeptide and an F1 polypeptide, wherein the F1 polypeptide is linked to the ferritin protein. Preferably, the encapsulin protein nanoparticle includes an immunogen according to the present invention comprising a recombinant RSV F protein or a fragment thereof including an F2 polypeptide and an F1 polypeptide, wherein the F1 polypeptide is linked to the encapsulin protein. Preferably, the SOR protein nanoparticle includes an immunogen according to the present invention comprising a recombinant RSV F protein or a fragment thereof including an F2 polypeptide and an F1 polypeptide, wherein the F1 polypeptide is linked to the SOR protein.

Thus, the immunogen according to the present invention (in particular the recombinant RSV F protein or the fragment thereof) may also be linked to an encapsulin polypeptide to construct an encapsulin nanoparticle, in particular wherein the encapsulin nanoparticle is specifically bound by a prefusion-specific antibody (e.g., D25, MPE8 or AM14 antibody), and/or includes an RSV F prefusion specific conformation (such as antigenic site Ø). Encapsulin proteins are a conserved family of bacterial proteins also known as linocin-like proteins that form large protein assemblies that function as a minimal compartment to package enzymes. The encapsulin assembly is made up of monomeric subunits, which are polypeptides having a molecule weight of approximately 30 kDa. An example of the sequence of one such monomeric subunit is provided as SEQ ID NO: 49:

```
encapsulin polypeptide:
                                       [SEQ ID NO: 49]
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF
```

Following production, the monomeric subunits self-assemble into the globular encapsulin assembly including 60 monomeric subunits. Methods of constructing encapsulin nanoparticles are known to the person of ordinary skill in the art, and further described herein (see, for example, Sutter et al., Nature Struct. and Mol. Biol., 15:939-947, 2008, which is incorporated by reference herein in its entirety). In specific examples, the encapsulin polypeptide is bacterial encapsulin, such as *E. coli* or *Thermotoga maritime* encapsulin.

An exemplary encapsulin sequence to be combined with the immunogen according to the present invention (in particular the recombinant RSV F protein or the fragment thereof) is set forth as SEQ ID NO: 49.

Moreover, any of the immunogens according to the present invention (in particular the recombinant RSV F proteins or the fragments thereof) may also be linked to a Sulfur Oxygenase Reductase (SOR) polypeptide to construct a SOR nanoparticle, in particular wherein the SOR nanoparticle is specifically bound by a prefusion-specific antibody (e.g., D25, MPE8 or AM14 antibody), and/or includes a RSV F prefusion specific conformation (such as antigenic site Ø). SOR proteins are microbial proteins (for example from the thermoacidophilic archaeon *Acidianus ambivalens* that form 24 subunit protein assemblies. Methods of constructing SOR nanoparticles are known to the person of ordinary skill in the art (see, e.g., Urich et al., Science, 311:996-1000, 2006, which is incorporated by reference herein in its entirety).

Furthermore, the immunogen according to the present invention (in particular the recombinant RSV F protein or the fragment thereof) may also be linked to a Lumazine synthase polypeptide to construct a Lumazine synthase nanoparticle, wherein the Lumazine synthase nanoparticle is specifically bound by a prefusion-specific antibody (e.g., D25, MPE8 or AM14 antibody), and/or includes a RSV F prefusion specific conformation (such as antigenic site Ø).

Moreover, the immunogen according to the present invention (in particular the recombinant RSV F protein or the fragment thereof) may also be linked to a pyruvate dehydrogenase polypeptide to construct a pyruvate dehydrogenase nanoparticle, wherein the pyruvate dehydrogenase nanoparticle is specifically bound by a prefusion-specific antibody (e.g., D25, MPE8 or AM14 antibody), and/or includes a RSV F prefusion specific conformation (such as antigenic site Ø).

Preferably, the immunogen according to the present invention (in particular the recombinant RSV F protein or the fragment thereof) is linked to the N- or C-terminus of a ferritin, encapsulin, SOR, lumazine synthase or pyruvate dehydrogenase protein, for example with a linker, such as a Ser-Gly linker or any of the linkers disclosed in Table 1. Constructs are preferably made in HEK 293 Freestyle cells, since the fusion proteins are secreted from those cells and self-assembled into nanoparticles. The nanoparticles can be purified using known techniques, for example by a few different chromatography procedures, e.g. Mono Q (anion exchange) followed by size exclusion (SUPEROSE® 6) chromatography.

Several embodiments include a monomeric subunit of a ferritin, encapsulin, SOR, lumazine synthase or pyruvate dehydrogenase protein, or any portion thereof which is capable of directing self-assembly of monomeric subunits into the globular form of the protein. Amino acid sequences from monomeric subunits of any known ferritin, encapsulin, SOR, lumazine synthase or pyruvate dehydrogenase protein can be used to produce fusion proteins with the immunogen according to the present invention (in particular the recombinant RSV F protein or the fragment thereof), in particular so long as the monomeric subunit is capable of self-assembling into a nanoparticle displaying the immunogen according to the present invention (in particular the recombinant RSV F protein or the fragment thereof) on its surface.

The fusion proteins need not comprise the full-length sequence of a monomeric subunit polypeptide of a ferritin, encapsulin, SOR, lumazine synthase or pyruvate dehydrogenase protein. Portions, or regions, of the monomeric subunit polypeptide can be utilized so long as the portion comprises amino acid sequences that direct self assembly of monomeric subunits into the globular form of the protein.

In some embodiments, it may be useful to engineer mutations into the amino acid sequence of the monomeric ferritin, encapsulin, SOR, lumazine synthase or pyruvate dehydrogenase subunits. For example, it may be useful to alter sites such as enzyme recognition sites or glycosylation sites in order to give the fusion protein beneficial properties (e.g., half-life).

It will be understood by those skilled in the art that fusion of the immunogen according to the present invention (in particular of the recombinant RSV F protein or of the fragment thereof) to the ferritin, encapsulin, SOR, lumazine synthase or pyruvate dehydrogenase protein should be done such that the immunogen/recombinant RSV F protein portion of the fusion protein does not interfere with self-assembly of the monomeric ferritin, encapsulin, SOR, lumazine synthase or pyruvate dehydrogenase subunits into the globular protein, and that the ferritin, encapsulin, SOR, lumazine synthase or pyruvate dehydrogenase protein portion of the fusion protein does not interfere with the ability of the immunogen according to the present invention (in particular of the recombinant RSV F protein or of the fragment thereof) to elicit an immune response to RSV.

For example, the ferritin, encapsulin, SOR, lumazine synthase or pyruvate dehydrogenase protein and the immunogen according to the present invention (in particular the recombinant RSV F protein or the fragment thereof) can be joined together directly without affecting the activity of either portion. In other embodiments, the ferritin, encapsulin, SOR, lumazine synthase or pyruvate dehydrogenase protein and the immunogen according to the present invention (in particular the recombinant RSV F protein or the fragment thereof) are joined using a linker (also referred to as a spacer) sequence. The linker sequence is designed to position the ferritin, encapsulin, SOR, lumazine synthase or pyruvate dehydrogenase portion of the fusion protein and the immunogen/recombinant RSV F protein portion of the fusion protein, with regard to one another, such that the fusion protein maintains the ability to assemble into nanoparticles, and also elicits an immune response to RSV.

Preferably, the linker sequences comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. One example of such a linker sequence is SGG. Amino acids can be added or subtracted as needed. Further examples of useful linker sequences are disclosed in Table 1. Those skilled in the art are capable of determining appropriate linker sequences for construction of protein nanoparticles.

Preferably, the protein nanoparticles has a molecular weight of from 100 to 5000 kDa, such as approximately 500 to 4600 kDa. More preferably, a Ferritin nanoparticle has an approximate molecular weight of about 650 kDa, an Encapsulin nanoparticle has an approximate molecular weight of about 2100 kDa, a SOR nanoparticle has an approximate molecular weight of about 1000 kDa, a lumazine synthase nanoparticle has an approximate molecular weight of about 4000 kDa, and a pyruvate dehydrogenase nanoparticle has an approximate molecular weight of about 4600 kDa, when the protein nanoparticle includes the immunogen according to the present invention (in particular the recombinant RSV F protein or the fragment thereof).

The disclosed recombinant RSV F proteins stabilized in a prefusion conformation linked to ferritin, encapsulin, SOR, lumazine synthase or pyruvate dehydrogenase proteins can self-assemble into multi-subunit protein nanoparticles, typically termed ferritin nanoparticles, encapsulin nanoparticles, SOR nanoparticles, lumazine synthase nanoparticles, and pyruvate dehydrogenase nanoparticles, respectively. The nanoparticles including the immunogen according to the present invention (in particular the recombinant RSV F protein or the fragment thereof) have substantially the same structural characteristics as the native ferritin, encapsulin, SOR, lumazine synthase or pyruvate dehydrogenase nanoparticles that do not include the immunogen according to the present invention (in particular the recombinant RSV F protein or the fragment thereof). That is, they contain 24, 60, 24, 60, or 60 subunits (respectively) and have similar corresponding symmetry. In the case of nanoparticles constructed of monomer subunits including the immunogen according to the present invention (in particular the recombinant RSV F protein or the fragment thereof), such nanoparticles are preferably specifically bound by a prefusion-specific antibody (e.g., D25 antibody), and/or include an RSV F prefusion specific conformation (such as antigenic site Ø).

Nucleic Acid Molecule, Vector and Host Cell

In a further aspect the present invention also provides a nucleic acid molecule comprising a polynucleotide encoding the immunogen, the virus-like particle, or protein nanoparticle according to the present invention as described herein.

As used herein, "nucleic acid molecule" (also referred to as "polynucleotide") refers in particular to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like.

Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). Typically, nucleotide is one monomer in a polynucleotide. A nucleotide sequence refers to the sequence of bases in a polynucleotide. Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences." "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system.

Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" or a "nucleic acid molecule encoding a certain peptide/protein" includes all nucleotide sequences that are degenerate versions of each other and that encode the same amino acid sequence. Nucleotide sequences that encode proteins and RNA may include introns.

A nucleic acid molecule comprising a polynucleotide encoding the immunogen, the virus-like particle or the protein nanoparticle according to the present invention as described herein thus in particular a nucleic acid molecule comprising a polynucleotide encoding at least a recombinant RSV F protein stabilized in a prefusion conformation as disclosed herein. Accordingly, the polynucleotide encodes at least a recombinant RSV F protein or a fragment thereof including an F2 polypeptide and an F1 polypeptide (such as an F1 polypeptide linked to a transmembrane domain); a disulfide bond between a pair of cysteines at positions 155 and 290; a cavity-filling amino acid substitution at position S190 and a cavity-filling amino acid substitution at position V207; a disulfide bond between a pair of cysteines at positions Q98C and Q361C, at positions A149C and Y458C, at positions N183GC and N428C, at positions N88C and N254C, at positions E92C and N254C, and/or at positions S238C and Q279C; wherein the recombinant RSV F protein or the fragment thereof does not comprise a pep27 polypeptide. Preferred embodiments of the nucleic acid molecule comprising a polynucleotide encoding the immunogen, the virus-like particle or the protein nanoparticle according to the present invention correspond to preferred embodiments of the immunogen, the virus-like particle or the protein nanoparticle according to the present invention.

Nucleic acid molecules comprising polynucleotides encoding the immunogen according to the present invention (in particular the recombinant RSV F protein or the fragment thereof) or virus-like particles or protein nanoparticles containing such immunogens include DNA, cDNA and RNA sequences which encode the antigen. Examples of nucleic acid molecules and/or polynucleotides include, e.g., a recombinant polynucleotide, a vector, an oligonucleotide, an RNA molecule such as an rRNA, an mRNA, an miRNA, an siRNA, or a tRNA, or a DNA molecule such as a cDNA.

Preferably, the nucleic acid molecule comprises a polynucleotide encoding the immunogen according to the present invention as described herein. It is also preferred that the nucleic acid molecule comprises a polynucleotide encoding the virus-like particle or the protein nanoparticle according to the present invention as described herein.

Preferably, the nucleic acid molecule encodes a precursor F0 polypeptide that, when expressed in an appropriate cell, is processed into the disclosed recombinant RSV F protein or the fragment thereof, in particular wherein the precursor F0 polypeptide includes, from N- to C-terminus, a signal peptide, a F2 polypeptide, a Pep27 polypeptide, and a F1 polypeptide. Accordingly, it is preferred that the polynucleotide encodes a precursor protein of the immunogen or protein nanoparticle. More preferably, the encoded precursor protein comprises, from N- to C-terminus, a signal peptide, a F2 polypeptide, and a F1 polypeptide. Even more preferably, the encoded precursor protein comprises, from N- to C-terminus, a signal peptide, a F2 polypeptide, a F1 polypeptide, and a trimerization domain.

Exemplary nucleic acid molecules comprising a polynucleotide encoding an immunogen according to the present invention (in particular a recombinant RSV F protein or a fragment thereof) have any of the following nucleic acid sequences (SEQ ID NOs 56-62) or share at least 70% sequence identity, preferably at least 75% sequence identity, preferably at least 80% sequence identity, more preferably at least 85% sequence identity, more preferably at least 88% sequence identity, even more preferably at least 90% sequence identity, even more preferably at least 92% sequence identity, still more preferably at least 95% sequence identity, still more preferably at least 96% sequence identity, particularly preferably at least 97% sequence identity, particularly preferably at least 98% sequence identity and most preferably at least 99% sequence identity with any of the following nucleic acid sequences (SEQ ID NOs 56-62):

```
391-2sc9-10DS-Cav1 Q98C-Q361C:
                                                                       [SEQ ID NO: 56]
atggctgctactgctatgcggatgattatctcaattattttatttcaacctacatgactcacattaccctgtgtcagaacattaccgaggaa ttctaccagagcacttgctccgccgtgtctagaggatacctgtctgctctgaggaccggctggtatacaagcgtggtcactattgagctg tccaagatccagaaaaacgtgtgtaagagtaccgattcaaaggtcaaactgatcaaacaggagctggaaaggtataacaatgccgt
```

-continued gattgagctgcagagcctgatgtgcaatgaacctgctagcgggtctggaagtgccatcgcttccggagtggccgtctgcaaggtgctg cacctggagggcgaagtcaacaagatcaagaatgccctgctgtctacaaacaaagctgtggtctcactgagcaatggcgtgagtgt cctgacttttaaggtgctggacctgaaaaactacatcgataaggagctgctgccaaaactgaacaatcatgactgtcggatcagcaat attgagacagtgattgaattccagcagaagaacaatcgactgctggagatcgcaagagaattttcagtgaacgccggcattaccaca cccctgagcacctacatgctgacaaattctgagctgctgagtctgattaacgacatgcctatcaccaatgatcagaagaaactgatga gctccaacgtgcagatcgtcagacagcagtcctattctattatgtgcgtggtcaaggaggaagtgatcgcctacgtggtccagctgcct atctacggcgtgatcgataccccatgctggaagctgcacacaagtccctgtgtactaccgacaacaaagagggctcaaatatctg cctgacaaggactgaccgcggctggtactgtgataacgcagggagtgtgtcattctttccacaggccgaaacttgcaaggtgtgctcc aacagggtcttctgtgataccatgaattctctgaccctgcccacagacgtgaacctgtgcaacactgatatctttaataccaagtacga ctgtaagattatgactagcaagaccgacatctctagttcagtgatcacctccattggagctatcgtctcttgctacggcaagacaaaatg tactgcatctaacaagaatcgcgggatcatcaagacattctctaacggatgtgattatgtcagtaataaggggggtcgacacagtgagc gtcggaaacactctgtactatgtgaataagctggagggcaaagccctgtacatcaaaggggaacctatcattaactactatgatccac tggtgttccccagtgacgagtttgatgcatcaattgcccaggtgaacgctaagatcaatcagtccctggccttcatccggagatcagac gagctgctgagcgcaattggcgggtacatccccgaagctcctcgcgatggccaggcatatgtgcgaaaagacggggagtgggtcct gctgagcaccttcctgggaggactggtgcctcgaggatcccaccatcaccatcaccatagcgcttggtcccatccacagtttgaaaa g 391-2sc9DS-Cav1 Q98C-Q361C:

[SEQ ID NO: 57]

atggctgctactgctatgcggatgattatctcaattattttatttcaacctacatgactcacattaccctgtgtcagaacattaccgaggaa ttctaccagagcacttgctccgccgtgtctagaggatacctgtctgctctgaggaccggctggtatacaagcgtggtcactattgagctg tccaagatccagaaaaacgtgtgtaagagtaccgattcaaaggtcaaactgatcaaacaggagctggaaaggtataacaatgccgt gattgagctgcagagcctgatgtgcaatgaacctgctagcttctccgggtctggaagtgccatcgcttccggagtggccgtctgcaag gtgctgcacctggagggcgaagtcaacaagatcaagaatgccctgctgtctacaaacaaagctgtggtctcactgagcaatggcgt gagtgtcctgacttttaaggtgctggacctgaaaaactacatcgataaggagctgctgccaaaactgaacaatcatgactgtcggatc agcaatattgagacagtgattgaattccagcagaagaacaatcgactgctggagatcgcaagagaattttcagtgaacgccggcatt accacacccctgagcacctacatgctgacaaattctgagctgctgagtctgattaacgacatgcctatcaccaatgatcagaagaaa ctgatgagctccaacgtgcagatcgtcagacagcagtcctattctattatgtgcgtggtcaaggaggaagtgatcgcctacgtggtcca gctgcctatctacggcgtgatcgataccccatgctggaagctgcacacaagtccctgtgtactaccgacaacaaagagggctcaa atatctgcctgacaaggactgaccgcggctggtactgtgataacgcagggagtgtgtcattctttccacaggccgaaacttgcaaggt gtgctccaacagggtcttctgtgataccatgaattctctgaccctgcccacagacgtgaacctgtgcaacactgatatctttaataccaa gtacgactgtaagattatgactagcaagaccgacatctctagttcagtgatcacctccattggagctatcgtacttgctacggcaagac aaaatgtactgcatctaacaagaatcgcgggatcatcaagacattctctaacggatgtgattatgtcagtaataaggggggtcgacaca gtgagcgtcggaaacactctgtactatgtgaataagctggagggcaaagccctgtacatcaaaggggaacctatcattaactactatg atccactggtgttccccagtgacgagtttgatgcatcaattgcccaggtgaacgctaagatcaatcagtccctggccttcatccggaga tcagacgagctgctgagcgcaattggcgggtacatccccgaagctcctcgcgatggccaggcatatgtgcgaaaagacggggagt gggtcctgctgagcaccttcctgggaggactggtgcctcgaggatcccaccatcaccatcaccatagcgcttggtcccatccacagt ttgaaaagtga ATue51908sc9-10DS-Cav1 A149C-Y458C:

[SEQ ID NO: 58]

atggattccaaggggagctcccagaaggatctaggctgctgctgctgctggtggtaccaacctgctgctgccacagggagtggtc ggacagaatatcacagaggaattctaccagagcacttgctccgcagtgtctcggggatacctgtctgccctgagaactggctggtata cctctgtggtcacaattgagctgagtaagatccagaagaacgtgtgcaaaagtaccgactcaaaggtcaaactgatcaagcaggag ctggaacggtataacaatgccgtggtcgagctgcagagcctgatgcagaacgaacctgcttctggcagcggatctgccgtgtgtagt -continued ggagtggccgtctgcaaagtgctgcatctggagggcgaagtcaacaagatcaagaatgcactgctgtctactaacaaggccgtggt
ctcactgagcaatggcgtgagtgtcctgacctttaaggtgctggacctgaaaaactacatcgataaggagctgctgcctcagctgaac
aatcacgattgtaggatctccaatattgagacagtgattgaattccagcagaagaacaatcgcctgctggagatcgctcgagagttca
gcgtgaacgcaggcattaccacaccactgtcaacatacatgctgactaattcagagctgctgagcctgattaacgacatgcccatca
ccaatgatcagaagaaactgatgtctagtaacgtgcagatcgtccgccagcagtcctattctattatgtgcgtggtcaaggaggaagtg
atcgcatacgtggtccagctgcctatctacggcgtgatcgataccccatgctggaaactgcatacatctcccctgtgcactaccgaca
acaaggaaggaagtaatatttgcctgacaagaactgacaggggctggtactgtgataacgctggcagcgtgagcttcttccctcaga
ccgaaacatgcaaggtgcagagcaaccgggtcttctgtgatacaatgaattccctgactctgccaaccgacgtgaacctgtgcaac
accgatatctttaatacaaagtacgactgtaagatcatgacaagcaagactgacatctcaagctccgtgatcacaagtattggagctat
cgtgtcatgctacggcaagaccaaatgtacagcatctaacaaaaacagagggatcattaagactttctcaaacggatgtgattatgtg
agcaacaagggggtcgacactgtgagcgtcggaaacaccctgtactgtgtgaataagctggagggcaaagccctgtacatcaagg
gggaacccatcattaactactatgatccactggtgttccccagcgacgagtttgatgcatccattgcccaggtgaacgccaaaatcaa
tcagtccctggcttttattaggcgctccgacgagctgctgtctgccattggcgggtacatccccgaagcccctagggatggccaggctt
atgtgcgcaaggacggggagtgggtcctgctgtcaaccttcctgggaggactggtgccaagaggctcccaccatcaccatcaccat
agcgcctggtcccaccctcagtttgaaaag RB94 DS-Cav1 sc9 A149C-Y458C:

[SEQ ID NO: 59]

atggattctaagggttccagccagaaaggttccaggctgctgctgctgctggtggtgagcaatctgctgctgcctcagggagtggtggg
acagaacatcaccgaggagttctaccagtcaacctgcagcgccgtgagccggggctacctgagcgcactgagaaccggatggtat
acatccgtggtcactattgagctgtctaagatccagaaaaacgtgtgtaattctacagatagtaacgtcaagctgatcaaacaggagct
ggaaaggtataacaatgctgtggtcgagctgcagtccctgatgcagaacgaacctgccagcagcagcggcagcggcagcgccat
ctgttctggggtggcagtctgcaaggtgctgcatctggagggagaagtcaacaagatcaaaaatgcactgctgagtactaacaaagc
cgtggtcagtctgtcaaatggggtgagcgtcctgacctttaaggtgctggacctgaaaaactacatcgataaggagctgctgcccaaa
ctgaacaatcacgactgtcagatcagcaatattgccactgtgattgagttccagcagaagaacaatcgcctgctggagatcgcccgg
gagttcagcgtgaacgcaggcattaccacaccactgtccacctacatgctgacaaatagtgagctgctgtcactgattaacgacatg
cccatcaccaatgatcagaagaaactgatgagttcaaacgtgcagatcgtcaggcagcagagctattccattatgtgcgtggtcaag
gaggaagtgatggcctacgtggtccagctgcctatctacggcgtgatcgatacaccatgctggaagctgcatacttcacccctgtgta
ctaccgacaacaaagaggggagcaatatctgcctgacaagaactgacaggggatggtactgtgataacgctggctctgtgagtttctt
tcctcaggcagaaacctgcaaggtgcagtctaaccgcgtcttctgtgatacaatgaatagtctgaccctgccaacagacgtgaacct
gtgcaatacagatatctttaatgccaagtacgactgtaagattatgacttccaagaccgacatcagctcctctgtgatcacttctattggg
gccatcgtcagttgctacggaaagacaaaatgtactgctagcaacaagaatcggggcatcatcaagacattcagtaacgggtgtgat
tatgtgtcaaatagaggcgtggacactgtgagcgtcgggaacaccctgtactgtgtgaataagctggagggaaaagctctgtacatca
agggcgaacctatcattaactactatgatccactggtgttcccctcagacgagtttgatgcaagcattgcccaggtgaacgccaaaat
caatcagtctctggcttttattaggcgcagcgacgagctgctgtccgcaattggcgggtacatccccgaagcccctagggatggaca
ggcttatgtgcgcaaggacggcgagtgggtcctgctgtccaccttcctgggaggcctggtgcccagaggctctcaccatcaccatca
ccattcagcctggagccaccctcagtttgaaaaa RB94 sc9 DS-Cav1 N183GC-N428C:

[SEQ ID NO: 60]

atggattctaagggttccagccagaaaggaccaggctgctgctgctgctggtggtgagcaatctgctgctgcctcagggagtggtggg
acagaacatcaccgaggagttctaccagtcaacctgcagcgccgtgagccggggctacctgagcgcactgagaaccggatggtat
acatccgtggtcactattgagctgtctaagatccagaaaaacgtgtgtaattctacagatagtaacgtcaagctgatcaaacaggagct
ggaaaggtataacaatgctgtggtcgagctgcagtccctgatgcagaacgaacctgccagcagcagcggcagcggcagcgccat -continued cgcttctggggtggcagtctgcaaggtgctgcatctggagggagaagtcaacaagatcaaaaatgcactgctgagtactaacaaag ccgtggtcagtctgtcaggttgtggggtgagcgtcctgacctttaaggtgctggacctgaaaaactacatcgataaggagctgctgccc aaactgaacaatcacgactgtcagatcagcaatattgccactgtgattgagttccagcagaagaacaatcgcctgctggagatcgcc cgggagttcagcgtgaacgcaggcattaccacaccactgtccacctacatgctgacaaatagtgagctgctgtcactgattaacgac atgcccatcaccaatgatcagaagaaactgatgagttcaaacgtgcagatcgtcaggcagcagagctattccattatgtgcgtggtca aggaggaagtgatggcctacgtggtccagctgcctatctacggcgtgatcgatacaccatgctggaagctgcatacttcacccctgtg tactaccgacaacaaagaggggagcaatatctgcctgacaagaactgacaggggatggtactgtgataacgctggctctgtgagttt ctttcctcaggcagaaacctgcaaggtgcagtctaaccgcgtcttctgtgatacaatgaatagtctgaccctgccaacagacgtgaac ctgtgcaatacagatatctttaatgccaagtacgactgtaagattatgacttccaagaccgacatcagctcctctgtgatcacttctattg gggccatcgtcagttgctacggaaagacaaaatgtactgctagcaacaagtgtcggggcatcatcaagacattcagtaacgggtgtg attatgtgtcaaatagaggcgtggacactgtgagcgtcgggaacaccctgtactatgtgaataagctggagggaaaagctctgtacat caagggcgaacctatcattaactactatgatccactggtgttcccctcagacgagtttgatgcaagcattgcccaggtgaacgccaaa atcaatcagtctctggcttttattaggcgcagcgacgagctgctgtccgcaattggcgggtacatccccgaagcccctagggatggac aggcttatgtgcgcaaggacggcgagtgggtcctgctgtccaccttcctgggaggcctggtgcccagaggctctcaccatcaccatc accattcagcctggagccaccctcagtttgaaaaa bRSV 391-2 sc9 DS-Cav1 A149C-Y458C:
[SEQ ID NO: 61]
atggctgctactgctatgcggatgattatctcaattattttatttcaacctacatgactcacattaccctgtgtcagaacattaccgaggaa ttctaccagagcacttgctccgccgtgtctagaggatacctgtctgctctgaggaccggctggtatacaagcgtggtcactattgagctg tccaagatccagaaaaacgtgtgtaagagtaccgattcaaaggtcaaactgatcaaacaggagctggaaaggtataacaatgccgt gattgagctgcagagcctgatgcagaatgaacctgctagcttctccgggtctggaagtgccatctgttccggagtggccgtctgcaag gtgctgcacctggagggcgaagtcaacaagatcaagaatgccctgctgtctacaaacaaagctgtggtctcactgagcaatggcgt gagtgtcctgacttttaaggtgctggacctgaaaaactacatcgataaggagctgctgccaaaactgaacaatcatgactgtcggatc agcaatattgagacagtgattgaattccagcagaagaacaatcgactgctggagatcgcaagagaattttcagtgaacgccggcatt accacaccctgagcacctacatgctgacaaattctgagctgctgagtctgattaacgacatgcctatcaccaatgatcagaagaaa ctgatgagctccaacgtgcagatcgtcagacagcagtcctattctattatgtgcgtggtcaaggaggaagtgatcgcctacgtggtcca gctgcctatctacggcgtgatcgataccccatgctggaagctgcacacaagtcccctgtgtactaccgacaacaaagagggctcaa atatctgcctgacaaggactgaccgcggctggtactgtgataacgcaggagtgtgtcattcttccacaggccgaaacttgcaaggt gcagtccaacagggtcttctgtgataccatgaattctctgaccctgcccacagacgtgaacctgtgcaacactgatatctttaatacca agtacgactgtaagattatgactagcaagaccgacatctctagttcagtgatcacctccattggagctatcgtctcttgctacggcaaga caaaatgtactgcatctaacaagaatcgcgggatcatcaagacattctctaacggatgtgattatgtcagtaataaggggtcgacac agtgagcgtcggaaacactctgtactgtgtgaataagctggagggcaaagccctgtacatcaaaggggaacctatcattaactactat gatccactggtgttccccagtgacgagtttgatgcatcaattgcccaggtgaacgctaagatcaatcagtccctggccttcatccggag atcagacgagctgctgagcgcaattggcgggtacatccccgaagctcctcgcgatggccaggcatatgtgcgaaaagacggggag tgggtcctgctgagcaccttcctgggaggactggtgcctcgaggatcccaccatcaccatcaccatagcgcttggtcccatccacag tttgaaaag bRSV ATue51908 sc9-10 DS-Cav1 N183GC-N428C:
[SEQ ID NO: 62]
atggattccaaggggagctcccagaaaggatctaggctgctgctgctgctggtggtctccaacctgctgctgccacagggagtggtc ggacagaatatcacagaggaattctaccagagcacttgctccgcagtgtctcggggatacctgtctgccctgagaactggctggtata cctctgtggtcacaattgagctgagtaagatccagaagaacgtgtgcaaaagtaccgactcaaaggtcaaactgatcaagcaggag ctggaacggtataacaatgccgtggtcgagctgcagagcctgatgcagaacgaacctgcttctggcagcggatctgccgtggctagt ggagtggccgtctgcaaagtgctgcatctggagggcgaagtcaacaagatcaagaatgcactgctgtctactaacaaggccgtggt -continued

```
ctcactgagcggctgcggcgtgagtgtcctgacctttaaggtgctggacctgaaaaactacatcgataaggagctgctgcctcagctg aacaatcacgattgtaggatctccaatattgagacagtgattgaattccagcagaagaacaatcgcctgctggagatcgctcgagagt tcagcgtgaacgcaggcattaccacaccactgtcaacatacatgctgactaattcagagctgctgagcctgattaacgacatgccca tcaccaatgatcagaagaaactgatgtctagtaacgtgcagatcgtccgccagcagtcctattctattatgtgcgtggtcaaggaggaa gtgatcgcatacgtggtccagctgcctatctacggcgtgatcgatacccatgctggaaactgcatacatctcccctgtgcactaccg acaacaaggaaggaagtaatatttgcctgacaagaactgacaggggctggtactgtgataacgctggcagcgtgagcttcttccctc agaccgaaacatgcaaggtgcagagcaaccgggtcttctgtgataacaatgaattccctgactctgccaaccgacgtgaacctgtgc aacaccgatatctttaatacaaagtacgactgtaagatcatgacaagcaagactgacatctcaagctccgtgatcacaagtattggag ctatcgtgtcatgctacggcaagaccaaatgtacagcatctaacaaatgcagagggatcattaagactttctcaaacggatgtgattat gtgagcaacaaggggtcgacactgtgagcgtcggaaacaccctgtactatgtgaataagctggagggcaaagccctgtacatcaa gggggaacccatcattaactactatgatccactggtgttcccagcgacgagtttgatgcatccattgcccaggtgaacgccaaaatc aatcagtccctggcttttattaggcgctccgacgagctgctgtctgccattggcgggtacatccccgaagcccctagggatggccagg cttatgtgcgcaaggacggggagtgggtcctgctgtcaaccttcctgggaggactggtgccaagaggctcccaccatcaccatcac catagcgcctggtcccaccctcagtttgaaaag
```

Methods for the manipulation and insertion of the nucleic acids of this disclosure into vectors are well known in the art (see for example, Sambrook et al., *Molecular Cloning a Laboratory Manual,* 2d edition, Cold Spring Harbor Press, Cold Spring Harbor, N.Y., 1989, and Ausubel et al., *Current Protocols in Molecular Biology, Greene Publishing Associates and* John Wiley & Sons, New York, N.Y., 1994).

A nucleic acid molecule comprising a polynucleotide encoding the immunogen, the virus-like particle or the protein nanoparticle according to the present invention can be cloned or amplified by in vitro methods, such as the polymerase chain reaction (PCR), the ligase chain reaction (LCR), the transcription-based amplification system (TAS), the self-sustained sequence replication system (3SR) and the QB replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology,* (Stockton Press, N Y, 1989). Polynucleotides also can be isolated by screening genomic or cDNA libraries with probes selected from the sequences of the desired polynucleotide under stringent hybridization conditions.

The nucleic acid molecule comprising a polynucleotide encoding the immunogen, the virus-like particle or the protein nanoparticle according to the present invention may be a recombinant DNA which is incorporated into a vector, into an autonomously replicating plasmid or virus, or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA. DNA sequences encoding the immunogen, the virus-like particle or the protein nanoparticle according to the present invention can be expressed in vitro by DNA transfer into a suitable host cell. The cell may be prokaryotic or eukaryotic. The term also includes any progeny of the subject host cell.

It is understood that all progeny may not be identical to the parental cell since there may be mutations that occur during replication. Methods of stable transfer, meaning that the foreign DNA is continuously maintained in the host, are known in the art.

Preferably, the nucleic acid molecule comprising a polynucleotide encoding the immunogen, the virus-like particle or the protein nanoparticle according to the present invention is codon optimized for expression in a bovine cell. This is particularly useful if the nucleic acid molecule is for use in cattle.

The nucleic acid molecule comprising a polynucleotide encoding the immunogen, the virus-like particle or the protein nanoparticle according to the present invention may be operably linked to expression control sequences.

As used herein, "expression control sequences" refers in particular to nucleic acid sequences that regulate the expression of a heterologous nucleic acid sequence to which it is operably linked. Expression control sequences are operably linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A nucleic acid molecule/polynucleotide can be inserted into an expression vector that contains a promoter sequence, which facilitates the efficient transcription of the inserted genetic sequence of the host. The expression vector typically contains an origin of replication, a promoter, as well as specific nucleic acid sequences that allow phenotypic selection of the transformed cells.

Preferably, the nucleic acid molecule comprising a polynucleotide encoding the immunogen, the virus-like particle or the protein nanoparticle according to the present invention is operably linked to a promoter.

As used herein, a first nucleic acid sequence is "operably linked" with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

An expression control sequence operably linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

In a further aspect the present invention thus also provides a vector comprising the nucleic acid molecule according to the present invention as described above.

As used herein, the term "vector" refers in particular to a nucleic acid molecule that is suitable for incorporating or harboring a desired nucleic acid sequence. In particular, a vector can be introduced into a host cell, thereby producing a transformed host cell.

In general, a transformed cell is a cell into which a nucleic acid molecule has been introduced by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

The vectors may be a storage vector, an expression vector, a cloning vector, a transfer vector etc. A storage vector is a vector which allows the convenient storage of a nucleic acid molecule. Thus, the vector may comprise a sequence corresponding, e.g., to a desired antibody or antibody fragment thereof according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses. A replication deficient viral vector that requires complementation of one or more regions of the viral genome required for replication, as a result of, for example a deficiency in at least one replication-essential gene function. For example, such that the viral vector does not replicate in typical host cells, especially those in a mammalian subject that could be infected by the viral vector in the course of a therapeutic method. Examples of replication-deficient viral vectors and systems for their use are known in the art and include; for example replication-deficient LCMV vectors (see, e.g., U.S. Pat. Pub. No. 2010/0297172, incorporated by reference herein in its entirety) and replication deficient adenoviral vectors (see, e.g., PCT App. Pub. No. WO 2000/00628, incorporated by reference herein).

Preferably, the vector including the nucleic acid molecule comprising a polynucleotide encoding the immunogen (in particular the recombinant RSV F protein or the fragment thereof), the virus-like particle or the protein nanoparticle is a viral vector. Such a viral vector may be used, for example for expression of the immunogen in a host cell, or for immunization of a subject as disclosed herein. In some embodiments, the viral vectors are administered to a subject as part of a prime-boost vaccination. Moreover, the viral vectors may be included in a vaccine, such as a primer vaccine or a booster vaccine for use in a prime-boost vaccination.

The viral vector including the nucleic acid molecule comprising a polynucleotide encoding the immunogen (in particular the recombinant RSV F protein or the fragment thereof), the virus-like particle or the protein nanoparticle may be replication-competent. For example, the viral vector can have a mutation (e.g., insertion of nucleic acid encoding the PreF antigen) in the viral genome that does not inhibit viral replication in host cells. The viral vector also can be conditionally replication-competent. In other examples, the viral vector is replication-deficient in host cells.

Preferably, the vector is a bovine parainfluenza virus vector, a human parainfluenza virus vector, a Newcastle disease virus vector, a Sendai virus vector, a measles virus vector, an attenuated RSV vector, a paramyxovirus vector, an adenovirus vector, an alphavirus vector, a Venezuelan equine encephalitis vector, a Semliki Forest virus vector, a Sindbis virus vector, an adeno-associated virus vector, a poxvirus vector, a rhabdovirus vector, a vesicular stomatitis virus vector, a picornovirus vector, or a herpes virus vector Preferably, the immunogen (in particular the recombinant RSV F protein or the fragment thereof) is expressed by a viral vector that can be delivered via the respiratory tract. For example, a paramyxovirus (PIV) vector, such as bovine parainfluenza virus (BPIV) vector (e.g., a BPIV-1, BPIV-2, or BPV-3 vector) or human PIV vector, a metapneumovirus (MPV) vector, a Sendia virus vector, or a measles virus vector, is used to express the immunogen (in particular the recombinant RSV F protein or the fragment thereof). A BPIV3 viral vector expressing the RSV F and the hPIV F proteins (MEDI-534) is currently in clinical trials as a RSV vaccine.

Examples of paramyxovirus (PIV) vector for expressing antigens are known to the person of skill in the art (see, e.g., U.S. Pat. App. Pubs. 2012/0045471, 2011/0212488, 2010/0297730, 2010/0278813, 2010/0167270, 2010/0119547, 2009/0263883, 2009/0017517, 2009/0004722, 2008/0096263, 2006/0216700, 2005/0147623, 2005/0142148, 2005/0019891, 2004/0208895, 2004/0005545, 2003/0232061, 2003/0095987, and 2003/0072773; each of which is incorporated by reference herein in its entirety).

In another example, a Newcastle disease viral vector is used to express the immunogen (in particular the recombinant RSV F protein or the fragment thereof) (see, e.g., McGinnes et al., J. Virol., 85: 366-377, 2011, describing RSV F and G proteins expressed on Newcastle disease like particles, incorporated by reference in its entirety).

In another example, a Sendai virus vector is used to express a disclosed antigen (see, e.g., Jones et al, Vaccine, 30:959-968, 2012, incorporated by reference herein in its entirety, which discloses use of a Sendai virus-based RSV vaccine to induce an immune response in primates).

Additional viral vectors are also available for expression of the disclosed antigens, including polyoma, i.e., SV40 (Madzak et al., 1992, J. Gen. Viral., 73:15331536), adenovirus (Berkner, 1992, Cur. Top. Microbial. Immunol., 158: 39-6; Berliner et al., 1988, Bio Techniques, 6:616-629; Gorziglia et al., 1992, J. Viral., 66:4407-4412; Quantin et al., 1992, Proc. Nat. Acad. Sci. USA, 89:2581-2584; Rosenfeld et al., 1992, Cell, 68:143-155; Wilkinson et al, 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbial. Immunol., 158:91-123; On et al., 1990, Gene, 89:279-282), herpes viruses including HSV and EBV and CMV (Margolskee, 1992, Cur. Top. Microbial. Immunol., 158:67-90; Johnson et al., 1992, J. Viral., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alpha viruses (S. Schlesinger, 1993, Trends Biotechnol. 11: 18-22; I. Frolov et al., 1996, Proc. Natl. Acad. Sci. USA 93: 11371-11377) and retroviruses of avian (Brandyopadhyay et al., 1984, Mol. Cell Biol., 4:749-754; Petropouplos et al., 1992, J. Viral., 66:3391-3397), murine (Miller, 1992, Curr. Top. Microbial. Immunol., 158:1-24; Miller et al., 1985, Mol. Cell Biol., 5:431-437; Sorge et al., 1984, Mol. Cell Biol., 4: 1730-1737; Mann et al., 1985, J. Viral., 54:401-407), and human origin (Page et al., 1990, J. Viral., 64:5370-5276; Buchschalcher et al., 1992, J. Viral., 66:2731-2739). Baculovirus (Autographa californica multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.). Additional viral vectors are familiar to the person of ordinary skill in the art.

Preferably, the vector is an adenoviral vector. Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) can be used to generate the adenoviral vector. For example, a simian adenovirus can be used as the source of the viral genome of the adenoviral vector. A simian adenovirus can be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. In some examples, a simian adenoviral vector is a simian adenoviral vector of serotype 3, 7, 11, 16, 18, 19, 20, 27, 33, 38, or 39. In one example, a chimpanzee serotype C Ad3 vector is used (see, e.g., Peruzzi et al., Vaccine, 27:1293-1300, 2009). Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. The person of ordinary skill in the art is familiar with replication competent and deficient adenoviral vectors (including singly and multiply replication deficient adenoviral vectors). Examples of replication-deficient adenoviral vectors, including multiply replication-deficient adenoviral vectors, are disclosed in U.S. Pat. Nos. 5,837,511; 5,851,806; 5,994,106; 6,127,175; 6,482,616; and 7,195,896, and International Patent Application Nos. WO 94/28152, WO 95/02697, WO 95/16772, WO 95/34671, WO 96/22378, WO 97112986, WO 97/21826, and WO 03/022311.

Preferably, the nucleic acid molecule or the vector according to the present invention as described herein comprise a nucleotide sequence as set forth in any of SEQ ID NOs: 56-62.

In a further aspect, the present invention also provides an isolated host cell comprising the nucleic acid molecule or the vector according to the present invention as described herein.

As used herein, the term "host cell" refers in particular to cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli*, *Bacillus subtilis*, *Saccharomyces cerevisiae*, *Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and W138, BHK, and COS cell lines, although cell lines may be used, such as cells designed to provide higher expression, desirable glycosylation patterns, or other features. Preferably, the host cell is a HEK293 cell or a derivative thereof, such as Gnn-1-cells (ATCC® No. CRL-3022).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Immunogenic Composition

In a further aspect the present invention also provides a pharmaceutical composition comprising
 (i) the immunogen according to the present invention as described herein;
 (ii) the virus-like particle according to the present invention as described herein;
 (iii) the protein nanoparticle according to the present invention as described herein;
 (iv) the nucleic acid molecule according to the present invention as described herein;
 (v) the vector according to the present invention as described herein; or
 (vi) the host cell according to the present invention as described herein;
and a pharmaceutically acceptable carrier.

Preferred embodiments of the pharmaceutical composition correspond to preferred embodiment of the immunogen according to the present invention as described herein, the virus-like particle according to the present invention as described herein, the protein nanoparticle according to the present invention as described herein, the nucleic acid molecule according to the present invention as described herein, the vector according to the present invention as described herein, and the host cell according to the present invention as described herein, respectively.

Preferably, the pharmaceutical composition (i.e., the immunogenic composition) comprises the virus-like particle according to the present invention as described herein or the protein nanoparticle according to the present invention as described herein. More preferably, the pharmaceutical composition (i.e., the immunogenic composition) comprises the host cell according to the present invention as described herein. Even more preferably, the pharmaceutical composition (i.e., the immunogenic composition) comprises the nucleic acid molecule according to the present invention as described herein or the vector according to the present invention as described herein. Most preferably, the pharmaceutical composition (i.e., the immunogenic composition) comprises the immunogen according to the present invention as described herein.

The immunogen according to the present invention as described herein, the virus-like particle according to the present invention as described herein, the protein nanoparticle according to the present invention as described herein, the nucleic acid molecule according to the present invention as described herein, the vector according to the present invention as described herein, and the host cell according to the present invention as described herein can be included in a pharmaceutical composition, including therapeutic and prophylactic formulations. It is understood that the immunogen according to the present invention as described herein, the virus-like particle according to the present invention as described herein, the protein nanoparticle according to the present invention as described herein, the nucleic acid molecule according to the present invention as described herein, the vector according to the present invention as described herein, and the host cell according to the present invention as described herein, respectively, constitutes in particular the active component of the pharmaceutical composition.

Preferably, the pharmaceutical composition is an immunogenic composition. In general, an immunogenic composition is a composition comprising an immunogen, i.e. an antigen that induces an immune response, such as a measurable CTL response against virus expressing the antigen, or a measurable B cell response (such as production of antibodies) against the antigen. As such, an immunogenic composition includes one or more immunogens (for example, polypeptide antigens) or antigenic epitopes. An immunogenic composition can also include one or more additional components capable of eliciting or enhancing an immune response, such as an excipient, carrier, and/or adjuvant. In certain instances, immunogenic compositions are administered to elicit an immune response that protects the subject against symptoms or conditions induced by a pathogen. In some cases, symptoms or disease caused by a pathogen is prevented (or reduced or ameliorated) by inhibiting replication of the pathogen (e.g., RSV) following exposure of the subject to the pathogen. In particular, an "immunogenic composition" includes the immunogen according to the present invention (in particular the recombinant RSV F protein or the fragment thereof), that induces a measurable CTL response against virus expressing RSV F protein, or induces a measurable B cell response (such as production of antibodies) against RSV F protein. It further refers to isolated nucleic acids encoding an immunogen, such as a nucleic acid that can be used to express the immunogen (and thus be used to elicit an immune response against this polypeptide). For in vitro use, an immunogenic composition may for example include the immunogen or the nucleic acid encoding the immunogen. For in vivo use, the immunogenic composition may for example include the immunogen according to the present invention as described herein, the virus-like particle according to the present invention as described herein, the protein nanoparticle according to the present invention as described herein, the nucleic acid molecule according to the present invention as described herein, the vector according to the present invention as described herein, and the host cell according to the present invention as described herein provided in pharmaceutically acceptable carriers, and/or other agents. Any particular peptide, such as the immunogen according to the present invention (in particular the recombinant RSV F protein or the fragment thereof) or a nucleic acid encoding the immunogen according to the present invention (in particular the recombinant RSV F protein or the fragment thereof), can be readily tested for its ability to induce a CTL or B cell response by art-recognized assays. Immunogenic compositions can include adjuvants, which are well known to one of skill in the art.

The pharmaceutical composition further comprises a pharmaceutically acceptable carrier. The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed immunogens. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired anti-RSV immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Preferably, the immunogen according to the present invention as described herein, the virus-like particle according to the present invention as described herein, the protein nanoparticle according to the present invention as described herein, the nucleic acid molecule according to the present invention as described herein, the vector according to the present invention as described herein, or the host cell according to the present invention as described herein can be combined in the pharmaceutical composition together with one or more adjuvants and, optionally, other therapeutic ingredients, such as antiviral drugs.

The composition may include a first immunogen according to the present invention (in particular the recombinant RSV F protein or the fragment thereof) and a second immunogen according to the present invention (in particular the recombinant RSV F protein or the fragment thereof), wherein the first and the second immunogen according to the present invention (in particular the recombinant RSV F protein or the fragment thereof) are distinct. The composition may include a first virus-like particle according to the present invention as described herein and a second virus-like particle according to the present invention as described herein, wherein the first and the second virus-like particle according to the present invention as described herein are distinct. The composition may include a first protein nanoparticle according to the present invention as described herein and a second protein nanoparticle according to the present invention as described herein, wherein the first and the second protein nanoparticle according to the present invention as described herein are distinct. The composition may include a first nucleic acid molecule according to the present invention as described herein and a second nucleic acid molecule according to the present invention as described herein, wherein the first and the second nucleic acid molecule according to the present invention as described herein are distinct. The composition may include a first vector according to the present invention as described herein and a second vector according to the present invention as described herein, wherein the first and the second vector according to the present invention as described herein are distinct. The composition may include a first host cell according to the present invention as described herein and a second host cell according to the present invention as described herein, wherein the first and the second host cell according to the present invention as described herein are distinct.

The pharmaceutical composition can be administered to subjects by a variety of administration modes known to the person of ordinary skill in the art, for example, nasal, pulmonary, intramuscular, subcutaneous, intravenous, intraperitoneal, or parenteral routes. Preferably, the pharmaceutical composition is administered intramuscularly.

To formulate the compositions, various pharmaceutically acceptable additives, as well as a base or vehicle for dispersion of the conjugate can be used. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, TWEEN® 80), solubility enhancing agents (for example, cyclodextrins and derivatives thereof), stabilizers (for example, serum albumin), and reducing agents (for example, glutathione) can be included. Adjuvants, such as Montanide™ ISA71 VG (Seppic), aluminum hydroxide (ALHYDROGEL®, available from Brenntag Biosector, Copenhagen, Denmark and AMPHOGEL®, Wyeth Laboratories, Madison, N.J.), Freund's adjuvant, MPL™ (3-0-deacylated monophosphoryl lipid A; Corixa, Hamilton, Ind.), IL-12 (Genetics Institute, Cambridge, Mass.) TLR agonists (such as TLR-9 agonists), among many other suitable adjuvants well known in the art, can be included in the compositions.

The pharmaceutical composition may be in liquid or in solid form. When the composition is a liquid, the tonicity of the formulation, as measured with reference to the tonicity of 0.9% (w/v) physiological saline solution taken as unity, may be adjusted to a value at which no substantial, irreversible tissue damage will be induced at the site of administration. Generally, the tonicity of the solution may be adjusted to a value of about 0.3 to about 3.0, such as about 0.5 to about 2.0, or about 0.8 to about 1.7.

The immunogen according to the present invention as described herein, the virus-like particle according to the present invention as described herein, the protein nanoparticle according to the present invention as described herein, the nucleic acid molecule according to the present invention as described herein, the vector according to the present invention as described herein, and the host cell according to the present invention as described herein, respectively, can be dispersed in a base or vehicle, which can include a hydrophilic compound having a capacity to disperse the antigens, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth) acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films, for examples for direct application to a mucosal surface.

The immunogen according to the present invention as described herein, the virus-like particle according to the present invention as described herein, the protein nanoparticle according to the present invention as described herein, the nucleic acid molecule according to the present invention as described herein, the vector according to the present invention as described herein, and the host cell according to the present invention as described herein, respectively, can be combined with the base or vehicle according to a variety of methods, and release of the antigens can be by diffusion, disintegration of the vehicle, or associated formation of water channels. In some circumstances, the immunogen according to the present invention as described herein, the virus-like particle according to the present invention as described herein, the protein nanoparticle according to the present invention as described herein, the nucleic acid molecule according to the present invention as described herein, the vector according to the present invention as described herein, and the host cell according to the present invention as described herein, respectively, is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The pharmaceutical compositions can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the disclosed immunogens can be brought about by including in the composition an agent which delays absorption, for example, monostearate salts and gelatin.

The immunogen according to the present invention as described herein, the virus-like particle according to the present invention as described herein, the protein nanoparticle according to the present invention as described herein, the nucleic acid molecule according to the present invention as described herein, the vector according to the present invention as described herein, and the host cell according to the present invention as described herein, respectively, may be administered in a time-release formulation, for example in a composition that includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include for example any biocompatible controlled release material which is inert to the active agent and which is capable of incorporating the disclosed antigen and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body. Numerous systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

Exemplary polymeric materials for use include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.aprolactone-CO-glycolic acid), poly(beta-hydroxy butyric acid), poly(alkyl-2- cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

Pharmaceutical compositions may in particular be sterile and stable under conditions of manufacture, storage and use. Sterile solutions can be prepared by incorporating the immunogen according to the present invention as described herein, the virus-like particle according to the present invention as described herein, the protein nanoparticle according to the present invention as described herein, the nucleic acid molecule according to the present invention as described herein, the vector according to the present invention as described herein, and the host cell according to the present invention as described herein, respectively, in the required amount in an appropriate solvent with one or a combination of ingredients enumerated herein, as required, followed by filtered sterilization. Generally, dispersions may be prepared by incorporating the disclosed antigen and/or other biologically active agent into a sterile vehicle that contains a basic dispersion medium and the required other ingredients from those enumerated herein. In the case of sterile powders, methods of preparation include vacuum drying and freeze-drying which yields a powder of the disclosed antigen plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

Actual methods for preparing administrable compositions will be known or apparent to those skilled in the art and are described in more detail in such publications as *Remingtons Pharmaceutical Sciences*, 19th Ed., Mack Publishing Company, Easton, Pa., 1995.

In several embodiments, the composition includes an adjuvant. As used herein, the term "adjuvant" refers in particular to a vehicle used to enhance antigenicity. Adjuvants include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants.

Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-IBBL and toll-like receptor (TLR) agonists, such as TLR-9 agonists. The person of ordinary skill in the art is familiar with adjuvants (see, e.g., Singh (ed.) Vaccine Adjuvants and Delivery Systems. Wiley-Interscience, 2007), for example, those that can be included in a pharmaceutical composition. Preferably, the adjuvant is selected to elicit a Th1 immune response in a subject administered the pharmaceutical composition In other words, the adjuvant comprised by the pharmaceutical composition preferably promotes a Th1 immune response. Preferably, the adjuvant is alum, an oil-in water composition, MF59, ASOI, AS03, AS04, MPL, QS21, a CpG oligonucleotide, a TLR7 agonist, a TLR4 agonist, a TLR3 agonist, or a combination of two or more thereof.

A particularly preferred adjuvant is Montanide™ ISA71 VG (Seppic). Montanide™ ISA71 VG is a ready-to-use oily vaccine adjuvant for water-in-oil (W/O) emulsion. It is based on specific enriched light mineral oil and is preferably used in bovine subjects. Montanide™ ISA71 VG increases the Th1 immune response. Montanide™ ISA 71 VG has some advantages over Freund's adjuvant (FA), as it is less viscous and more stable (Aucouturier J, Dupuis L, Ganne V. Adjuvants designed for veterinary and human vaccines. Vaccine 2001; 19:2666-72). Montanide™ ISA71 VG is based on mineral oil with a refined, non-ionic surfactant from an ester of the sugar mannitol and purified oleic acid of vegetable origin. According to the manufacturer's data sheet, Montanide™ ISA 71 VG is based on a specific enriched light mineral oil, designed to raise the TH1 response and to improve significantly the IgG2 production, even if the antigen is of low intrinsic immunogenicity. Montanide™ ISA 71 VG has been demonstrated to stimulate humoral and cellular immune responses. Because Montanide™ ISA 71 VG contains no ingredients of animal or bacterial origin, it is considered safe and possesses the European Council Regulation-allowance for the animal market so far. Preferably, an water in oil emulsion is prepared with Montanide™ ISA71 VG in a ratio of 70:30 adjuvant to aqueous phase.

Another preferred adjuvant is ISA 206 (Seppic). ISA 206 is based on a high-grade injectable mineral oil and provides a water-in-oil-in-water emulsion and is supposed to induce both, a short- and a long-term protective immune response.

A further suitable adjuvant is a non-toxic bacterial lipopolysaccharide derivative. An example of a suitable nontoxic derivative of lipid A, is monophosphoryl lipid A or more particularly 3-Deacylated monophoshoryl lipid A (3DMPL). See, for example, U.S. Pat. Nos. 4,436,727; 4,877,611; 4,866,034 and 4,912,094. 3D-MPL primarily promotes CD4+ T cell responses with an IFN-y (Th1) phenotype. Chemically it is a mixture of 3-deacylated monophosphoryl lipid A with 3, 4, 5 or 6 acylated chains. In the compositions, small particle 3D-MPL can be used. Small particle 3D-MPL has a particle size such that it can be sterile-filtered through a 0.22 μm filter. Such preparations are described in WO94/21292. Alternatively, the lipopolysaccharide can be a B(I-6) glucosamine disaccharide, as described in U.S. Pat. No. 6,005,099 and EP Patent No. 0 729 473 B1. One of skill in the art would be readily able to produce various lipopolysaccharides, such as 3D-MPL, based on the teachings of these references.

In addition to the aforementioned immunostimulants (that are similar in structure to that of LPS or MPL or 3D-MPL), acylated monosaccharide and disaccharide derivatives that are a sub-portion to the above structure of MPL are also suitable adjuvants.

In several embodiments, a Toll-like receptor (TLR) agonist is used as an adjuvant. For example, the pharmaceutical composition comprises a TLR agonist. For example, the TLR agonist can be a TLR-4 agonist such as a synthetic derivative of lipid A (see, e.g., WO 95/14026, and WO 01/46127) an alkyl Glucosaminide phosphate (AGP; see, e.g., WO 98/50399 or U.S. Pat. Nos. 6,303,347; 6,764,840). Other suitable TLR-4 ligands, capable of causing a signaling response through TLR-4 are, for example, lipopolysaccharide from gram-negative bacteria and its derivatives, or fragments thereof, in particular a non-toxic derivative of LPS (such as 3D-MPL). Other suitable TLR agonists are: heat shock protein (HSP) 10, 60, 65, 70, 75 or 90; surfactant Protein A, hyaluronan oligosaccharides, heparin sulphate fragments, fibronectin fragments, fibrinogen peptides and B-defensin-2, and muramyl dipeptide (MDP). For example, the TLR agonist is HSP 60, 70 or 90. Other suitable TLR-4 ligands are as described in WO 2003/011223 and in WO 2003/099195.

Additional TLR agonists (such as an agent that is capable of causing a signaling response through a TLR signaling pathway) are also useful as adjuvants, such as agonists for TLR2, TLR3, TLR7, TLR8 and/or TLR9. Accordingly, the composition may further include an adjuvant which is selected from the group consisting of: a TLR-1 agonist, a TLR-2 agonist, TLR-3 agonist, a TLR-4 agonist, TLR-5 agonist, a TLR-6 agonist, TLR-7 agonist, a TLR-8 agonist, TLR-9 agonist, or a combination thereof. For example, a TLR agonist is used that is capable of causing a signaling response through TLR-1, for example one or more of from: Tri-acylated lipopeptides (LPs); phenol-soluble modulin; *Mycobacterium tuberculosis* LP; S-(2,3-bis(palmitoyloxy)-(2-RS)-propyl)-N-palmitoyl-(R)-Cys-(S)-Ser-(S)-L-ys(4)-OH, trihydrochloride (Pam3Cys) LP which mimics the acetylated amino terminus of a bacterial lipoprotein and OspA LP from *Borrelia burgdorferi*. For example, a TLR agonist is used that is capable of causing a signaling response through TLR-2, such as one or more of a lipoprotein, a peptidoglycan, a bacterial lipopeptide from *M tuberculosis, B burgdorferi* or *T pallidum*; peptidoglycans from species including *Staphylococcus aureus*; lipoteichoic acids, mannuronic acids, Neisseria porins, bacterial fimbriae, Yersina virulence factors, CMV virions, measles haemagglutinin, and zymosan from yeast. Furthermore, a TLR agonist may be used that is capable of causing a signaling response through TLR-3, such as one or more of double stranded RNA (dsRNA), or polyinosinicpolycytidylic acid (Poly IC), a molecular nucleic acid pattern associated with viral infection. Moreover, a TLR agonist may be used that is capable of causing a signaling response through TLR-5, such as bacterial flagellin. Also, a TLR agonist may be used that is capable of causing a signaling response through TLR-6, such as one or more of mycobacterial lipoprotein, di-acylated LP, and phenol-soluble modulin. Additional TLR6 agonists are described in WO 2003/043572. For example, a TLR agonist is used that is capable of causing a signaling response through TLR-7, such as one or more of a single stranded RNA (ssRNA), loxoribine, a guanosine analogue at positions N7 and CS, or an imidazoquinoline compound, or derivative thereof. In one embodiment, the TLR agonist is imiquimod. Further TLR7 agonists are described in WO 2002/085905.

Moreover, a TLR agonist may be used that is capable of causing a signaling response through TLR-8. Suitably, the TLR agonist capable of causing a signaling response through TLR-8 is a single stranded RNA (ssRNA), an imidazoquinoline molecule with anti-viral activity, for example resiquimod (R848); resiquimod is also capable of recognition by TLR-7. Other TLR-8 agonists which can be used include those described in WO 2004/071459. Furthermore, an adjuvant may include a TLR agonist capable of inducing a signaling response through TLR-9. For example, the adjuvant can include HSP90, bacterial or viral DNA, and/or DNA containing unmethylated CpG nucleotides (e.g., a CpG oligonucleotide). For example, CpG-containing oligonucleotides induces a predominantly Th1 response. Such oligonucleotides are well known and are described, for example, in WO 95/26204, WO 96/02555, WO 99/33488 and U.S. Pat. Nos. 5,278,302, 5,666,153, and. 6,008,200 and 5,856,462. Accordingly, oligonucleotides for use as adjuvants in the disclosed compositions include CpG containing oligonucleotides, for example, containing two or more dinucleotide CpG motifs. Also included are oligonucleotides with mixed internucleotide linkages.

Other adjuvants that can be used in the pharmaceutical compositions are saponins, such as QS21. In some examples, saponins are used as an adjuvant, e.g., for systemic administration of a PreF antigen. Use of saponins (e.g., use of Quil A, derived from the bark of the South American tree *Quillaja Saponaria Molina*) as adjuvants is familiar to the person of ordinary skill in the art (see, e.g., U.S. Pat. No. 5,057,540 and EP0 362 279 B1. EP0 109 942 B1; WO 96/11711; WO 96/33739). The haemolytic saponins QS21 and QS 17 (HPLC purified fractions of Quil A) have been described as potent systemic adjuvants, and the method of their production is disclosed in U.S. Pat. No. 5,057,540 and EP 0 362279B1.

The adjuvant can also include mineral salts such as an aluminum or calcium salts, in particular aluminum hydroxide, aluminum phosphate and calcium phosphate.

Another class of suitable Th1 biasing adjuvants for use in compositions includes outer membrane proteins (OMP)-based immunostimulatory compositions. OMP-based immunostimulatory compositions are particularly suitable as mucosal adjuvants, e.g., for intranasal administration. OMP-based immunostimulatory compositions are a genus of preparations of (OMPs), including some porins) from Gram-negative bacteria, e.g., *Neisseria* species, which are useful as a carrier or in compositions for immunogens, such as bacterial or viral antigens (see, e.g., U.S. Pat. Nos. 5,726,292; 4,707,543). Further, proteosomes have the capability to auto-assemble into vesicle or vesicle-like OMP clusters of about 20 nm to about 800 nm, and to noncovalently incorporate, coordinate, associate (e.g., electrostatically or hydrophobically), or otherwise cooperate with protein antigens (Ags), particularly antigens that have a hydrophobic moiety. Proteosomes can be prepared, for example, as described in the art (see, e.g., U.S. Pat. No. 5,726,292 or 5,985,284; 2003/0044425.). Proteosomes are composed primarily of chemically extracted outer membrane proteins (OMPs) from *Neisseria meningitidis* (mostly porins A and B as well as class 4 OMP), maintained in solution by detergent (Lowell G H. Proteosomes for Improved Nasal, Oral, or Injectable Vaccines. In: Levine M M, Woodrow G C, Kaper J B, Cobon G S, eds, New Generation Vaccines. New York: Marcel Dekker, Inc. 1997; 193-206). Proteosomes can be formulated with a variety of antigens such as purified or recombinant proteins derived from viral sources, including the immunogens according to the present invention. The gradual removal of detergent allows the formation of particulate hydrophobic complexes of approximately 100-200 nm in diameter (Lowell G H. Proteosomes for Improved Nasal, Oral, or Injectable Vaccines. In: Levine M M, Woodrow G C, Kaper J B, Cobon G S, eds, New Generation Vaccines. New York: Marcel Dekker, Inc. 1997; 193-206).

Combinations of different adjuvants can also be used in the pharmaceutical compositions described herein. For example, as already noted, QS21 can be formulated together with 3D-MPL. The ratio of QS21:3D-MPL will typically be in the order of 1:10 to 10:1; such as 1:5 to 5:1, and often substantially 1:1. Typically, the ratio is in the range of 2.5:1 to 1:1 3D-MPL:QS21 (such as AS01 (GlaxoSmithKline). Another combination adjuvant formulation includes 3D-MPL and an aluminum salt, such as aluminum hydroxide (such as ASO4 (GlaxoSmithKline). When formulated in combination, this combination can enhance an antigen-specific Th1 immune response. The adjuvant formulation may comprise a mineral salt, such as a calcium or aluminum (alum) salt, for example calcium phosphate, aluminum phosphate or aluminum hydroxide. Moreover, the adjuvant may include an oil and water emulsion, e.g., an oil-in-water emulsion (such as MF59 (Novartis) or AS03 (GlaxoSmithKline). One example of an oil-in-water emulsion comprises a metabolisable oil, such as squalene, a tocol such as a tocopherol, e.g., alpha-tocopherol, and a surfactant, such as sorbitan trioleate (Span 85) or polyoxyethylene sorbitan monooleate (Tween 80), in an aqueous carrier.

The pharmaceutical composition typically contains a therapeutically effective amount of the immunogen according to the present invention as described herein, the virus-like particle according to the present invention as described herein, the protein nanoparticle according to the present invention as described herein, the nucleic acid molecule according to the present invention as described herein, the vector according to the present invention as described herein, or the host cell according to the present invention as described herein, respectively.

As used herein, a "therapeutically effective amount" refers to the amount of an agent, such as the immunogen according to the present invention as described herein, the virus-like particle according to the present invention as described herein, the protein nanoparticle according to the present invention as described herein, the nucleic acid molecule according to the present invention as described herein, the vector according to the present invention as described herein, or the host cell according to the present invention as described herein, respectively, that is sufficient to prevent, treat (including prophylaxis), reduce and/or ameliorate the symptoms and/or underlying causes of any of a disorder or disease, for example to prevent, inhibit, and/or treat RSV infection. A therapeutically effective amount may be sufficient to reduce or eliminate a symptom of a disease, such as RSV infection. For instance, this can be the amount necessary to inhibit viral replication or to measurably alter outward symptoms of the viral infection. In general, this amount will be sufficient to measurably inhibit virus (for example, RSV) replication or infectivity. When administered to a subject, a dosage will generally be used that will achieve target tissue concentrations that has been shown to achieve in vitro inhibition of viral replication. It is understood that to obtain a protective immune response against a pathogen can require multiple administrations of the immunogenic composition. Thus, a therapeutically effective amount encompasses a fractional dose that contributes in combination with previous or subsequent administrations to attaining a protective immune response.

Preparation of the pharmaceutical compositions is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757. Typically, the amount of antigen in each dose of the pharmaceutical composition is selected as an amount which induces an immune response without significant, adverse side effects.

The amount of the immunogen according to the present invention as described herein, the virus-like particle according to the present invention as described herein, the protein nanoparticle according to the present invention as described herein, the nucleic acid molecule according to the present invention as described herein, the vector according to the present invention as described herein, or the host cell according to the present invention as described herein, respectively, can thus vary depending upon the specific immunogen employed, the route and protocol of administration, and the target population, for example.

Preferably, each bovine dose will comprise 1 ng-10 g of protein (such as the immunogen, in particular the recombinant RSV F protein or the fragment thereof), preferably from about 0.1 µg to about 5 g; more preferably from about 1 µg to about 1000 µg; even more preferably from about 10 µg to about 100 µg; still more preferably from about 25 µg to about 75 µg; and most preferably each bovine dose comprises about 50 µg of protein (such as the immunogen, in particular the recombinant RSV F protein or the fragment thereof).

The amount utilized in a pharmaceutical composition is selected based on the subject population (e.g., calf or adult cattle). An optimal amount for a particular composition can be ascertained by standard studies involving observation of antibody titers and other responses in subjects. It is understood that a therapeutically effective amount of an antigen in a pharmaceutical composition can include an amount that is ineffective at eliciting an immune response by administration of a single dose, but that is effective upon administration of multiple dosages, for example in a prime-boost administration protocol.

As used herein, a "prime-boost protocol" (or "prime-boost vaccination") refers to an immunotherapy including administration of a first immunogenic composition (the primer vaccine) followed by administration of a second immunogenic composition (the booster vaccine) to a subject to induce an immune response. The primer vaccine and/or the booster vaccine may optionally include a vector (such as a viral vector, RNA, or DNA vector) expressing the antigen to which the immune response is directed. The booster vaccine is typically administered to the subject after the primer vaccine; the skilled artisan will understand a suitable time interval between administration of the primer vaccine and the booster vaccine, and examples of such timeframes are disclosed herein. Preferably, the primer vaccine, the booster vaccine, or both primer vaccine and the booster vaccine additionally include an adjuvant. In one non-limiting example, the primer vaccine is a DNA-based vaccine (or other vaccine based on gene delivery), and the booster vaccine is a protein or protein nanoparticle based vaccine.

Accordingly, administration of the immunogen according to the present invention as described herein, the virus-like particle according to the present invention as described herein, the protein nanoparticle according to the present invention as described herein, the nucleic acid molecule according to the present invention as described herein, the vector according to the present invention as described herein, the host cell according to the present invention as described herein, or the pharmaceutical composition according to the present invention as described herein, respectively, in a prime-boost protocol (prime-boost vaccination) is preferred.

In several examples, pharmaceutical compositions for eliciting an immune response against RSV in cattle include a therapeutically effective amount of the immunogen according to the present invention as described herein, the virus-like particle according to the present invention as described herein, the protein nanoparticle according to the present invention as described herein, the nucleic acid molecule according to the present invention as described herein, the vector according to the present invention as described herein, or the host cell according to the present invention as described herein, for administration to calves (e.g., calves between birth and 1 year, such as between 0 and 6 months, at the age of initial dose) or adult cattle. It will be appreciated that the choice of adjuvant can be different in these different applications, and the optimal adjuvant and concentration for each situation can be determined empirically by those of skill in the art.

Preferably, the pharmaceutical compositions are vaccines that reduce or prevent infection with RSV, in particular with bRSV. It is also preferred that the pharmaceutical compositions are vaccines that reduce or prevent a pathological response following infection with RSV. Optionally, the pharmaceutical compositions are formulated with at least one additional antigen of a pathogenic organism other than RSV. For example, the pathogenic organism can be a pathogen of the respiratory tract (such as a virus or bacterium that causes a respiratory infection). The pharmaceutical composition may contain an antigen derived from a pathogenic virus other than RSV, such as a virus that causes an infection of the respiratory tract, such as influenza or parainfluenza. Alternatively or additionally, the additional antigens is selected to facilitate administration or reduce the number of inoculations required to protect a subject against a plurality of infectious organisms. For example, the antigen can be derived from any one or more of influenza, hepatitis B, diphtheria, tetanus, pertussis, *Hemophilus* influenza, poliovirus, *Streptococcus* or *Pneumococcus*, among others. Preferably, the pharmaceutical composition comprises a RSV F prefusion-specific antibody that specifically binds the immunogen according to the present invention as described herein. Exemplary antibodies are the RSV F prefusion-specific antibodies as described herein.

Methods and Uses

In a further aspect the present invention provides the immunogen according to the present invention as described herein, the virus-like particle according to the present invention as described herein, the protein nanoparticle according to the present invention as described herein, the nucleic acid molecule according to the present invention as described herein, the vector according to the present invention as described herein, the host cell according to the present invention as described herein, or the pharmaceutical composition according to the present invention as described herein for use in generating an immune response to RSV F in a subject, in particular in cattle. Preferably, the immune response comprises a Th1 immune response as described herein.

Accordingly, the present invention also provides a method for generating an immune response to RSV F in a subject, comprising administering to the subject an effective amount of the immunogen according to the present invention as described herein; the virus-like particle according to the present invention as described herein; the protein nanoparticle according to the present invention as described herein; the nucleic acid molecule according to the present invention as described herein; the vector according to the present invention as described herein; or the pharmaceutical composition according to the present invention as described herein; to generate the immune response. Preferably, the immune response comprises a Th1 immune response as described herein.

Thus, a therapeutically effective amount of an immunogenic composition including one or more of the immunogen according to the present invention as described herein, the virus-like particle according to the present invention as described herein, the protein nanoparticle according to the present invention as described herein, the nucleic acid molecule according to the present invention as described herein, the vector according to the present invention as described herein, and the host cell according to the present invention as described herein, can be administered to a subject in order to generate an immune response to RSV, in particular to bRSV.

The present invention also provides the immunogen according to the present invention as described herein, the virus-like particle according to the present invention as described herein, the protein nanoparticle according to the present invention as described herein, the nucleic acid molecule according to the present invention as described herein, the vector according to the present invention as described herein, the host cell according to the present invention as described herein, or the pharmaceutical composition according to the present invention as described herein for use in prevention and/or treatment of RSV infection in a subject, in particular in cattle. Preferably, the RSV infection to be prevented and/or treated is bRSV infection.

Accordingly, the present invention provides a method for treating or preventing a RSV infection in a subject, comprising administering to the subject a therapeutically effective amount of the immunogen according to the present invention as described herein, the virus-like particle according to the present invention as described herein, the protein nanoparticle according to the present invention as described herein, the nucleic acid molecule according to the present invention as described herein, the vector according to the present invention as described herein, the host cell according to the present invention as described herein, or the pharmaceutical composition according to the present invention as described herein; thereby treating or preventing RSV infection in the subject.

Preferably, a subject is selected for treatment that has, or is at risk for developing, an RSV infection, for example, because of exposure or the possibility of exposure to RSV. Following administration of a therapeutically effective amount of the disclosed pharmaceutical compositions, the subject can be monitored for RSV infection, symptoms associated with RSV infection, or both. Accordingly, in the use and method described herein, the subject is preferably at risk of or has an RSV infection.

Preferably, in the use and method described herein, the subject is a bovine subject, such as cattle (cow). In the context of the subject, the term "bovine" refers to the subfamily Bovinae, which includes domestic cattle, bison, African buffalo, the water buffalo, the yak, and the four-horned and spiral-horned antelopes. Accordingly, the subject is preferably of the subfamily Bovinae, more preferably cattle, in particular domestic cattle.

Preferably the subject is a calf, i.e. an animal of the subfamily Bovinae, which is no more than one year old. More preferably, the subject is a calf of (domestic) cattle.

In more general, typical subjects include humans, as well as non-human primates and other animals, such as cattle. To identify subjects for prophylaxis or treatment as described herein, screening methods may be employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize RSV infection. These and other routine methods allow the veterinarian or the clinician to select subjects in need of therapy or prevention as disclosed herein.

An pharmaceutical composition can be administered as an independent prophylaxis or treatment program, or as a follow-up, adjunct or coordinate treatment regimen to other treatments. The pharmaceutical composition can be used in coordinate vaccination protocols or combinatorial formulations. For example, combinatorial pharmaceutical compositions and coordinate immunization protocols may employ separate immunogens or formulations, each directed toward eliciting an immune response to an RSV immunogen, such as an immune response to RSV F protein. Separate pharmaceutical compositions that elicit the immune response to the RSV immunogen can be combined in a polyvalent pharmaceutical composition administered to a subject in a single immunization step, or they can be administered separately (in monovalent pharmaceutical compositions) in a coordinate immunization protocol.

The administration of the pharmaceutical compositions can be for prophylactic and/or therapeutic purpose. When provided prophylactically, the pharmaceutical composition is typically provided in advance of any symptom, for example in advance of infection. The prophylactic administration of the pharmaceutical compositions usually serves to prevent or ameliorate any (subsequent) infection. When provided therapeutically, the pharmaceutical composition is provided at or after the onset of a symptom of disease or infection, for example after development of a symptom of RSV infection, or after diagnosis of RSV infection. The pharmaceutical composition can thus be provided prior to the anticipated exposure to RSV so as to attenuate the anticipated severity, duration or extent of an infection and/or associated disease symptoms, after exposure or suspected exposure to the virus, or after the actual initiation of an infection.

Administration typically induces a sufficient immune response to treat or prevent the pathogenic infection, for example, to inhibit the infection and/or reduce the signs and/or symptoms of the infection. Amounts effective for this use will depend upon the severity of the disease, the general state of the subject's health, and the robustness of the subject's immune system. As described in detail above, a therapeutically effective amount is that which provides for example subjective relief of a symptom(s) or an objectively identifiable improvement as noted by the clinician or other qualified observer. For example, effective amounts are amounts that are effective to elicit a desired immune response or alleviate one or more symptoms of a targeted disease. Furthermore, an effective amount or effective dose of the may simply inhibit or enhance one or more selected biological activities correlated with a disease or condition, as set forth herein, for either therapeutic or diagnostic purposes.

For prophylactic and therapeutic purposes, the immunogen according to the present invention as described herein, the virus-like particle according to the present invention as described herein, the protein nanoparticle according to the present invention as described herein, the nucleic acid molecule according to the present invention as described herein, the vector according to the present invention as described herein, the host cell according to the present invention as described herein, or the pharmaceutical composition according to the present invention as described herein can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). Preferably, the immunogen according to the present invention as described herein, the virus-like particle according to the present invention as described herein, the protein nanoparticle according to the present invention as described herein, the nucleic acid molecule according to the present invention as described herein, the vector according to the present invention as described herein, the host cell according to the present invention as described herein, or the pharmaceutical composition according to the present invention as described herein is administered repeatly, i.e. at least twice. One example of repeated administration is prime-boost administration as described herein.

The therapeutically effective dosage of the pharmaceutical composition can thus be provided as repeated doses within a prolonged prophylaxis or treatment regimen that will yield clinically significant results to alleviate one or more symptoms or detectable conditions associated with a targeted disease or condition, such as RSV infection, in particular bRSV infection. Determination of effective dosages in this context is typically guided by administration protocols that significantly reduce the occurrence or severity of targeted disease symptoms or conditions in the subject.

A suitable immunization regimen may for example include at least three separate inoculations with one or more pharmaceutical compositions, with a second inoculation being administered more than about two, about three to eight, or about four, weeks following the first inoculation. Generally, the third inoculation can be administered several months after the second inoculation, and in specific embodiments, more than about five months after the first inoculation, more than about six months to about two years after the first inoculation, or about eight months to about one year after the first inoculation. Periodic inoculations beyond the third are also desirable to enhance the subject's "immune memory." The adequacy of the vaccination parameters chosen, e.g., formulation, dose, regimen and the like, can be determined by taking aliquots of serum from the subject and assaying antibody titers during the course of the immunization program. If such monitoring indicates that vaccination is sub-optimal, the subject can be boosted with an additional dose of pharmaceutical composition, and the vaccination parameters can be modified in a fashion expected to potentiate the immune response. It is contemplated that there can be several boosts, and that each boost can include the same or a different RSV preF immunogen.

For prime-boost protocols as described herein, the prime can be administered as a single dose or multiple doses, for example two doses, three doses, four doses, five doses, six doses or more can be administered to a subject over days, weeks or months. The boost can be administered as a single dose or multiple doses, for example two to six doses, or more can be administered to a subject over a day, a week or months. Multiple boosts can also be given, such one to five, or more. Different dosages can be used in a series of sequential inoculations. For example a relatively large dose in a primary inoculation and then a boost with relatively smaller doses. The immune response against the selected antigenic surface can be generated by one or more inoculations of a subject.

Immunization protocols using a DNA plasmid prime and ferritin nanoparticle boost are known to the person of ordinary skill in the art (see, e.g., Wei et al., Science, 329(5995): 1060-4, 2010, which is incorporated by reference herein in its entirety).

Accordingly, it is preferred that the administration comprises a prime-boost administration of the immunogen, the virus-like particle, the protein nanoparticle, the nucleic acid molecule, the vector, the host cell, or the pharmaceutical composition, respectively.

The actual dosage of the pharmaceutical composition will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the pharmaceutical composition for eliciting the desired activity or biological response in the subject. Dosage regimens can be adjusted to provide an optimum prophylactic or therapeutic response. As described above, an effective amount is also one in which any toxic or detrimental side effects of the disclosed antigen and/or other biologically active agent is outweighed in clinical terms by therapeutically beneficial effects.

Preferably, the immunogen according to the present invention as described herein, the virus-like particle according to the present invention as described herein, the protein nanoparticle according to the present invention as described herein, the nucleic acid molecule according to the present invention as described herein, the vector according to the present invention as described herein, the host cell according to the present invention as described herein, or the pharmaceutical composition according to the present invention as described herein is administered intravenously or intramuscularly.

A preferred range for a therapeutically effective amount of the disclosed PreF antigens (immunogens) within the methods and pharmaceutical compositions of the disclosure is about 0.0001 mg/kg body weight to about 10 mg/kg body weight, such as about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 4 mg/kg, about 5 mg/kg, or about 10 mg/kg, for example 0.01 mg/kg to about 1 mg/kg body weight, about 0.05 mg/kg to about 5 mg/kg body weight, about 0.2 mg/kg to about 2 mg/kg body weight, or about 1.0 mg/kg to about 10 mg/kg body weight.

More preferably, a single dose comprises 1 ng-10 g of the immunogen, preferably 100 ng-5 g of the immunogen, more preferably 1-1000 μg of the immunogen, even more preferably 10-100 μg of the immunogen, and most preferably 50 μg of the immunogen.

The dosage and number of doses will depend on the setting, for example, in an adult or anyone primed by prior RSV infection or immunization, a single dose may be a sufficient booster. In naive calves, for example, at least two doses may be given, such as at least three doses.

An annual boost may be given once per year, for example, along with other annual vaccination.

Methods for preparing administrable compositions will be known or apparent to those skilled in the art and are described in more detail in such publications as *Remingtons Pharmaceutical Sciences,* 19th Ed., Mack Publishing Company, Easton, Pa., 1995.

Dosage can be varied by the attending veterinarian or clinician to maintain a desired concentration at a target site (for example, systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth. To achieve the same serum concentration level, for example, slow-release particles with a release rate of 5 nanomolar (under standard conditions) would be administered at about twice the dosage of particles with a release rate of 10 nanomolar.

Upon administration of the immunogen according to the present invention as described herein, the virus-like particle according to the present invention as described herein, the protein nanoparticle according to the present invention as described herein, the nucleic acid molecule according to the present invention as described herein, the vector according to the present invention as described herein, the host cell according to the present invention as described herein, or the pharmaceutical composition according to the present invention as described herein, the immune system of the subject typically responds by producing antibodies specific for the prefusion conformation of the RSV F protein. Such a response signifies that an effective dose of the pharmaceutical composition was delivered.

It may be advantageous to administer the pharmaceutical compositions disclosed herein with other agents such as proteins, peptides, antibodies, and other antiviral agents, such as anti-RSV agents. Accordingly, it is preferred that the immunogen, the virus-like particle, the protein nanoparticle, the nucleic acid molecule, the vector, the host cell, or the pharmaceutical composition is administered in combination with an anti-RSV agent.

Non-limiting examples of anti-RSV agents include the monoclonal antibody palivizumab (SYNAGIS®; Medimmune, Inc.) and the small molecule anti-viral drug ribavirin (manufactured by many sources, e.g., Warrick Pharmaceuticals, Inc.). Pharmaceutical compositions can be administered concurrently with other anti-RSV agents. The pharmaceutical compositions can also be administered sequentially with other anti-RSV therapeutic agents, such as before or after the other agent. One of ordinary skill in the art would know that sequential administration can mean immediately following or after an appropriate period of time, such as hours, days, or weeks later.

Furthermore, a therapeutically effective amount of a pharmaceutical composition including a nucleic acid encoding a disclosed PreF antigen can be administered to a subject in order to generate an immune response.

Moreover, a therapeutically effective amount of a nucleic acid encoding a disclosed immunogen can be administered to a subject to treat or prevent or inhibit RSV infection. One approach to administration of nucleic acids can be direct immunization with plasmid DNA, such as with a mammalian expression plasmid. As described above, the nucleotide sequence encoding a disclosed antigen can be placed under the control of a promoter to increase expression of the molecule. Another approach would use RNA (such as Nonviral delivery of self-amplifying RNA vaccines, see e.g., Geall et al., Proc Natl Acad Sci USA, 109:14604-9, 2012. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil ATM (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce Class I mediated CTL responses (Takahashi et al., *Nature* 344:873, 1990).

In another approach to using nucleic acids for immunization, a disclosed antigen can also be expressed by attenuated viral hosts or vectors or bacterial vectors. Recombinant vaccinia virus, adenovirus, adeno-associated virus (AAV), herpes virus, retrovirus, cytomegalovirus or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

For example, a nucleic acid encoding a disclosed PreF antigen is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 µg/kg to about 50 mg/kg, and typically are about 0.005 mg/kg to about 5 mg/kg (see, e.g., U.S. Pat. No. 5,589,466).

In addition to the preventive and therapeutic methods and uses provided above, any of the immunogen according to the present invention as described herein, the virus-like particle according to the present invention as described herein, the protein nanoparticle according to the present invention as described herein, the nucleic acid molecule according to the present invention as described herein, the vector according to the present invention as described herein, the host cell according to the present invention as described herein, or the pharmaceutical composition according to the present invention as described herein, can be utilized to produce antigen specific immunodiagnostic reagents, for example, for sero-surveillance. Immunodiagnostic reagents can be designed from any of the antigens described herein. For example, in the case of the disclosed antigens, the presence of serum antibodies to RSV is monitored using the isolated antigens disclosed herein, such as to detect an RSV infection and/or the presence of antibodies that specifically bind to the prefusion conformation of RSV F protein.

Accordingly, the present invention also provides a method for detecting or isolating an RSV F binding antibody in a subject, comprising:
  (a) providing the immunogen according to the present invention as described herein; the virus-like particle according to the present invention as described herein; the protein nanoparticle according to the present invention as described herein; the nucleic acid molecule according to the present invention as described herein; the vector according to the present invention as described herein; the host cell according to the present invention as described herein; or the pharmaceutical composition according to the present invention as described herein;
  (b) contacting a biological sample from the subject with the recombinant RSV F protein or with the fragment thereof under conditions sufficient to form an immune complex between the recombinant RSV F protein or the fragment thereof and the RSV F binding antibody; and
  (c) detecting the immune complex, thereby detecting or isolating the RSV F binding antibody in the subject.

Preferably, such a method is an in-vitro method for detecting an RSV F binding antibody in an isolated biological sample of a subject.

Generally, the method includes contacting a sample from a subject, such as, but not limited to a blood, serum, plasma, urine or sputum sample from the subject with one or more of the RSV F protein antigen stabilized in a prefusion conformation disclosed herein and detecting binding of antibodies in the sample to the disclosed immunogens. The binding can be detected by any means known to one of skill in the art, including the use of labeled secondary antibodies that specifically bind the antibodies from the sample. Labels include radiolabels, enzymatic labels, and fluorescent labels. In addition, the detection of the prefusion RSV F binding antibody also allows the response of the subject to immunization with the disclosed antigen to be monitored.

Preferably, the titer of the prefusion RSV F antibody binding antibodies can be determined. The binding can be detected by any means known to one of skill in the art, including the use of labeled secondary antibodies that specifically bind the antibodies from the sample. Labels include radiolabels, enzymatic labels, and fluorescent labels. In other embodiments, a disclosed immunogen is used to isolate antibodies present in a subject or biological sample obtained from a subject.

Kit

In a further aspect the present invention also provides a kit comprising
  (i) the immunogen according to the present invention as described herein;
  (ii) the virus-like particle according to the present invention as described herein;
  (iii) the protein nanoparticle according to the present invention as described herein;
  (iv) the nucleic acid molecule according to the present invention as described herein;
  (v) the vector according to the present invention as described herein;
  (vi) the host cell according to the present invention as described herein; and/or
  (vii) the pharmaceutical composition according to the present invention as described herein;
and instructions for using the kit.

For example, the kit may be used for treating or preventing an RSV infection in a subject, or for detecting the presence of RSV F protein prefusion specific antibodies in the sera of a subject.

Preferably, the kit includes a container and/or a label or package insert on or associated with the container. Suitable containers include, for example, bottles, vials, syringes, etc. The containers may be formed from a variety of materials such as glass or plastic. The container typically holds a composition including one or more of the immunogen according to the present invention as described herein, the virus-like particle according to the present invention as described herein, the protein nanoparticle according to the present invention as described herein, the nucleic acid molecule according to the present invention as described herein, the vector according to the present invention as described herein, the host cell according to the present invention as described herein, or the pharmaceutical composition according to the present invention as described herein.

The container may optionally have a sterile access port (for example the container may be an intravenous solution bag or a vial having a stopper pierceable by a hypodermic injection needle). The label or package insert indicates that the composition is used for treating the particular condition, in particular RSV infection, such as bRSV infection. The label or package insert typically will further include instructions for use of the immunogen according to the present invention as described herein, the virus-like particle according to the present invention as described herein, the protein nanoparticle according to the present invention as described herein, the nucleic acid molecule according to the present invention as described herein, the vector according to the present invention as described herein, the host cell according to the present invention as described herein, or the pharmaceutical composition according to the present invention as described herein, for example, in a method of treating or preventing an RSV infection, such as a bRSV infection. The package insert may include instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. The kits may additionally include buffers and other reagents routinely used for the practice of a particular method. Such kits and appropriate contents are well known to those of skill in the art.

BRIEF DESCRIPTION OF THE FIGURES

In the following a brief description of the appended figures will be given. The figures are intended to illustrate the present invention in more detail. However, they are not intended to limit the subject matter of the invention in any way.

FIG. 1 shows for Example 1 a ClustalOmega sequence alignment of hRSVF strain A2 with RSV F from nine bovine strains (corresponding to SEQ ID NOs: 1-9) as indicated. Each row covers 60 positions. Residue positions completely conserved are designated by a "*", homologous residues by a ":" and variable residues by a space.

FIG. 2 shows for Example 1 strain names and accession numbers for human and bovine RSV F proteins.

FIG. 4 shows for Example 1 the expression screen for bDS-Cav1 RSV F in seven different strains.

FIG. 5 shows for Example 1 the antigenic screening of bRSV F single chain immunogens.

FIG. 6 shows for Example 1 the antigenic screening of bRSVF single chain immunogens with interprotomer disulfides.

FIG. 7 shows for Example 1 the yields of bRSV single chain immunogens in liter-scale production.

FIG. 8 shows the antigenic and physical characterization of bRSV F glycoprotein immunogens.

FIG. 10 shows for Example 4 crystallographic data collection and refinement statistics.

FIG. 11 shows the crystal structures of pre-F-stabilized bRSV F immunogens. a, Crystal structure of bRSV F ATue51908 DS-Cav1 depicted by a Cα-worm representation color-coded by atomic mobility factors, with thick, red worm for flexible regions and thin, blue worm for more rigid regions. Atomic level details are shown in insets on the right with stick representations and 2Fo-Fc electron density (blue) for regions that were mutated to stabilize the pre-F conformation. The upper left inset shows a ribbon superposition of the antigenic site Ø region of ATue51908 DS-Cav1 (lime) with the structure of hRSV F DS-Cav1 (gray; PDB ID 4MMU). b, Crystal structure of the DS2 immunogen bRSV F 391-2 DS-Cav1 sc9 Q98C-Q361C, depicted as in (a).

FIG. 13 shows bRSV neutralization EC50 titers measured from week 5 mouse sera.

FIG. 15 shows biographical data for immunized calves.

FIG. 16 shows bRSV neutralization $EC_{50}$ titers measured from calf sera.

FIG. 19 shows viral titers as a measure of bRSV replication in nasopharyngeal secretion.

FIG. 21 shows the effect of vaccination on bRSV replication in the respiratory tract of calves and clinical signs of disease. a, Clinical sore at day 6 post RSV challenge. Each dot represents the score from each animal obtained at day 6 post challenge. DS2-v1 (391-2 sc9 DS-Cav1Q98C-Q361C), Post-F (391-2 post-F), PBS (Placebo). Geometric mean scores are indicated by black horizontal lines. b, Effect of F protein vaccination on proportion of neutrophils in BAL, 6 days after challenge with bRSV. P≤0.0105 for calves vaccinated with pre-F compared to controls. P values were determined by two-tailed Mann-Whitney tests. * indicates P≤0.05,  indicates P≤0.01, * indicates P≤0.001 and **** indicates P≤0.0001.

FIG. 22 shows the clinical scores and signs of immunized calves.

FIG. 23 shows the definition of clinical scores.

FIG. 24 shows the effect of bRSV F vaccination on pulmonary pathology.

EXAMPLES

Figure 3:
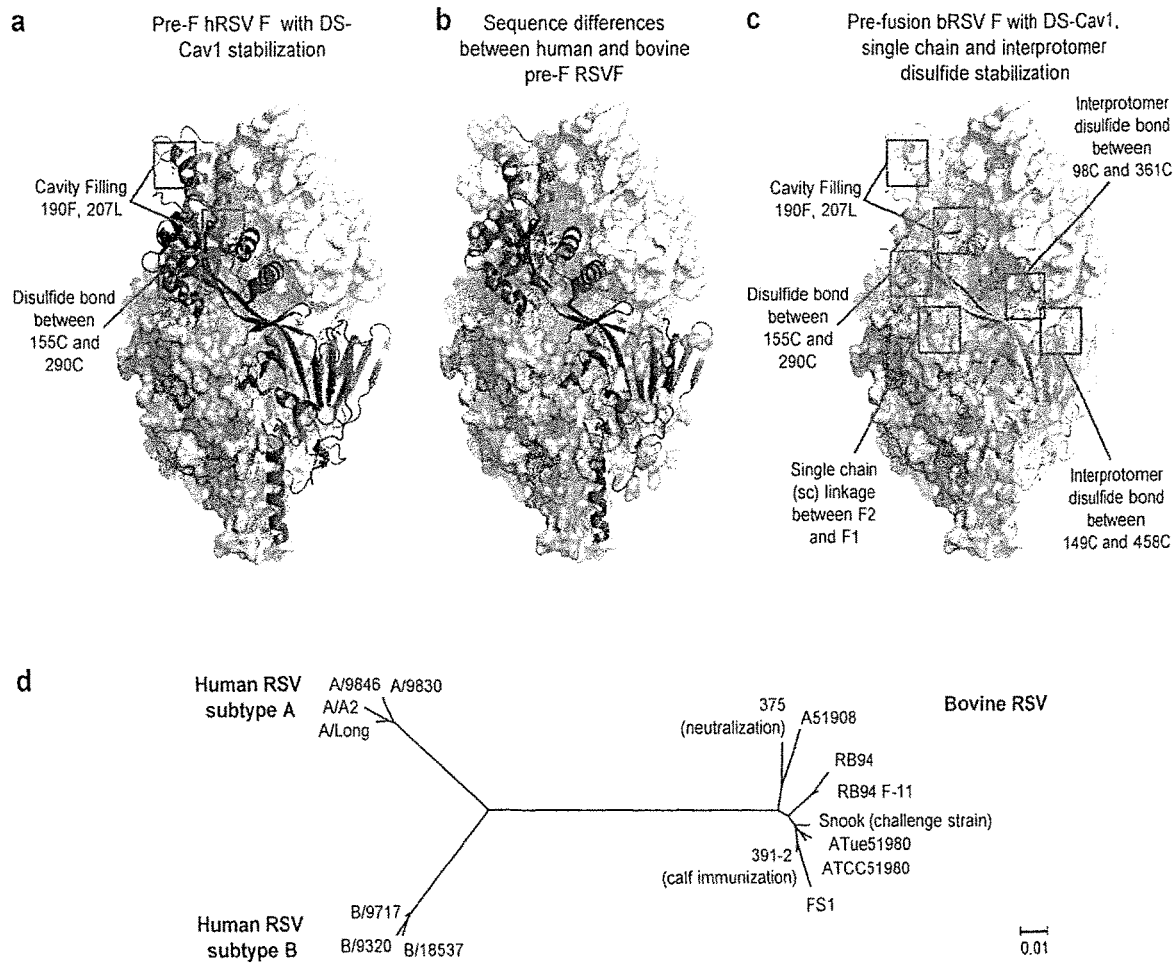
FIG. 3 shows for Example 1 the translation of pre-F hRSV F stabilization to bRSV F. a, Structural model of a pre-F hRSV F trimer stabilized by DS-Cav1 mutations (PDB ID 4MMU). One monomer is depicted by a blue ribbon model with the four DS-Cav1 mutations shown by red stick models outlined by red squares. The other two monomers are depicted by gray surface representations. b, Sequence variation between hRSV strain A2 and eight different bRSV strains is mapped (orange surface representation) onto a blue ribbon model of one monomer of a DS-Cav1 pre-F RSV F trimer colored as in (a). c, The locations of the DS-Cav1 mutations (red), the sc linkage (green) and interprotomer disulfide stabilization mutations (green) introduced into bovine RSV F protein are indicated by boxed stick models for one RSV F monomer. In (b) and (c), the other two monomers of the trimer are shown as gray surface representations. d, Phylogenetic tree for human and bovine RSV F proteins. Names shown indicate the virus strain or isolate. GenBank accession numbers for all strains used in this study are shown in FIG. 2.

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Experimental: Material and Methods

Protein Expression, Purification

RSV F variants were expressed by transient transfection of Expi293F cells using 293Fectin (Invitrogen). Cell culture supernatants were harvested five days post transfection and centrifuged at 10,000 g to remove cell debris. The supernatants were sterile-filtered, and RSV F variants were purified by nickel (Roche) and Strep-Tactin (iba) affinity chromatography followed by size-exclusion chromatography (SEC. The foldon domain was removed only when proteins were prepared for animal immunization. The C-terminal tags were removed from the variants by digestion with 2 U/ml restriction-grade thrombin (Novagen) overnight at 4° C. The bRSV F glycoprotein with purification tags removed were then purified by a second round of size-exclusion chromatography in PBS.

Expression and Purification of Antibodies and Antigen-Binding Fragments (Fabs).

Antibodies were expressed by transient co-transfection of Expi293F cells (Thermo Fisher Scientific, MA) with both heavy- and light-chain plasmids using 293 fectin (Thermo Fisher Scientific, MA). Cell supernatants were harvested after 4-5 days and passed over Protein A agarose (GE Healthcare, PA). Bound antibodies were washed with PBS and eluted with IgG elution buffer (Pierce, Ill.) into 1/10th volume of 1 M Tris-HCl pH 8.0. Fabs were generated by digesting the IgG with Lys-C or HRV3C protease, and the cleaved Fc region was removed by passing the mixture over Protein A agarose. Final purification of Fabs was performed by SEC.

Antigenic Screening of bRSV F Immunogens

Initial assessment of all constructs were performed using a 96-well microplate format for high throughput expression followed by an ELISA-based antigenic evaluation as described previously 17. Briefly, 24 h prior to transfection HEK 293T cells (Thermo Fisher Scientific, MA) were seeded in each well of a 96-well microplate at a density of $2.5 \times 10^5$ cells/ml in expression medium (high glucose DMEM supplemented with 10% ultra-low IgG fetal bovine serum and 1×-non-essential amino acids), and incubated at 37° C., 5% CO2 for 20 h. Plasmid DNA and TrueFect-Max (United BioSystems, MD) were mixed and added to the growing cells, and the 96-well plate incubated at 37° C., 5% CO2. One day post transfection, enriched medium (high glucose DMEM plus 25% ultra-low IgG fetal bovine serum, 2× nonessential amino acids, 1× glutamine) was added to each well, and the 96-well plate was returned to the incubator for continuous culture. Five days post transfection supernatants with the expressed bRSV F variants were harvested and tested by ELISA for binding to D25, MPE8 and motavizumab antibodies using Ni2+-NTA microplates.

RSV F Antigenic Characterization

A fortéBio Octet Red384 instrument was used to measure binding kinetics of RSV F variants to antibodies that target the pre-F or post-F form (D25, AM14, MPE8 and Mota). All assays were performed with agitation set to 1,000 rpm in phosphate-buffered saline (PBS) supplemented with 1% bovine serum albumin (BSA) to minimize nonspecific interactions. The final volume for all solutions was 50 µl/well. Assays were performed at 30° C. in tilted black 384-well plates (Geiger Bio-One). Ni-NTA sensor tips were used to capture relevant RSV F variants. Typical capture levels for each loading step were between 1.4 and 1.5 nm, and variability within a row of eight tips did not exceed 0.1 nm for each of these steps. The nm unit is a measure of the change in the interference pattern of white light reflected from the surface of the biosensor tip compared to an internal reference. This was measured in real-time and correlated with a change in the thickness of bound molecules on the biosensor tip surface. This can also be defined as a change in response units measured in nm. Biosensor tips were equilibrated for 120 s in PBS+1% BSA prior to loading bRSV F variants. Biosensor tips were then equilibrated for 120 s in PBS+1% BSA prior to measuring association with antigen binding fragments (Fabs) in solution (0.007 µM to 0.5 µM) for 300 s; Fabs were then allowed to dissociate for 300-1200 s depending on the observed dissociation rate. Parallel correction to subtract systematic baseline drift was carried out by subtracting the measurements recorded for a loaded sensor incubated in PBS+1% BSA. Data analysis and curve fitting were carried out using Octet software, version 9.0. Experimental data were fitted with the binding equations describing a 1:1 interaction. Global analysis of the data sets assuming reversible binding (full dissociation) were carried out using nonlinear least-squares fitting allowing a single set of binding parameters to be obtained simultaneously for all of the concentrations used in each experiment.

Physical Stability of RSV F Variants

To assess the physical stability of the pre-fusion conformation of designed bRSV F glycoproteins under various stress conditions, the proteins were treated with a variety of pharmaceutically relevant stresses such as extreme pH, high temperature, low and high osmolarity, and repeated freeze/thaw cycles while at a concentration of 50 µg/ml. The physical stability of treated bRSV F variants was evaluated by the preservation of antigenic site Ø after treatment as assessed by binding of the site Ø-specific antibody D25. In pH treatments, the bRSV F glycoprotein solution was adjusted to pH 3.5 and pH 10 with appropriate buffers and incubated at room temperature for 60 minutes and subsequently neutralized to pH 7.5. Temperature treatments were carried out by incubating the bRSV F glycoprotein solutions at 50° C. and 70° C. for 60 minutes in a PCR cycler with heated lid. In osmolarity treatments, bRSV F glycoprotein solutions originally containing 150 mM NaCl were either diluted with 2.5 mM Tris buffer (pH 7.5) to an osmolarity of 10 mM NaCl or adjusted with 4.5 M MgCl2 to a final concentration of 3.0 M MgCl2. Protein solutions were incubated for 60 minutes at room temperature and then returned to 150 mM salt by adding 5.0 M NaCl or dilution with 2.5 mM Tris buffer, respectively, and concentrated to 50 µg/ml. The freeze/thaw treatment was carried out by repeatedly freezing bRSV F glycoprotein solutions in liquid nitrogen and thawing at 37° C. ten times in the presence of 10% glycerol. All bRSV F glycoproteins were diluted to 40 µg/ml with PBS+1% BSA, and their ability to bind D25 Fab was measured with an Octet instrument using the protocol described above. The degree of physical stability is reported as the ratio of steady state D25-binding level before and after stress treatment.

Negative Stain Electron Microscopy

Samples were diluted to approximately 0.01 mg/ml, adsorbed to freshly glow-discharged carbon-coated grids, rinsed with several drops of buffer containing 10 mM HEPES, pH 7.0, and 150 mM KCl, and stained with 0.75% uranyl formate. Images were recorded on an FEI T20 microscope with a 2 k×2 k Eagle CCD camera at a pixel size of 2.2 Å. Reference-free 2D classification and averaging were performed with EMAN2 (Tang, G., et al. EMAN2: An extensible image processing suite for electron microscopy. *Journal of structural biology* 157, 38-46 (2007)) and SPIDER.

Crystallization and X-Ray Data Collection of Pre-F-Stabilized bRSV F Proteins

Crystallization conditions were screened by vapor diffusion using a Mosquito crystallization robot (TTP labtech) that generated sitting drops at 20° C. by mixing 0.2 µl of bRSV immunogens with 0.2 µl of reservoir solution. Optimized crystals for data collection were grown by manually setting up hanging drops combining 0.5 µl protein with 0.5 µl of reservoir solution. ATue51908 DS-Cav1 crystals were grown in 12% (w/v) PEG 3350, and 0.1M sodium acetate pH 5.5, and 391-2 sc9 DS-Cav1Q98C Q361C crystals were grown in 0.9 M K/Na tartrate, 0.16 M Li2SO4, and 0.1 M CHES pH 9.5. Prior to data collection, ATue51908 DS-Cav1 crystals were transferred to 15% (v/v) 2R,3R-butanediol, 18% (w/v) PEG 3350, and 0.1M sodium acetate pH 5.5 and 391-2 sc9 DS-Cav1Q98C Q361C crystals were transferred to 15% (v/v) 2R,3R-butanediol, 1.3 M K/Na tartrate, 0.16 M Li2SO4, and 0.1 M CHES pH 9.5 followed by flash freezing in liquid nitrogen. X-ray diffraction data were collected at a wavelength of 1.00 Å at the SER-CAT beamline ID-22 (Advanced Photon Source, Argonne National Laboratory).

Structure Determination, Refinement and Analysis of Pre-F-Stabilized bRSV F

Diffraction data were integrated and scaled with the HKL2000 suite, and a molecular replacement solutions for both structures were obtained by PHASER using the pre-F RSV F structure (PDB ID: 4MMS) as a search model. Manual model building was carried out using COOT, with secondary structure elements built first. Refinement of individual coordinates, TLS parameters, and individual B-factors was performed in PHENIX. Final data collection and refinement statistics are presented in FIG. 10. All structural images were created using PyMol (The PyMol Molecular Graphics System, version 1.1; Schrödinger, LLC).

Mouse Immunizations

All mouse experiments were reviewed and approved by the Animal Care and Use Committee of the Vaccine Research Center, NIAID, NIH, under animal protocol 13-454, and all animals were housed and cared for in accordance with local, state, federal, and institute policies in an American Association for Accreditation of Laboratory Animal Care (AAALAC)-accredited facility at the NIH. Mice were randomized into groups of ten and these groups were not blinded to the investigators. As in previous experiments, hybrid female mice that were the first filial offspring of a cross between BALB/cJ females (C) and C57BL6) males (B6) (The Jackson Laboratory) known as CB6F1/J at ages 6 weeks to 12 weeks were intramuscularly injected with RSV F immunogens at week 0 and week 3. The frozen RSV F variant immunogen proteins were thawed on ice and mixed with 5-fold w/w poly I:C (Invivogen) adjuvant (i.e. 10 μg RSV F, 50 μg Poly I:C per animal per immunization), with injections taking place within 1 h of immunogen: adjuvant preparation. No adverse effect from immunization was observed. Blood was collected at least three days before immunization, and at week 2, week 5 and week 7 post initial immunization.

bRSV Neutralization Assays bRSV microneutralization assay was performed using BT cells (ATCC CRL1390) and 500-1000 TCID50 (50% tissue culture infectious doses) of bRSV, strain 375 (ATCC VR1339). Briefly, immune sera were serially diluted in quadruplicates prior to mixing with 500-1000 TCID50 of bRSV for 1 hour at 37° C. in a humidified 5% CO2 atmosphere prior to addition to monolayers of BT cells seeded the day before at 8,000 cells/well. Cells were then incubated for 7 days, fixed with 70% methanol, stained with 1% crystal violet and examined at the microscope for syncytia formation and cytophatic effect (CPE). Neutralizing titer was defined as the reciprocal of the highest sera dilution at which the infectivity of bRSV was completely neutralized in 50% of the wells. Infectivity was identified by the presence of CPE and syncytia on day 7, and the titer was calculated by the Reed-Muench method.

ELISA Binding Assays

A standard ELISA was used to determine binding of immune sera to bRSV pre- and post-bRSV F proteins. Briefly, ELISA plates were coated with antigens at 5 μg/ml, blocked with 1% BSA in PBS, incubated with serial dilutions of sera and washed. Bound mAbs were detected by incubation with AP-conjugated Goat Anti-Mouse adsorbed against human IgG (Southern Biotech) or goat anti-bovine IgG (Southern Biotech). Plates were then washed, substrate (4-Nitrophenyl phosphate disodium salt hexahydrate, Sigma) was added and plates were read at 405 nm. The relative titer of sera binding to respective coated antigens were determined by measuring the concentration of each serum required to achieve 50% binding relative to the maximum (ED50). The ED50 values were calculated by interpolation of binding curves fitted with a four-parameter nonlinear regression with a variable slope.

Calf Immunization

The calf experiment was performed under the regulations of the Home Office Scientific Procedures Act (1986) of the United Kingdom. The study had been reviewed and approved by the Animal and Plant Health Agency (APHA) Ethical Review Committee. Calve groups were not blinded to the investigators. Male calves were obtained from local farms and were removed from their mothers at birth to ensure that they did not receive any colostrum and transported to APHA at ~1 day of age. Calves were bled on arrival at APHA and were fed 250 ml of colostrum, 48 hrs after birth, in order produce calves with little or no maternally derived bRSV-specific serum antibodies. Sera obtained before and after colostrum intake was analyzed for bRSV-specific and prefusion bRSV F protein-specific antibodies by ELISA. All but two calves were free from bRSV-specific serum antibodies. Calves were allocated to three groups of 5 to give groups matched for calf age, and the two animals with maternally derived bRSV-specific antibodies were allocated to the control group. Calves were 3 to 6 weeks old at the time of vaccination. The frozen bRSV F proteins, pre-F (DS2) and post-F (391-2 post-F) were thawed on ice and mixed with Montanide™ ISA71 VG (Seppic, France) in a water in oil emulsion in a ratio of 70:30 adjuvant to aqueous phase. Calves were inoculated intramuscularly with 50 μg protein in a volume of 2 ml on two occasions 4 weeks apart. As controls, calves were inoculated with 2 ml PBS in ISA71 VG. Vaccinations took place within 3 h of immunogen: adjuvant preparation. Calves developed a transient fever 24 h after vaccination and no or only mild diffuse swelling at the injection sites. Calves were bled at defined time points for analysis of bRSV-specific serum antibody responses.

Calf Challenge Virus

Virulent bRSV used to challenge calves consisted of bronchoalveolar lavage (BAL) prepared from a gnotobiotic calf inoculated 6 days previously with the Snook strain of bRSV, which had been passaged on four previous occasions in gnotobiotic or specific pathogen free calves. The BAL was free from other viruses, mycoplasmas, and bacteria as assessed by inoculation of tissue culture cells, mycoplasmal or bacterial media. Virus titers were determined by plaque assay on fetal calf kidney cells.

Calf Challenge

Four weeks after the last vaccination, calves were challenged by intranasal and intratracheal administration of $10^4$ pfu of bRSV, Snook strain, in BAL. Following bRSV challenge, nasopharyngeal swabs were obtained daily to monitor bRSV excretion, and calves were examined daily for clinical signs of disease. The severity of disease was given a score as shown in FIG. 22. The clinical scores are defined in FIG. 23. Calves were euthanized 6 days after challenge to determine the extent of gross pneumonic consolidation and the extent of virus infection in the lower respiratory tract as described previously. Titers of virus in the trachea were determined by scraping the epithelium from a piece of trachea approximately 3 cm long into 2 ml of Hanks balanced salt solution (Sigma) containing 1% bovine serum albumin (BSA) (Sigma). The apical and cardiac lung lobes were clamped and the lungs lavaged with ~1 liter of PBS to obtain bronchalveolar lavage (BAL). Cytospin preparations of BAL cells were fixed and stained with Diff Quik (Thermo Fisher Scientific) and differential cell counts made using oil immersion microscopy. Samples of lung taken from three different apical lung lobes were homogenized to give a 20% w/v suspension. Lung tissue for histology was also taken from 3 different apical lobes and fixed in 10% neutral buffered formalin, paraffin wax embedded and sections were stained with haematoxylin and eosin.
Statistical Analysis Statistical analyses were performed using two-tailed Mann-Whitney tests with GraphPad Prism 6.0 software (La Jolla, Calif.). Differences were considered statistically significant at P≤0.05.

Example 1: Design and Initial Characterization of bRSV F Immunogens

The RSV F glyoprotein is conserved between bRSV and hRSV, with sequence identities of ~80% (FIGS. 1 and 2, and FIG. 3 b,d) and multiple F-directed antibodies able to neutralize both hRSV and bRSV. Based on the success of the prior engineering of pre-F hRSV F trimer (McLellan, J. S., et al. Structure-based design of a fusion glycoprotein vaccine for respiratory syncytial virus. Science 342, 592-598 (2013)), bRSV F was modified to create thermostable pre-F trimers. A disulfide between residues 155 and 290 (DS) along with cavity-filling mutations S190F and V207L (Cav1) and a C-terminal T4 foldon trimerization domain (foldon) were incorporated into bRSV F from seven different strains to make bovine versions of DS-Cav1 (bDS-Cav1 s) (FIG. 3 a, b and FIG. 4), which included cleavable C-terminal His and Strep tags for purification.

Upon expression in Expi293F cells only three of the seven bDS-Cav1s (strains 391-2, ATue51908, and RB94 respectively) expressed at greater than 0.5 mg/L of culture (FIG. 4). Amino acid sequences of those three bDS-Cav1 s are shown in the following:

bRSV 391-2 DSCav1:

[SEQ ID NO: 36]
MAATAMRMIISIIFISTYMTHITLCQNITEEFYQSTCSAVSRGYLSALRT

GWYTSVVTIELSKIQKNVCKSTDSKVKLIKQELERYNNAVIELQSLMQNE

PASFSRAKRGIPELIHYTRNSTKRFYGLMGKKRKRRFLGFLLGIGSAIAS

GVAVCKVLHLEGEVNKIKNALLSTNKAVVSLSNGVSVLTFKVLDLKNYID

KELLPKLNNHDCRISNIETVIEFQQKNNRLLEIAREFSVNAGITTPLSTY

MLTNSELLSLINDMPITNDQKKLMSSNVQIVRQQSYSIMCVVKEEVIAYV

VQLPIYGVIDTPCWKLHTSPLCTTDNKEGSNICLTRTDRGWYCDNAGSVS

FEPQAETCKVQSNRVFCDTMNSLTLPTDVNLCNTDIFNTKYDCKIMTSKT

DISSSVITSIGAIVSCYGKTKCTASNKNRGIIKTFSNGCDYVSNKGVDTV

SVGNTLYYVNKLEGKALYIKGEPIINYYDPLVFPSDEFDASIAQVNAKIN

QSLAFIRRSDELLSAIGGYIPEAPRDGQAYVRKDGEWVLLSTFLGGLVPR

GSHHHHHHSAWSHPQFEK bRSV ATue51908 DSCav1:

[SEQ ID NO: 37]
MDSKGSSQKGSRLLLLLVVSNLLLPQGVVGQNITEEFYQSTCSAVSRGYL

SALRTGWYTSVVTIELSKIQKNVCKSTDSKVKLIKQELERYNNAVVELQS

LMQNEPASFSRAKRGIPELIHYTRNSTKKFYGLMGKKRKRRFLGFLLGIG

SAVASGVAVCKVLHLEGEVNKIKNALLSTNKAVVSLSNGVSVLTFKVLDL

KNYIDKELLPQLNNHDCRISNIETVIEFQQKNNRLLEIAREFSVNAGITT

PLSTYMLTNSELLSLINDMPITNDQKKLMSSNVQIVRQQSYSIMCVVKEE

VIAYVVQLPIYGVIDTPCWKLHTSPLCTTDNKEGSNICLTRTDRGWYCDN

AGSVSFFPQTETCKVQSNRVFCDTMNSLTLPTDVNLCNTDIFNTKYDCKI

MTSKTDISSSVITSIGAIVSCYGKTKCTASNKNRGIIKTFSNGCDYVSNK

GVDTVSVGNTLYYVNKLEGKALYIKGEPIINYYDPLVFPSDEFDASIAQV

NAKINQSLAFIRRSDELLSAIGGYIPEAPRDGQAYVRKDGEWVLLSTFLG

GLVPRGSHHHHHHSAWSHPQFEK bRSV RB94 DSCav1:

[SEQ ID NO: 38]
MPMGSLQPLATLYLLGMLVASVLAAQNITEEFYQSTCSAVSRGYLSALRT

GWYTSVVTIELSKIQKNVCNSTDSNVKLIKQELERYNNAVVELQSLMQNE

PASSSRAKRGIPELIHYKRNSTKKFYGLMGKKRKRRFLGFLLGIGSAIAS

GVAVCKVLHLEGEVNKIKNALLSTNKAVVSLSNGVSVLTFKVLDLKNYID

KELLPKLNNHDCQISNIATVIEFQQKNNRLLEIAREFSVNAGITTPLSTY

MLTNSELLSLINDMPITNDQKKLMSSNVQIVRQQSYSIMCVVKEEVMAYV

VQLPIYGVIDTPCWKLHTSPLCTTDNKEGSNICLTRTDRGWYCDNAGSVS

FFPQAETCKVQSNRVFCDTMNSLTLPTDVNLCNTDIFNAKYDCKIMTSKT

DISSSVITSIGAIVSCYGKTKCTASNKNRGIIKTFSNGCDYVSNRGVDTV

SVGNTLYYVNKLEGKALYIKGEPIINYYDPLVFPSDEFDASIAQVNAKIN

QSLAFIRRSDELLSAIGGYIPEAPRDGQAYVRKDGEWVLLSTFLGGLVPR

GSHHHHHHSAWSHPQFEK

All three of these bDS-Cav1 s were recognized by pre-F-specific mAbs D25 (McLellan, J. S., et al. Structure of RSV fusion glycoprotein trimer bound to a prefusion-specific neutralizing antibody. Science 340, 1113-1117 (2013)) and MPE8 (Corti, D., et al. Cross-neutralization of four paramyxoviruses by a human monoclonal antibody. Nature 501, 439-443 (2013)) as well as by mAb motavizumab (Mota; McLellan, J. S., et al. Structural basis of respiratory syncytial virus neutralization by motavizumab. Nat Struct Mol Biol 17, 248-250 (2010)) (FIG. 4).

To enhance immunogenicity, next bDS-Cav1 thermostability was sought to be optimized. To minimize the number of designs evaluated, two RSV strains (391-2 and RB94) were selected to optimize initially, with the intent to introduce the best mutations from the final set into the third strain, ATue51908. Previous investigations (Georgiev, I. S., et al. Single-Chain Soluble BG505.SOSIP gp140 Trimers as Structural and Antigenic Mimics of Mature Closed HIV-1 Env. Journal of virology 89, 5318-5329 (2015); Sharma, S. K., et al. Cleavage-Independent HIV-1 Env Trimers Engineered as Soluble Native Spike Mimetics for Vaccine Design. Cell Rep 11, 539-550 (2015); Krarup, A., et al. A highly stable prefusion RSV F vaccine derived from structural analysis of the fusion mechanism. Nat Commun 6, 8143 (2015); Chen, J., et al. Structure of the hemagglutinin precursor cleavage site, a determinant of influenza pathogenicity and the origin of the labile conformation. Cell 95, 409-417 (1998)) of type 1 fusion machines have indicated that removal of the cleavage site to create sc variants can improve pre-F stability. Therefore, with a focus on that aforementioned type of stabilizations and on the introduction of interprotomer disulfide bonds (DS2), 92 variants of bDS-Cav1 were designed, all of which employed a sc topology and 32 of which contained an interprotomer disulfide ("DS2" variants). Additionally, many of the 92 designs incorporated internal cavity-filling mutations, core residues from hRSV F for increased stability, and additional sites of N-linked glycosylation to mask irrelevant epitopes.

All 92 bDS-Cav1 designs were evaluated for expression and antigenic recognition by mAbs D25, MPE8 and Mota in a 96 well-microplate transient transfection format (McLellan, J. S., et al. Structure-based design of a fusion glycoprotein vaccine for respiratory syncytial virus. *Science* 342, 592-598 (2013)). Each design was scored by summing ELISA readings for the pre-F-specific mAbs D25 and MPE8 (FIGS. 5 and 6). The top three-scoring DS2 designs (391-2 DS-Cav1 sc9 Q98C-Q361C [SEQ ID NO: 32], RB94 DS-Cav1 sc9 A149C Y458C [SEQ ID NO: 39], and RB94 sc9 DS-Cav1 N183GC-N428C [SEQ ID NO: 40]) and the top two-scoring 391-2 and RB94 sc designs without interprotomer disulfides (sc9-10_bRSV(RB94) DS-Cav1_fd_hp2_fp2_ig1 [SEQ ID NO: 41] and 391-2-site Ø hRSV bovsurf DS-Cav1-BZGJ9 Long [SEQ ID NO: 42]) were selected for additional evaluation (FIGS. 5 and 6). To expand the dimensions of our search for optimal immunogens, interprotomer disulfides (Q98C-Q361C, A149C-Y458C and N183GC-N428C) and sc formats (sc9 and sc9-10) from the top five designs were mixed and matched and the ATue51908 strain was added to generate additional designs for a total of nine constructs, which were expressed in 1 liter Expi293F cultures (FIG. 7). Amino acid sequences of those nine constructs are shown in the following:

bRSV 391-2 sc9-10 DS-Cav1 Q98C-Q361C:
[SEQ ID NO: 31]
MAATAMRMIISIIFISTYMTHITLCQNITEEFYQSTCSAVSRGYLSALRT
GWYTSVVTIELSKIQKNVCKSTDSKVKLIKQELERYNNAVIELQSLMCNE
PASgsGSAIASGVAVCKVLHLEGEVNKIKNALLSTNKAVVSLSNGVSVLT
FKVLDLKNYIDKELLPKLNNHDCRISNIETVIEFQQKNNRLLEIAREFSV
NAGITTPLSTYMLTNSELLSLINDMPITNDQKKLMSSNVQIVRQQSYSIM
CVVKEEVIAYVVQLPIYGVIDTPCWKLHTSPLCTTDNKEGSNICLTRTDR
GWYCDNAGSVSFFPQAETCKVCSNRVFCDTMNSLTLPTDVNLCNTDIFNT
KYDCKIMTSKTDISSSVITSIGAIVSCYGKTKCTASNKNRGIIKTFSNGC
DYVSNKGVDTVSVGNTLYYVNKLEGKALYIKGEPIINYYDPLVFPSDEFD
ASIAQVNAKINQSLAFIRRSDELLSaiggyipeaprdgqayvrkdgewvl
lstflgglvprgshhhhhhsawshpqfek bRSV 391-2 sc9 DS-Cav1 Q98C-Q361C:
[SEQ ID NO: 32]
MAATAMRMIISIIFISTYMTHITLCQNITEEFYQSTCSAVSRGYLSALRT
GWYTSVVTIELSKIQKNVCKSTDSKVKLIKQELERYNNAVIELQSLMCNE
PASFSgsGSAIASGVAVCKVLHLEGEVNKIKNALLSTNKAVVSLSNGVSV
LTFKVLDLKNYIDKELLPKLNNHDCRISNIETVIEFQQKNNRLLEIAREF
SVNAGITTPLSTYMLTNSELLSLINDMPITNDQKKLMSSNVQIVRQQSYS
IMCVVKEEVIAYVVQLPIYGVIDTPCWKLHTSPLCTTDNKEGSNICLTRT
DRGWYCDNAGSVSFFPQAETCKVCSNRVFCDTMNSLTLPTDVNLCNTDIF
NTKYDCKIMTSKTDISSSVITSIGAIVSCYGKTKCTASNKNRGIIKTFSN GCDYVSNKGVDTVSVGNTLYYVNKLEGKALYIKGEPIINYYDPLVFPSDE
FDASIAQVNAKINQSLAFIRRSDELLSaiggyipeaprdgqayvrkdgew
vllstflgglyprgshhhhhhsawshpqfek bRSV 391-2 sc9 DS-Cav1 A149C-Y458C:
[SEQ ID NO: 43]
MAATAMRMIISIIFISTYMTHITLCQNITEEFYQSTCSAVSRGYLSALRT
GWYTSVVTIELSKIQKNVCKSTDSKVKLIKQELERYNNAVIELQSLMQNE
PASFSGSGSA1cSGVAVCKVLHLEGEVNKIKNALLSTNKAVVSLSNGVSV
LTFKVLDLKNYIDKELLPKLNNHDCRISNIETVIEFQQKNNRLLEIAREF
SVNAGITTPLSTYMLTNSELLSLINDMPITNDQKKLMSSNVQIVRQQSYS
IMCVVKEEVIAYVVQLPIYGVIDTPCWKLHTSPLCTTDNKEGSNICLTRT
DRGWYCDNAGSVSFFPQAETCKVQSNRVFCDTMNSLTLPTDVNLCNTDIE
NTKYDCKIMTSKTDISSSVITSIGAIVSCYGKTKCTASNKNRGIIKTFSN
GCDYVSNKGVDTVSVGNTLYcVNKLEGKALYIKGEPIINYYDPLVFPSDE
FDASIAQVNAKINQSLAFIRRSDELLSaiggyipeaprdgqayvrkdgew
vllstflgglvprgshhhhhhsawshpqfek bRSV ATue51908 sc9-10 DS-Cav1 A149C-Y458C:
[SEQ ID NO: 33]
MDSKGSSQKGSRLLLLLVVSNLLLPQGVVGQNITEEFYQSTCSAVSRGYL
SALRTGWYTSVVTIELSKIQKNVCKSTDSKVKLIKQELERYNNAVVELQS
LMQNEPASgsGSAVcSGVAVCKVLHLEGEVNKIKNALLSTNKAVVSLSNG
VSVLIFKVLDLKNYIDKELLPQLNNHDCRISNIETVIEFQQKNNRLLEIA
REFSVNAGITTPLSTYMLTNSELLSLINDMPITNDQKKLMSSNVQIVRQQ
SYSIMCVVKEEVIAYVVQLPIYGVIDTPCWKLHTSPLCTTDNKEGSNICL
TRTDRGWYCDNAGSVSFFPQTETCKVQSNRVFCDTMNSLTLPTDVNLCNT
DIFNTKYDCKIMTSKTDISSSVITSIGAIVSCYGKTKCTASNKNRGIIKT
FSNGCDYVSNKGVDTVSVGNTLYcVNKLEGKALYIKGEPIINYYDPLVFP
SDEFDASIAQVNAKINQSLAFIRRSDELLSAIGGYIPEAPRDGQAYVRKD
GEWVLLSTFLGGLVPRGSHHHHHHSAWSHPQFEK bRSV ATue51908 sc9-10 DS-Cav1 N183GC-N428C:
[SEQ ID NO: 44]
MDSKGSSQKGSRLLLLLVVSNLLLPQGVVGQNITEEFYQSTCSAVSRGYL
SALRTGWYTSVVTIELSKIQKNVCKSTDSKVKLIKQELERYNNAVVELQS
LMQNEPASgsGSAVASGVAVCKVLHLEGEVNKIKNALLSTNKAVVSLSgc
GVSVLTFKVLDLKNYIDKELLPQLNNHDCRISNIETVIEFQQKNNRLLEI
AREFSVNAGITTPLSTYMLTNSELLSLINDMPITNDQKKLMSSNVQIVRQ
QSYSIMCVVKEEVIAYVVQLPIYGVIDTPCWKLHTSPLCTTDNKEGSNIC
LTRTDRGWYCDNAGSVSFFPQTETCKVQSNRVFCDTMNSLTLPTDVNLCN
TDIFNTKYDCKIMTSKTDISSSVITSIGAIVSCYGKTKCTASNKcRGIIK
TFSNGCDYVSNKGVDTVSVGNTLYYVNKLEGKALYIKGEPIINYYDPLVF
PSDEFDASIAQVNAKINQSLAFIRRSDELLSaiggyipeaprdgqayvrk
dgewvllstflgglvprgshhhhhhsawshpqfek bRSV RB94 sc9 DS-Cav1 A149C-Y458C:
[SEQ ID NO: 39]
MDSKGSSQKGSRLLLLLVVSNLLLPQGVVGQNITEEFYQSTCSAVSRGYL

SALRTGWYTSVVTIELSKIQKNVCNSTDSNVKLIKQELERYNNAVVELQS

LMQNEPASSSgsGSAlcSGVAVCKVLHLEGEVNKIKNALLSTNKAVVSLS

NGVSVLTFKVLDLKNYIDKELLPKNNHDCQISNIATVIEFQQKNNRLLEI

AREFSVNAGITTPLSTYMLTNSELLSLINDMPITNDQKKLMSSNVQIVRQ

QSYSIMCVVKEEVMAYVVQLPIYGVIDTPCWKLHTSPLCTTDNKEGSNIC

LTRTDRGWYCDNAGSVSFFPQAETCKVQSNRVFCDTMNSLTLPTDVNLCN

TDIFNAKYDCKIMTSKTDISSSVITSIGAIVSCYGKTKCTASNKNRGIIK

TFSNGCDYVSNRGVDTVSVGNTLYcVNKLEGKALYIKGEPIINYYDPLVF

PSDEFDASIAQVNAKINQSLAFIRRSDELLSAIGGYIPEAPRDGQAYVRK

DGEWVLLSTFLGGLVPRGSHHHHHHSAWSHPQFEK bRSV RB94 sc9 DS-Cav1 N183GC-N428C:
[SEQ ID NO: 40]
MDSKGSSQKGSRLLLLLVVSNLLLPQGVVGQNITEEFYQSTCSAVSRGYL

SALRTGWYTSVVTIELSKIQKNVCNSTDSNVKLIKQELERYNNAVVELQS

LMQNEPASSSgsGSAIASGVAVCKVLHLEGEVNKIKNALLSTNKAVVSLS gcGVSVLTFKVLDLKNYIDKELLPKLNNHDCQISNIATVIEFQQKNNRLL

EIAREFSVNAGITTPLSTYMLTNSELLSLINDMPITNDQKKLMSSNVQIV

RQQSYSIMCVVKEEVMAYVVQLPIYGVIDTPCWKLHTSPLCTTDNKEGSN

ICLTRTDRGWYCDNAGSVSFFPQAETCKVQSNRVFCDTMNSLTLPTDVNL

CNTDIFNAKYDCKIMTSKTDISSSVITSIGAIVSCYGKTKCTASNKcRGI

IKTFSNGCDYVSNRGVDTVSVGNTLYYVNKLEGKALYIKGEPIINYYDPL

VFPSDEFDASIAQVNAKINQSLAFIRRSDELLSAIGGYIPEAPRDGQAYV

RKDGEWVLLSTFLGGLVPRGSHHHHHHSAWSHPQFEK sc9-10_bRSV(RB94) DS-Cav1_fd_hp2_fp2_ig1:
[SEQ ID NO: 41]
MELLILKANAITTILTAVTFCFASGQNITEEFYQSTCSAVSRGYLSALRT

GWYTSVITIELSKIQKNVCNSTDSNVKLIKQELERYNNAVVELQSLMQST

PATGSGSAIASGVAVCKVLHLEGEVNKIKNALLSTNKAVVSLSNGVSVLI

TKVLDLKNYIDKELLPILNNHDCQISNIATVIEFQQKNNRLLEIAREFSV

NAGVTTPVSTYMLTNSELLSLINDMPITNDQKKLMSSNVQIVRQQSYSIM

CIIKEEVLAYVVQLPIYGVIDTPCWKLHTSPLCTTDNKEGSNICLTRTDR

GWYCDNAGSVSFFPQAETCKVQSNRVFCDTMNSLTLPTDVNLCNTDIFNA

KYDCKIMTSKTDVSSSVITSLGAIVSCYGKTKCTASNKNRGIIKTFSNGC

DYVSNRGVDTVSVGNTLYYVNKQEGKSLYIKGEPIINYYDPLVFPSDEFD

ASIAQVNAKINQSLAFIRRSDELLSAIGGYIPEAPRDGQAYVRKDGEWVL

LSTFLGGLVPRGSHHHHHHSAWSHPQFEK 391-2-site Ø' hRSV bovsurf DS-Cav1-BZGJ9 Long:
[SEQ ID NO: 42]
MDSKGSSQKGSRLLLLLVVSNLLLPQGVVGqniteefyqstcsavsrgyl salrtgwytsvitielsKIQKNVCKSTDSKVKLIKQELERYNNAVlelql lmqstpatnngsgsaiasgVAVCKylhlegevnkiknallstnkavvsls ngvsVLTFKvldlknyidkELLPKLNNHDCRISNIEtviefqqknnrlle itrefsvnagvttpvstymltnsellslindmpitndqkklmssnvqivr qqsySIMCllkeevlayvvqlpiygvidtpcwklhtsplcttdnkegsni cltrtdrgwycdnagsvsffpqaetckvqsnrvfcdtmnsrtlptdvnlc ntdifntkydckimtsktdvsssvitslgaivscygktkctasnknrgii ktfsngcdyvsnkgvdtvsygntlyyvnkqegkslyvkgepiinfydplv fpsdefdasisqvnekinqslafirrsdeLLhnvnagksttGGYIPEAPR

DGQAYVRKDGEWVLLSTFLGGLVPRGSHHHHHHSAWSHPQFEK

The sc designs sc9 and sc9-10 differed only in two residues, with a GS linker replacing $F_2F1$ cleavage and fusion residues 106-144 or 104-144, respectively. Of these nine designs, the two sc-only variants, namely bRSV 391-2 sc9 DS-Cav1Q98C-Q361C (SEQ ID NO: 32) and bRSV 391-2 sc9-10 DS-Cav1Q98C-Q361C (SEQ ID NO: 31) gave 7-9 fold higher expression yields as compared to the other variants (FIG. 7). However, size exclusion chromatography revealed that their respective sizes were compatible with aggregation. Therefore, three of the remaining five DS2 designs were chosen (each with sc topology and added interprotomer disulfides) with the highest yield (FIG. 7) for immunogenic, antigenic, physical, and structural characterizations.

Additionally, as benchmarks, the DS-Cav1 variant of each of the three strains and also the post-F form of each of the three strains (the latter created by removing the RSV F fusion loop residues 137-146), as previously described (McLellan, J. S., Yang, Y., Graham, B. S. & Kwong, P. D. Structure of respiratory syncytial virus fusion glycoprotein in the postfusion conformation reveals preservation of neutralizing epitopes. *Journal of virology* 85, 7788-7796 (2011)), were used. Altogether the sc-DS2, DS-Cav1 and post-F immunogens of each of the three strains totals nine final immunogen constructs (cf. FIG. 8). Namely, the following nine immunogen constructs were used: bRSV 391-2 DSCav1 (SEQ ID NO: 36), bRSV ATue51908 DSCav1 (SEQ ID NO: 37), bRSV 391-2 DSCav1 (SEQ ID NO: 38), bRSV 391-2 sc9-10 DS-Cav1Q98C-Q361C (SEQ ID NO: 31), bRSV 391-2 sc9 DS-Cav1 Q98C-Q361C (SEQ ID NO: 32), bRSV ATue51908 sc9-10 DS-Cav1 A149C-Y458C (SEQ ID NO: 33), bRSV 391-2 postF (SEQ ID NO: 45), bRSV ATue51908 postF (SEQ ID NO: 46), and bRSV 391-2 postF (SEQ ID NO: 47).

bRSV 391-2 postF:
[SEQ ID NO: 45]
MAATAMRMIISIIFISTYMTHITLCQNITEEFYQSTCSAVSRGYLSALRT

GWYTSVVTIELSKIQKNVCKSTDSKVKLIKQELERYNNAVIELQSLMQNE

PASFSRAKRGIPELIHYTRNSTKRFYGLMGKKRKRRAIASGVAVSKVLHL

EGEVNKIKNALLSTNKAVVSLSNGVSVLTSKVLDLKNYIDKELLPKVNNH

DCRISNIETVIEFQQKNNRLLEIAREFSVNAGITTPLSTYMLTNSELLSL

INDMPITNDQKKLMSSNVQIVRQQSYSIMSVVKEEVIAYVVQLPIYGVID

TPCWKLHTSPLCTTDNKEGSNICLTRTDRGWYCDNAGSVSFFPQAETCKV

QSNRVFCDTMNSLTLPTDVNLCNTDIFNTKYDCKIMTSKTDISSSVITSI

GAIVSCYGKTKCTASNKNRGIIKTFSNGCDYVSNKGVDTVSVGNTLYYVN

-continued

KLEGKALYIKGEPIINYYDPLVFPSDEFDASIAQVNAKINQSLAFIRRSD

ELLGLEVLFQGPHHHHHHHHSAWSHPQFEK bRSV ATue51908 postF:
[SEQ ID NO: 46]
MDSKGSSQKGSRLLLLLVVSNLLLPQGVVGQNITEEFYQSTCSAVSRGYL

SALRTGWYTSVVTIELSKIQKNVCKSTDSKVKLIKQELERYNNAVVELQS

LMQNEPASFSRAKRGIPELIHYTRNSTKKFYGLMGKKRKRRAVASGVAVS

KVLHLEGEVNKIKNALLSTNKAVVSLSNGVSVLTSKVLDLKNYIDKELLP

QVNNHDCRISNIETVIEFQQKNNRLLEIAREFSVNAGITTPLSTYMLTNS

ELLSLINDMPITNDQKKLMSSNVQIVRQQSYSIMSVVKEEVIAYVVQLPI

YGVIDTPCWKLHTSPLCTTDNKEGSNICLTRTDRGWYCDNAGSVSFFPQT

ETCKVQSNRVFCDTMNSLTLPTDVNLCNTDIPNTKYDCKIMTSKTDISSS

VITSIGAIVSCYGKTKCTASNKNRGIIKTFSNGCDYVSNKGVDTVSVGNT

LYYVNKLEGKALYIKGEPIINYYDPLVFPSDEFDASIAQVNAKINQSLAF

IRRSDELLGLEVLFQGPHHHHHHHHSAWSHPQFEK bRSV RB94 postF:
[SEQ ID NO: 47]
MDSKGSSQKGSRLLLLLVVSNLLLPQGVVGQNITEEFYQSTCSAVSRGYL

SALRTGWYTSVVTIELSKIQKNVCNSTDSNVKLIKQELERYNNAVVELQS

LMQNEPASSSRAKRGIPELIHYKRNSTKKFYGLMGKKRKRRAIASGVAVS

KVLHLEGEVNKIKNALLSTNKAVVSLSNGVSVLTSKVLDLKNYIDKELLP

KVNNHDCQISNIATVIEFQQKNNRLLEIAREFSVNAGITTPLSTYMLTNS

ELLSLINDMPITNDQKKLMSSNVQIVRQQSYSIMSVVKEEVMAYVVQLPI

YGVIDTPCWKLHTSPLCTTDNKEGSNICLTRTDRGWYCDNAGSVSFFPQA

ETCKVQSNRVFCDTMNSLTLPTDVNLCNTDIFNAKYDCKIMTSKTDISSS

VITSIGAIVSCYGKTKCTASNKNRGIIKTFSNGCDYVSNRGVDTVSVGNT

LYYVNKLEGKALYIKGEPIINYYDPLVFPSDEFDASIAQVNAKINQSLAF

IRRSDELLGLEVLFQGPHHHHHHHHSAWSHPQFEK

Figure 9:
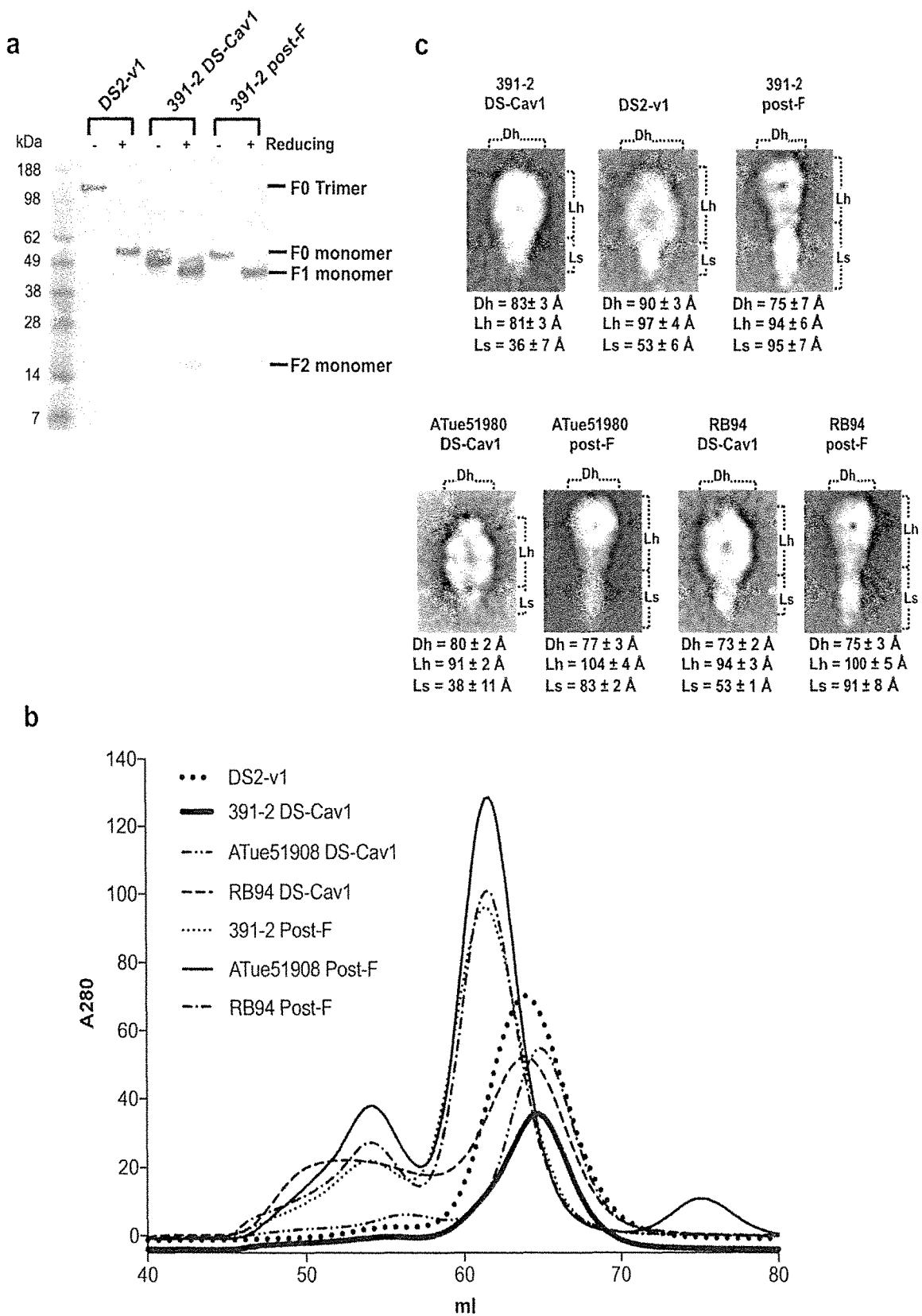
FIG. 9 shows protein purification and electron microscopy analysis. a, Representative SDS PAGE gel analysis for engineered bRSV F glycoproteins. DS2-v1 (391-2 sc9 DS-Cav1 Q98C-Q361, 391-2 DS-Cav1 and 391-2 post-F. Proteins are observed to collapse to smaller molecular weight bands in the presence of a reducing agent, confirming disulfide bond formation. b, Gel filtration chromatograms of bRSV F glycoprotein variants. Variants stabilized in pre-F conformation had longer retention times than variants with post-F conformation. c, Negative stain electron microscopy of pre-fusion and post-fusion forms of bovine RSV F. Images shown here are 2D class averages of variants with measured dimensions. Dh, diameter of head; Lh, length of head; Ls, length of stalk.

All nine of these constructs gave expression yields of 2-5 mg/L except for ATue51908 sc9-10 DS-Cav1 A149C-Y458C (0.24 mg/L) and RB94 DS-Cav1 (0.76 mg/L) (FIG. 8), and the post-F forms consistently gave the highest expression (3-5 mg/L). After purification on nickel and Strep-Tactin affinity columns, and subsequent cleavage of C-terminal affinity tags, all nine immunogens behaved well when analyzed by size-exclusion chromatography, eluting with peaks consistent with trimer formation (FIG. 9 a, b), with post-F forms eluting at slightly larger sizes than pre-F forms due to their elongated shape (McLellan, J. S., et al. Structure of RSV fusion glycoprotein trimer bound to a prefusion-specific neutralizing antibody. Science 340, 1113-1117 (2013); McLellan, J. S., Yang, Y., Graham, B. S. & Kwong, P. D. Structure of respiratory syncytial virus fusion glycoprotein in the postfusion conformation reveals preservation of neutralizing epitopes. Journal of virology 85, 7788-7796 (2011)).

Example 2: Antigenic Characteristics of bRSV F Immunogens

The antigenicity of each purified immunogen was evaluated with biolayer interferometry to assess recognition by the antigenic site Ø-directed mAb D25 (McLellan, J. S., et al. Structure of RSV fusion glycoprotein trimer bound to a prefusion-specific neutralizing antibody. Science 340, 1113-1117 (2013)), antigenic site II-directed mAb Mota (McLellan, J. S., et al. Structural basis of respiratory syncytial virus neutralization by motavizumab. Nat Struct Mol Biol 17, 248-250 (2010)) and quaternary-specific mAbs AM14 (Gilman, M. S. A., et al. Characterization of a Prefusion-Specific Antibody That Recognizes a Quaternary, Cleavage-Dependent Epitope on the RSV Fusion Glycoprotein. PloS pathogens 11, e1005035 (2015)) and MPE8 (Corti, D., et al. Cross-neutralization of four paramyxoviruses by a human monoclonal antibody. Nature 501, 439-443 (2013)) (FIG. 8). The three pre-F-specific mAbs, D25, MPE8 and AM14 recognized all six immunogens containing pre-F stabilizing mutations, confirming stabilization of their pre-F conformations. Moreover, recognition by the quaternary-specific mAbs MPE8 and AM14 substantiated the formation of native-like trimers. In contrast, these mAbs did not recognize any of the post-F immunogens. As expected, Mota recognized all nine immunogens since its site II epitope is not affected by pre- and post-F conformational changes. Notably, all mAbs except for D25, recognized the pre-F immunogens with nanomolar affinity (0.2-12.8 nM) even though these mAbs were elicited by hRSV F. D25 recognized the pre-F immunogens with affinities ranging from 0.4-420 nM, suggesting that antigenic site Ø may be adversely effected by some of the stabilizing mutations. Interestingly, the three DS-Cav1-only immunogens which also had the least number of mutations had the highest affinity for D25.

Example 3: Physical Characteristics of bRSV F Immunogens

Next, the stability of purified immunogens was assessed by subjecting them to high temperature, pH extremes, osmolarity extremes and cycles of freeze-thaw and quantifying their subsequent recognition by D25 (FIG. 8). All nine immunogens were observed to generally tolerate pH and osmolarity extremes and freeze-thaw cycles. The three DS-Cav1-only immunogens, 391-2 DS-Cav1, Atue51908 DS-Cav1 and RB94 DS-Cav1, were most susceptible to physical extremes and lost 25-60% of their D25 reactivity upon exposure to high (3M) osmolarity. Curiously, the majority of immunogens actually increased reactivity to D25 after exposure to high pH. Although none of the DS-Cav1-only immunogens were able to survive exposure to high temperature (70° C.), all three of the DS2 immunogens tolerated high temperature. Not surprisingly, all three post-F immunogens were heat resistant.

Example 4: Structural Characteristics of bRSV F Immunogens

To further confirm the pre- and post-F conformations of the engineered bRSV F immunogens, they were examined by negative stain electron microscopy (EM), followed by reference-free 2D class averaging of the images (FIG. 9c). Each of the pre-F immunogens displayed bulb-like trimer structures with a short stem-like structure at one end, whereas the post-F immunogens displayed longer and more slender structures each of which were consistent with known crystal structures of pre- and post-F hRSV F (McLellan, J. S., et al. Structure-based design of a fusion glycoprotein vaccine for respiratory syncytial virus. Science 342, 592-598 (2013); McLellan, J. S., et al. Structure of RSV fusion glycoprotein trimer bound to a prefusion-specific neutralizing antibody. *Science* 340, 1113-1117 (2013); McLellan, J. S., Yang, Y., Graham, B. S. & Kwong, P. D. Structure of respiratory syncytial virus fusion glycoprotein in the postfusion conformation reveals preservation of neutralizing epitopes. *Journal of virology* 85, 7788-7796 (2011); Swanson, K. A., et al. Structural basis for immunization with postfusion respiratory syncytial virus fusion F glycoprotein (RSV F) to elicit high neutralizing antibody titers. *Proceedings of the National Academy of Sciences of the United States of America* 108, 9619-9624 (2011)).

The crystal structures of two pre-F-stabilized bRSV F immunogens, ATue51908 DS-Cav1 (SEQ ID NO: 37) and 391-2 DS-Cav1 sc9 Q98C-Q361C (SEQ ID NO: 32) were determined to 2.65 and 3.6 Å resolution, respectively (FIG. 10). ATue51908 DS-Cav1 crystallized in a monoclinic lattice not previously observed with hRSV F immunogens. The overall structure of ATue51908 DS-Cav1 was similar to that of hRSV DS-Cav1 (McLellan, J. S., et al. Structure-based design of a fusion glycoprotein vaccine for respiratory syncytial virus. *Science* 342, 592-598 (2013)) with a root mean square deviation (rmsd) of 1.0 Å for 437 Cα atoms excluding residues 209-215 in a membrane distal loop adjacent to antigenic site Ø (FIG. 11a). In this crystal form, the appended C-terminal foldon trimerization domain was visible in the electron density map, although its three-fold axis was misaligned by ~17 degrees relative to the three-fold axis of bRSV pre-F due to crystal packing (FIG. 11a). The introduced DS and S190F mutations showed strong electron density, while V207L showed weaker but detectable electron density (FIG. 11a). The DS2 immunogen 391-2 DS-Cav1 sc9 Q98C-Q361C (SEQ ID NO: 32) crystallized in the cubic lattice commonly observed with hRSV F pre-F immunogens and like ATue51908 DS-Cav1, its structure was similar to hRSV DS-Cav1 with an rsmd of 1.1 Å for 435 Cα atoms. Although side chains for the DS-Cav1 mutations were not clearly apparent in the electron density, partly due to the 3.6-Å resolution of structure, the DS2 interprotomer Q98C-Q361C disulfide and nearby sc linker showed traceable electron density (FIG. 11b). Comparison of the two bRSV pre-F-stabilized structures at the backbone level revealed high structural similarity with an rmsd of 0.9 Å between 434 equivalent Cα atoms excluding the $F_2F_1$ linker region. The greatest structural differences between the hRSV and bRSV pre-F immunogens were observed in residues 206-215 at the apical loop between α4 and α5 near antigenic site Ø (FIGS. 11a, b, left panels), which is also the region of highest sequence divergence (50% identity) between the two species (FIG. 1). These structural and sequence difference may explain the lower binding affinity of D25 to bRSV pre-F (FIG. 8) relative to hRSV pre-F (McLellan, J. S., et al. Structure-based design of a fusion glycoprotein vaccine for respiratory syncytial virus. *Science* 342, 592-598 (2013)).

Example 5: Immunogenic Characterization of bRSV F Immunogens in Mice

Figure 12:
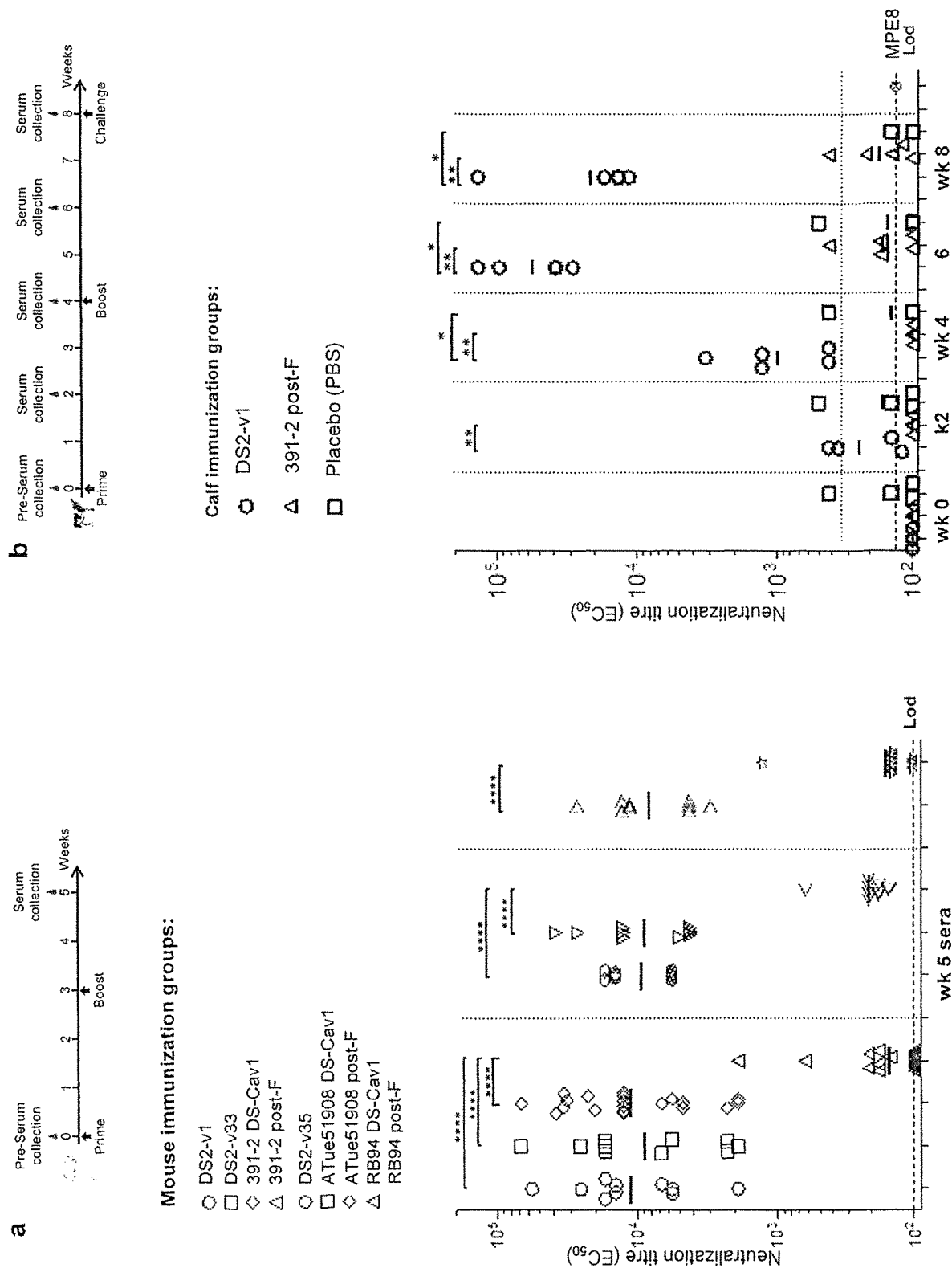
FIG. 12 shows serum neutralizing antibody titers elicited by engineered bRSV F pre-F trimers. Pre-F-stabilized bRSV F glycoproteins elicited geometric mean $EC_5$s neutralization titers between 43-344 fold higher than post-F in mice and calves respectively. Schematic immunization procedures for bRSV F variants in seronegative mice (a) and calves (b). Neutralization titer from each animal is shown as an individual dot, and geometric means are indicated by black horizontal lines. Immunization groups are shape-coded. Lod, limit of detection (titer=100) is indicated with a horizontal dashed line. Vertical dotted lines separate immunogen strains in (a) and weeks post prime in (b). Serum antibody binding ELISA data is summarized in FIG. 14. P values were determined by two-tailed Mann-Whitney tests. * indicates P≤0.05,  indicates P≤0.01, * indicates P≤0.001 and **** indicates P≤0.0001. There are 10 mice per group for the mouse immunizations. For calf immunizations, the DS2-v1 (391-2 sc9 DS-Cav1Q98C-Q361C) and post-F (391-2 post-F) groups each contained 5 animals and the placebo group contained 4 animals.
Figure 14:
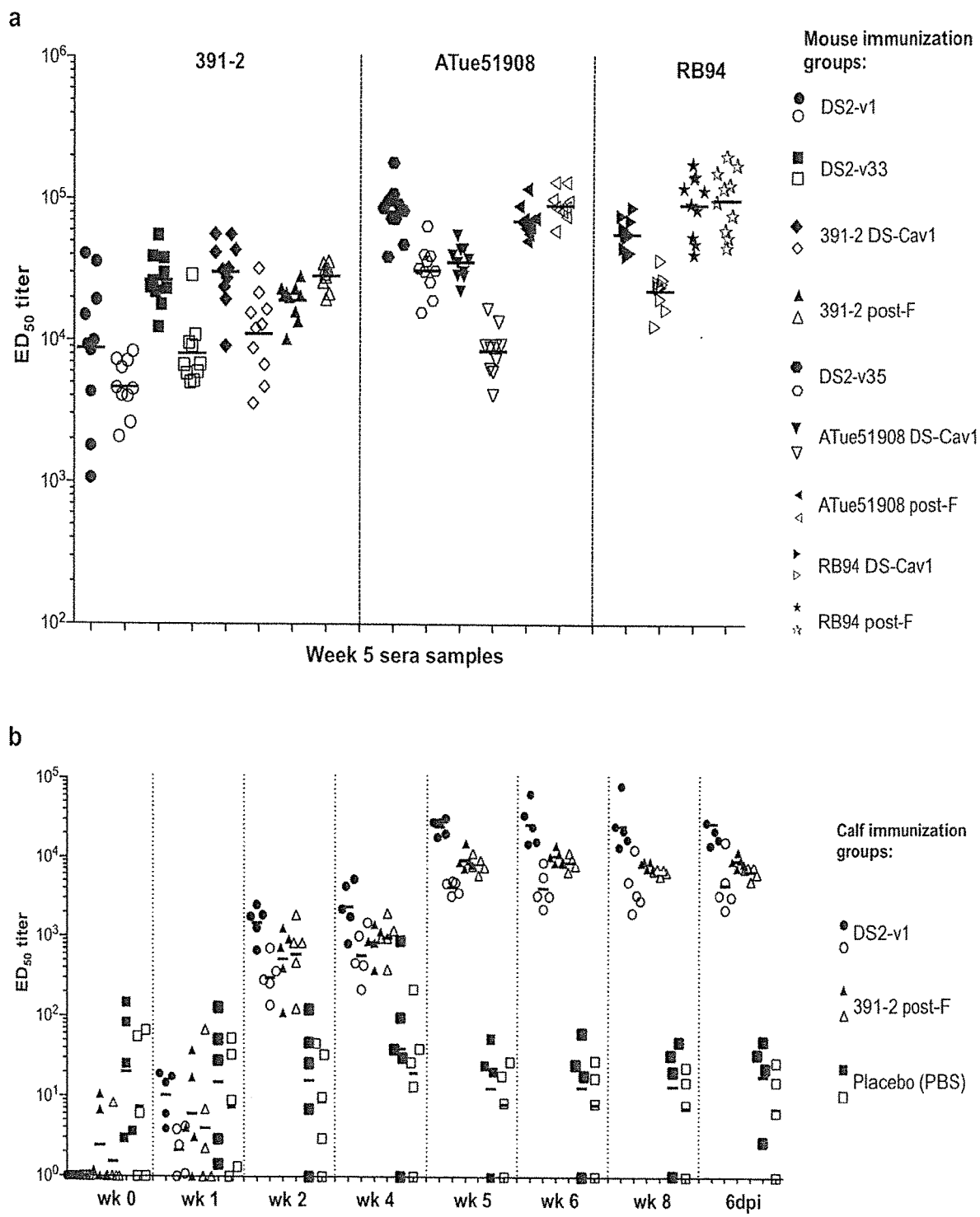
FIG. 14 shows immunogenicity of engineered bovine RSV F pre-F trimers. ELISA binding titers of week five sera from mice (a) and longitudinal sera samples from calves (b) immunized with bRSV F variants. titers from each animal are represented by shape-coded symbols. Solid symbols indicate sera recognition of immobilized 391-2 sc9 DS-Cav1Q98C-Q361C RSV F trimers and open symbols indicate recognition of immobilized 391-2 post-F RSV F trimers. Vertical dotted lines separate immunogen strains in (a) and weeks post prime in (b). 6 dpi, 6 days post inoculation for calf challenge study in (b). Geometric mean titers are indicated by black horizontal lines. Calf immunization groups: DS2-v1 (391-2 sc9 DS-Cav1 Q98C-Q361C), 391-2 post-F and placebo (PBS).

To evaluate immunogenicity, each of the nine bRSV F immunogens were used to immunize a group of 10 CB6F1/J mice. Each immunogen dose comprised 10 g of protein adjuvanted with 50 g of polyinosinic:polycytidylic acid (PolyI:C). Mice were primed and boosted intramuscularly at weeks 0 and 3 respectively. Analysis of week five sera revealed geometric mean reciprocal $IC_{50}$ neutralization titers of 6,880-11,453 for pre-F immunogen-immunized mice, which were 33- to 55-fold higher (P≤0.0001) than the titers (geometric mean 100-210) observed for the post-F immunogen-immunized mice (FIG. 12a and FIG. 13). Neutralization titers elicited from pre-F-immunized mice were 82-110 fold greater than the calibrated protective titer of 100 (McLellan, J. S., et al. Structure-based design of a fusion glycoprotein vaccine for respiratory syncytial virus. *Science* 342, 592-598 (2013)). 391-2 DS-Cav1 sc9 Q98C-Q361C (SEQ ID NO: 32) elicited the highest titers (geometric mean 11,453). Thus the 1000-fold difference in D25 mAb binding affinities observed between various pre-F immunogens (FIG. 8) did not appear to impact the neutralization titers of elicited sera. To gauge the overall immunogenicity of each immunogen, the sera binding response to pre-F and post-F immunogens was assessed using an ELISA (FIG. 14a). The binding titers of pre-F elicited sera to the six pre-F immunogens were statistically comparable to each other with geometric mean endpoint binding titers ranging from 4,687 to 100,323. Intriguingly, sera from 391-2 sc9 Q98C-Q361C (SEQ ID NO: 32)-immunized mice displayed the lowest titers for pre-F immunogen even though it had the highest titers of neutralizing antibodies. As expected, sera elicited by pre-F immunogens displayed lower binding titers to post-F immunogens.

Example 6: Immunogenic Characterization of bRSV F Immunogens in Calves

Figure 17:
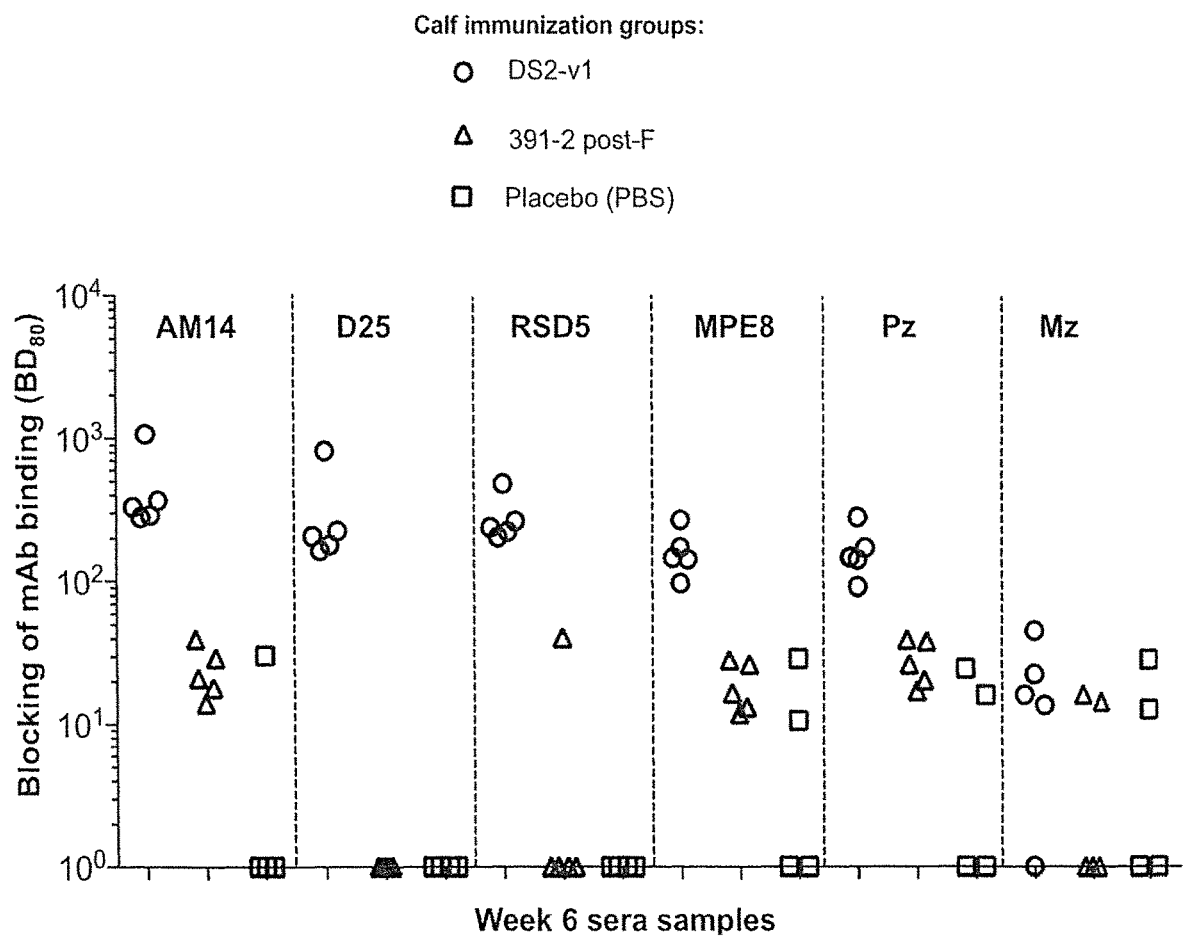
FIG. 17 shows blocking of neutralizing antibody binding. ELISA plates coated with 391-2 sc9 DS-Cav1Q98C-Q361C pre-F bRSV F trimer were incubated with serial dilutions of week 6 calf sera followed by biotinylated mAbs. The serum dilution that blocked mAb binding by 80% (defined as BD80) was determined. Higher BD80 values indicate the presence of sera that specifically blocks the respective mAbs. Vertical dotted lines separate the six different biotinylated mAbs (indicated above) used for pre-F trimer detection. Blocking of mAb binding titer of serum from each animal are represented by shape-coded symbols. Calf immunization groups: DS2-v1 (391-2 sc9 DS-Cav1Q98C-Q361C), 391-2 post-F and placebo (PBS).

To investigate the effectiveness of pre-F-stabilized RSV F vaccines in bRSV-seronegative calves, the highly stable DS2 immunogen (391-2 DS-Cav1 sc9 Q98C-Q361C; SEQ ID NO: 32), which in mice elicited the highest neutralization titers (geometric mean reciprocal $IC_{50}$ 11,453), was selected. As controls post-F 391-2 were chose and phosphate buffered saline (PBS) was used to immunize a placebo group. Groups of five 3-6 week old male calves (FIG. 15) were immunized twice at weeks 0 and 4, and sera were collected two weeks after each immunization. Each injection consisted of 50 g protein in 0.6 ml PBS adjuvanted with 1.4 ml of ISA 71G. The reciprocal $IC_{50}$ neutralization titers from the DS2-immunized calves were observed to increase exponentially at weeks 2, 4 and 6 relative to week 0, resulting in a final geometric mean titer of 56,055 two weeks after the boost (FIG. 12b and FIG. 16). By week 8, however, four weeks after the boost, titers had dropped to a geometric mean of 21,849. In contrast, by week 8, post-F immunogen elicited minimal titers (geometric mean 172) within the same range as two of the saline control-immunized calves (141 and 100 respectively), which appeared to have maternally-derived serum antibodies at the start of the study. Results from ELISA analysis of sera from DS2-immunized calves mirrored the neutralization titers with titers steadily increasing and then slightly decreasing from weeks 6 to 8 (FIG. 14b). As expected, sera from 391-2 post-F-immunized calves followed a similar trend, reaching geometric mean titers approximately 3.0 and 3.8-fold lower than pre-F by weeks 6 and 8 respectively. It is also clear from the neutralization data (FIG. 12b) that post-F elicited significantly lower levels of neutralizing antibodies. Not surprisingly, sera elicited by 391-2 pre-F immunogen displayed lower binding titers to 391-2 post-F immunogen and 391-2 post-F-elicited sera recognized both pre- and post-F with comparable titers. Results from a competition ELISA showed that the sera from DS2-immunized calves competed with the broadly neutralizing mAbs AM14, D25, RSD5, MPE8 and palivizumab (pali), suggesting that antigenic sites 0, II and V were all targeted (FIG. 17). Although the mAb mota showed considerably less competition than the other antigenic site II mAb, pali, it's high 34.6 µM affinity (Wu, H., et al. Development of motavizumab, an ultra-potent antibody for the prevention of respiratory syncytial virus infection in the upper and lower respiratory tract. Journal of molecular biology 368, 652-665 (2007)) for RSV F likely limited sera competition. As expected, sera from 391-2 post-F-immunized calves competed to a much lower extent with the pre-F-specific mAbs AM14, RSD5, MPE8, and did not compete at all with D25. Interestingly, two mAbs compatible with post-F RSV F, mota and pali also competed to a much lower extent with post-F-elicited sera. This suggests that a minority of the post-F-elicited sera was directed against site II.

Example 7: bRSV Challenge of Immunized Calves

Figure 18:
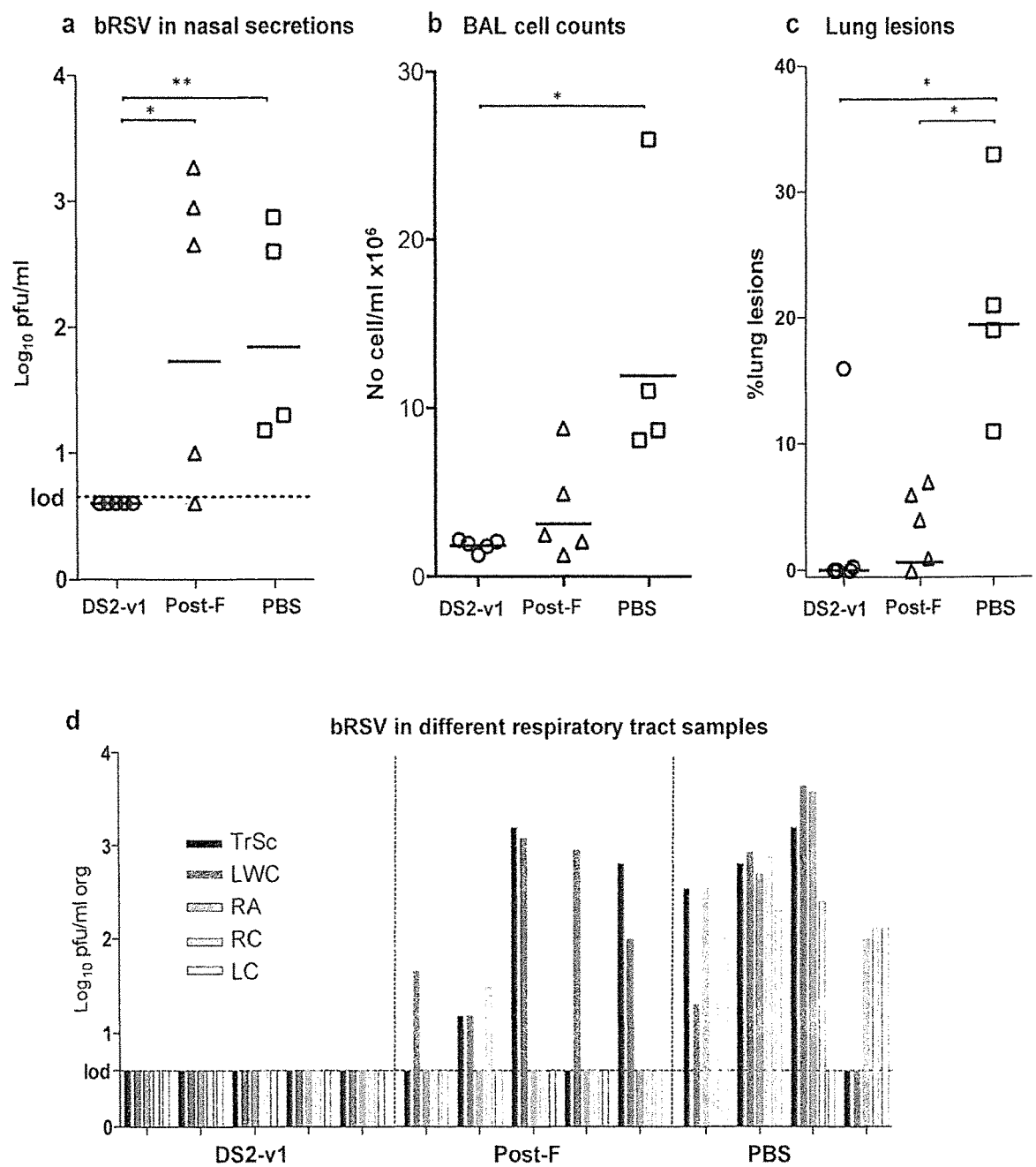
FIG. 18 shows the effect of vaccination on bRSV replication in the respiratory tract of calves and on pulmonary pathology. a, Peak titers of bRSV in nasal secretions. Each dot represents the virus titer from nasopharyngeal swabs obtained at day 6 post challenge. Groups of 5 calves were vaccinated with DS2-v1 (391-2 DS-Cav1 sc9 Q98C-Q361C) and Post-F (391-2 post-F), and 4 calves were vaccinated with PBS (Placebo in adjuvant). Geometric mean peak titers are indicated by black horizontal lines. b, Effect of F protein vaccination on numbers of cells in BAL, 6 days after challenge with bRSV. c, Analysis of percentage of lung with macroscopic lung lesions from photographs of lungs. d, bRSV titers in samples of tracheal epithelium (TrSc), lung wash cells (LWC), and homogenates of samples taken from the right apical (RA), right cardiac (RC) and left cardiac (LC) lobes of the lung, 6 days post-infection. Each bar represents the bRSV titer of a lung sample. Each group of five bars is from an individual calf. Titers are expressed as $\log_{10}$ pfu/ml or g. The limit of detection (lod) is $\log_{10}$ 0.7 pfu/ml (a and d). Virus titers for each individual testing point are listed in FIG. 15. P values were determined by two-tailed Mann-Whitney tests. ns indicates not significant (P>0.05), * indicates P≤0.05,  indicates P≤0.01, * indicates P≤0.001 and **** indicates P≤0.0001
Figure 20:
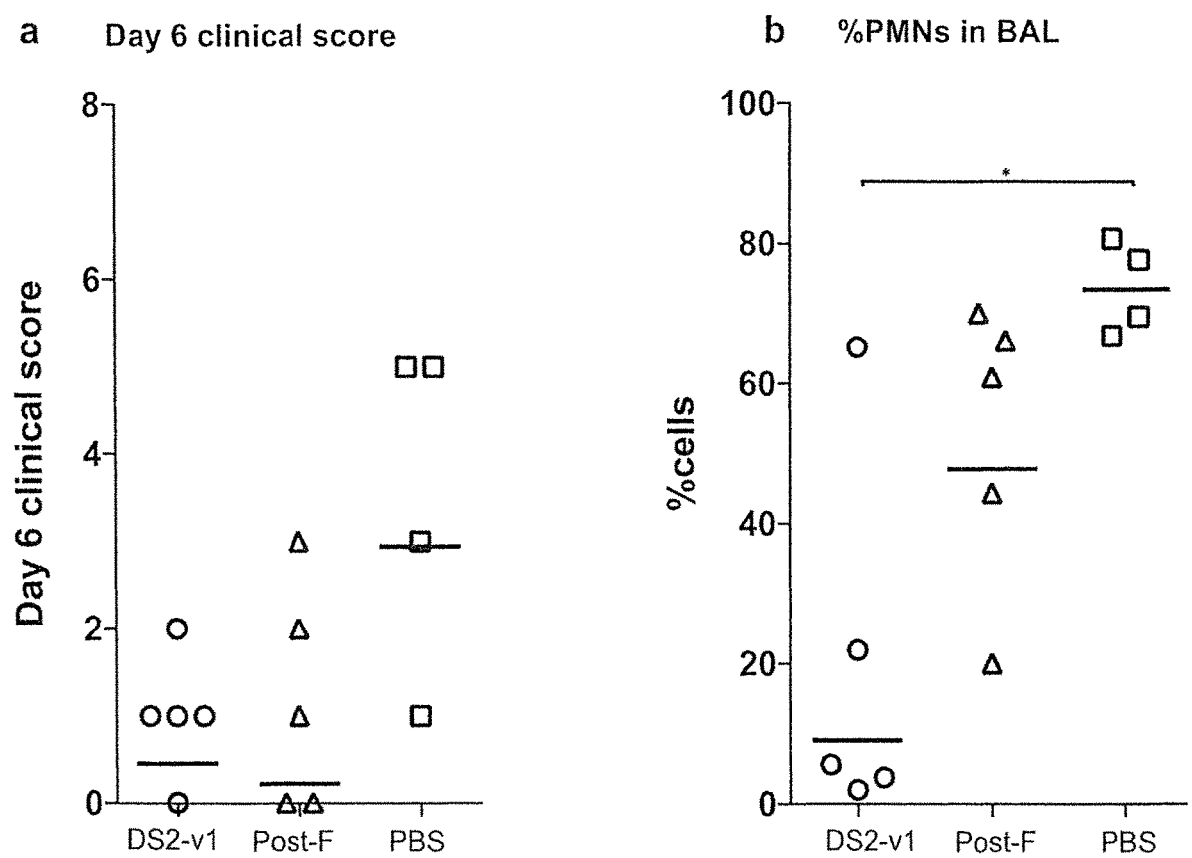
FIG. 20 shows viral titers as a measure of bRSV replication in the respiratory tract of calves.

Next, all calves were challenged by intranasal and intratracheal routes with the heterologous Snook strain of bRSV, four weeks after the boost. Calves were monitored daily for clinical signs of disease and for viral titers in the nasopharynx for six days after challenge. At day six after challenge, calves were euthanized and bronchoalveolar lavage (BAL) and lung biopsies from three regions of the lung were obtained to determine viral titers, neutrophil infiltration, and the extent of microscopic and macroscopic lesions. Remarkably, calves vaccinated with DS2 (391-2 DS-Cav1 sc9 Q98C-Q361C; SEQ ID NO: 32) had no detectable bRSV viral titers in nasopharyngeal secretions (FIG. 18a and FIG. 19). No detectable bRSV titers were observed from a postmortem lung wash, samples of tracheal epithelium, right apical, right cardiac or left cardiac regions of the lung (FIG. 12d and FIG. 20). In contrast, geometric mean viral titers of up to 1.78 and 1.67 ($\log_{10}$ pfu/ml) were observed in the daily nasal secretions from the post-F and PBS vaccinated calves respectively. Likewise, virus was isolated post mortem from BAL cells of all of the post-F-immunized and PBS-immunized calves with the greatest extent of lung virus replication in the PBS-immunized control animals (FIG. 18d). Thus, all DS2-immunized calves were protected from bRSV viral replication in both the upper and lower respiratory tracts.

Figure 25:
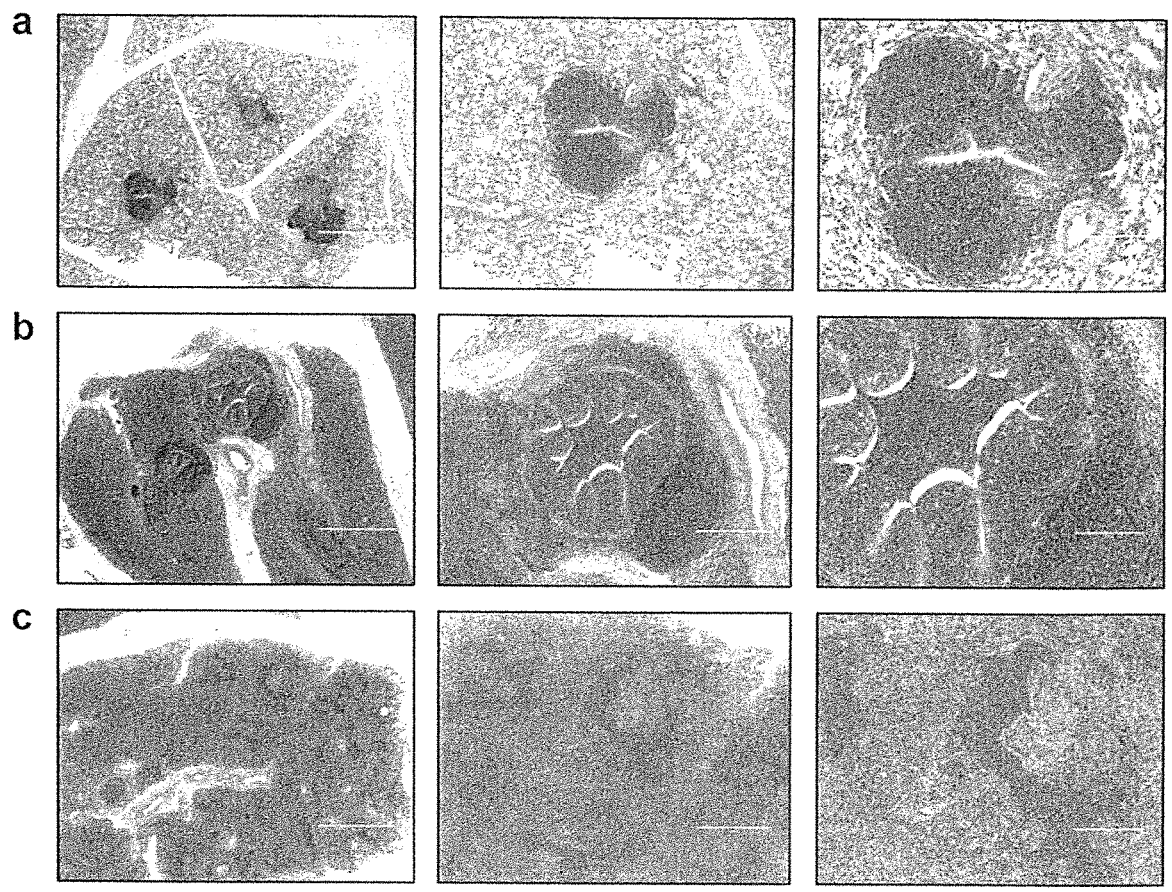
FIG. 25 shows the histology of lung sections from vaccinated calves. Haematoxylin and eosin stained lung sections (left panel 4× objective, middle panel 10× objective and right panel 20× objective) from calves vaccinated with 50 μg of adjuvanted pre-F (a), post-F (b) and PBS (c), 6 days after challenge with bRSV. White scale bars represent 1000 μm (left panel), 400 μm (middle panel) 200 μm (right panel).

Furthermore, four out of five of the DS2-immunized calves were also protected from clinical signs of disease, lung inflammation and macroscopic lung lesions (FIG. 18b-c, FIG. 21 and FIG. 22-24). Clinical scores, based mainly on differences in respiratory rate and body temperature, were minimal for most the pre-F- and post-F-immunized calves. Scores trended higher for the PBS-immunized controls, but were not significantly different from the other two groups (FIG. 22-23). However, both respiratory rate (RR) and body temperature increased in all PBS-immunized calves, 6 days after bRSV challenge, whereas the RR increased in only 2 post-F-immunized and one pre-F-immunized calves at this time (FIG. 21a). Although the one calf in the pre-F-immunized group that had developed a raised RR and body temperature also exhibited signs of lung inflammation, the geometric mean number of cells observed in the BAL, the percentage of polymorph nuclear neutrophils (PMNs) in BAL, and the percentage of macroscopic lung lesions were all statistically lower than in the placebo group (FIG. 18b-c and FIG. 22-24). The post-F-immunized calves displayed intermediate levels of lung inflammation. Although the extent of macroscopic lung lesions in the post-F-immunized calves was less that in the placebo group, the percentage of PMNs in BAL was similar to that seen in BAL from calves in the placebo group. Microscopic lung lesions in the placebo group, six days post challenge, were typical of bRSV bronchiolitis and alveolitis and were characterized by epithelial hypertrophy of small bronchioles, bronchiolar exudate containing desquamated epithelial cells, neutrophils and macrophages, and thickening of alveolar walls due to infiltration by mononuclear cells and granulocytes (FIG. 25c). Bronchiolitis and alveolitis were also seen in in three of the post-F-immunized calves (FIG. 25b). In addition, a peribronchiolar lymphoreticular hyperplasia was seen in all lung sections from these animals. In contrast, bronchiolitis and alveolitis were absent from all but one of the DS2-immunized calves, and the histopathology was essentially restricted to a peribronchiolar lymphoreticular hyperplasia (FIG. 25a).

TABLE OF SEQUENCES AND SEQ ID NUMBERS (SEQUENCE LISTING):

| SEQ ID NO | Sequence | Remarks |
|---|---|---|
| SEQ ID NO: 1 | maatamrmiisiifistymthitlcqniteefyqstcsaysrgylsalr tgwytsvvtielskiqknvckstdskvklikqelerynnavielqsl mqnepasfsrakrgipelihytrnstkrfyglmgkkrkrrflgfllgig saiasgvavskvlhlegevnkiknallstnkavvslsngvsvltskvl dlknyidkellpkvnnhdcrisnietviefqqknnrlleiarefsvn agittplstymltnsellslindmpitndqkklmssnvqivrqqsys imsvvkeeviayvvqlpiygvidtpcwklhtsplcttdnkegsni cltrtdrgwycdnagsvsffpqaetckvqsnrvfcdtmnsltlptd vnlcntdifntkydckimtsktdisssvitsigaivscygktkctasn knrgiiktfsngcdyvsnkgvdtvsvgntlyyvnklegkalyikge piinyydplvfpsdefdasiaqvnakinqslafirrsdellhsvdvg ksttnvvittiiivivvvilmliavgllfycktrstpimlgkdqlsginnl sfsk | bRSV 391-2 F0 (GenBank Acc. No: AAA42808.1) |
| SEQ ID NO: 2 | mattamrmiisiifistyvthitlcqniteefyqstcsavsrgylsalrt gwytsvvtielskiqknvckstdskvklikqelerynnavvelqsl mqnepasfsrakrgipelihytrnstkkfyglmgkkrkrrflgfllgi gsavasgvavskvlhlegeynkiknallstnkavvslsngvsvlts kvldlknyidkellpqynnhdcrisnietviefqqknnrlleiaref svnagittplstymltnsellslindmpitndqkklmssnvqivrq qsysimsvvkeeviayvvqlpiygvidtpcwklhtsplcttdnke gsnicltrtdrgwycdnagsvsffpqtetckvqsnrvfcdtmnsltl ptdvnlcntdifntkydckimtsktdisssvitsigaivscygktkct asnknrgiiktfsngcdyvsnkgvdtvsvgntlyyvnklegkalyi | bRSV ATue51908 F0 (NCBI reference sequence: NP_048055.1) |

TABLE OF SEQUENCES AND SEQ ID NUMBERS (SEQUENCE LISTING):

| SEQ ID NO | Sequence | Remarks |
|---|---|---|
| | kgepiinyydplvfpsdefdasiaqvnakinqslafirrsdellhsv dvgksttnvvittiiivivvvilmliavgllfycktkstpimlgkdqls ginnlsfsk | |
| SEQ ID NO: 3 | matttmrmiisiiiifiyvqhitlcqniteefyqstcsavsrgylsalrt gwytsvvtielskiqknvcnstdsnvklikqelerynnavvelqsl mqnepasssrakrgipelihykrnstkkfyglmgkkrkrrflgfllg igsaiasgvavskvlhlegevnkiknallstnkavvslsngvsvlts kvldlknyidkellpkvnnhdcqisniatviefqqknnrlleiaref svnagittplstymltnsellslindmpitndqkklmssnvqivrq qsysimsvvkeevmayvvqlpiygvidtpcwklhtsplcttdnk egsnicltrtdrgwycdnagsvsffpqaetckvqsnrvfcdtmns ltlptdvnlcntdifnakydckimtsktdisssvitsigaivscygkt kctasnknrgiiktfsngcdyvsnrgvdtvsvgntlyyvnklegka lyikgepiinyydplvfpsdefdasiaqvnakinqslafirrsdell hsvdvgksttnvvittiiivivvvilmliavgllfyskrtstpimlgkd qlsginnlsfsk | bRSV RB94 F0 (GenBank Acc. No: CAN90052.1) |
| SEQ ID NO: 4 | mattamrmiisiifistyvthitlcqniteefyqstcsavsrgylsalrt gwytsvvtielskiqknvcnstdsnvklikqelerynnavvelqsl mqnepasssrakrgipelihykrnstkkfyglmgkkrkrrflgfllg igsaiasgvavskvlhlegevnkiknallstnkavvslsngvsvlts kvldlknyidkellpkvnnhdckisniatviefqqknnrlleiaref svnagittplstymltnsellslindmpitndqkklmssnvqivrq qsysimsvvkeevmayvvqlpiygvidtpcwklhtsplcttdnk egsnicltrtdrgwycdnagsvsffpqaetckvqsnrvfcdtmns ltlptdvnlcntdifnakydckimtsktdisssvitsigaivscygkt kctasnknrgiiktfsngcdyvsnrgvdtvsvgntlyyvnklegka lyikgepiinyydplvfpsdefdasiaqvnakinqslafirrsdell hsvdvgksttnvvittiiivivvvilmliavgllfyskrtstpimlgkd qlsginnlsfsk | bRSV RB94 F-11 F0 (GenBank Acc. No: BAA00798.1) |
| SEQ ID NO: 5 | matttmrmiisiilistyvphitlcqniteefyqstcsavsrgylsalrt gwytsvvtielskiqknvcngtdskvklikqelerynnavaelqsl mqneptsssrakrgipesihytrnstkkfyglmgkkrkrrflgfllgi gsaiasgvavskvlhlegevnkiknallstnkavvslsngvsvltsk vldlknyidkellpkvnnhdcrisniatviefqqknnrlleiarefsv nagittplstymltnsellsiindmpitndqkklmsvcqivrqqsys imsvlreviayvvqlplygvidtpcwklhtsplcttdnkegsniclt rtdrgwycdnagsvsffpqaetckvqsnrvfcdtmnsltlptdvnl cntdifnskydckimtsktdisssvitsigaivscygktkctasnknr giiktfsngcdvsnkgvdtvsvgntlyyvnklegkalyikgepiin yynplvfpsdefdasiaqvnakinqslafirrsdellhsvdvgkstt nvvittiiivivvvilmlitvgllfycktrstpimlgkdqlssinnlsfsk | bRSV A51908 F0 (GenBank Acc. No: AAA42804.1) |
| SEQ ID NO: 6 | mrmiisiilistyvphitlcqniteefyqstcsaysrgylsalrtgwyts vvtielskiqknvcngtdskvklikqelerynnavvelqslmqne ptsssrakrgipesihytrnstkkfyglmgkkrkrrflgfllgigsaias gvayskvlhlegevnkiknallstnkavvslsngvsvltskvldlkn yidkkllpkvnnhdcrisnietviefqqknnrlleiarefsvnagitt plstymltnsellslindmpitndqkklmssnvqivrqqsysims vvkeeviayvvqlpiygvidtpcwkvhtsplcttdnkegsnicltr tdrgwycdnagsvsffpqaetckvqsnrvfcdtmnsltlptdvnl cntdifntkydckimtsktdisssvitsigaivscygktkctasnknr giiktfsngcdyvsnkgvdtvsvgntlyyvnklegkalyikgepiin yynplvfgtyefdasiaqvnak | bRSV A375 F0 (GenBank Acc. No: ACL80037.1) |
| SEQ ID NO: 7 | mgttamrmvisiifistyvthitlcqniteefyqstcsaysrgylsalrt gwytsvvtielskiqknvckstdskvklikqelerynnavielqsl mqnepasfsrakrgipelihyprnstkrfyglmgkkrkrrflgfllgi gsaiasgvayskvlhlegevnkiknallstnkavvslsngvsvltsk yldlknyidkellpkvnnhdcrisnigtviefqqknnrlleiarefsv nagittplstymltnsellslindmpitndqkklmssnvqivrqqs ysimsvvkeeviayevqlpiygvidtpcwkihtsplcttdnkegs nicltrtdrgwycdnagsvsffpqaetckvqsnrvfcdtmnsltlpt dvnlcntdifntkydckimtsktdisssvitsigaivscygktkctas nknrgiiktfpigcdyvsnkgvdtvsvgntlyyvnklegkalyikg epiinyydplvfpsdefdasiaqvnakinqslafirrsdellhsvdv gksttnvvittiiivivvvilmliavgllfycktrstpimlgkdqlsgin nlsfsk | bRSV FS1 F0 (GenBank Acc. No: AAB28458.1) |
| SEQ ID NO: 8 | mattamtmiisiifistyvthitlcqniteefyqstcsaysrgylsalrt gwytsvvtielskiqknvckstdskvklikqelerynnavvelqsl mqnepasfsrakrsipelihytrnstkkfyglmgkkrkrrflgfllgi | bRSV Snook F0 (GenBank Acc. No: CAA76980.1) |

-continued

TABLE OF SEQUENCES AND SEQ ID NUMBERS (SEQUENCE LISTING):

| SEQ ID NO | Sequence | Remarks |
|---|---|---|
| | gsaiasgvayskvlhlegevnkiknallstnkavvslsngvsvltsk vldlknyidkellpkvnnhdcrisniatviefqqknnrlleiarefs vnagittplstymltnsellslindmpitndqkklmssnvqivrqq sysimsvvkeeviayvvqlpiygvidtpcwklhtsplcttdnkeg snicltrtdrgwycdnagsysffpqaetckvqsnrvfcdtmnsltl ptdvnlcntdifntkydckimtsktdisssvitsigaivscygktkct asnknrgiiktfsngcdyvsnkgvdtvsvgntlyyvnklegkalyi kgepiinyydplvfpsdefdasiaqvnakinqslafirrsdellhsv dvgksttnvvittiiivivvvilmliavgllfycktrstpimlgkdqlsg innlsfsk | |
| SEQ ID NO: 9 | mattamrmiisiifistyvthitlcqniteefyqstcsaysrgylsalrt gwytsvvtielskiqknycnstdskvklikqelerynnavvelqsl mqnepasfsrakrgipelihytrnstkkfyglmgkkrkrrflgfllgi gsaiasgvavskvlhlegevnkiknallstnkavvslsngvsvltsk vldlknyidkellpkvnnhdcriskietviefqqknnrlleiarefs vnagittplstymltnsellslindmpitndqkklmssnvqivrqq sysimsvvkeeviayvvqlpiygvidtpcwklhtsplcttdnkeg snicltrtdrgwycdnagsysffpqtetckvqsnrvfcdtmnsltlp tdvnlcntdifntkydckimtsktdisssvitsigaivscygktkcta snknrgiiktfsngcdyvsnkgvdtvsvgntlyyvnklegkalyik gepiinyydplvfpsdefdasiaqvnakinqslafirrsdellhsvd vgksttnvvittiiivivvvilmliavgllfycktkstpimlgkdqlsgi nnlsfsk | bRSV ATCC51908 F0 (GenBan Acc. No: AAL49399.1) |
| SEQ ID NO: 10 | GSGNVGLGG | Linker |
| SEQ ID NO: 11 | GSGNWGLGG | Linker |
| SEQ ID NO: 12 | GSGNIGLGG | Linker |
| SEQ ID NO: 13 | GSGGNGIGLGG | Linker |
| SEQ ID NO: 14 | GSGGSGGSGG | Linker |
| SEQ ID NO: 15 | GSGNVLGG | Linker |
| SEQ ID NO: 16 | GGSG | Linker |
| SEQ ID NO: 17 | GGSGGS | Linker |
| SEQ ID NO: 18 | GGSGGSG | Linker |
| SEQ ID NO: 19 | GGSGSGG | Linker |
| SEQ ID NO: 20 | GGSGGGGSGGSG | Linker |
| SEQ ID NO: 21 | GGSGG | Linker |
| SEQ ID NO: 22 | GGSGSGSG | Linker |
| SEQ ID NO: 23 | GSGGGSG | Linker |
| SEQ ID NO: 24 | GGPGG | Linker |
| SEQ ID NO: 25 | GGGSGGGSGGGSGGG | Linker |

TABLE OF SEQUENCES AND SEQ ID NUMBERS (SEQUENCE LISTING):

| SEQ ID NO | Sequence | Remarks |
| --- | --- | --- |
| SEQ ID NO: 26 | GGGSGGGSGGG | Linker |
| SEQ ID NO: 27 | GYIPEAPRDGQAYVRKDGEWVLLSTF | Trimerization domain |
| SEQ ID NO: 28 | SAIGGYIPEAPRDGQAYVRKDGEWVLLSTF | Trimerization domain |
| SEQ ID NO: 29 | SAIGGYIPEAPRDGQAYVRKDGEWVLLSTFLGG LVPRGSH | Trimerization domain |
| SEQ ID NO: 30 | LVPRGS | Thrombin site |
| SEQ ID NO: 31 | MAATAMRMIISIIFISTYMTHITLCQNITEEFYQST CSAVSRGYLSALRTGWYTSVVTIELSKIQKNVCKS TDSKVKLIKQELERYNNAVIELQSLMCNEPASgsG SAIASGVAVCKVLHLEGEVNKIKNALLSTNKAVV SLSNGVSVLTFKVLDLKNYIDKELLPKLNNHDCRI SNIETVIEFQQKNRLLEIAREFSVNAGITTPLSTY MLTNSELLSLINDMPITNDQKKLMSSNVQIVRQ QSYSIMCVVKEEVIAYVVQLPIYGVIDTPCWKLH TSPLCTTDNKEGSNICLTRTDRGWYCDNAGSVS FFPQAETCKVCSNRVFCDTMNSLTLPTDVNLCN TDIFNTKYDCKIMTSKTDISSSVITSIGAIVSCYGKT KCTASNKNRGIIKTFSNGCDYVSNKGVDTVSVG NTLYYVNKLEGKALYIKGEPIINYYDPLVFPSDEF DASIAQVNAKINQSLAFIRRSDELLSaiggyipeaprd gqayvrkdgewvllstflgglvprgshhhhhhsawshpqfek | 391-2sc9-10DS-Cav1 Q98C Q361C |
| SEQ ID NO: 32 | MAATAMRMIISIIFISTYMTHITLCQNITEEFYQST CSAVSRGYLSALRTGWYTSVVTIELSKIQKNVCKS TDSKVKLIKQELERYNNAVIELQSLMCNEPASFSgs GSAIASGVAVCKVLHLEGEVNKIKNALLSTNKAV VSLSNGVSVLTFKVLDLKNYIDKELLPKLNNHDC RISNIETVIEFQQKNRLLEIAREFSVNAGITTPLST YMLTNSELLSLINDMPITNDQKKLMSSNVQIVRQ QSYSIMCVVKEEVIAYVVQLPIYGVIDTPCWKLH TSPLCTTDNKEGSNICLTRTDRGWYCDNAGSVS FFPQAETCKVCSNRVFCDTMNSLTLPTDVNLCN TDIFNTKYDCKIMTSKTDISSSVITSIGAIVSCYGKT KCTASNKNRGIIKTFSNGCDYVSNKGVDTVSVG NTLYYVNKLEGKALYIKGEPIINYYDPLVFPSDEF DASIAQVNAKINQSLAFIRRSDELLSaiggyipeaprd gqayvrkdgewvllstflgglvprgshhhhhhsawshpqfek | 391-2sc9DS-Cav1Q98C Q361C |
| SEQ ID NO: 33 | MDSKGSSQKGSRLLILLVVSNLLLPQGVVGQNI TEEFYQSTCSAVSRGYLSALRTGWYTSVVTIELSKI QKNVCKSTDSKVKLIKQELERYNNAVVELQSLM QNEPASgsGSAVcSGVAVCKVLHLEGEVNKIKNA LLSTNKAVVSLSNGVSVLTFKVLDLKNYIDKELLP QLNNHDCRISNIETVIEFQQKNRLLEIAREFSVN AGITTPLSTYMLTNSELLSLINDMPITNDQKKLMS SNVQIVRQQSYSIMCVVKEEVIAYVVQLPIYGVI DTPCWKLHTSPLCTTDNKEGSNICLTRTDRGWY CDNAGSVSFFPQTETCKVQSNRVFCDTMNSLTL PTDVNLCNTDIENTKYDCKIMTSKTDISSSVITSIG AIVSCYGKTKCTASNKNRGIIKTFSNGCDYVSNK GVDTVSVGNTLYcVNKLEGKALYIKGEPIINYYD PLVFPSDEFDASIAQVNAKINQSLAFIRRSDELLSA IGGYIPEAPRDGQAYVRKDGEWVLLSTFLGGLV PRGSHHHHHHSAWSHPQFEK | ATue51908sc9-10DS-Cav1 A149C-Y458C |
| SEQ ID NO: 34 | HHHHHH | His tag |
| SEQ ID NO: 35 | WSHPQFEK | Strep tag |
| SEQ ID NO: 36 | MAATAMRMIISIIFISTYMTHITLCQNITEEFYQST CSAVSRGYLSALRTGWYTSVVTIELSKIQKNVCKS TDSKVKLIKQELERYNNAVIELQSLMQNEPASFSR | bRSV 391-2 DSCav1 |

TABLE OF SEQUENCES AND SEQ ID NUMBERS (SEQUENCE LISTING):

| SEQ ID NO | Sequence | Remarks |
|---|---|---|
| | AKRGIPELIHYTRNSTKRFYGLMGKKRKRRFLGFL<br>LGIGSAIASGVAVCKVLHLEGEVNKIKNALLSTNK<br>AVVSLSNGVSVLTFKVLDLKNYIDKELLPKLNNH<br>DCRISNIETVIEFQQKNRLLEIAREFSVNAGITTP<br>LSTYMLINSELLSLINDMPITNDQKKLMSSNVQI<br>VRQQSYSIMCVVKEEVIAYVVQLPIYGVIDTPCW<br>KLHTSPLCTTDNKEGSNICLTRTDRGWYCDNAG<br>SVSFFPQAETCKVQSNRVFCDTMNSLTLPTDVN<br>LCNTDIFNTKYDCKIMTSKTDISSSVITSIGAIVSCY<br>GKTKCTASNKNRGIIKTFSNGCDYVSNKGVDTV<br>SVGNTLYYVNKLEGKALYIKGEPIINYYDPLVFPS<br>DEFDASIAQVNAKINQSLAFIRRSDELLSAIGGYIP<br>EAPRDGQAYVRKDGEWVLLSTFLGGLVPRGSH<br>HHHHHSAWSHPQFEK | |
| SEQ ID NO: 37 | MDSKGSSQKGSRLLLLLVVSNLLLPQGVVGQNI<br>TEEFYQSTCSAVSRGYLSALRTGWYTSVVTIELSKI<br>QKNVCKSTDSKVKLIKQELERYNNAVVELQSLM<br>QNEPASFSRAKRGIPELIHYTRNSTKKFYGLMGKK<br>RKRRFLGFLLGIGSAVASGVAVCKVLHLEGEVNK<br>IKNALLSTNKAVVSLSNGVSVLTFKVLDLKNYIDK<br>ELLPQLNNHDCRISNIETVIEFQQKNRLLEIAREF<br>SVNAGITTPLSTYMLTNSELLSLINDMPITNDQKK<br>LMSSNVQIVRQQSYSIMCVVKEEVIAYVVQLPIY<br>GVIDTPCWKLHTSPLCTTDNKEGSNICLTRTDRG<br>WYCDNAGSVSFFPQTETCKVQSNRVFCDTMNS<br>LTLPTDVNLCNTDIFNTKYDCKIMTSKTDISSSVIT<br>SIGAIVSCYGKTKCTASNKNRGIIKTFSNGCDYVS<br>NKGVDTVSVGNTLYYVNKLEGKALYIKGEPIINY<br>YDPLVFPSDEFDASIAQVNAKINQSLAFIRRSDEL<br>LSAIGGYIPEAPRDGQAYVRKDGEWVLLSTFLG<br>GLVPRGSHHHHHHSAWSHPQFEK | bRSV ATue51908 DSCav1 |
| SEQ ID NO: 38 | MPMGSLQPLATLYLLGMLVASVLAAQNITEEFY<br>QSTCSAVSRGYLSALRTGWYTSVVTIELSKIQKNV<br>CNSTDSNVKLIKQELERYNNAVVELQSLMQNEP<br>ASSSRAKRGIPELIHYKRNSTKKFYGLMGKKRKRR<br>FLGFLLGIGSAIASGVAVCKVLHLEGEVNKIKNAL<br>LSTNKAVVSLSNGVSVLTFKVLDLKNYIDKELLPK<br>LNNHDCQISNIATVIEFQQKNRLLEIAREFSVN<br>AGITTPLSTYMLTNSELLSLINDMPITNDQKKLMS<br>SNVQIVRQQSYSIMCVVKEEVMAYVVQLPIYGVI<br>DTPCWKLHTSPLCTTDNKEGSNICLTRTDRGWY<br>CDNAGSVSFFPQAETCKVQSNRVFCDTMNSLTL<br>PTDVNLCNTDIFNAKYDCKIMTSKTDISSSVITSIG<br>AIVSCYGKTKCTASNKNRGIIKTFSNGCDYVSNR<br>GVDTVSVGNTLYYVNKLEGKALYIKGEPIINYYD<br>PLVFPSDEFDASIAQVNAKINQSLAFIRRSDELLSA<br>IGGYIPEAPRDGQAYVRKDGEWVLLSTFLGGLV<br>PRGSHHHHHHSAWSHPQFEK | bRSV RB94DSCav1 |
| SEQ ID NO: 39 | MDSKGSSQKGSRLLLLLVVSNLLLPQGVVGQNI<br>TEEFYQSTCSAVSRGYLSALRTGWYTSVVTIELSKI<br>QKNVCNSTDSNVKLIKQELERYNNAVVELQSLM<br>QNEPASSSgsGSAlcSGVAVCKVLHLEGEVNKIKN<br>ALLSTNKAVVSLSNGVSVLTFKVLDLKNYIDKELL<br>PKLNNHDCQISNIATVIEFQQKNRLLEIAREFSV<br>NAGITTPLSTYMLTNSELLSLINDMPITNDQKKL<br>MSSNVQIVRQQSYSIMCVVKEEVMAYVVQLPIY<br>GVIDTPCWKLHTSPLCTTDNKEGSNICLTRTDRG<br>WYCDNAGSVSFFPQAETCKVQSNRVFCDTMNS<br>LTLPTDVNLCNTDIFNAKYDCKIMTSKTDISSSVIT<br>SIGAIVSCYGKTKCTASNKNRGIIKTFSNGCDYVS<br>NRGVDTVSVGNTLYcVNKLEGKALYIKGEPIINY<br>YDPLVFPSDEFDASIAQVNAKINQSLAFIRRSDEL<br>LSAIGGYIPEAPRDGQAYVRKDGEWVLLSTFLG<br>GLVPRGSHHHHHHSAWSHPQFEK | RB94 DS-Cav1 sc9 A149C Y458C |
| SEQ ID NO: 40 | MDSKGSSQKGSRLLLLLVVSNLLLPQGVVGQNI<br>TEEFYQSTCSAVSRGYLSALRTGWYTSVVTIELSKI<br>QKNVCNSTDSNVKLIKQELERYNNAVVELQSLM<br>QNEPASSSgsGSAIASGVAVCKVLHLEGEVNKIKN<br>ALLSTNKAVVSLSgcGVSVLTFKVLDLKNYIDKELL<br>PKLNNHDCQISNIATVIEFQQKNRLLEIAREFSV | RB94 sc9 DS-Cav1 N183GC N428C |

-continued

TABLE OF SEQUENCES AND SEQ ID NUMBERS (SEQUENCE LISTING):

| SEQ ID NO | Sequence | Remarks |
|---|---|---|
| | NAGITTPLSTYMLTNSELLSLINDMPITNDQKKL MSSNVQ1VRQQSYSIMCVVKEEVMAYVVQLPIY GVIDTPCWKLHTSPLCTTDNKEGSNICLTRTDRG WYCDNAGSVSFFPQAETCKVQSNRVFCDTMNS LTLPTDVNLCNTDIFNAKYDCKIMTSKTDISSSVIT SIGAIVSCYGKTKCTASNKcRGIIKTFSNGCDYVS NRGVDTVSVGNTLYYVNKLEGKALYIKGEPIINY YDPLVFPSDEFDASIAQVNAKINQSLAFIRRSDEL LSAIGGYIPEAPRDGQAYVRKDGEWVLLSTFLG GLVPRGSHHHHHHSAWSHPQFEK | |
| SEQ ID NO: 41 | MELLILKANAITTILTAVTFCFASGQNITEEFYQST CSAVSRGYLSALRTGWYTSVITIELSKIQKNVCNS TDSNVKLIKQELERYNNAVVELQSLMQSTPATGS GSAIASGVAVCKVLHLEGEVNKIKNALLSTNKAV VSLSNGVSVLTFKVLDLKNYIDKELLPILNNHDC QISNIATVIEFQQKNNRLLEIAREFSVNAGVTTPV STYMLTNSELLSLINDMPITNDQKKLMSSNVQIV RQQSYSIMCIIKEEVLAYVVQLPIYGVIDTPCWKL HTSPLCTTDNKEGSNICLTRTDRGWYCDNAGS VSFFPQAETCKVQSNRVFCDTMNSLTLPTDVNL CNTDIFNAKYDCKIMTSKTDVSSSVITSLGAIVSC YGKTKCTASNKNRGIIKTFSNGCDYVSNRGVDT VSVGNTLYYVNKQEGKSLYIKGEPIINYYDPLVFP SDEFDASIAQVNAKINQSLAFIRRSDELLSAIGGYI PEAPRDGQAYVRKDGEWVLLSTFLGGLVPRGS HHHHHHSAWSHPQFEK | sc9-10_bRSV(RB94) DS-Cav1_fd_hp2_fp2_ig1 |
| SEQ ID NO: 42 | MDSKGSSQKGSRLLLLLVVSNLLLPQGVVGqnite efyqstcsaysrgylsalrtgwytsvitielsKIQKNVCKSTDSK VKLIKQELERYNNAVlelqllmqstpatnngsgsaiasgVA VCKvlhlegevnkiknallstnkavvslsngvsVLTFkvldlkny idkELLPKLNNHDCRISNIEtviefqqknnrlleitrefsvna gvttpvstymltnsellslindmpitndqkklmssnvqivrqqsyS IMCllkeevlayvvqlpiygvidtpcwklhtsplcttdnkegsnic ltrtdrgwycdnagsvsffpqaetckvqsnrvfcdtmnsrtlptdv nlcntdifntkydckimtsktdvsssvitslgaivscygktkctasnk nrgiiktfsngcdyvsnkgvdtvsvgntlyyvnkqegkslyvkgep iinfydplvfpsdefdasisqvnekinqslafirrsdeLLhnvnagk sttGGYIPEAPRDGQAYVRKDGEWVLLSTFLGGL VPRGSHHHHHHSAWSHPQFEK | 391-2-site Ø hRSV bovsurf DS-Cav1-BZGJ9 Long |
| SEQ ID NO: 43 | MAATAMRMIISIIFISTYMTHITLCQNITEEFYQST CSAVSRGYLSALRTGWYTSVVTIELSKIQKNVCKS TDSKVKLIKQELERYNNAVIELQSLMQNEPASFS GSGSAlcSGVAVCKVLHLEGEVNKIKNALLSTNK AVVSLSNGVSVLITKVLDLKNYIDKELLPKLNNH DCRISNIETVIEFQQKNNRLLEIAREFSVNAGITTP LSTYMLTNSELLSLINDMPITNDQKKLMSSNVQI VRQQSYSIMCVVKEEVIAYVVQLPIYGVIDTPCW KLHTSPLCTTDNKEGSNICLTRTDRGWYCDNAG SVSFFPQAETCKVQSNRVFCDTMNSLTLPTDVN LCNTDIFNTKYDCKIMTSKTDISSSVITSIGAIVSCY GKTKCTASNKNRGIIKTFSNGCDYVSNKGVDTV SVGNTLYcVNKLEGKALYIKGEPIINYYDPLVFPS DEFDASIAQVNAKINQSLAFIRRSDELLsaiggyipea prdgqayvrkdgewvllstflgglvprgshhhhhhsawshpqfe k | bRSV 391-2 sc9 DS-Cav1 A149C Y458C |
| SEQ ID NO: 44 | MDSKGSSQKGSRLLLLLVVSNLLLPQGVVGQNI TEEFYQSTCSAVSRGYLSALRTGWYTSVVTIELSKI QKNVCKSTDSKVKLIKQELERYNNAVVELQSLM QNEPASgsGSAVASGVAVCKVLHLEGEVNKIKN ALLSTNKAVVSLSgcGVSVLTFKVLDLKNYIDKELL PQLNNHDCRISNIETVIEFQQKNNRLLEIAREFSV NAGITTPLSTYMLTNSELLSLINDMPITNDQKKL MSSNVQIVRQQSYSIMCVVKEEVIAYVVQLPIYG VIDTPCWKLHTSPLCTTDNKEGSNICLTRTDRG WYCDNAGSVSFFPQTETCKVQSNRVFCDTMNS LTLPTDVNLCNTDIFNTKYDCKIMTSKTDISSSVIT SIGAIVSCYGKTKCTASNKcRGIIKTFSNGCDYVS NKGVDTVSVGNTLYYVNKLEGKALYIKGEPIINY | bRSV ATue51908 sc9-10 DS-Cav1 N183GC N428C |

| TABLE OF SEQUENCES AND SEQ ID NUMBERS (SEQUENCE LISTING): | | |
|---|---|---|
| SEQ ID NO | Sequence | Remarks |
| | YDPLVFPSDEFDASIAQVNAKINQSLAFIRRSDEL Lsaiggyipeaprdgqayvrkdgewvllstflgglvprgshhhh hsawshpqfek | |
| SEQ ID NO: 45 | MAATAMRMIISIIFISTYMTHITLCQNITEEFYQST CSAVSRGYLSALRTGWYTSVVTIELSKIQKNVCKS TDSKVKLIKQELERYNNAVIELQSLMQNEPASFSR AKRGIPELIHYTRNSTKRFYGLMGKKRKRRAIASG VAVSKVLHLEGEVNKIKNALLSTNKAVVSLSNGV SVLTSKVLDLKNYIDKELLPKVNNHDCRISNIETVI EFQQKNNRLLEIAREFSVNAGITTPLSTYMLTNSE LLSLINDMPITNDQKKLMSSNVQIVRQQSYSIMS VVKEEVIAYVVQLPIYGVIDTPCWKLHTSPLCTTD NKEGSNICLTRTDRGWYCDNAGSVSFFPQAETC KVQSNRVFCDTMNSLTLPTDVNLCNTDIFNTKY DCKIMTSKTDISSSVITSIGAIVSCYGKTKCTASNK NRGIIKTFSNGCDYVSNKGVDTVSVGNTLYYVN KLEGKALYIKGEPIINYYDPLVFPSDEFDASIAQVN AKINQSLAFIRRSDELLGLEVLFQGPHHHHHHH HSAWSHPQFEK | bRSV 391-2 postF |
| SEQ ID NO: 46 | MDSKGSSQKGSRLLLLLVVSNLLLPQGVVGQNI TEEFYQSTCSAVSRGYLSALRTGWYTSVVTIELSKI QKNVCKSTDSKVKLIKQELERYNNAVVELQSLM QNEPASFSRAKRGIPELIHYTRNSTKKFYGLMGKK RKRRAVASGVAVSKVLHLEGEVNKIKNALLSTNK AVVSLSNGVSVLTSKVLDLKNYIDKELLPQVNNH DCRISNIETVIEFQQKNNRLLEIAREFSVNAGITTP LSTYMLTNSELLSLINDMPITNDQKKLMSSNVQI VRQQSYSIMSVVKEEVIAYVVQLPIYGVIDTPCW KLHTSPLCTTDNKEGSNICLTRTDRGWYCDNAG SVSFFPQTETCKVQSNRVFCDTMNSLTLPTDVNL CNTDIFNTKYDCKIMTSKTDISSSVITSIGAIVSCY GKTKCTASNKNRGIIKTFSNGCDYVSNKGVDTV SVGNTLYYVNKLEGKALYIKGEPIINYYDPLVFPS DEFDASIAQVNAKINQSLAFIRRSDELLGLEVLFQ GPHHHHHHHHSAWSHPQFEK | bRSV ATue51908 postF |
| SEQ ID NO: 47 | MDSKGSSQKGSRLLLLLVVSNLLLPQGVVGQNI TEEFYQSTCSAVSRGYLSALRTGWYTSVVTIELSKI QKNVCNSTDSNVKLIKQELERYNNAVIELQSLM QNEPASSSRAKRGIPELIHYKRNSTKKFYGLMGK KRKRRAIASGVAVSKVLHLEGEVNKIKNALLSTNK AVVSLSNGVSVLTSKVLDLKNYIDKELLPKVNNH DCQISNIATVIEFQQKNNRLLEIAREFSVNAGITTP LSTYMLTNSELLSLINDMPITNDQKKLMSSNVQI VRQQSYSIMSVVKEEVMAYVVQLPIYGVIDTPC WKLHTSPLCTTDNKEGSNICLTRTDRGWYCDN AGSVSFFPQAETCKVQSNRVFCDTMNSLTLPTD VNLCNTDIFNAKYDCKIMTSKTDISSSVITSIGAIV SCYGKTKCTASNKNRGIIKTFSNGCDYVSNRGV DTVSVGNTLYYVNKLEGKALYIKGEPIINYYDPLV FPSDEFDASIAQVNAKINQSLAFIRRSDELLGLEVL FQGPHHHHHHHSAWSHPQFEK | bRSV RB94 postF |
| SEQ ID NO: 48 | MLSKDIIKLLNEQVNKEMNSSNLYMSMSSWCYT HSLDGAGLFLFDHAAEEYEHAKKLIVFLNENNVP VQLTSISAPEHKFEGLTQIFQKAYEHEQHISESINN IVDHAIKGKDHATFNFLQWYVAEQHEEEVLFKD ILDKIELIGNENHGLYLADQYVKGIAKSRKS | ferritin polypeptide |
| SEQ ID NO: 49 | MEFLKRSFAPLTEKQWQEIDNRAREIFKTQLYGR KFVDVEGPYGWEYAAHPLGEVEVLSDENEVVK WGLRKSLPLIELRATFTLDLWELDNLERGKPNVD LSSLEETVRKVAEFEDEVIFRGCEKSGVKGLLSFEER KIECGSTPKDLLEAIVRALSIFSKDGIEGPYTLVINT DRWINFLKEEAGHYPLEKRVEECLRGGKIITTPRIE DALVVSERGGDFKLILGQDLSIGYEDREKDAVRL FITETFTFQVVNPEALILLKF | encapsulin polypeptide |
| SEQ ID NO: 50 | EVQLVESGGGLVKPGGSLRLSCAASGFTFSSYSM NWVRQAPGKGLEWVSSISASSSYSDYADSAKGR FTISRDNAKTSLFLQMNSLRAEDTAIYFCARARAT GYSSITPYFDIWGQGTLVTVSS | MPE8 Heavy Chain Variable region |

TABLE OF SEQUENCES AND SEQ ID NUMBERS (SEQUENCE LISTING):

| SEQ ID NO | Sequence | Remarks |
|---|---|---|
| SEQ ID NO: 51 | QSVVTQTPSVSGAPGQRVTISCTGSSSNIGAGY DVHWYQQLPGTAPKLLIYDNNNRPSGVPDRFS ASKSGTSASLAITGLQAEDEADYYCQSYDRNLSG VFGTGTKVTVL | MPE8 Light Chain Variable region |
| SEQ ID NO: 52 | DIQMTQSPSSLSASVGDRVTITCQASQDIKKYLN WYHQKPGKVPELLMHDASNLETGVPSRFSGRG SGTDFTLTISSLQPEDIGTYYCQQYDNLPPLTFG GGTKVEIKR | AM14 Light Chain Variable region |
| SEQ ID NO: 53 | EVQLVESGGGVVQPGRSLRLSCAASGFSFSHYA MHWVRQAPGKGLEWVAVISYDGENTYYADSV KGRFSISRDNSKNTVSLQMNSLRPEDTALYYCAR DRIVDDYYYYGMDVWGQGATVTVSS | AM14 Heavy Chain Variable region |
| SEQ ID NO: 54 | DIQMTQSPSSLSAAVGDRVTITCQASQDIVNYL NWYQQKPGKAPKLLIYVASNLETGVPSRFSGSG SGTDFSLTISSLQPEDVATYYCQQYDNLPLTFGG GTKVEIK | D25 Light Chain Variable region |
| SEQ ID NO: 55 | QVQLVQSGAEVKKPGSSVMVSCQASGGPLRNY IINWLRQAPGQGPEWMGGIIPVLGTVHYAPKF QGRVTITADESTDTAYIHLISLRSEDTAMYYCATE TALVVSTTYLPHYFDNWGQGTLVTVSS | D25 Heavy Chain Variable region |
| SEQ ID NO: 56 | atggctgctactgctatgcggatgattatctcaattattttttatttcaacct acatgactcacattaccctgtgtcagaacattaccgaggaattctac cagagcacttgctccgccgtgtctagaggatacctgtctgctctgag gaccggctggtatacaagcgtggtcactattgagctgtccaagatcc agaaaaacgtgtgtaagagtaccgattcaaaggtcaaactgatcaa acaggagctggaaaggtataacaatgccgtgattgagctgcagag cctgatgtgcaatgaacctgctagcggggtctggaagtgccatcgctt ccggagtggccgtctgcaaggtgctgcacctggagggcgaagtca acaagatcaagaatgccctgctgtctacaaacaaagctgtggtctc actgagcaatggcgtgagtgtcctgactttttaaggtgctggacctgaa aaactacatcgataaggagctgctgccaaaactgaacaatcatga ctgtcggatcagcaatattgagacagtgattgaattccagcagaaga acaatcgactgctggagatcgcaagagaattttcagtgaacgccgg cattaccacaccctgagcacctacatgctgacaaattctgagctg ctgagtctgattaacgacatgcctatcaccaatgatcagaagaaact gatgagctccaacgtgcagatcgtcagacagcagtcctattctattat gtgcgtggtcaaggaggaagtgatcgcctacgtggtccagctgcct atctacggcgtgatcgataccccatgctggaagctgcacacaagtc ccctgtgtactaccgacaacaaagagggctcaaatatctgcctgac aaggactgaccgcggctggtactgtgataacgcagggagtgtgtca ttcttccacaggccgaaacttgcaaggtgtgctccaacagggtcttc tgtgataccatgaattctctgaccctgcccacagacgtgaacctgtg caacactgatatctttaataccaagtacgactgtaagattatgactag caagaccgacatctctagttcagtgatcacctccattggagctatcgt ctcttgctacggcaagacaaaatgtactgcatctaacaagaatcgc gggatcatcaagacattctctaacggatgtgattatgtcagtaataag ggggtcgacacagtgagcgtcggaaacactctgtactatgtgaata agctggagggcaaagccctgtacatcaaaggggaacctatcatta actactatgatccactggtgttcccagtgacgagtttgatgcatcaa ttgcccaggtaacgctaagatcaatcagtccctggccttcatccgg agatcagacgagctgctgagcgcaattggcgggtacatccccgaa gctcctcgcgatggccaggcatatgtgcgaaaagacggggagtgg gtcctgctgagcaccttcctgggaggactggtgcctcgaggatccc accatcaccatcaccatagcgcttggtccatccacagtttgaaaa g | 391-2 sc9-10DS-Cav1Q98C-Q361C_nuc |
| SEQ ID NO: 57 | atggctgctactgctatgcggatgattatctcaattattttttatttcaacct acatgactcacattaccctgtgtcagaacattaccgaggaattctac cagagcacttgctccgccgtgtctagaggatacctgtctgctctgag gaccggctggtatacaagcgtggtcactattgagctgtccaagatcc agaaaaacgtgtgtaagagtaccgattcaaaggtcaaactgatcaa acaggagctggaaaggtataacaatgccgtgattgagctgcagag cctgatgtgcaatgaacctgctagctctccgggtctggaagtgccat cgcttccggagtggccgtctgcaaggtgctgcacctggagggcga agtcaacaagatcaagaatgccctgctgtctacaaacaaagctgtg gtctcactgagcaatggcgtgagtgtcctgactttttaaggtgctggac ctgaaaaactacatcgataaggagctgctgccaaaactgaacaat catgactgtcggatcagcaatattgagacagtgattgaattccagca | 391-2sc9DS-Cav1 Q98C-Q361C_nuc |

TABLE OF SEQUENCES AND SEQ ID NUMBERS (SEQUENCE LISTING):

| SEQ ID NO | Sequence | Remarks |
|---|---|---|
| | gaagaacaatcgactgctggagatcgcaagagaattttcagtgaac gccggcattaccacaccctgagcacctacatgctgacaaattctg agctgctgagtctgattaacgacatgcctatcaccaatgatcagaag aaactgatgagctccaacgtgcagatcgtcagacagcagtcctatt ctattatgtgcgtggtcaaggaggaagtgatcgcctacgtggtccag ctgcctatctacggcgtgatcgatacccatgctggaagctgcaca caagtcccctgtgtactaccgacaacaagagggctcaaatatctg cctgacaaggactgaccgcggctggtactgtgataacgcagggag tgtgtcattcttccacaggccgaaacttgcaaggtgtgctccaacag ggtcttctgtgataccatgaattctctgaccctgcccacagacgtgaa cctgtgcaacactgatatctttaataccaagtacgactgtaagattat gactagcaagaccgacatctctagttcagtgatcacctccattggag ctatcgtctcttgctacggcaagacaaaatgtactgcatctaacaag aatcgcgggatcatcaagacattctctaacggatgtgattatgtcagt aataaggggtcgacacagtgagcgtcggaaacactctgtactatg tgaataagctggagggcaaagccctgtacatcaaggggaaccta tcattaactactatgatccactggtgttcccagtgacgagtttgatgc atcaattgcccaggtgaacgctaagatcaatcagtccctggccttca tccggagatcagacgagctgctgagcgcaattggcgggtacatcc ccgaagctcctcgcgatggccaggcatatgtgcgaaaagacggg gagtgggtcctgctgagcaccttcctggggaggactggtgcctcgag gatcccaccatcaccatcaccatagcgcttggtcccatccacagttt gaaaagtga | |
| SEQ ID NO: 58 | atggattccaaggggagctcccagaaaggatctaggctgctgctgc tgctggtggtctccaacctgctgctgccacagggagtggtcggaca gaatatcacagaggaattctaccagagcacttgctccgcagtgtctc ggggatacctgtctgccctgagaactggctggtatacctctgtggtca caattgagctgagtaagatccagaagaacgtgtgcaaaagtaccg actcaaaggtcaaactgatcaagcaggagctggaacggtataaca atgccgtggtcgagctgcagagcctgatgcagaacgaacctgcttc tggcagcggatctgccgtgtgtagtggagtggccgtctgcaaagtgc tgcatctggagggcgaagtcaacaagatcaagaatgcactgctgtc tactaacaaggccgtggtctcactgagcaatggcgtgagtgtcctga ccttttaaggtgctggacctgaaaaactacatcgataaggagctgctg cctcagctgaacaatcacgattgtaggatctccaatattgagacagt gattgaattccagcagaagaacaatcgcctgctggagatcgctcga gagttcagcgtgaacgcaggcattaccacaccactgtcaacatac atgctgactaattcagagctgctgagcctgattaacgacatgcccat caccaatgatcagaagaaactgatgtctagtaacgtgcagatcgtc cgccagcagtcctattctattatgtgcgtggtcaaggaggaagtgatc gcatacgtggtccagctgcctatctacggcgtgatcgatacccatg ctggaaactgcatacatctcccctgtgcactaccgacaacaagga aggaagtaatatttgcctgacaagaactgacaggggctggtactgtg ataacgctggcagcgtgagcttcttccctcagaccgaaacatgcaa ggtgcagagcaacggggtcttctgtgatacaatgaattccctgactct gccaaccgacgtgaacctgtgcaacaccgatatctttaatacaaag tacgactgtaagatcatgacaagcaagactgacatctcaagctccg tgatcacaagtattggagctatcgtgtcatgctacggcaagaccaaa tgtacagcatctaacaaaaaacagagggatcattaagactttctcaaa cggatgtgattatgtgagcaacaaggggtcgacactgtgagcgtc ggaaacaccctgtactgtgtgaataagctggagggcaaagccctgt acatcaagggggaacccatcattaactactatgatccactggtgttc cccagcgacgagtttgatgcatccattgcccaggtgaacgccaaa atcaatcagtccctggcttttattaggcgctccgacgagctgctgtct gccattggcgggtacatccccgaagcccctagggatggccaggct tatgtgcgcaaggacggggagtgggtcctgctgtcaaccttcctggg aggactggtgccaagaggctccaccatcaccatcaccatagcg cctggtcccaccctcagtttgaaaag | ATue51908sc9-10DS-Cav1 A149C-Y458C_nuc |
| SEQ ID NO: 59 | atggattctaagggttccagccagaaaggttccaggctgctgctgct gctggtggtgagcaatctgctgctgcctcagggagtggtgggacag aacatcaccgaggagttctaccagtcaacctgcagcgccgtgagc cggggctacctgagcgcctgagaaccggatggtatacatccgtg gtcactattgagctgtctaagatccagaaaaacgtgtgtaattctaca gatagtaacgtcaagctgatcaaacaggagctggaaaggtataac aatgctgtggtcgagctgcagtccctgatgcagaacgaacctgcca gcagcagcggcagcggcagcgccatctgttctggggtggcagtct gcaaggtgctgcatctggagggagaagtcaacaagatcaaaaatg cactgctgagtactaacaaagccgtggtcagtctgtcaaatggggtg agcgtcctgacctttaaggtgctggacctgaaaaactacatcgataa ggagctgctgcccaaactgaacaatcacgactgtcagatcagcaa tattgccactgtgattgagttccagcagaagaacaatcgcctgctgg agatcgcccgggagttcagcgtgaacgcaggcattaccacacca | RB94 DS-Cav1 sc9 A149C-Y458C_nuc |

-continued

TABLE OF SEQUENCES AND SEQ ID NUMBERS (SEQUENCE LISTING):

| SEQ ID NO | Sequence | Remarks |
|---|---|---|
| | ctgtccacctacatgctgacaaatagtgagctgctgtcactgattaac<br>gacatgcccatcaccaatgatcagaagaaactgatgagttcaaac<br>gtgcagatcgtcaggcagcagagctattccattatgtgcgtggtcaa<br>ggaggaagtgatggcctacgtggtccagctgcctatctacggcgtg<br>atcgatacaccatgctggaagctgcatacttcacccctgtgctac<br>cgacaacaaagaggggagcaatatctgcctgacaagaactgaca<br>ggggatggtactgtgataacgctggctctgtgagtttctttcctcaggc<br>agaaacctgcaaggtgcagtctaaccgcgtcttctgtgatacaatga<br>atagtctgaccctgccaacagacgtgaacctgtgcaatacagatat<br>ctttaatgccaagtacgactgtaagattatgacttccaagaccgacat<br>cagctcctctgtgatcacttctattggggccatcgtcagttgctacgg<br>aaagacaaaatgtactgctagcaacaagaatcggggcatcatcaa<br>gacattcagtaacgggtgtgattatgtgtcaaatagaggcgtggaca<br>ctgtgagcgtcgggaacaccctgtactgtgtgaataagctggaggg<br>aaaagctctgtacatcaagggcgaacctatcattaactactatgatc<br>cactggtgttcccctcagacgagtttgatgcaagcattgcccaggtg<br>aacgccaaaatcaatcagtctctggcttttattaggcgcagcgacga<br>gctgctgtccgcaattggcgggtacatccccgaagcccctagggat<br>ggacaggcttatgtgcgcaaggacggcgagtgggtcctgctgtcca<br>ccttcctgggaggcctggtgcccagaggctctcaccatcaccatca<br>ccattcagcctggagccaccctcagtttgaaaaa | |
| SEQ ID NO: 60 | atggattctaagggttccagccagaaaggttccaggctgctgctgct<br>gctggtggtgagcaatctgctgctgcctcagggagtggtgggacag<br>aacatcaccgaggagttctaccagtcaacctgcagcgccgtgagc<br>cggggctacctgagcgcactgagaaccggatggtatacatccgtg<br>gtcactattgagctgtctaagatccagaaaaacgtgtgtaattctaca<br>gatagtaacgtcaagctgatcaaacaggagctggaaaggtataac<br>aatgctgtggtcgagctgcagtccctgatgcagaacgaacctgcca<br>gcagcagcggcagcggcagcgccatcgcttctggggtggcagtct<br>gcaaggtgctgcatctggaggagaagtcaacaagatcaaaaatg<br>cactgctgagtactaacaaagccgtggtcagtctgtcaggttgtggg<br>gtgagcgtcctgacctttaaggtgctggacctgaaaaactacatcga<br>taaggagctgctgcccaaactgaacaatcacgactgtcagatcag<br>caatattgccactgtgattgagttccagcagaagaacaatcgcctgc<br>tggagatcgcccgggagttcagcgtgaacgcaggcattaccacac<br>cactgtccacctacatgctgacaaatagtgagctgctgtcactgatta<br>acgacatgcccatcaccaatgatcagaagaaactgatgagttcaa<br>acgtgcagatcgtcaggcagcagagctattccattatgtgcgtggtc<br>aaggaggaagtgatggcctacgtggtccagctgcctatctacggcg<br>tgatcgataccatgctggaagctgcatacttcacccctgtgtacta<br>ccgacaacaaagaggggagcaatatctgcctgacaagaactgac<br>aggggatggtactgtgataacgctggctctgtgagtttctttcctcagg<br>cagaaacctgcaaggtgcagtctaaccgcgtcttctgtgatacaatg<br>aatagtctgaccctgccaacagacgtgaacctgtgcaatacagata<br>tctttaatgccaagtacgactgtaagattatgacttccaagaccgaca<br>tcagctcctctgtgatcacttctattggggccatcgtcagttgctacgg<br>aaagacaaaatgtactgctagcaacaagtgtcggggcatcatcaa<br>gacattcagtaacgggtgtgattatgtgtcaaatagaggcgtggaca<br>ctgtgagcgtcgggaacaccctgtactatgtgaataagctggaggg<br>aaaagctctgtacatcaagggcgaacctatcattaactactatgatc<br>cactggtgttcccctcagacgagtttgatgcaagcattgcccaggtg<br>aacgccaaaatcaatcagtctctggcttttattaggcgcagcgacga<br>gctgctgtccgcaattggcgggtacatccccgaagcccctagggat<br>ggacaggcttatgtgcgcaaggacggcgagtgggtcctgctgtcca<br>ccttcctgggaggcctggtgcccagaggctctcaccatcaccatca<br>ccattcagcctggagccaccctcagtttgaaaaa | RB94 sc9 DS-Cav1<br>N183GC-N428C_<br>nuc |
| SEQ ID NO: 61 | atggctgctactgctatgcggatgattatctcaattatttttatttcaacct<br>acatgactcacattaccctgtgtcagaacattaccgaggaattctac<br>cagagcacttgctccgccgtgtctagaggatacctgtctgctctgag<br>gaccggctggtatacaagcgtggtcactattgagctgtccaagatcc<br>agaaaaacgtgtgtaagagtaccgattcaaaggtcaaactgatcaa<br>acaggagctggaaaggtataacaatgccgtgattgagctgcagag<br>cctgatgcagaatgaacctgctagcttctccgggtctggaagtgcca<br>tctgttccggagtggccgtctgcaaggtgctgcacctggagggcga<br>agtcaacaagatcaagaatgccctgctgtctacaaacaaagctgtg<br>gtctcactgagcaatggcgtgagtgtcctgacttttaaggtgctggac<br>ctgaaaactacatcgataaggagctgctgccaaaactgaacaat<br>catgactgtcggatcagcaatattgagacagtgattgaattccagca<br>gaagaacaatcgactgctggagatcgcaagagaattttcagtgaac<br>gccggcattaccacaccctgagcacctacatgctgacaaattctg<br>agctgctgagtctgattaacgacatgcctatcaccaatgatcagaag<br>aaactgatgagctccaacgtgcagatcgtcagacagcagtcctatt | bRSV 391-2 sc9<br>DS-Cav1<br>A149C-<br>Y458C_nuc |

-continued

TABLE OF SEQUENCES AND SEQ ID NUMBERS (SEQUENCE LISTING):

| SEQ ID NO | Sequence | Remarks |
|---|---|---|
| | ctattatgtgcgtggtcaaggaggaagtgatcgcctacgtggtccag ctgcctatctacggcgtgatcgataccccatgctggaagctgcaca caagtcccctgtgtactaccgacaacaaagagggctcaaatatctg cctgacaaggactgaccgcggctggtactgtgataacgcagggag tgtgtcattctttccacaggccgaaacttgcaaggtgcagtccaaca gggtcttctgtgataccatgaattctctgaccctgcccacagacgtga acctgtgcaacactgatatctttaataccaagtacgactgtaagatta tgactagcaagaccgacatctctagttcagtgatcacctccattgga gctatcgtctcttgctacggcaagacaaaatgtactgcatctaacaa gaatcgcgggatcatcaagacattctctaacggatgtgattatgtcag taataaggggtcgacacagtgagcgtcggaaacactctgtactgt gtgaataagctggagggcaaagccctgtacatcaaaggggaacct atcattaactactatgatccactggtgttccccagtgacgagtttgatg catcaattgcccaggtgaacgctaagatcaatcagtccctggccttc atccggagatcagacgagctgctgagcgcaattggcgggtacatc cccgaagctcctcgcgatggccaggcatatgtgcgaaaagacgg ggagtgggtcctgctgagcaccttcctgggaggactggtgcctcga ggatcccaccatcaccatcaccatagcgcttggtcccatccacagt ttgaaaag | |
| SEQ ID NO: 62 | atggattccaaggggagctcccagaaaggatctaggctgctgctgc tgctggtggtctccaacctgctgctgccacagggagtggtcggaca gaatatcacagaggaattctaccagagcacttgctccgcagtgtctc ggggatacctgtctgccctgagaactggctggtatacctctgtggtca caattgagctgagtaagatccagaagaacgtgtgcaaaagtaccg actcaaaggtcaaactgatcaagcaggagctggaacggtataaca atgccgtggtcgagctgcagagcctgatgcagaacgaacctgcttc tggcagcggatctgccgtggctagtggagtggccgtctgcaaagtg ctgcatctggagggcgaagtcaacaagatcaagaatgcactgctgt ctactaacaaggccgtggtctcactgagcggctgcggcgtgagtgt cctgacctttaaggtgctggacctgaaaaactacatcgataaggag ctgctgcctcagctgaacaatcacgattgtaggatctccaatattgag acagtgattgaattccagcagaagaacaatcgcctgctggagatcg ctcgagagttcagcgtgaacgcaggcattaccacaccactgtcaa catacatgctgactaattcagagctgctgagcctgattaacgacatg cccatcaccaatgatcagaagaaactgatgtctagtaacgtgcaga tcgtccgccagcagtcctattctattatgtgcgtggtcaaggaggaag tgatcgcatacgtggtccagctgcctatctacggcgtgatcgatacc ccatgctggaaactgcatacatctcccctgtgcactaccgacaaca aggaaggaagtaatatttgcctgacaagaactgacaggggctggta ctgtgataacgctggcagcgtgagcttcttccctcagaccgaaacat gcaaggtgcagagcaaccgggtcttctgtgatacaatgaattccctg actctgccaaccgacgtgaacctgtgcaacaccgatatctttaatac aaagtacgactgtaagatcatgacaagcaagactgacatctcaag ctccgtgatcacaagtattggagctatcgtgtcatgctacggcaaga ccaaatgtacagcatctaacaaatgcagagggatcattaagactttc tcaaacggatgtgattatgtgagcaacaaggggtcgacactgtga gcgtcggaaacaccctgtactatgtgaataagctggagggcaaag ccctgtacatcaaggggggaacccatcattaactactatgatccactg gtgttccccagcgacgagtttgatgcatccattgcccaggtgaacgc caaaatcaatcagtccctggcttttattaggcgctccgacgagctgct gtctgccattggcgggtacatccccgaagcccctagggatggcca ggcttatgtgcgcaaggacggggagtgggtcctgctgtcaaccttcc tgggaggactggtgccaagaggctcccaccatcaccatcaccata gcgcctggtcccaccctcagtttgaaaag | bRSV ATue51908 sc9-10 DS-Cav1 N183GC-N428C_ nuc |
| SEQ ID NO: 63 | MAATAMRMIISIIFISTYMTHITLCQNITEEFYQST CSAVSRGYLSALRTGWYTSVVTIELSKIQKNVCKS TDSKVKLIKQELERYNcAVIELQSLMQNEPASFSgs GSAIASGVAVCKVLHLEGEVNKIKNALLSTNKAV VSLSNGVSVLTFKVLDLKNYIDKELLPKLNNHDC RISNIETVIEFQQKNNRLLEIAREFSVNAGITTPLST YMLTcSELLSLINDMPITNDQKKLMSSNVQIVRQ QSYSIMCVVKEEVIAYVVQLPIYGVIDTPCWKLH TSPLCTTDNKEGSNICLTRTDRGWYCDNAGSVS FFPQAETCKVQSNRVFCDTMNSLTLPTDVNLCN TDIFNTKYDCKIMTSKTDISSSVITSIGAIVSCYGKT KCTASNKNRGIIKTFSNGCDYVSNKGVDTVSVG NTLYYVNKLEGKALYIKGEPIINYYDPLVFPSDEF DASIAQVNAKINQSLAFIRRSDELLSAIGGYIPEAP RDGQAYVRKDGEWVLLSTFLGGLVPRGSHHH HHHSAWSHPQFEK | 391-2 sc9 DS-Cav1 N88C N254C |

| TABLE OF SEQUENCES AND SEQ ID NUMBERS (SEQUENCE LISTING): | | |
|---|---|---|
| SEQ ID NO | Sequence | Remarks |
| SEQ ID NO: 64 | MAATAMRMIISIIFISTYMTHITLCQNITEEFYQST CSAVSRGYLSALRTGWYTSVVTIELSKIQKNVCKS TDSKVKLIKQELERYNNAVlcLQSLMQNEPASFSg sGSAIASGVAVCKVLHLEGEVNKIKNALLSTNKA VVSLSNGVSVLITKVLDLKNYIDKELLPKLNNHD CRISNIETVIEFQQKNNRLLEIAREFSVNAGITTPLS TYMLTcSELLSLINDMPITNDQKKLMSSNVQIVR QQSYSIMCVVKEEVIAYVVQLPIYGVIDTPCWKL HTSPLCTTDNKEGSNICLTRTDRGWYCDNAGS VSFFPQAETCKVQSNRVFCDTMNSLTLPTDVNL CNTDIFNTKYDCKIMTSKTDISSSVITSIGAIVSCY GKTKCTASNKNRGIIKTFSNGCDYVSNKGVDTV SVGNTLYYVNKLEGKALYIKGEPIINYYDPLVFPS DEFDASIAQVNAKINQSLAFIRRSDELLSAIGGYIP EAPRDGQAYVRKDGEWVLLSTFLGGLVPRGSH HHHHHSAWSHPQFEK | 391-2 sc9 DS-Cav1 sc9 E92C N254C |
| SEQ ID NO: 65 | MAATAMRMIISIIFISTYMTHITLCQNITEEFYQST CSAVSRGYLSALRTGWYTSVVTIELSKIQKNVCKS TDSKVKLIKQELERYNNAVIELQSLMQNEPASFSg sGSAIASGVAVCKVLHLEGEVNKIKNALLSTNKA VVSLSNGVSVLTFKVLDLKNYIDKELLPKLNNHD CRISNIETVIEFQQKNNRLLEIAREFcVNAGITTPLS TYMLTNSELLSLINDMPITNDQKKLMSSNVcIVR QQSYSIMCVVKEEVIAYVVQLPIYGVIDTPCWKL HTSPLCTTDNKEGSNICLTRTDRGWYCDNAGS VSFFPQAETCKVQSNRVFCDTMNSLTLPTDVNL CNTDIFNTKYDCKIMTSKTDISSSVITSIGAIVSCY GKTKCTASNKNRGIIKTFSNGCDYVSNKGVDTV SVGNTLYYVNKLEGKALYIKGEPIINYYDPLVFPS DEFDASIAQVNAKINQSLAFIRRSDELLSAIGGYIP EAPRDGQAYVRKDGEWVLLSTFLGGLVPRGSH HHHHHSAWSHPQFEK | 391-2 sc9 DS-Cav1 sc9 S238C Q279C |

The invention claimed is:

1. An immunogen comprising a recombinant respiratory syncytial virus (RSV) F protein or a fragment thereof specifically binding to an RSV F prefusion-specific antibody,
wherein the recombinant RSV F protein or the fragment thereof comprises an F1 polypeptide and an F2 polypeptide of any RSV F protein characterized by the following substitutions at amino acid positions corresponding to the following amino acid positions in SEQ ID NO: 1 as a reference sequence:
(i) S155C and S290C substitutions, which form a non-natural disulfide bond;
(ii) a substitution at one or both of positions S190 and V207 by amino acids selected from the group consisting of F, L, W, Y, H, and M; and
(iii) a pair of substitutions forming a non-natural disulfide bond selected from the group consisting of the following substitution pairs: Q98C and Q361C, A149C and Y458C, N183GC and N428C, N88C and N254C, E92C and N254C, and S238C and Q279C;
wherein the recombinant RSV F protein or the fragment thereof does not comprise a pep27 polypeptide; and
wherein (a) the recombinant RSV F protein or the fragment thereof comprises or consists of an F2 polypeptide comprising or consisting of amino acids 26-103 of SEQ ID NO: 31, and an F1 polypeptide comprising or consisting of amino acids 106-474 of SEQ ID NO: 31; or
(b) the recombinant RSV F protein or the fragment thereof comprises or consists of an F2 polypeptide comprising or consisting of amino acids 26-105 of SEQ ID NO: 32; and
an F1 polypeptide comprising or consisting of amino acids 108-476 of SEQ ID NO: 32.

2. The immunogen according to claim 1, wherein the F1 polypeptide and the F2 polypeptide of the recombinant RSV F protein or of the fragment thereof share at least 80% sequence identity with the F1 polypeptide and the F2 polypeptide, respectively, of a native bovine RSV F protein.

3. The immunogen according to claim 2, wherein the native bovine RSV F protein comprises an amino acid sequence according to any of SEQ ID NOs: 1-9.

4. The immunogen according to claim 1, wherein the recombinant RSV F protein, or the fragment thereof, comprises:
(i) an antigenic site Ø that specifically binds to the RSV F prefusion-specific antibody, wherein the antigenic site Ø comprises residues 62-69 and 196-209 of a native bovine RSV F protein sequence set forth in any one of SEQ ID NOs: 1-9;
(ii) an epitope recognized by AM14 antibody, wherein the epitope recognized by AM14 antibody comprises at least residues L160, N183, N426, R429, H514 and H515 of a native bovine RSV F protein sequence set forth in any one of SEQ ID NOs: 1-9; and/or
(iii) an epitope recognized by MPE8 antibody, wherein the epitope recognized by MPE8 antibody comprises at least residues T50, D310, L305, G307, and 1309 of a native bovine RSV F protein sequence set forth in any one of SEQ ID NOs: 1-9.

5. The immunogen according to claim 1, wherein the F2 polypeptide and the F1 polypeptide are linked by a heterologous peptide linker or are directly linked.

6. The immunogen according to claim 1, wherein the recombinant RSV F protein is linked to a trimerization domain.

7. The immunogen according to claim 1, wherein the immunogen comprises or consists of
an F2 polypeptide comprising or consisting of amino acids 26-103 of SEQ ID NO: 31;
an F1 polypeptide comprising or consisting of amino acids 106-474 of SEQ ID NO: 31; and
a foldon domain comprising or consisting of amino acids 475-513 of SEQ ID NO: 31, which is preferably directly linked to the C-terminus of the F1 polypeptide.

8. The immunogen according to claim 1, wherein the recombinant RSV F protein or the fragment thereof comprises or consists of
an F2 polypeptide comprising or consisting of amino acids 26-105 of SEQ ID NO: 32;
an F1 polypeptide comprising or consisting of amino acids 108-476 of SEQ ID NO: 32; and
a foldon domain comprising or consisting of amino acids 477-515 of SEQ ID NO: 32, which is preferably directly linked to the C-terminus of the F1 polypeptide.

9. The immunogen according to claim 1, wherein the immunogen comprises or consists of amino acids 26-474 of SEQ ID NO: 31.

10. The immunogen according to claim 1, wherein the immunogen comprises or consists of an amino acid sequence according to SEQ ID NO: 31.

11. The immunogen according to claim 1, wherein the immunogen comprises or consists of amino acids 26-476 of SEQ ID NO: 32.

12. The immunogen according to claim 1, wherein the immunogen comprises or consists of an amino acid sequence according to SEQ ID NO: 32.

13. A virus-like particle comprising the immunogen according to claim 1.

14. A protein nanoparticle comprising the immunogen according to claim 1.

15. A nucleic acid molecule comprising a polynucleotide encoding the immunogen of claim 1, a virus-like particle comprising the immunogen, or a protein nanoparticle comprising the immunogen.

16. A vector comprising the nucleic acid molecule according to claim 15.

17. An isolated host cell comprising the nucleic acid molecule of claim 15 or a vector comprising the nucleic acid molecule.

18. An immunogenic composition comprising
(i) the immunogen according to claim 1;
(ii) a virus-like particle comprising the immunogen according to (i);
(iii) a protein nanoparticle comprising the immunogen according to (i);
(iv) a nucleic acid molecule comprising a polynucleotide encoding the immunogen according to (i), the virus-like particle according to (ii), or the protein nanoparticle according to (iii);
(v) a vector comprising the nucleic acid molecule according to (iv); or
(vi) a host cell comprising the nucleic acid molecule according to (iv) or the vector according to (v);
and a pharmaceutically acceptable carrier.

* * * * *

SEQUENCE LISTING

<160> NUMBER OF SEQ ID NOS: 65

<210> SEQ ID NO 1
<211> LENGTH: 574
<212> TYPE: PRT
<213> ORGANISM: Artificial Sequence
<220> FEATURE:
<223> OTHER INFORMATION: bRSV 391-2 F0

<400> SEQUENCE: 1

Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Gln Asn Glu Pro Ala Ser Phe Ser Arg Ala Lys Arg Gly Ile Pro
            100                 105                 110

Glu Leu Ile His Tyr Thr Arg Asn Ser Thr Lys Arg Phe Tyr Gly Leu

-continued

```
            115                 120                 125
Met Gly Lys Lys Arg Lys Arg Arg Phe Leu Gly Phe Leu Leu Gly Ile
    130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Lys Val Asn
        195                 200                 205

Asn His Asp Cys Arg Ile Ser Asn Ile Glu Thr Val Ile Glu Phe Gln
        210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Val Val Lys Glu Glu Val Ile Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Thr Asp Val Asn Leu Cys Asn Thr
        370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
        450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
        515                 520                 525

Thr Ile Ile Ile Val Ile Val Val Ile Leu Met Leu Ile Ala Val
        530                 535                 540
```

```
Gly Leu Leu Phe Tyr Cys Lys Thr Arg Ser Thr Pro Ile Met Leu Gly
545                 550                 555                 560

Lys Asp Gln Leu Ser Gly Ile Asn Asn Leu Ser Phe Ser Lys
                565                 570

<210> SEQ ID NO 2
<211> LENGTH: 574
<212> TYPE: PRT
<213> ORGANISM: artificial sequence
<220> FEATURE:
<223> OTHER INFORMATION: bRSV ATue51908 F0

<400> SEQUENCE: 2

Met Ala Thr Thr Ala Met Arg Met Ile Ile Ser Ile Ile Phe Ile Ser
1               5                   10                  15

Thr Tyr Val Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Val Glu Leu Gln Ser Leu
                85                  90                  95

Met Gln Asn Glu Pro Ala Ser Phe Ser Arg Ala Lys Arg Gly Ile Pro
            100                 105                 110

Glu Leu Ile His Tyr Thr Arg Asn Ser Thr Lys Lys Phe Tyr Gly Leu
        115                 120                 125

Met Gly Lys Lys Arg Lys Arg Arg Phe Leu Gly Phe Leu Leu Gly Ile
    130                 135                 140

Gly Ser Ala Val Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Gln Val Asn
        195                 200                 205

Asn His Asp Cys Arg Ile Ser Asn Ile Glu Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Val Val Lys Glu Glu Val Ile Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335
```

Thr Asp Arg Gly Trp Tyr Cys Asp Asn Ala Gly Ser Val Ser Phe Phe
                340                 345                 350

Pro Gln Thr Glu Thr Cys Lys Val Gln Ser Asn Arg Val Phe Cys Asp
            355                 360                 365

Thr Met Asn Ser Leu Thr Leu Pro Thr Asp Val Asn Leu Cys Asn Thr
        370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
        515                 520                 525

Thr Ile Ile Val Ile Val Val Ile Leu Met Leu Ile Ala Val
    530                 535                 540

Gly Leu Leu Phe Tyr Cys Lys Thr Lys Ser Thr Pro Ile Met Leu Gly
545                 550                 555                 560

Lys Asp Gln Leu Ser Gly Ile Asn Asn Leu Ser Phe Ser Lys
                565                 570

<210> SEQ ID NO 3
<211> LENGTH: 574
<212> TYPE: PRT
<213> ORGANISM: artificial sequence
<220> FEATURE:
<223> OTHER INFORMATION: bRSV RB94 F0

<400> SEQUENCE: 3

Met Ala Thr Thr Thr Met Arg Met Ile Ile Ser Ile Ile Ile Ile Phe
1               5                   10                  15

Ile Tyr Val Gln His Ile Thr Leu Cys Gln Asn Ile Thr Glu Glu Phe
                20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Val Thr Ile Glu Leu Ser Lys Ile
        50                  55                  60

Gln Lys Asn Val Cys Asn Ser Thr Asp Ser Asn Val Lys Leu Ile Lys
65                  70                  75                  80

Gln Glu Leu Glu Arg Tyr Asn Asn Ala Val Val Glu Leu Gln Ser Leu
                85                  90                  95

Met Gln Asn Glu Pro Ala Ser Ser Ser Arg Ala Lys Arg Gly Ile Pro
            100                 105                 110

Glu Leu Ile His Tyr Lys Arg Asn Ser Thr Lys Lys Phe Tyr Gly Leu
        115                 120                 125

Met Gly Lys Lys Arg Lys Arg Arg Phe Leu Gly Phe Leu Leu Gly Ile
130             135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Lys Val Asn
        195                 200                 205

Asn His Asp Cys Gln Ile Ser Asn Ile Ala Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Val Val Lys Glu Glu Val Met Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Thr Asp Val Asn Leu Cys Asn Thr
    370                 375                 380

Asp Ile Phe Asn Ala Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Arg Gly Val Asp
        435                 440                 445

Thr Val Ser Val Gly Asn Thr Leu Tyr Tyr Val Asn Lys Leu Glu Gly
    450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
        515                 520                 525

Thr Ile Ile Ile Val Ile Val Val Ile Leu Met Leu Ile Ala Val
    530                 535                 540

```
Gly Leu Leu Phe Tyr Ser Lys Thr Arg Ser Thr Pro Ile Met Leu Gly
545                 550                 555                 560

Lys Asp Gln Leu Ser Gly Ile Asn Asn Leu Ser Phe Ser Lys
                565                 570

<210> SEQ ID NO 4
<211> LENGTH: 574
<212> TYPE: PRT
<213> ORGANISM: artificial sequence
<220> FEATURE:
<223> OTHER INFORMATION: bRSV RB94 F-11 F0

<400> SEQUENCE: 4

Met Ala Thr Thr Ala Met Arg Met Ile Ile Ser Ile Ile Phe Ile Ser
1               5                   10                  15

Thr Tyr Val Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Asn Ser Thr Asp Ser Asn Val Lys Leu Ile Lys
65                  70                  75                  80

Gln Glu Leu Glu Arg Tyr Asn Asn Ala Val Val Glu Leu Gln Ser Leu
                85                  90                  95

Met Gln Asn Glu Pro Ala Ser Ser Ser Arg Ala Lys Arg Gly Ile Pro
            100                 105                 110

Glu Leu Ile His Tyr Lys Arg Asn Ser Thr Lys Lys Phe Tyr Gly Leu
        115                 120                 125

Met Gly Lys Lys Arg Lys Arg Arg Phe Leu Gly Phe Leu Leu Gly Ile
    130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Lys Val Asn
        195                 200                 205

Asn His Asp Cys Lys Ile Ser Asn Ile Ala Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Val Val Lys Glu Glu Val Met Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335
```

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Thr Asp Val Asn Leu Cys Asn Thr
        370                 375                 380

Asp Ile Phe Asn Ala Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Arg Gly Val Asp
                435                 440                 445

Thr Val Ser Val Gly Asn Thr Leu Tyr Tyr Val Asn Lys Leu Glu Gly
            450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
                500                 505                 510

Leu His Ser Val Asp Val Gly Lys Ser Thr Thr Asn Val Val Ile Thr
            515                 520                 525

Thr Ile Ile Ile Val Ile Val Val Ile Leu Met Leu Ile Ala Val
            530                 535                 540

Gly Leu Leu Phe Tyr Ser Lys Thr Arg Ser Thr Pro Ile Met Leu Gly
545                 550                 555                 560

Lys Asp Gln Leu Ser Gly Ile Asn Asn Leu Ser Phe Ser Lys
                565                 570

```
<210> SEQ ID NO 5
<211> LENGTH: 572
<212> TYPE: PRT
<213> ORGANISM: artificial sequence
<220> FEATURE:
<223> OTHER INFORMATION: bRSV A51908 F0

<400> SEQUENCE: 5
```

Met Ala Thr Thr Thr Met Arg Met Ile Ile Ser Ile Ile Leu Ile Ser
1               5                   10                  15

Thr Tyr Val Pro His Ile Thr Leu Cys Gln Asn Ile Thr Glu Glu Phe
                20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Val Thr Ile Glu Leu Ser Lys Ile
        50                  55                  60

Gln Lys Asn Val Cys Asn Gly Thr Asp Ser Lys Val Lys Leu Ile Lys
65                  70                  75                  80

Gln Glu Leu Glu Arg Tyr Asn Asn Ala Val Ala Glu Leu Gln Ser Leu
                85                  90                  95

Met Gln Asn Glu Pro Thr Ser Ser Ser Arg Ala Lys Arg Gly Ile Pro
                100                 105                 110

Glu Ser Ile His Tyr Thr Arg Asn Ser Thr Lys Lys Phe Tyr Gly Leu
            115                 120                 125

```
Met Gly Lys Lys Arg Lys Arg Arg Phe Leu Gly Phe Leu Leu Gly Ile
    130                 135                 140
Gly Ser Ala Ile Ala Ser Gly Val Ala Val Ser Lys Val Leu His Leu
145                 150                 155                 160
Glu Gly Glu Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asp Lys Glu Leu Leu Pro Lys Val Asn
        195                 200                 205
Asn His Asp Cys Arg Ile Ser Asn Ile Ala Thr Val Ile Glu Phe Gln
210                 215                 220
Gln Lys Asn Asn Arg Leu Leu Glu Ile Ala Arg Glu Phe Ser Val Asn
225                 230                 235                 240
Ala Gly Ile Thr Thr Pro Leu Ser Thr Tyr Met Leu Thr Asn Ser Glu
                245                 250                 255
Leu Leu Ser Ile Ile Asn Asp Met Pro Ile Thr Asn Asp Gln Lys Lys
            260                 265                 270
Leu Met Ser Val Cys Gln Ile Val Arg Gln Gln Ser Tyr Ser Ile Met
        275                 280                 285
Ser Val Leu Arg Glu Val Ile Ala Tyr Val Val Gln Leu Pro Leu Tyr
    290                 295                 300
Gly Val Ile Asp Thr Pro Cys Trp Lys Leu His Thr Ser Pro Leu Cys
305                 310                 315                 320
Thr Thr Asp Asn Lys Glu Gly Ser Asn Ile Cys Leu Thr Arg Thr Asp
                325                 330                 335
Arg Gly Trp Tyr Cys Asp Asn Ala Gly Ser Val Ser Phe Phe Pro Gln
            340                 345                 350
Ala Glu Thr Cys Lys Val Gln Ser Asn Arg Val Phe Cys Asp Thr Met
        355                 360                 365
Asn Ser Leu Thr Leu Pro Thr Asp Val Asn Leu Cys Asn Thr Asp Ile
370                 375                 380
Phe Asn Ser Lys Tyr Asp Cys Lys Ile Met Thr Ser Lys Thr Asp Ile
385                 390                 395                 400
Ser Ser Ser Val Ile Thr Ser Ile Gly Ala Ile Val Ser Cys Tyr Gly
                405                 410                 415
Lys Thr Lys Cys Thr Ala Ser Asn Lys Asn Arg Gly Ile Ile Lys Thr
            420                 425                 430
Phe Ser Asn Gly Cys Asp Tyr Val Ser Asn Lys Gly Val Asp Thr Val
        435                 440                 445
Ser Val Gly Asn Thr Leu Tyr Tyr Val Asn Lys Leu Glu Gly Lys Ala
    450                 455                 460
Leu Tyr Ile Lys Gly Glu Pro Ile Ile Asn Tyr Tyr Asn Pro Leu Val
465                 470                 475                 480
Phe Pro Ser Asp Glu Phe Asp Ala Ser Ile Ala Gln Val Asn Ala Lys
                485                 490                 495
Ile Asn Gln Ser Leu Ala Phe Ile Arg Arg Ser Asp Glu Leu Leu His
            500                 505                 510
Ser Val Asp Val Gly Lys Ser Thr Thr Asn Val Val Ile Thr Thr Ile
        515                 520                 525
Ile Ile Val Ile Val Val Ile Leu Met Leu Ile Thr Val Gly Leu
    530                 535                 540
Leu Phe Tyr Cys Lys Thr Arg Ser Thr Pro Ile Met Leu Gly Lys Asp
```

```
                545                 550                 555                 560
          Gln Leu Ser Ser Ile Asn Asn Leu Ser Phe Ser Lys
                          565                 570

<210> SEQ ID NO 6
<211> LENGTH: 493
<212> TYPE: PRT
<213> ORGANISM: artificial sequence
<220> FEATURE:
<223> OTHER INFORMATION: bRSV A375 F0

<400> SEQUENCE: 6

Met Arg Met Ile Ile Ser Ile Ile Leu Ile Ser Thr Tyr Val Pro His
1               5                   10                  15

Ile Thr Leu Cys Gln Asn Ile Thr Glu Glu Phe Tyr Gln Ser Thr Cys
            20                  25                  30

Ser Ala Val Ser Arg Gly Tyr Leu Ser Ala Leu Arg Thr Gly Trp Tyr
        35                  40                  45

Thr Ser Val Val Thr Ile Glu Leu Ser Lys Ile Gln Lys Asn Val Cys
    50                  55                  60

Asn Gly Thr Asp Ser Lys Val Lys Leu Ile Lys Gln Glu Leu Glu Arg
65                  70                  75                  80

Tyr Asn Asn Ala Val Val Glu Leu Gln Ser Leu Met Gln Asn Glu Pro
                85                  90                  95

Thr Ser Ser Ser Arg Ala Lys Arg Gly Ile Pro Glu Ser Ile His Tyr
            100                 105                 110

Thr Arg Asn Ser Thr Lys Lys Phe Tyr Gly Leu Met Gly Lys Lys Arg
        115                 120                 125

Lys Arg Arg Phe Leu Gly Phe Leu Leu Gly Ile Gly Ser Ala Ile Ala
    130                 135                 140

Ser Gly Val Ala Val Ser Lys Val Leu His Leu Glu Gly Glu Val Asn
145                 150                 155                 160

Lys Ile Lys Asn Ala Leu Leu Ser Thr Asn Lys Ala Val Val Ser Leu
                165                 170                 175

Ser Asn Gly Val Ser Val Leu Thr Ser Lys Val Leu Asp Leu Lys Asn
            180                 185                 190

Tyr Ile Asp Lys Lys Leu Leu Pro Lys Val Asn Asn His Asp Cys Arg
        195                 200                 205

Ile Ser Asn Ile Glu Thr Val Ile Glu Phe Gln Gln Lys Asn Asn Arg
    210                 215                 220

Leu Leu Glu Ile Ala Arg Glu Phe Ser Val Asn Ala Gly Ile Thr Thr
225                 230                 235                 240

Pro Leu Ser Thr Tyr Met Leu Thr Asn Ser Glu Leu Leu Ser Leu Ile
                245                 250                 255

Asn Asp Met Pro Ile Thr Asn Asp Gln Lys Lys Leu Met Ser Ser Asn
            260                 265                 270

Val Gln Ile Val Arg Gln Gln Ser Tyr Ser Ile Met Ser Val Val Lys
        275                 280                 285

Glu Glu Val Ile Ala Tyr Val Val Gln Leu Pro Ile Tyr Gly Val Ile
    290                 295                 300

Asp Thr Pro Cys Trp Lys Val His Thr Ser Pro Leu Cys Thr Thr Asp
305                 310                 315                 320

Asn Lys Glu Gly Ser Asn Ile Cys Leu Thr Arg Thr Asp Arg Gly Trp
                325                 330                 335

Tyr Cys Asp Asn Ala Gly Ser Val Ser Phe Phe Pro Gln Ala Glu Thr
```

```
                340              345              350
Cys Lys Val Gln Ser Asn Arg Val Phe Cys Asp Thr Met Asn Ser Leu
            355              360              365
Thr Leu Pro Thr Asp Val Asn Leu Cys Asn Thr Asp Ile Phe Asn Thr
        370              375              380
Lys Tyr Asp Cys Lys Ile Met Thr Ser Lys Thr Asp Ile Ser Ser Ser
385              390              395              400
Val Ile Thr Ser Ile Gly Ala Ile Val Ser Cys Tyr Gly Lys Thr Lys
            405              410              415
Cys Thr Ala Ser Asn Lys Asn Arg Gly Ile Ile Lys Thr Phe Ser Asn
        420              425              430
Gly Cys Asp Tyr Val Ser Asn Lys Gly Val Asp Thr Val Ser Val Gly
        435              440              445
Asn Thr Leu Tyr Tyr Val Asn Lys Leu Glu Gly Lys Ala Leu Tyr Ile
        450              455              460
Lys Gly Glu Pro Ile Ile Asn Tyr Tyr Asn Pro Leu Val Phe Gly Thr
465              470              475              480
Tyr Glu Phe Asp Ala Ser Ile Ala Gln Val Asn Ala Lys
            485              490

<210> SEQ ID NO 7
<211> LENGTH: 574
<212> TYPE: PRT
<213> ORGANISM: artificial sequence
<220> FEATURE:
<223> OTHER INFORMATION: bRSV FS1 F0

<400> SEQUENCE: 7

Met Gly Thr Th

```
                   210                 215                 220
Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                    245                 250                 255

Leu Leu Ser Leu Ile Asn Asp Met Pro Ile Thr Asn Asp Gln Lys Lys
                260                 265                 270

Leu Met Ser Ser Asn Val Gln Ile Val Arg Gln Ser Tyr Ser Ile
            275                 280                 285

Met Ser Val Val Lys Glu Val Ile Ala Tyr Glu Val Gln Leu Pro
290                 295                 300

Ile Tyr Gly Val Ile Asp Thr Pro Cys Trp Lys Ile His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Thr Asp Val Asn Leu Cys Asn Thr
370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Pro Ile Gly Cys Asp Tyr Val Ser Asn Lys Gly Val Asp
                435                 440                 445

Thr Val Ser Val Gly Asn Thr Leu Tyr Tyr Val Asn Lys Leu Glu Gly
450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
                500                 505                 510

Leu His Ser Val Asp Val Gly Lys Ser Thr Thr Asn Val Val Ile Thr
            515                 520                 525

Thr Ile Ile Ile Val Ile Val Val Ile Leu Met Leu Ile Ala Val
530                 535                 540

Gly Leu Leu Phe Tyr Cys Lys Thr Arg Ser Thr Pro Ile Met Leu Gly
545                 550                 555                 560

Lys Asp Gln Leu Ser Gly Ile Asn Asn Leu Ser Phe Ser Lys
                565                 570

<210> SEQ ID NO 8
<211> LENGTH: 574
<212> TYPE: PRT
<213> ORGANISM: artificial sequence
<220> FEATURE:
<223> OTHER INFORMATION: bRSV Snook F0

<400> SEQUENCE: 8

Met Ala Thr Thr Ala Met Thr Met Ile Ile Ser Ile Ile Phe Ile Ser
```

```
1               5                   10                  15
Thr Tyr Val Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Val Thr Ile Glu Leu Ser Lys Ile
50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Val Glu Leu Gln Ser Leu
            85                  90                  95

Met Gln Asn Glu Pro Ala Ser Phe Ser Arg Ala Lys Arg Ser Ile Pro
            100                 105                 110

Glu Leu Ile His Tyr Thr Arg Asn Ser Thr Lys Lys Phe Tyr Gly Leu
            115                 120                 125

Met Gly Lys Lys Arg Lys Arg Arg Phe Leu Gly Phe Leu Leu Gly Ile
            130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Lys Val Asn
            195                 200                 205

Asn His Asp Cys Arg Ile Ser Asn Ile Ala Thr Val Ile Glu Phe Gln
            210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Ser Val Val Lys Glu Glu Val Ile Ala Tyr Val Val Gln Leu Pro
            290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Thr Asp Val Asn Leu Cys Asn Thr
            370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
            405                 410                 415

Tyr Gly Lys Thr Lys Cys Thr Ala Ser Asn Lys Asn Arg Gly Ile Ile
            420                 425                 430
```

```
Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
        515                 520                 525

Thr Ile Ile Ile Val Ile Val Val Ile Leu Met Leu Ile Ala Val
        530                 535                 540

Gly Leu Leu Phe Tyr Cys Lys Thr Arg Ser Thr Pro Ile Met Leu Gly
545                 550                 555                 560

Lys Asp Gln Leu Ser Gly Ile Asn Asn Leu Ser Phe Ser Lys
                565                 570

<210> SEQ ID NO 9
<211> LENGTH: 574
<212> TYPE: PRT
<213> ORGANISM: artificial sequence
<220> FEATURE:
<223> OTHER INFORMATION: bRSV ATCC51908 F0

<400> SEQUENCE: 9

Met Ala Thr Thr Ala Met Arg Met Ile Ile Ser Ile Ile Phe Ile Ser
1               5                   10                  15

Thr Tyr Val Thr His Ile Thr Leu Cys Gln Asn Ile Thr Glu Glu Phe
            20                  25                  30

Ty

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
        260                 265                 270

Leu Met Ser Ser Asn Val Gln Ile Val Arg Gln Gln Ser Tyr Ser Ile
    275                 280                 285

Met Ser Val Val Lys Glu Val Ile Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Thr Glu Thr Cys Lys Val Gln Ser Asn Arg Val Phe Cys Asp
        355                 360                 365

Thr Met Asn Ser Leu Thr Leu Pro Thr Asp Val Asn Leu Cys Asn Thr
    370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Leu Glu Gly
    450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
        515                 520                 525

Thr Ile Ile Ile Val Ile Val Val Ile Leu Met Leu Ile Ala Val
    530                 535                 540

Gly Leu Leu Phe Tyr Cys Lys Thr Lys Ser Thr Pro Ile Met Leu Gly
545                 550                 555                 560

Lys Asp Gln Leu Ser Gly Ile Asn Asn Leu Ser Phe Ser Lys
                565                 570

<210> SEQ ID NO 10
<211> LENGTH: 9
<212> TYPE: PRT
<213> ORGANISM: Artificial Sequence
<220> FEATURE:
<223> OTHER INFORMATION: Linker

<400> SEQUENCE: 10

Gly Ser Gly Asn Val Gly Leu Gly Gly
1               5

<210> SEQ ID NO 11
<211> LENGTH: 9
<212> TYPE: PRT
<213> ORGANISM: Artificial Sequence
<220> FEATURE:
<223> OTHER INFORMATION: Linker

<400> SEQUENCE: 11

Gly Ser Gly Asn Trp Gly Leu Gly Gly
1               5

<210> SEQ ID NO 12
<211> LENGTH: 9
<212> TYPE: PRT
<213> ORGANISM: Artificial Sequence
<220> FEATURE:
<223> OTHER INFORMATION: Linker

<400> SEQUENCE: 12

Gly Ser Gly Asn Ile Gly Leu Gly Gly
1               5

<210> SEQ ID NO 13
<211> LENGTH: 11
<212> TYPE: PRT
<213> ORGANISM: Artificial Sequence
<220> FEATURE:
<223> OTHER INFORMATION: Linker

<400> SEQUENCE: 13

Gly Ser Gly Gly Asn Gly Ile Gly Leu Gly Gly
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Linker

<400> SEQUENCE: 14

Gly Ser Gly Gly Ser Gly Gly Ser Gly Gly
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Linker

<400> SEQUENCE: 15

Gly Ser Gly Asn Val Leu Gly Gly
1               5

<210> SEQ ID NO 16
<211> LENGTH: 4
<212> TYPE: PRT
<213> ORGANISM: Artificial Sequence
<220> FEATURE:
<223> OTHER INFORMATION: Linker

<400> SEQUENCE: 16

Gly Gly Ser Gly
1

```
<210> SEQ ID NO 17
<211> LENGTH: 6
<212> TYPE: PRT
<213> ORGANISM: Artificial Sequence
<220> FEATURE:
<223> OTHER INFORMATION: Linker

<400> SEQUENCE: 17

Gly Gly Ser Gly Gly Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Linker

<400> SEQUENCE: 18

Gly Gly Ser Gly Gly Ser Gly
1               5

<210> SEQ ID NO 19
<211> LENGTH: 7
<212> TYPE: PRT
<213> ORGANISM: Artificial Sequence
<220> FEATURE:
<223> OTHER INFORMATION: Linker

<400> SEQUENCE: 19

Gly Gly Ser Gly Ser Gly Gly
1               5

<210> SEQ ID NO 20
<211> LENGTH: 12
<212> TYPE: PRT
<213> ORGANISM: Artificial Sequence
<220> FEATURE:
<223> OTHER INFORMATION: Linker

<400> SEQUENCE: 20

Gly Gly Ser Gly Gly Gly Gly Ser Gly Gly Ser Gly
1               5                   10

<210> SEQ ID NO 21
<211> LENGTH: 5
<212> TYPE: PRT
<213> ORGANISM: Artificial Sequence
<220> FEATURE:
<223> OTHER INFORMATION: Linker

<400> SEQUENCE: 21

Gly Gly Ser Gly Gly
1               5

<210> SEQ ID NO 22
<211> LENGTH: 8
<212> TYPE: PRT
<213> ORGANISM: Artificial Sequence
<220> FEATURE:
<223> OTHER INFORMATION: Linker

<400> SEQUENCE: 22

Gly Gly Ser Gly Ser Gly Ser Gly
1               5
```

-continued

```
<210> SEQ ID NO 23
<211> LENGTH: 7
<212> TYPE: PRT
<213> ORGANISM: Artificial Sequence
<220> FEATURE:
<223> OTHER INFORMATION: Linker

<400> SEQUENCE: 23

Gly Ser Gly Gly Gly Ser Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Linker

<400> SEQUENCE: 24

Gly Gly Pro Gly Gly
1               5

<210> SEQ ID NO 25
<211> LENGTH: 15
<212> TYPE: PRT
<213> ORGANISM: Artificial Sequence
<220> FEATURE:
<223> OTHER INFORMATION: Linker

<400> SEQUENCE: 25

Gly Gly Gly Ser Gly Gly Gly Ser Gly Gly Gly Ser Gly Gly Gly
1               5                   10                  15

<210> SEQ ID NO 26
<211> LENGTH: 11
<212> TYPE: PRT
<213> ORGANISM: Artificial Sequence
<220> FEATURE:
<223> OTHER INFORMATION: Linker

<400> SEQUENCE: 26

Gly Gly Gly Ser Gly Gly Gly Ser Gly Gly Gly
1               5                   10

<210> SEQ ID NO 27
<211> LENGTH: 26
<212> TYPE: PRT
<213> ORGANISM: Artificial Sequence
<220> FEATURE:
<223> OTHER INFORMATION: Trimerization domain

<400> SEQUENCE: 27

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe
            20                  25

<210> SEQ ID NO 28
<211> LENGTH: 30
<212> TYPE: PRT
<213> ORGANISM: Artificial Sequence
<220> FEATURE:
<223> OTHER INFORMATION: Trimerization domain

<400> SEQUENCE: 28

Ser Ala Ile Gly Gly Tyr Ile Pro Glu Ala Pro Arg Asp Gly Gln Ala
1               5                   10                  15
```

Tyr Val Arg Lys Asp Gly Glu Trp Val Leu Leu Ser Thr Phe
            20                  25                  30

<210> SEQ ID NO 29
<211> LENGTH: 40
<212> TYPE: PRT
<213> ORGANISM: Artificial Sequence
<220> FEATURE:
<223> OTHER INFORMATION: Trimerization domain

<400> SEQUENCE: 29

Ser Ala Ile Gly Gly Tyr Ile Pro Glu Ala Pro Arg Asp Gly Gln Ala
1               5                   10                  15

Tyr Val Arg Lys Asp Gly Glu Trp Val Leu Leu Ser Thr Phe Leu Gly
            20                  25                  30

Gly Leu Val Pro Arg Gly Ser His
        35                  40

<210> SEQ ID NO 30
<211> LENGTH: 6
<212> TYPE: PRT
<213> ORGANISM: Artificial Sequence
<220> FEATURE:
<223> OTHER INFORMATION: Thrombin site

<400> SEQUENCE: 30

Leu Val Pro Arg Gly Ser
1               5

<210> SEQ ID NO 31
<211> LENGTH: 529
<212> TYPE: PRT
<213> ORGANISM: Artificial Sequence
<220> FEATURE:
<223> OTHER INFORMATION: 391-2 sc9-10 DS-Cav1 Q98C Q361C

<400> SEQUENCE: 31

Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Cys Asn Glu Pro Ala Ser Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Asn Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Glu Leu Leu Pro Lys Leu Asn Asn His Asp Cys Arg Ile Ser
                165                 170                 175

Asn Ile Glu Thr Val Ile Glu Phe Gln Gln Lys Asn Asn Arg Leu Leu
            180                 185                 190

Glu Ile Ala Arg Glu Phe Ser Val Asn Ala Gly Ile Thr Thr Pro Leu
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Cys Val Val Lys Glu Glu
                245                 250                 255

Val Ile Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asp Asn Lys
        275                 280                 285

Glu Gly Ser Asn Ile Cys Leu Thr Arg Thr Asp Arg Gly Trp Tyr Cys
290                 295                 300

Asp Asn Ala Gly Ser Val Ser Phe Phe Pro Gln Ala Glu Thr Cys Lys
305                 310                 315                 320

Val Cys Ser Asn Arg Val Phe Cys Asp Thr Met Asn Ser Leu Thr Leu
                325                 330                 335

Pro Thr Asp Val Asn Leu Cys Asn Thr Asp Ile Phe Asn Thr Lys Tyr
            340                 345                 350

Asp Cys Lys Ile Met Thr Ser Lys Thr Asp Ile Ser Ser Ser Val Ile
        355                 360                 365

Thr Ser Ile Gly Ala Ile Val Ser Cys Tyr Gly Lys Thr Lys Cys Thr
370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Leu Glu Gly Lys Ala Leu Tyr Ile Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ala Gln Val Asn Ala Lys Ile Asn Gln Ser Leu
450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His Ser Ala Trp Ser His Pro Gln Phe Glu
        515                 520                 525

Lys

<210> SEQ ID NO 32
<211> LENGTH: 531
<212> TYPE: PRT
<213> ORGANISM: Artificial Sequence
<220> FEATURE:
<223> OTHER INFORMATION: 391-2 sc9 DS-Cav1 Q98C Q361C

<400> SEQUENCE: 32

Met Ala Ala Thr Ala Met Arg Met Ile Ile Ser Ile Ile Phe Ile Ser

-continued

```
1               5                   10                  15
Thr Tyr Met Thr His Ile Thr Leu Cys Gln Asn Ile Thr Glu Glu Phe
                20                  25                  30

Tyr Gln Ser Thr Cys Ser Ala Val Ser Arg Gly Tyr Leu Ser Ala Leu
                35                  40                  45

Arg Thr Gly Trp Tyr Thr Ser Val Val Thr Ile Glu Leu Ser Lys Ile
 50                  55                  60

Gln Lys Asn Val Cys Lys Ser Thr Asp Ser Lys Val Lys Leu Ile Lys
 65                  70                  75                  80

Gln Glu Leu Glu Arg Tyr Asn Asn Ala Val Ile Glu Leu Gln Ser Leu
                85                  90                  95

Met Cys Asn Glu Pro Ala Ser Phe Ser Gly Ser Gly Ser Ala Ile Ala
                100                 105                 110

Ser Gly Val Ala Val Cys Lys Val Leu His Leu Glu Gly Glu Val Asn
                115                 120                 125

Lys Ile Lys Asn Ala Leu Leu Ser Thr Asn Lys Ala Val Val Ser Leu
        130                 135                 140

Ser Asn Gly Val Ser Val Leu Thr Phe Lys Val Leu Asp Leu Lys Asn
145                 150                 155                 160

Tyr Ile Asp Lys Glu Leu Leu Pro Lys Leu Asn Asn His Asp Cys Arg
                165                 170                 175

Ile Ser Asn Ile Glu Thr Val Ile Glu Phe Gln Gln Lys Asn Asn Arg
                180                 185                 190

Leu Leu Glu Ile Ala Arg Glu Phe Ser Val Asn Ala Gly Ile Thr Thr
                195                 200                 205

Pro Leu Ser Thr Tyr Met Leu Thr Asn Ser Glu Leu Leu Ser Leu Ile
 210                 215                 220

Asn Asp Met Pro Ile Thr Asn Asp Gln Lys Lys Leu Met Ser Ser Asn
225                 230                 235                 240

Val Gln Ile Val Arg Gln Gln Ser Tyr Ser Ile Met Cys Val Val Lys
                245                 250                 255

Glu Glu Val Ile Ala Tyr Val Val Gln Leu Pro Ile Tyr Gly Val Ile
                260                 265                 270

Asp Thr Pro Cys Trp Lys Leu His Thr Ser Pro Leu Cys Thr Thr Asp
                275                 280                 285

Asn Lys Glu Gly Ser Asn Ile Cys Leu Thr Arg Thr Asp Arg Gly Trp
                290                 295                 300

Tyr Cys Asp Asn Ala Gly Ser Val Ser Phe Phe Pro Gln Ala Glu Thr
305                 310                 315                 320

Cys Lys Val Cys Ser Asn Arg Val Phe Cys Asp Thr Met Asn Ser Leu
                325                 330                 335

Thr Leu Pro Thr Asp Val Asn Leu Cys Asn Thr Asp Ile Phe Asn Thr
                340                 345                 350

Lys Tyr Asp Cys Lys Ile Met Thr Ser Lys Thr Asp Ile Ser Ser Ser
                355                 360                 365

Val Ile Thr Ser Ile Gly Ala Ile Val Ser Cys Tyr Gly Lys Thr Lys
                370                 375                 380

Cys Thr Ala Ser Asn Lys Asn Arg Gly Ile Ile Lys Thr Phe Ser Asn
385                 390                 395                 400

Gly Cys Asp Tyr Val Ser Asn Lys Gly Val Asp Thr Val Ser Val Gly
                405                 410                 415

Asn Thr Leu Tyr Tyr Val Asn Lys Leu Glu Gly Lys Ala Leu Tyr Ile
                420                 425                 430
```

```
Lys Gly Glu Pro Ile Ile Asn Tyr Tyr Asp Pro Leu Val Phe Pro Ser
        435                 440                 445

Asp Glu Phe Asp Ala Ser Ile Ala Gln Val Asn Ala Lys Ile Asn Gln
450                 455                 460

Ser Leu Ala Phe Ile Arg Arg Ser Asp Glu Leu Leu Ser Ala Ile Gly
465                 470                 475                 480

Gly Tyr Ile Pro Glu Ala Pro Arg Asp Gly Gln Ala Tyr Val Arg Lys
                485                 490                 495

Asp Gly Glu Trp Val Leu Leu Ser Thr Phe Leu Gly Gly Leu Val Pro
            500                 505                 510

Arg Gly Ser His His His His His His Ser Ala Trp Ser His Pro Gln
        515                 520                 525

Phe Glu Lys
    530

<210> SEQ ID NO 33
<211> LENGTH: 534
<212> TYPE: PRT
<213> ORGANISM: Artificial Sequence
<220> FEATURE:
<223> OTHER INFORMATION: ATue51908 sc9-10 DS-Cav1 A149C-Y458C

<400> SEQUENCE: 33

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Val Gly Gln Asn
                20                  25                  30

Ile Thr Glu Glu Phe Tyr Gln Ser Thr Cys Ser Ala Val Ser Arg Gly
            35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Lys Ser Thr Asp Ser Lys
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Glu Pro Ala Ser Gly Ser Gly Ser
            100                 105                 110

Ala Val Cys Ser Gly Val Ala Val Cys Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Gln Leu Asn Asn His
                165                 170                 175

Asp Cys Arg Ile Ser Asn Ile Glu Thr Val Ile Glu Phe Gln Gln Lys
            180                 185                 190

Asn Asn Arg Leu Leu Glu Ile Ala Arg Glu Phe Ser Val Asn Ala Gly
        195                 200                 205

Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240

Ser Ser Asn Val Gln Ile Val Arg Gln Gln Ser Tyr Ser Ile Met Cys
                245                 250                 255
```

```
Val Val Lys Glu Glu Val Ile Ala Tyr Val Val Gln Leu Pro Ile Tyr
            260                 265                 270

Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
290                 295                 300

Arg Gly Trp Tyr Cys Asp Asn Ala Gly Ser Val Ser Phe Phe Pro Gln
305                 310                 315                 320

Thr Glu Thr Cys Lys Val Gln Ser Asn Arg Val Phe Cys Asp Thr Met
                325                 330                 335

Asn Ser Leu Thr Leu Pro Thr Asp Val Asn Leu Cys Asn Thr Asp Ile
            340                 345                 350

Phe Asn Thr Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Lys Gly Val Asp Thr Val
                405                 410                 415

Ser Val Gly Asn Thr Leu Tyr Cys Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
    450                 455                 460

Ile Asn Gln Ser Leu Ala Phe Ile Arg Arg Ser Asp Glu Leu Leu Ser
465                 470                 475                 480

Ala Ile Gly Gly Tyr Ile Pro Glu Ala Pro Arg Asp Gly Gln Ala Tyr
                485                 490                 495

Val Arg Lys Asp Gly Glu Trp Val Leu Leu Ser Thr Phe Leu Gly Gly
            500                 505                 510

Leu Val Pro Arg Gly Ser His His His His His Ser Ala Trp Ser
        515                 520                 525

His Pro Gln Phe Glu Lys
    530

<210> SEQ ID NO 34
<211> LENGTH: 6
<212> TYPE: PRT
<213> ORGANISM: Artificial Sequence
<220> FEATURE:
<223> OTHER INFORMATION: His tag

<400> SEQUENCE: 34

His His His His His His
1               5

<210> SEQ ID NO 35
<211> LENGTH: 8
<212> TYPE: PRT
<213> ORGANISM: Artificial Sequence
<220> FEATURE:
<223> OTHER INFORMATION: Strep tag

<400> SEQUENCE: 35

Trp Ser His Pro Gln Phe Glu Lys
```

<210> SEQ ID NO 36
<211> LENGTH: 568
<212> TYPE: PRT
<213> ORGANISM: Artificial Sequence
<220> FEATURE:
<223> OTHER INFORMATION: bRSV 391-2 DSCav1

<400> SEQUENCE: 36

```
Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Gln Asn Glu Pro Ala Ser Phe Ser Arg Ala Lys Arg Gly Ile Pro
            100                 105                 110

Glu Leu Ile His Tyr Thr Arg Asn Ser Thr Lys Arg Phe Tyr Gly Leu
        115                 120                 125

Met Gly Lys Lys Arg Lys Arg Arg Phe Leu Gly Phe Leu Leu Gly Ile
    130                 135                 140

Gly Ser Ala Ile Ala Ser Gly Val Ala Val Cys Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Glu Leu Leu Pro Lys Leu Asn
        195                 200                 205

Asn His Asp Cys Arg Ile Ser Asn Ile Glu Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Cys Val Val Lys Glu Glu Val Ile Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
```

```
                    355                 360                 365
Thr Met Asn Ser Leu Thr Leu Pro Thr Asp Val Asn Leu Cys Asn Thr
        370                 375                 380

Asp Ile Phe Asn Thr Lys Tyr Asp Cys Lys Ile Met Thr Ser Lys Thr
385                 390                 395                 400

Asp Ile Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Leu Glu Gly
                450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
                500                 505                 510

Leu Ser Ala Ile Gly Gly Tyr Ile Pro Glu Ala Pro Arg Asp Gly Gln
                515                 520                 525

Ala Tyr Val Arg Lys Asp Gly Glu Trp Val Leu Leu Ser Thr Phe Leu
                530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 37
<211> LENGTH: 573
<212> TYPE: PRT
<213> ORGANISM: Artificial Sequence
<220> FEATURE:
<223> OTHER INFORMATION: bRSV ATue51908 DSCav1

<400> SEQUENCE: 37

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Val Gly Gln Asn
                20                  25                  30

Ile Thr Glu Glu Phe Tyr Gln Ser Thr Cys Ser Ala Val Ser Arg Gly
                35                  40                  45

Tyr Leu Ser Ala Leu Arg Thr Gly Trp Tyr Thr Ser Val Val Thr Ile
        50                  55                  60

Glu Leu Ser Lys Ile Gln Lys Asn Val Cys Lys Ser Thr Asp Ser Lys
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Glu Pro Ala Ser Phe Ser Arg Ala
                100                 105                 110

Lys Arg Gly Ile Pro Glu Leu Ile His Tyr Thr Arg Asn Ser Thr Lys
                115                 120                 125

Lys Phe Tyr Gly Leu Met Gly Lys Lys Arg Lys Arg Arg Phe Leu Gly
                130                 135                 140

Phe Leu Leu Gly Ile Gly Ser Ala Val Ala Ser Gly Val Ala Val Cys
```

-continued

```
            145                 150                 155                 160
Lys Val Leu His Leu Glu Gly Glu Val Asn Lys Ile Lys Asn Ala Leu
                    165                 170                 175
Leu Ser Thr Asn Lys Ala Val Val Ser Leu Ser Asn Gly Val Ser Val
                    180                 185                 190
Leu Thr Phe Lys Val Leu Asp Leu Lys Asn Tyr Ile Asp Lys Glu Leu
                    195                 200                 205
Leu Pro Gln Leu Asn Asn His Asp Cys Arg Ile Ser Asn Ile Glu Thr
            210                 215                 220
Val Ile Glu Phe Gln Gln Lys Asn Asn Arg Leu Leu Glu Ile Ala Arg
225                 230                 235                 240
Glu Phe Ser Val Asn Ala Gly Ile Thr Thr Pro Leu Ser Thr Tyr Met
                    245                 250                 255
Leu Thr Asn Ser Glu Leu Leu Ser Leu Ile Asn Asp Met Pro Ile Thr
                    260                 265                 270
Asn Asp Gln Lys Lys Leu Met Ser Ser Asn Val Gln Ile Val Arg Gln
                    275                 280                 285
Gln Ser Tyr Ser Ile Met Cys Val Val Lys Glu Val Ile Ala Tyr
            290                 295                 300
Val Val Gln Leu Pro Ile Tyr Gly Val Ile Asp Thr Pro Cys Trp Lys
305                 310                 315                 320
Leu His Thr Ser Pro Leu Cys Thr Thr Asp Asn Lys Glu Gly Ser Asn
                    325                 330                 335
Ile Cys Leu Thr Arg Thr Asp Arg Gly Trp Tyr Cys Asp Asn Ala Gly
                    340                 345                 350
Ser Val Ser Phe Phe Pro Gln Thr Glu Thr Cys Lys Val Gln Ser Asn
                    355                 360                 365
Arg Val Phe Cys Asp Thr Met Asn Ser Leu Thr Leu Pro Thr Asp Val
            370                 375                 380
Asn Leu Cys Asn Thr Asp Ile Phe Asn Thr Lys Tyr Asp Cys Lys Ile
385                 390                 395                 400
Met Thr Ser Lys Thr Asp Ile Ser Ser Ser Val Ile Thr Ser Ile Gly
                    405                 410                 415
Ala Ile Val Ser Cys Tyr Gly Lys Thr Lys Cys Thr Ala Ser Asn Lys
                    420                 425                 430
Asn Arg Gly Ile Ile Lys Thr Phe Ser Asn Gly Cys Asp Tyr Val Ser
                    435                 440                 445
Asn Lys Gly Val Asp Thr Val Ser Val Gly Asn Thr Leu Tyr Tyr Val
            450                 455                 460
Asn Lys Leu Glu Gly Lys Ala Leu Tyr Ile Lys Gly Glu Pro Ile Ile
465                 470                 475                 480
Asn Tyr Tyr Asp Pro Leu Val Phe Pro Ser Asp Glu Phe Asp Ala Ser
                    485                 490                 495
Ile Ala Gln Val Asn Ala Lys Ile Asn Gln Ser Leu Ala Phe Ile Arg
            500                 505                 510
Arg Ser Asp Glu Leu Leu Ser Ala Ile Gly Gly Tyr Ile Pro Glu Ala
            515                 520                 525
Pro Arg Asp Gly Gln Ala Tyr Val Arg Lys Asp Gly Glu Trp Val Leu
            530                 535                 540
Leu Ser Thr Phe Leu Gly Gly Leu Val Pro Arg Gly Ser His His
545                 550                 555                 560
His His His Ser Ala Trp Ser His Pro Gln Phe Glu Lys
                    565                 570
```

<210> SEQ ID NO 38
<211> LENGTH: 568
<212> TYPE: PRT
<213> ORGANISM: Artificial Sequence
<220> FEATURE:
<223> OTHER INFORMATION: bRSV RB94DSCav1

<400> SEQUENCE: 38

Met Pro Met Gly Ser Leu Gln Pro Leu Ala Thr Leu Tyr Leu Leu Gly
1               5                   10                  15

Met Leu Val Ala Ser Val Leu Ala Ala Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Asn Ser Thr Asp Ser Asn Val Lys Leu Ile Lys
65                  70                  75                  80

Gln Glu Leu Glu Arg Tyr Asn Asn Ala Val Val Glu Leu Gln Ser Leu
                85                  90                  95

Met Gln Asn Glu Pro Ala Ser Ser Arg Ala Lys Arg Gly Ile Pro
            100                 105                 110

Glu Leu Ile His Tyr Lys Arg Asn Ser Thr Lys Lys Phe Tyr Gly Leu
        115                 120                 125

Met Gly Lys Lys Arg Lys Arg Arg Phe Leu Gly Phe Leu Leu Gly Ile
    130                 135                 140

Gly Ser Ala Ile Ala Ser Gly Val Ala Val Cys Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Glu Leu Leu Pro Lys Leu Asn
        195                 200                 205

Asn His Asp Cys Gln Ile Ser Asn Ile Ala Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Cys Val Val Lys Glu Glu Val Met Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

```
Thr Met Asn Ser Leu Thr Leu Pro Thr Asp Val Asn Leu Cys Asn Thr
    370                 375                 380

Asp Ile Phe Asn Ala Lys Tyr Asp Cys Lys Ile Met Thr Ser Lys Thr
385                 390                 395                 400

Asp Ile Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Arg Gly Val Asp
        435                 440                 445

Thr Val Ser Val Gly Asn Thr Leu Tyr Tyr Val Asn Lys Leu Glu Gly
    450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser His His His His His His Ser Ala
545                 550                 555                 560

Trp Ser His Pro Gln Phe Glu Lys
                565

<210> SEQ ID NO 39
<211> LENGTH: 536
<212> TYPE: PRT
<213> ORGANISM: Artificial Sequence
<220> FEATURE:
<223> OTHER INFORMATION: RB94 DS-Cav1 sc9 A149C Y458C

<400> SEQUENCE: 39

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Val Gly Gln Asn
                20                  25                  30

Ile Thr Glu Glu Phe Tyr Gln Ser Thr Cys Ser Ala Val Ser Arg Gly
            35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Asn Ser Thr Asp Ser Asn
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Glu Pro Ala Ser Ser Ser Gly Ser
            100                 105                 110

Gly Ser Ala Ile Cys Ser Gly Val Ala Val Cys Lys Val Leu His Leu
        115                 120                 125

Glu Gly Glu Val Asn Lys Ile Lys Asn Ala Leu Leu Ser Thr Asn Lys
    130                 135                 140

Ala Val Val Ser Leu Ser Asn Gly Val Ser Val Leu Thr Phe Lys Val
145                 150                 155                 160
```

Leu Asp Leu Lys Asn Tyr Ile Asp Lys Glu Leu Leu Pro Lys Leu Asn
            165                 170                 175

Asn His Asp Cys Gln Ile Ser Asn Ile Ala Thr Val Ile Glu Phe Gln
        180                 185                 190

Gln Lys Asn Asn Arg Leu Leu Glu Ile Ala Arg Glu Phe Ser Val Asn
    195                 200                 205

Ala Gly Ile Thr Thr Pro Leu Ser Thr Tyr Met Leu Thr Asn Ser Glu
210                 215                 220

Leu Leu Ser Leu Ile Asn Asp Met Pro Ile Thr Asn Asp Gln Lys Lys
225                 230                 235                 240

Leu Met Ser Ser Asn Val Gln Ile Val Arg Gln Gln Ser Tyr Ser Ile
                245                 250                 255

Met Cys Val Val Lys Glu Val Met Ala Tyr Val Val Gln Leu Pro
            260                 265                 270

Ile Tyr Gly Val Ile Asp Thr Pro Cys Trp Lys Leu His Thr Ser Pro
        275                 280                 285

Leu Cys Thr Thr Asp Asn Lys Glu Gly Ser Asn Ile Cys Leu Thr Arg
    290                 295                 300

Thr Asp Arg Gly Trp Tyr Cys Asp Asn Ala Gly Ser Val Ser Phe Phe
305                 310                 315                 320

Pro Gln Ala Glu Thr Cys Lys Val Gln Ser Asn Arg Val Phe Cys Asp
                325                 330                 335

Thr Met Asn Ser Leu Thr Leu Pro Thr Asp Val Asn Leu Cys Asn Thr
            340                 345                 350

Asp Ile Phe Asn Ala Lys Tyr Asp Cys Lys Ile Met Thr Ser Lys Thr
        355                 360                 365

Asp Ile Ser Ser Ser Val Ile Thr Ser Ile Gly Ala Ile Val Ser Cys
    370                 375                 380

Tyr Gly Lys Thr Lys Cys Thr Ala Ser Asn Lys Asn Arg Gly Ile Ile
385                 390                 395                 400

Lys Thr Phe Ser Asn Gly Cys Asp Tyr Val Ser Asn Arg Gly Val Asp
                405                 410                 415

Thr Val Ser Val Gly Asn Thr Leu Tyr Cys Val Asn Lys Leu Glu Gly
            420                 425                 430

Lys Ala Leu Tyr Ile Lys Gly Glu Pro Ile Ile Asn Tyr Tyr Asp Pro
        435                 440                 445

Leu Val Phe Pro Ser Asp Glu Phe Asp Ala Ser Ile Ala Gln Val Asn
    450                 455                 460

Ala Lys Ile Asn Gln Ser Leu Ala Phe Ile Arg Arg Ser Asp Glu Leu
465                 470                 475                 480

Leu Ser Ala Ile Gly Gly Tyr Ile Pro Glu Ala Pro Arg Asp Gly Gln
                485                 490                 495

Ala Tyr Val Arg Lys Asp Gly Glu Trp Val Leu Leu Ser Thr Phe Leu
            500                 505                 510

Gly Gly Leu Val Pro Arg Gly Ser His His His His His His Ser Ala
        515                 520                 525

Trp Ser His Pro Gln Phe Glu Lys
    530                 535

<210> SEQ ID NO 40
<211> LENGTH: 537
<212> TYPE: PRT
<213> ORGANISM: Artificial Sequence
<220> FEATURE:

<223> OTHER INFORMATION: RB94 sc9 DS-Cav1 N183GC N428C

<400> SEQUENCE: 40

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
                20                  25                  30

Ile Thr Glu Glu Phe Tyr Gln Ser Thr Cys Ser Ala Val Ser Arg Gly
            35                  40                  45

Tyr Leu Ser Ala Leu Arg Thr Gly Trp Tyr Thr Ser Val Val Thr Ile
        50                  55                  60

Glu Leu Ser Lys Ile Gln Lys Asn Val Cys Asn Ser Thr Asp Ser Asn
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Glu Pro Ala Ser Ser Ser Gly Ser
            100                 105                 110

Gly Ser Ala Ile Ala Ser Gly Val Ala Val Cys Lys Val Leu His Leu
        115                 120                 125

Glu Gly Glu Val Asn Lys Ile Lys Asn Ala Leu Leu Ser Thr Asn Lys
130                 135                 140

Ala Val Val Ser Leu Ser Gly Cys Gly Val Ser Val Leu Thr Phe Lys
145                 150                 155                 160

Val Leu Asp Leu Lys Asn Tyr Ile Asp Lys Glu Leu Leu Pro Lys Leu
                165                 170                 175

Asn Asn His Asp Cys Gln Ile Ser Asn Ile Ala Thr Val Ile Glu Phe
            180                 185                 190

Gln Gln Lys Asn Asn Arg Leu Leu Glu Ile Ala Arg Glu Phe Ser Val
        195                 200                 205

Asn Ala Gly Ile Thr Thr Pro Leu Ser Thr Tyr Met Leu Thr Asn Ser
210                 215                 220

Glu Leu Leu Ser Leu Ile Asn Asp Met Pro Ile Thr Asn Asp Gln Lys
225                 230                 235                 240

Lys Leu Met Ser Ser Asn Val Gln Ile Val Arg Gln Gln Ser Tyr Ser
                245                 250                 255

Ile Met Cys Val Val Lys Glu Val Met Ala Tyr Val Val Gln Leu
            260                 265                 270

Pro Ile Tyr Gly Val Ile Asp Thr Pro Cys Trp Lys Leu His Thr Ser
        275                 280                 285

Pro Leu Cys Thr Thr Asp Asn Lys Glu Gly Ser Asn Ile Cys Leu Thr
290                 295                 300

Arg Thr Asp Arg Gly Trp Tyr Cys Asp Asn Ala Gly Ser Val Ser Phe
305                 310                 315                 320

Phe Pro Gln Ala Glu Thr Cys Lys Val Gln Ser Asn Arg Val Phe Cys
                325                 330                 335

Asp Thr Met Asn Ser Leu Thr Leu Pro Thr Asp Val Asn Leu Cys Asn
            340                 345                 350

Thr Asp Ile Phe Asn Ala Lys Tyr Asp Cys Lys Ile Met Thr Ser Lys
        355                 360                 365

Thr Asp Ile Ser Ser Ser Val Ile Thr Ser Ile Gly Ala Ile Val Ser
370                 375                 380

Cys Tyr Gly Lys Thr Lys Cys Thr Ala Ser Asn Lys Cys Arg Gly Ile
385                 390                 395                 400
```

```
Ile Lys Thr Phe Ser Asn Gly Cys Asp Tyr Val Ser Asn Arg Gly Val
                405                 410                 415

Asp Thr Val Ser Val Gly Asn Thr Leu Tyr Tyr Val Asn Lys Leu Glu
            420                 425                 430

Gly Lys Ala Leu Tyr Ile Lys Gly Glu Pro Ile Ile Asn Tyr Tyr Asp
        435                 440                 445

Pro Leu Val Phe Pro Ser Asp Glu Phe Asp Ala Ser Ile Ala Gln Val
    450                 455                 460

Asn Ala Lys Ile Asn Gln Ser Leu Ala Phe Ile Arg Arg Ser Asp Glu
465                 470                 475                 480

Leu Leu Ser Ala Ile Gly Gly Tyr Ile Pro Glu Ala Pro Arg Asp Gly
                485                 490                 495

Gln Ala Tyr Val Arg Lys Asp Gly Glu Trp Val Leu Leu Ser Thr Phe
            500                 505                 510

Leu Gly Gly Leu Val Pro Arg Gly Ser His His His His His His Ser
        515                 520                 525

Ala Trp Ser His Pro Gln Phe Glu Lys
    530                 535

<210> SEQ ID NO 41
<211> LENGTH: 529
<212> TYPE: PRT
<213> ORGANISM: Artificial Sequence
<220> FEATURE:
<223> OTHER INFORMATION: sc9-10_bRSV(RB94) DS-Cav1_fd_hp2_fp2_ig1

<400> SEQUENCE: 41

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Lys Ile
    50                  55                  60

Gln Lys Asn Val Cys Asn Ser Thr Asp Ser Asn Val Lys Leu Ile Lys
65                  70                  75                  80

Gln Glu Leu Glu Arg Tyr Asn Asn Ala Val Val Glu Leu Gln Ser Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Asn Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Glu Leu Leu Pro Ile Leu Asn Asn His Asp Cys Gln Ile Ser
                165                 170                 175

Asn Ile Ala Thr Val Ile Glu Phe Gln Gln Lys Asn Asn Arg Leu Leu
            180                 185                 190

Glu Ile Ala Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220
```

```
Met Pro Ile Thr Asn Asp Gln Lys Lys Leu Met Ser Ser Asn Val Gln
225                 230                 235                 240

Ile Val Arg Gln Gln Ser Tyr Ser Ile Met Cys Ile Ile Lys Glu Glu
            245                 250                 255

Val Leu Ala Tyr Val Val Gln Leu Pro Ile Tyr Gly Val Ile Asp Thr
        260                 265                 270

Pro Cys Trp Lys Leu His Thr Ser Pro Leu Cys Thr Thr Asp Asn Lys
    275                 280                 285

Glu Gly Ser Asn Ile Cys Leu Thr Arg Thr Asp Arg Gly Trp Tyr Cys
290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Leu Thr Leu
            325                 330                 335

Pro Thr Asp Val Asn Leu Cys Asn Thr Asp Ile Phe Asn Ala Lys Tyr
        340                 345                 350

Asp Cys Lys Ile Met Thr Ser Lys Thr Asp Val Ser Ser Ser Val Ile
    355                 360                 365

Thr Ser Leu Gly Ala Ile Val Ser Cys Tyr Gly Lys Thr Lys Cys Thr
370                 375                 380

Ala Ser Asn Lys Asn Arg Gly Ile Ile Lys Thr Phe Ser Asn Gly Cys
385                 390                 395                 400

Asp Tyr Val Ser Asn Arg Gly Val Asp Thr Val Ser Val Gly Asn Thr
            405                 410                 415

Leu Tyr Tyr Val Asn Lys Gln Glu Gly Lys Ser Leu Tyr Ile Lys Gly
        420                 425                 430

Glu Pro Ile Ile Asn Tyr Tyr Asp Pro Leu Val Phe Pro Ser Asp Glu
    435                 440                 445

Phe Asp Ala Ser Ile Ala Gln Val Asn Ala Lys Ile Asn Gln Ser Leu
450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
            485                 490                 495

Glu Trp Val Leu Leu Ser Thr Phe Leu Gly Gly Leu Val Pro Arg Gly
        500                 505                 510

Ser His His His His His His Ser Ala Trp Ser His Pro Gln Phe Glu
    515                 520                 525

Lys
```

<210> SEQ ID NO 42
<211> LENGTH: 543
<212> TYPE: PRT
<213> ORGANISM: Artificial Sequence
<220> FEATURE:
<223> OTHER INFORMATION: 391-2-site ? hRSV bovsurf DS-Cav1-BZGJ9 Long

<400> SEQUENCE: 42

```
Met Asp Ser Lys Gly Ser Ser Gln Lys Gly Ser Arg Leu Leu Leu Leu
1               5                   10                  15

Leu Val Val Ser Asn Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Ile Thr Ile
```

```
                50                  55                  60
Glu Leu Ser Lys Ile Gln Lys Asn Val Cys Lys Ser Thr Asp Ser Lys
 65                  70                  75                  80

Val Lys Leu Ile Lys Gln Glu Leu Glu Arg Tyr Asn Asn Ala Val Ile
                 85                  90                  95

Glu Leu Gln Leu Leu Met Gln Ser Thr Pro Ala Thr Asn Asn Gly Ser
            100                 105                 110

Gly Ser Ala Ile Ala Ser Gly Val Ala Val Cys Lys Val Leu His Leu
        115                 120                 125

Glu Gly Glu Val Asn Lys Ile Lys Asn Ala Leu Leu Ser Thr Asn Lys
    130                 135                 140

Ala Val Val Ser Leu Ser Asn Gly Val Ser Val Leu Thr Phe Lys Val
145                 150                 155                 160

Leu Asp Leu Lys Asn Tyr Ile Asp Lys Glu Leu Leu Pro Lys Leu Asn
                165                 170                 175

Asn His Asp Cys Arg Ile Ser Asn Ile Glu Thr Val Ile Glu Phe Gln
            180                 185                 190

Gln Lys Asn Asn Arg Leu Leu Glu Ile Thr Arg Glu Phe Ser Val Asn
        195                 200                 205

Ala Gly Val Thr Thr Pro Val Ser Thr Tyr Met Leu Thr Asn Ser Glu
    210                 215                 220

Leu Leu Ser Leu Ile Asn Asp Met Pro Ile Thr Asn Asp Gln Lys Lys
225                 230                 235                 240

Leu Met Ser Ser Asn Val Gln Ile Val Arg Gln Gln Ser Tyr Ser Ile
                245                 250                 255

Met Cys Ile Ile Lys Glu Glu Val Leu Ala Tyr Val Val Gln Leu Pro
            260                 265                 270

Ile Tyr Gly Val Ile Asp Thr Pro Cys Trp Lys Leu His Thr Ser Pro
        275                 280                 285

Leu Cys Thr Thr Asp Asn Lys Glu Gly Ser Asn Ile Cys Leu Thr Arg
    290                 295                 300

Thr Asp Arg Gly Trp Tyr Cys Asp Asn Ala Gly Ser Val Ser Phe Phe
305                 310                 315                 320

Pro Gln Ala Glu Thr Cys Lys Val Gln Ser Asn Arg Val Phe Cys Asp
                325                 330                 335

Thr Met Asn Ser Arg Thr Leu Pro Thr Asp Val Asn Leu Cys Asn Thr
            340                 345                 350

Asp Ile Phe Asn Thr Lys Tyr Asp Cys Lys Ile Met Thr Ser Lys Thr
        355                 360                 365

Asp Val Ser Ser Ser Val Ile Thr Ser Leu Gly Ala Ile Val Ser Cys
    370                 375                 380

Tyr Gly Lys Thr Lys Cys Thr Ala Ser Asn Lys Asn Arg Gly Ile Ile
385                 390                 395                 400

Lys Thr Phe Ser Asn Gly Cys Asp Tyr Val Ser Asn Lys Gly Val Asp
                405                 410                 415

Thr Val Ser Val Gly Asn Thr Leu Tyr Tyr Val Asn Lys Gln Glu Gly
            420                 425                 430

Lys Ser Leu Tyr Val Lys Gly Glu Pro Ile Ile Asn Phe Tyr Asp Pro
        435                 440                 445

Leu Val Phe Pro Ser Asp Glu Phe Asp Ala Ser Ile Ser Gln Val Asn
    450                 455                 460

Glu Lys Ile Asn Gln Ser Leu Ala Phe Ile Arg Arg Ser Asp Glu Leu
465                 470                 475                 480
```

Leu His Asn Val Asn Ala Gly Lys Ser Thr Thr Gly Gly Tyr Ile Pro
            485                 490                 495

Glu Ala Pro Arg Asp Gly Gln Ala Tyr Val Arg Lys Asp Gly Glu Trp
        500                 505                 510

Val Leu Leu Ser Thr Phe Leu Gly Gly Leu Val Pro Arg Gly Ser His
    515                 520                 525

His His His His His Ser Ala Trp Ser His Pro Gln Phe Glu Lys
530                 535                 540

<210> SEQ ID NO 43
<211> LENGTH: 531
<212> TYPE: PRT
<213> ORGANISM: Artificial Sequence
<220> FEATURE:
<223> OTHER INFORMATION: bRSV 391-2 sc9 DS-Cav1 A149C Y458

Tyr Cys Asp Asn Ala Gly Ser Val Ser Phe Phe Pro Gln Ala Glu Thr
305                 310                 315                 320

Cys Lys Val Gln Ser Asn Arg Val Phe Cys Asp Thr Met Asn Ser Leu
            325                 330                 335

Thr Leu Pro Thr Asp Val Asn Leu Cys Asn Thr Asp Ile Phe Asn Thr
        340                 345                 350

Lys Tyr Asp Cys Lys Ile Met Thr Ser Lys Thr Asp Ile Ser Ser Ser
    355                 360                 365

Val Ile Thr Ser Ile Gly Ala Ile Val Ser Cys Tyr Gly Lys Thr Lys
370                 375                 380

Cys Thr Ala Ser Asn Lys Asn Arg Gly Ile Ile Lys Thr Phe Ser Asn
385                 390                 395                 400

Gly Cys Asp Tyr Val Ser Asn Lys Gly Val Asp Thr Val Ser Val Gly
            405                 410                 415

Asn Thr Leu Tyr Cys Val Asn Lys Leu Glu Gly Lys Ala Leu Tyr Ile
        420                 425                 430

Lys Gly Glu Pro Ile Ile Asn Tyr Tyr Asp Pro Leu Val Phe Pro Ser
    435                 440                 445

Asp Glu Phe Asp Ala Ser Ile Ala Gln Val Asn Ala Lys Ile Asn Gln
450                 455                 460

Ser Leu Ala Phe Ile Arg Arg Ser Asp Glu Leu Leu Ser Ala Ile Gly
465                 470                 475                 480

Gly Tyr Ile Pro Glu Ala Pro Arg Asp Gly Gln Ala Tyr Val Arg Lys
            485                 490                 495

Asp Gly Glu Trp Val Leu Leu Ser Thr Phe Leu Gly Leu Val Pro
        500                 505                 510

Arg Gly Ser His His His His His His Ser Ala Trp Ser His Pro Gln
    515                 520                 525

Phe Glu Lys
    530

<210> SEQ ID NO 44
<211> LENGTH: 535
<212> TYPE: PRT
<213> ORGANISM: Artificial Sequence
<220> FEATURE:
<223> OTHER INFORMATION: bRSV ATue51908 sc9-10 DS-Cav1 N183GC N428C

<400> SEQUENCE: 44

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Gl

```
Glu Val Asn Lys Ile Lys Asn Ala Leu Leu Ser Thr Asn Lys Ala Val
    130                 135                 140
Val Ser Leu Ser Gly Cys Gly Val Ser Val Leu Thr Phe Lys Val Leu
145                 150                 155                 160
Asp Leu Lys Asn Tyr Ile Asp Lys Glu Leu Leu Pro Gln Leu Asn Asn
                165                 170                 175
His Asp Cys Arg Ile Ser Asn Ile Glu Thr Val Ile Glu Phe Gln Gln
            180                 185                 190
Lys Asn Asn Arg Leu Leu Glu Ile Ala Arg Glu Phe Ser Val Asn Ala
        195                 200                 205
Gly Ile Thr Thr Pro Leu Ser Thr Tyr Met Leu Thr Asn Ser Glu Leu
    210                 215                 220
Leu Ser Leu Ile Asn Asp Met Pro Ile Thr Asn Asp Gln Lys Lys Leu
225                 230                 235                 240
Met Ser Ser Asn Val Gln Ile Val Arg Gln Gln Ser Tyr Ser Ile Met
                245                 250                 255
Cys Val Val Lys Glu Glu Val Ile Ala Tyr Val Val Gln Leu Pro Ile
            260                 265                 270
Tyr Gly Val Ile Asp Thr Pro Cys Trp Lys Leu His Thr Ser Pro Leu
        275                 280                 285
Cys Thr Thr Asp Asn Lys Glu Gly Ser Asn Ile Cys Leu Thr Arg Thr
    290                 295                 300
Asp Arg Gly Trp Tyr Cys Asp Asn Ala Gly Ser Val Ser Phe Phe Pro
305                 310                 315                 320
Gln Thr Glu Thr Cys Lys Val Gln Ser Asn Arg Val Phe Cys Asp Thr
                325                 330                 335
Met Asn Ser Leu Thr Leu Pro Thr Asp Val Asn Leu Cys Asn Thr Asp
            340                 345                 350
Ile Phe Asn Thr Lys Tyr Asp Cys Lys Ile Met Thr Ser Lys Thr Asp
        355                 360                 365
Ile Ser Ser Ser Val Ile Thr Ser Ile Gly Ala Ile Val Ser Cys Tyr
    370                 375                 380
Gly Lys Thr Lys Cys Thr Ala Ser Asn Lys Cys Arg Gly Ile Ile Lys
385                 390                 395                 400
Thr Phe Ser Asn Gly Cys Asp Tyr Val Ser Asn Lys Gly Val Asp Thr
                405                 410                 415
Val Ser Val Gly Asn Thr Leu Tyr Tyr Val Asn Lys Leu Glu Gly Lys
            420                 425                 430
Ala Leu Tyr Ile Lys Gly Glu Pro Ile Ile Asn Tyr Tyr Asp Pro Leu
        435                 440                 445
Val Phe Pro Ser Asp Glu Phe Asp Ala Ser Ile Ala Gln Val Asn Ala
    450                 455                 460
Lys Ile Asn Gln Ser Leu Ala Phe Ile Arg Arg Ser Asp Glu Leu Leu
465                 470                 475                 480
Ser Ala Ile Gly Gly Tyr Ile Pro Glu Ala Pro Arg Asp Gly Gln Ala
                485                 490                 495
Tyr Val Arg Lys Asp Gly Glu Trp Val Leu Leu Ser Thr Phe Leu Gly
            500                 505                 510
Gly Leu Val Pro Arg Gly Ser His His His His His Ser Ala Trp
        515                 520                 525
Ser His Pro Gln Phe Glu Lys
    530                 535
```

```
<210> SEQ ID NO 45
<211> LENGTH: 530
<212> TYPE: PRT
<213> ORGANISM: artificial sequence
<220> FEATURE:
<223> OTHER INFORMATION: bRSV 391-2 postF

<400> SEQUENCE: 45
```

| Met | Ala | Ala | Thr | Ala | Met | Arg | Met | Ile | Ile | Ser | Ile | Ile | Phe | Ile | Ser |
|---|---|---|---|---|---|---|---|---|---|---|---|---|---|---|---|
| 1 | | | | 5 | | | | | 10 | | | | | 15 | |

| Thr | Tyr | Met | Thr | His | Ile | Thr | Leu | Cys | Gln | Asn | Ile | Thr | Glu | Glu | Phe |
| | | | 20 | | | | | 25 | | | | | 30 | | |

| Tyr | Gln | Ser | Thr | Cys | Ser | Ala | Val | Ser | Arg | Gly | Tyr | Leu | Ser | Ala | Leu |
| | | 35 | | | | | 40 | | | | | 45 | | | |

| Arg | Thr | Gly | Trp | Tyr | Thr | Ser | Val | Val | Thr | Ile | Glu | Leu | Ser | Lys | Ile |
| | 50 | | | | | 55 | | | | | 60 | | | | |

| Gln | Lys | Asn | Val | Cys | Lys | Ser | Thr | Asp | Ser | Lys | Val | Lys | Leu | Ile | Lys |
| 65 | | | | | 70 | | | | | 75 | | | | | 80 |

| Gln | Glu | Leu | Glu | Arg | Tyr | Asn | Asn | Ala | Val | Ile | Glu | Leu | Gln | Ser | Leu |
| | | | | 85 | | | | | 90 | | | | | 95 | |

| Met | Gln | Asn | Glu | Pro | Ala | Ser | Phe | Ser | Arg | Ala | Lys | Arg | Gly | Ile | Pro |
| | | | 100 | | | | | 105 | | | | | 110 | | |

| Glu | Leu | Ile | His | Tyr | Thr | Arg | Asn | Ser | Thr | Lys | Arg | Phe | Tyr | Gly | Leu |
| | | 115 | | | | | 120 | | | | | 125 | | | |

| Met | Gly | Lys | Lys | Arg | Lys | Arg | Arg | Ala | Ile | Ala | Ser | Gly | Val | Ala | Val |
| | 130 | | | | | 135 | | | | | 140 | | | | |

| Ser | Lys | Val | Leu | His | Leu | Glu | Gly | Glu | Val | Asn | Lys | Ile | Lys | Asn | Ala |
| 145 | | | | | 150 | | | | | 155 | | | | | 160 |

| Leu | Leu | Ser | Thr | Asn | Lys | Ala | Val | Val | Ser | Leu | Ser | Asn | Gly | Val | Ser |
| | | | | 165 | | | | | 170 | | | | | 175 | |

| Val | Leu | Thr | Ser | Lys | Val | Leu | Asp | Leu | Lys | Asn | Tyr | Ile | Asp | Lys | Glu |
| | | | 180 | | | | | 185 | | | | | 190 | | |

| Leu | Leu | Pro | Lys | Val | Asn | Asn | His | Asp | Cys | Arg | Ile | Ser | Asn | Ile | Glu |
| | | 195 | | | | | 200 | | | | | 205 | | | |

| Thr | Val | Ile | Glu | Phe | Gln | Gln | Lys | Asn | Asn | Arg | Leu | Leu | Glu | Ile | Ala |
| | 210 | | | | | 215 | | | | | 220 | | | | |

| Arg | Glu | Phe | Ser | Val | Asn | Ala | Gly | Ile | Thr | Thr | Pro | Leu | Ser | Thr | Tyr |
| 225 | | | | | 230 | | | | | 235 | | | | | 240 |

| Met | Leu | Thr | Asn | Ser | Glu | Leu | Leu | Ser | Leu | Ile | Asn | Asp | Met | Pro | Ile |
| | | | | 245 | | | | | 250 | | | | | 255 | |

| Thr | Asn | Asp | Gln | Lys | Lys | Leu | Met | Ser | Ser | Asn | Val | Gln | Ile | Val | Arg |
| | | | 260 | | | | | 265 | | | | | 270 | | |

| Gln | Gln | Ser | Tyr | Ser | Ile | Met | Ser | Val | Val | Lys | Glu | Glu | Val | Ile | Ala |
| | | 275 | | | | | 280 | | | | | 285 | | | |

| Tyr | Val | Val | Gln | Leu | Pro | Ile | Tyr | Gly | Val | Ile | Asp | Thr | Pro | Cys | Trp |
| | 290 | | | | | 295 | | | | | 300 | | | | |

| Lys | Leu | His | Thr | Ser | Pro | Leu | Cys | Thr | Thr | Asp | Asn | Lys | Glu | Gly | Ser |
| 305 | | | | | 310 | | | | | 315 | | | | | 320 |

| Asn | Ile | Cys | Leu | Thr | Arg | Thr | Asp | Arg | Gly | Trp | Tyr | Cys | Asp | Asn | Ala |
| | | | | 325 | | | | | 330 | | | | | 335 | |

| Gly | Ser | Val | Ser | Phe | Phe | Pro | Gln | Ala | Glu | Thr | Cys | Lys | Val | Gln | Ser |
| | | | 340 | | | | | 345 | | | | | 350 | | |

| Asn | Arg | Val | Phe | Cys | Asp | Thr | Met | Asn | Ser | Leu | Thr | Leu | Pro | Thr | Asp |
| | | 355 | | | | | 360 | | | | | 365 | | | |

```
Val Asn Leu Cys Asn Thr Asp Ile Phe Asn Thr Lys Tyr Asp Cys Lys
    370                 375                 380

Ile Met Thr Ser Lys Thr Asp Ile Ser Ser Val Ile Thr Ser Ile
385                 390                 395                 400

Gly Ala Ile Val Ser Cys Tyr Gly Lys Thr Lys Cys Thr Ala Ser Asn
                405                 410                 415

Lys Asn Arg Gly Ile Ile Lys Thr Phe Ser Asn Gly Cys Asp Tyr Val
            420                 425                 430

Ser Asn Lys Gly Val Asp Thr Val Ser Val Gly Asn Thr Leu Tyr Tyr
        435                 440                 445

Val Asn Lys Leu Glu Gly Lys Ala Leu Tyr Ile Lys Gly Glu Pro Ile
    450                 455                 460

Ile Asn Tyr Tyr Asp Pro Leu Val Phe Pro Ser Asp Glu Phe Asp Ala
465                 470                 475                 480

Ser Ile Ala Gln Val Asn Ala Lys Ile Asn Gln Ser Leu Ala Phe Ile
                485                 490                 495

Arg Arg Ser Asp Glu Leu Leu Gly Leu Glu Val Leu Phe Gln Gly Pro
            500                 505                 510

His His His His His His His Ser Ala Trp Ser His Pro Gln Phe
        515                 520                 525

Glu Lys
    530

<210> SEQ ID NO 46
<211> LENGTH: 535
<212> TYPE: PRT
<213> ORGANISM: artificial sequence
<220> FEATURE:
<223> OTHER INFORMATION: bRSV ATue51908 postF

<400> SEQUENCE: 46

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Val Gly Gln Asn
            20                  25                  30

Ile Thr Glu Glu Phe Tyr Gln Ser Thr Cys Ser Ala Val Ser Arg Gly
            35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Lys Ser Thr Asp Ser Lys
65              70                  75                  80

Val Lys Leu Ile Lys Gln Glu Leu Glu Arg Tyr Asn Asn Ala Val Val
                85                  90                  95

Glu Leu Gln Ser Leu Met Gln Asn Glu Pro Ala Ser Phe Ser Arg Ala
            100                 105                 110

Lys Arg Gly Ile Pro Glu Leu Ile His Tyr Thr Arg Asn Ser Thr Lys
        115                 120                 125

Lys Phe Tyr Gly Leu Met Gly Lys Lys Arg Lys Arg Arg Ala Val Ala
    130                 135                 140

Ser Gly Val Ala Val Ser Lys Val Leu His Leu Glu Gly Glu Val Asn
145                 150                 155                 160

Lys Ile Lys Asn Ala Leu Leu Ser Thr Asn Lys Ala Val Val Ser Leu
                165                 170                 175

Ser Asn Gly Val Ser Val Leu Thr Ser Lys Val Leu Asp Leu Lys Asn
            180                 185                 190
```

```
Tyr Ile Asp Lys Glu Leu Leu Pro Gln Val Asn Asn His Asp Cys Arg
            195                 200                 205

Ile Ser Asn Ile Glu Thr Val Ile Glu Phe Gln Gln Lys Asn Asn Arg
    210                 215                 220

Leu Leu Glu Ile Ala Arg Glu Phe Ser Val Asn Ala Gly Ile Thr Thr
225                 230                 235                 240

Pro Leu Ser Thr Tyr Met Leu Thr Asn Ser Glu Leu Leu Ser Leu Ile
                245                 250                 255

Asn Asp Met Pro Ile Thr Asn Asp Gln Lys Lys Leu Met Ser Ser Asn
            260                 265                 270

Val Gln Ile Val Arg Gln Gln Ser Tyr Ser Ile Met Ser Val Val Lys
            275                 280                 285

Glu Glu Val Ile Ala Tyr Val Val Gln Leu Pro Ile Tyr Gly Val Ile
        290                 295                 300

Asp Thr Pro Cys Trp Lys Leu His Thr Ser Pro Leu Cys Thr Thr Asp
305                 310                 315                 320

Asn Lys Glu Gly Ser Asn Ile Cys Leu Thr Arg Thr Asp Arg Gly Trp
                325                 330                 335

Tyr Cys Asp Asn Ala Gly Ser Val Ser Phe Phe Pro Gln Thr Glu Thr
            340                 345                 350

Cys Lys Val Gln Ser Asn Arg Val Phe Cys Asp Thr Met Asn Ser Leu
            355                 360                 365

Thr Leu Pro Thr Asp Val Asn Leu Cys Asn Thr Asp Ile Phe Asn Thr
        370                 375                 380

Lys Tyr Asp Cys Lys Ile Met Thr Ser Lys Thr Asp Ile Ser Ser Ser
385                 390                 395                 400

Val Ile Thr Ser Ile Gly Ala Ile Val Ser Cys Tyr Gly Lys Thr Lys
                405                 410                 415

Cys Thr Ala Ser Asn Lys Asn Arg Gly Ile Ile Lys Thr Phe Ser Asn
            420                 425                 430

Gly Cys Asp Tyr Val Ser Asn Lys Gly Val Asp Thr Val Ser Val Gly
            435                 440                 445

Asn Thr Leu Tyr Tyr Val Asn Lys Leu Glu Gly Lys Ala Leu Tyr Ile
        450                 455                 460

Lys Gly Glu Pro Ile Ile Asn Tyr Tyr Asp Pro Leu Val Phe Pro Ser
465                 470                 475                 480

Asp Glu Phe Asp Ala Ser Ile Ala Gln Val Asn Ala Lys Ile Asn Gln
                485                 490                 495

Ser Leu Ala Phe Ile Arg Arg Ser Asp Glu Leu Leu Gly Leu Glu Val
            500                 505                 510

Leu Phe Gln Gly Pro His His His His His His Ser Ala Trp
            515                 520                 525

Ser His Pro Gln Phe Glu Lys
            530                 535

<210> SEQ ID NO 47
<211> LENGTH: 535
<212> TYPE: PRT
<213> ORGANISM: artificial sequence
<220> FEATURE:
<223> OTHER INFORMATION: bRSV RB94 postF

<400> SEQUENCE: 47

Met Asp Ser Lys Gly Ser Ser Gln Lys Gly Ser Arg Leu Leu Leu Leu
1               5                   10                  15
```

-continued

Leu Val Val Ser Asn Leu Leu Pro Gln Gly Val Val Gly Gln Asn
             20                25                30

Ile Thr Glu Glu Phe Tyr Gln Ser Thr Cys Ser Ala Val Ser Arg Gly
                 35                40                45

Tyr Leu Ser Ala Leu Arg Thr Gly Trp Tyr Thr Ser Val Val Thr Ile
         50                55                60

Glu Leu Ser Lys Ile Gln Lys Asn Val Cys Asn Ser Thr Asp Ser Asn
65                   70                75                80

Val Lys Leu Ile Lys Gln Glu Leu Glu Arg Tyr Asn Asn Ala Val Val
                 85                90                95

Glu Leu Gln Ser Leu Met Gln Asn Glu Pro Ala Ser Ser Ser Arg Ala
                100               105               110

Lys Arg Gly Ile Pro Glu Leu Ile His Tyr Lys Arg Asn Ser Thr Lys
        115               120               125

Lys Phe Tyr Gly Leu Met Gly Lys Arg Lys Arg Arg Ala Ile Ala
        130               135               140

Ser Gly Val Ala Val Ser Lys Val Leu His Leu Glu Gly Glu Val Asn
145                 150               155               160

Lys Ile Lys Asn Ala Leu Leu Ser Thr Asn Lys Ala Val Val Ser Leu
                 165               170               175

Ser Asn Gly Val Ser Val Leu Thr Ser Lys Val Leu Asp Leu Lys Asn
         180               185               190

Tyr Ile Asp Lys Glu Leu Leu Pro Lys Val Asn Asn His Asp Cys Gln
         195               200               205

Ile Ser Asn Ile Ala Thr Val Ile Glu Phe Gln Gln Lys Asn Asn Arg
210               215               220

Leu Leu Glu Ile Ala Arg Glu Phe Ser Val Asn Ala Gly Ile Thr Thr
225               230               235               240

Pro Leu Ser Thr Tyr Met Leu Thr Asn Ser Glu Leu Leu Ser Leu Ile
             245               250               255

Asn Asp Met Pro Ile Thr Asn Asp Gln Lys Lys Leu Met Ser Ser Asn
             260               265               270

Val Gln Ile Val Arg Gln Gln Ser Tyr Ser Ile Met Ser Val Val Lys
         275               280               285

Glu Glu Val Met Ala Tyr Val Val Gln Leu Pro Ile Tyr Gly Val Ile
290               295               300

Asp Thr Pro Cys Trp Lys Leu His Thr Ser Pro Leu Cys Thr Thr Asp
305               310               315               320

Asn Lys Glu Gly Ser Asn Ile Cys Leu Thr Arg Thr Asp Arg Gly Trp
             325               330               335

Tyr Cys Asp Asn Ala Gly Ser Val Ser Phe Phe Pro Gln Ala Glu Thr
             340               345               350

Cys Lys Val Gln Ser Asn Arg Val Phe Cys Asp Thr Met Asn Ser Leu
         355               360               365

Thr Leu Pro Thr Asp Val Asn Leu Cys Asn Thr Asp Ile Phe Asn Ala
         370               375               380

Lys Tyr Asp Cys Lys Ile Met Thr Ser Lys Thr Asp Ile Ser Ser Ser
385               390               395               400

Val Ile Thr Ser Ile Gly Ala Ile Val Ser Cys Tyr Gly Lys Thr Lys
                 405               410               415

Cys Thr Ala Ser Asn Lys Asn Arg Gly Ile Ile Lys Thr Phe Ser Asn
             420               425               430

Gly Cys Asp Tyr Val Ser Asn Arg Gly Val Asp Thr Val Ser Val Gly

```
                435                 440                 445
Asn Thr Leu Tyr Tyr Val Asn Lys Leu Glu Gly Lys Ala Leu Tyr Ile
    450                 455                 460

Lys Gly Glu Pro Ile Ile Asn Tyr Tyr Asp Pro Leu Val Phe Pro Ser
465                 470                 475                 480

Asp Glu Phe Asp Ala Ser Ile Ala Gln Val Asn Ala Lys Ile Asn Gln
                485                 490                 495

Ser Leu Ala Phe Ile Arg Arg Ser Asp Glu Leu Leu Gly Leu Glu Val
            500                 505                 510

Leu Phe Gln Gly Pro His His His His His His Ser Ala Trp
        515                 520                 525

Ser His Pro Gln Phe Glu Lys
    530                 535

<210> SEQ ID NO 48
<211> LENGTH: 167
<212> TYPE: PRT
<213> ORGANISM: Artificial Sequence
<220> FEATURE:
<223> OTHER INFORMATION: ferritin polypeptide

<400> SEQUENCE: 48

Met Leu Ser Lys Asp Ile Ile Lys Leu Leu Asn Glu Gln Val Asn Lys
1               5                   10                  15

Glu Met Asn Ser Ser Asn Leu Tyr Met Ser Met Ser Ser Trp Cys Tyr
            20                  25                  30

Thr His Ser Leu Asp Gly Ala Gly Leu Phe Leu Phe Asp His Ala Ala
        35                  40                  45

Glu Glu Tyr Glu His Ala Lys Lys Leu Ile Val Phe Leu Asn Glu Asn
    50                  55                  60

Asn Val Pro Val Gln Leu Thr Ser Ile Ser Ala Pro Glu His Lys Phe
65                  70                  75                  80

Glu Gly Leu Thr Gln Ile Phe Gln Lys Ala Tyr Glu His Glu Gln His
                85                  90                  95

Ile Ser Glu Ser Ile Asn Asn Ile Val Asp His Ala Ile Lys Gly Lys
            100                 105                 110

Asp His Ala Thr Phe Asn Phe Leu Gln Trp Tyr Val Ala Glu Gln His
        115                 120                 125

Glu Glu Glu Val Leu Phe Lys Asp Ile Leu Asp Lys Ile Glu Leu Ile
    130                 135                 140

Gly Asn Glu Asn His Gly Leu Tyr Leu Ala Asp Gln Tyr Val Lys Gly
145                 150                 155                 160

Ile Ala Lys Ser Arg Lys Ser
            165

<210> SEQ ID NO 49
<211> LENGTH: 265
<212> TYPE: PRT
<213> ORGANISM: Artificial Sequence
<220> FEATURE:
<223> OTHER INFORMATION: encapsulin polypeptide

<400> SEQUENCE: 49

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30
```

```
Gly Arg Lys Phe Val Asp Val Glu Gly Pro Tyr Gly Trp Glu Tyr Ala
            35                  40                  45

Ala His Pro Leu Gly Glu Val Glu Val Leu Ser Asp Glu Asn Glu Val
 50                  55                  60

Val Lys Trp Gly Leu Arg Lys Ser Leu Pro Leu Ile Glu Leu Arg Ala
 65                  70                  75                  80

Thr Phe Thr Leu Asp Leu Trp Glu Leu Asp Asn Leu Glu Arg Gly Lys
                 85                  90                  95

Pro Asn Val Asp Leu Ser Ser Leu Glu Glu Thr Val Arg Lys Val Ala
             100                 105                 110

Glu Phe Glu Asp Glu Val Ile Phe Arg Gly Cys Glu Lys Ser Gly Val
             115                 120                 125

Lys Gly Leu Leu Ser Phe Glu Glu Arg Lys Ile Glu Cys Gly Ser Thr
         130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Lys Ile Ile Thr Thr Pro Arg
        195                 200                 205

Ile Glu Asp Ala Leu Val Val Ser Glu Arg Gly Gly Asp Phe Lys Leu
            210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265

<210> SEQ ID NO 50
<211> LENGTH: 124
<212> TYPE: PRT
<213> ORGANISM: Artificial Sequence
<220> FEATURE:
<223> OTHER INFORMATION: MPE8 Heavy Chain Variable region

<400> SEQUENCE: 50

Glu Val Gln Leu Val Glu Ser Gly Gly Leu Val Lys Pro Gly Gly
 1               5                  10                  15

Ser Leu Arg Leu Ser Cys Ala Ala Ser Gly Phe Thr Phe Ser Ser Tyr
                 20                  25                  30

Ser Met Asn Trp Val Arg Gln Ala Pro Gly Lys Gly Leu Glu Trp Val
             35                  40                  45

Ser Ser Ile Ser Ala Ser Ser Tyr Ser Asp Tyr Ala Asp Ser Ala
         50                  55                  60

Lys Gly Arg Phe Thr Ile Ser Arg Asp Asn Ala Lys Thr Ser Leu Phe
 65                  70                  75                  80

Leu Gln Met Asn Ser Leu Arg Ala Glu Asp Thr Ala Ile Tyr Phe Cys
                 85                  90                  95

Ala Arg Ala Arg Ala Thr Gly Tyr Ser Ser Ile Thr Pro Tyr Phe Asp
             100                 105                 110

Ile Trp Gly Gln Gly Thr Leu Val Thr Val Ser Ser
             115                 120
```

<210> SEQ ID NO 51
<211> LENGTH: 110
<212> TYPE: PRT
<213> ORGANISM: Artificial Sequence
<220> FEATURE:
<223> OTHER INFORMATION: MPE8 Light Chain Variable region

<400> SEQUENCE: 51

```
Gln Ser Val Val Thr Gln Thr Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Asn Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Arg Asn
                85                  90                  95

Leu Ser Gly Val Phe Gly Thr Gly Thr Lys Val Thr Val Leu
            100                 105                 110
```

<210> SEQ ID NO 52
<211> LENGTH: 109
<212> TYPE: PRT
<213> ORGANISM: Artificial Sequence
<220> FEATURE:
<223> OTHER INFORMATION: AM14 Light Chain Variable region

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Lys Lys Tyr
            20                  25                  30

Leu Asn Trp Tyr His Gln Lys Pro Gly Lys Val Pro Glu Leu Leu Met
        35                  40                  45

His Asp Ala Ser Asn Leu Glu Thr Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Ile Gly Thr Tyr Tyr Cys Gln Gln Tyr Asp Asn Leu Pro Pro
                85                  90                  95

Leu Thr Phe Gly Gly Gly Thr Lys Val Glu Ile Lys Arg
            100                 105
```

<210> SEQ ID NO 53
<211> LENGTH: 123
<212> TYPE: PRT
<213> ORGANISM: Artificial Sequence
<220> FEATURE:
<223> OTHER INFORMATION: AM14 Heavy Chain Variable region

<400> SEQUENCE: 53

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser His Tyr
            20                  25                  30

Ala Met His Trp Val Arg Gln Ala Pro Gly Lys Gly Leu Glu Trp Val
```

```
                35                  40                  45
Ala Val Ile Ser Tyr Asp Gly Glu Asn Thr Tyr Tyr Ala Asp Ser Val
        50                  55                  60

Lys Gly Arg Phe Ser Ile Ser Arg Asp Asn Ser Lys Asn Thr Val Ser
 65                 70                  75                  80

Leu Gln Met Asn Ser Leu Arg Pro Glu Asp Thr Ala Leu Tyr Tyr Cys
                85                  90                  95

Ala Arg Asp Arg Ile Val Asp Asp Tyr Tyr Tyr Gly Met Asp Val
            100                 105                 110

Trp Gly Gln Gly Ala Thr Val Thr Val Ser Ser
            115                 120

<210> SEQ ID NO 54
<211> LENGTH: 107
<212> TYPE: PRT
<213> ORGANISM: Artificial Sequence
<220> FEATURE:
<223> OTHER INFORMATION: D25 Light Chain Variable region

<400> SEQUENCE: 54

Asp Ile Gln Met Thr Gln Ser Pro Ser Ser Leu Ser Ala Ala Val Gly
 1               5                  10                  15

Asp Arg Val Thr Ile Thr Cys Gln Ala Ser Gln Asp Ile Val Asn Tyr
            20                  25                  30

Leu Asn Trp Tyr Gln Gln Lys Pro Gly Lys Ala Pro Lys Leu Leu Ile
        35                  40                  45

Tyr Val Ala Ser Asn Leu Glu Thr Gly Val Pro Ser Arg Phe Ser Gly
    50                  55                  60

Ser Gly Ser Gly Thr Asp Phe Ser Leu Thr Ile Ser Ser Leu Gln Pro
 65                 70                  75                  80

Glu Asp Val Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105

<210> SEQ ID NO 55
<211> LENGTH: 126
<212> TYPE: PRT
<213> ORGANISM: Artificial Sequence
<220> FEATURE:
<223> OTHER INFORMATION: D25 Heavy Chain Variable region

<400> SEQUENCE: 55

Gln Val Gln Leu Val Gln Ser Gly Ala Glu Val Lys Lys Pro Gly Ser
 1               5                  10                  15

Ser Val Met Val Ser Cys Gln Ala Ser Gly Gly Pro Leu Arg Asn Tyr
            20                  25                  30

Ile Ile Asn Trp Leu Arg Gln Ala Pro Gly Gln Gly Pro Glu Trp Met
        35                  40                  45

Gly Gly Ile Ile Pro Val Leu Gly Thr Val His Tyr Ala Pro Lys Phe
    50                  55                  60

Gln Gly Arg Val Thr Ile Thr Ala Asp Glu Ser Thr Asp Thr Ala Tyr
 65                 70                  75                  80

Ile His Leu Ile Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
            100                 105                 110
```

Phe Asp Asn Trp Gly Gln Gly Thr Leu Val Thr Val Ser Ser
              115                 120                 125

<210> SEQ ID NO 56
<211> LENGTH: 1587
<212> TYPE: DNA
<213> ORGANISM: Artificial Sequence
<220> FEATURE:
<223> OTHER INFORMATION: 391-2sc9-10DS-Cav1 Q98C-Q361C_nuc

<400> SEQUENCE: 56

| | | | | | |
|---|---|---|---|---|---|
| atggctgcta | ctgctatgcg | gatgattatc | tcaattattt | ttatttcaac | ctacatgact | 60 |
| cacattaccc | tgtgtcagaa | cattaccgag | gaattctacc | agagcacttg | ctccgccgtg | 120 |
| tctagaggat | acctgtctgc | tctgaggacc | ggctggtata | aagcgtggt | cactattgag | 180 |
| ctgtccaaga | tccagaaaaa | cgtgtgtaag | agtaccgatt | caaaggtcaa | actgatcaaa | 240 |
| caggagctgg | aaaggtataa | caatgccgtg | attgagctgc | agagcctgat | gtgcaatgaa | 300 |
| cctgctagcg | ggtctggaag | tgccatcgct | tccggagtgg | ccgtctgcaa | ggtgctgcac | 360 |
| ctggagggcg | aagtcaacaa | gatcaagaat | gccctgctgt | ctacaaacaa | agctgtggtc | 420 |
| tcactgagca | atggcgtgag | tgtcctgact | tttaaggtgc | tggacctgaa | aaactacatc | 480 |
| gataaggagc | tgctgccaaa | actgaacaat | catgactgtc | ggatcagcaa | tattgagaca | 540 |
| gtgattgaat | ccagcagaa | gaacaatcga | ctgctggaga | tcgaagaga | attttcagtg | 600 |
| aacgccggca | ttaccacacc | cctgagcacc | tacatgctga | caaattctga | gctgctgagt | 660 |
| ctgattaacg | acatgcctat | caccaatgat | cagaagaaac | tgatgagctc | caacgtgcag | 720 |
| atcgtcagac | agcagtccta | ttctattatg | tgcgtggtca | aggaggaagt | gatcgcctac | 780 |
| gtggtccagc | tgcctatcta | cggcgtgatc | gataccccat | gctggaagct | gcacacaagt | 840 |
| cccctgtgta | ctaccgacaa | caaagagggc | tcaaatatct | gcctgacaag | gactgaccgc | 900 |
| ggctggtact | gtgataacgc | agggagtgtg | tcattctttc | cacaggccga | aacttgcaag | 960 |
| gtgtgctcca | acagggtctt | ctgtgatacc | atgaattctc | tgaccctgcc | cacagacgtg | 1020 |
| aacctgtgca | acactgatat | ctttaatacc | aagtacgact | gtaagattat | gactagcaag | 1080 |
| accgacatct | ctagttcagt | gatcacctcc | attggagcta | tcgtctcttg | ctacggcaag | 1140 |
| acaaaatgta | ctgcatctaa | caagaatcgc | gggatcatca | agacattctc | taacggatgt | 1200 |
| gattatgtca | gtaataaggg | ggtcgacaca | gtgagcgtcg | gaaacactct | gtactatgtg | 1260 |
| aataagctgg | agggcaaagc | cctgtacatc | aaaggggaac | ctatcattaa | ctactatgat | 1320 |
| ccactggtgt | tccccagtga | cgagtttgat | gcatcaattg | cccaggtgaa | cgctaagatc | 1380 |
| aatcagtccc | tggccttcat | ccggagatca | gacgagctgc | tgagcgcaat | ggcgggtac | 1440 |
| atccccgaag | ctcctcgcga | tggccaggca | tatgtgcgaa | agacgggga | gtgggtcctg | 1500 |
| ctgagcacct | tcctgggagg | actggtgcct | cgaggatccc | accatcacca | tcaccatagc | 1560 |
| gcttggtccc | atccacagtt | tgaaaag | | | | 1587 |

<210> SEQ ID NO 57
<211> LENGTH: 1596
<212> TYPE: DNA
<213> ORGANISM: Artificial Sequence
<220> FEATURE:
<223> OTHER INFORMATION: 391-2sc9DS-Cav1 Q98C-Q361C_nuc

<400> SEQUENCE: 57

| | | | | | |
|---|---|---|---|---|---|
| atggctgcta | ctgctatgcg | gatgattatc | tcaattattt | ttatttcaac | ctacatgact | 60 |

| | |
|---|---|
| cacattaccc tgtgtcagaa cattaccgag gaattctacc agagcacttg ctccgccgtg | 120 |
| tctagaggat acctgtctgc tctgaggacc ggctggtata caagcgtggt cactattgag | 180 |
| ctgtccaaga tccagaaaaa cgtgtgtaag agtaccgatt caaaggtcaa actgatcaaa | 240 |
| caggagctgg aaaggtataa caatgccgtg attgagctgc agagcctgat gtgcaatgaa | 300 |
| cctgctagct tctccgggtc tggaagtgcc atcgcttccg gagtggccgt ctgcaaggtg | 360 |
| ctgcacctgg agggcgaagt caacaagatc aagaatgccc tgctgtctac aaacaaagct | 420 |
| gtggtctcac tgagcaatgg cgtgagtgtc ctgactttta aggtgctgga cctgaaaaac | 480 |
| tacatcgata ggagctgct gccaaaactg aacaatcatg actgtcggat cagcaatatt | 540 |
| gagacagtga ttgaattcca gcagaagaac aatcgactgc tggagatcgc aagagaattt | 600 |
| tcagtgaacg ccggcattac cacacccctg agcacctaca tgctgacaaa ttctgagctg | 660 |
| ctgagtctga ttaacgacat gcctatcacc aatgatcaga gaaactgat gagctccaac | 720 |
| gtgcagatcg tcagacagca gtcctattct attatgtgcg tggtcaagga ggaagtgatc | 780 |
| gcctacgtgg tccagctgcc tatctacggc gtgatcgata ccccatgctg gaagctgcac | 840 |
| acaagtcccc tgtgtactac cgacaacaaa gagggctcaa atatctgcct gacaaggact | 900 |
| gaccgcggct ggtactgtga taacgcaggg agtgtgtcat tctttccaca ggccgaaact | 960 |
| tgcaaggtgt gctccaacag ggtcttctgt gataccatga attctctgac cctgcccaca | 1020 |
| gacgtgaacc tgtgcaacac tgatatcttt aataccaagt acgactgtaa gattatgact | 1080 |
| agcaagaccg acatctctag ttcagtgatc acctccattg gagctatcgt ctcttgctac | 1140 |
| ggcaagacaa aatgtactgc atctaacaag aatcgcggga tcatcaagac attctctaac | 1200 |
| ggatgtgatt atgtcagtaa taaggggggtc gacacagtga gcgtcggaaa cactctgtac | 1260 |
| tatgtgaata agctggaggg caaagccctg tacatcaaag gggaacctat cattaactac | 1320 |
| tatgatccac tggtgttccc cagtgacgag tttgatgcat caattgccca ggtgaacgct | 1380 |
| aagatcaatc agtccctggc cttcatccgg agatcagacg agctgctgag cgcaattggc | 1440 |
| gggtacatcc ccgaagctcc tcgcgatggc caggcatatg tgcgaaaaga cggggagtgg | 1500 |
| gtcctgctga gcaccttcct gggaggactg gtgcctcgag gatcccacca tcaccatcac | 1560 |
| catagcgctt ggtcccatcc acagtttgaa aagtga | 1596 |

<210> SEQ ID NO 58
<211> LENGTH: 1602
<212> TYPE: DNA
<213> ORGANISM: Artificial Sequence
<220> FEATURE:
<223> OTHER INFORMATION: ATue51908sc9-10DS-Cav1 A149C-Y458C_nuc

<400> SEQUENCE: 58

| | |
|---|---|
| atggattcca aggggagctc ccagaaagga tctaggctgc tgctgctgct ggtggtctcc | 60 |
| aacctgctgc tgccacaggg agtggtcgga cagaatatca cagaggaatt ctaccagagc | 120 |
| acttgctccg cagtgtctcg gggataccTg tctgccctga aactggctg gtataccTct | 180 |
| gtggtcacaa ttgagctgag taagatccag aagaacgtgt gcaaaagtac cgactcaaag | 240 |
| gtcaaactga tcaagcagga gctggaacgg tataacaatg ccgtggtcga gctgcagagc | 300 |
| ctgatgcaga acgaacctgc ttctggcagc ggatctgccg tgtgtagtgg agtggccgtc | 360 |
| tgcaaagtgc tgcatctgga gggcgaagtc aacaagatca agaatgcact gctgtctact | 420 |
| aacaaggccg tggtctcact gagcaatggc gtgagtgtcc tgacctttaa ggtgctggac | 480 |
| ctgaaaaact acatcgataa ggagctgctg cctcagctga acaatcacga ttgtaggatc | 540 |

```
tccaatattg agacagtgat tgaattccag cagaagaaca atcgcctgct ggagatcgct    600
cgagagttca gcgtgaacgc aggcattacc acaccactgt caacatacat gctgactaat    660
tcagagctgc tgagcctgat taacgacatg cccatcacca atgatcagaa gaaactgatg    720
tctagtaacg tgcagatcgt ccgccagcag tcctattcta ttatgtgcgt ggtcaaggag    780
gaagtgatcg catacgtggt ccagctgcct atctacggcg tgatcgatac cccatgctgg    840
aaactgcata catctcccct gtgcactacc gacaacaagg aaggaagtaa tatttgcctg    900
acaagaactg acaggggctg gtactgtgat aacgctggca gcgtgagctt cttccctcag    960
accgaaacat gcaaggtgca gagcaaccgg gtcttctgtg atacaatgaa ttccctgact   1020
ctgccaaccg acgtgaacct gtgcaacacc gatatcttta atacaaagta cgactgtaag   1080
atcatgacaa gcaagactga catctcaagc tccgtgatca caagtattgg agctatcgtg   1140
tcatgctacg gcaagaccaa atgtacagca tctaacaaaa acagagggat cattaagact   1200
ttctcaaacg gatgtgatta tgtgagcaac aaggggggtcg acactgtgag cgtcggaaac   1260
accctgtact gtgtgaataa gctggagggc aaagccctgt acatcaaggg ggaacccatc   1320
attaactact atgatccact ggtgttcccc agcgacgagt ttgatgcatc cattgcccag   1380
gtgaacgcca aaatcaatca gtccctggct tttattaggc gctccgacga gctgctgtct   1440
gccattggcg gtacatccc cgaagcccct agggatggcc aggcttatgt gcgcaaggac   1500
ggggagtggg tcctgctgtc aaccttcctg gaggactgg tgccaagagg ctcccaccat   1560
caccatcacc atagcgcctg gtcccaccct cagtttgaaa ag                     1602

<210> SEQ ID NO 59
<211> LENGTH: 1608
<212> TYPE: DNA
<213> ORGANISM: Artificial Sequence
<220> FEATURE:
<223> OTHER INFORMATION: RB94 DS-Cav1 sc9 A149C-Y458C_nuc

<400> SEQUENCE: 59
atggattcta agggttccag ccagaaaggt tccaggctgc tgctgctgct ggtggtgagc     60
aatctgctgc tgcctcaggg agtggtggga cagaacatca ccgaggagtt ctaccagtca    120
acctgcagcg ccgtgagccg gggctacctg agcgcactga aaccggatg gtatacatcc    180 gtggtcacta ttgagctgtc taagatccag aaaaacgtgt gtaattctac agatagtaac    240
gtcaagctga tcaaacagga gctggaaagg tataacaatg ctgtggtcga gctgcagtcc    300
ctgatgcaga acgaacctgc cagcagcagc ggcagcggca gcgccatctg ttctggggtg    360
gcagtctgca aggtgctgca tctggaggga gaagtcaaca agatcaaaaa tgcactgctg    420
agtactaaca aagccgtggt cagtctgtca aatggggtga gcgtcctgac ctttaaggtg    480
ctggacctga aaaactacat cgataaggag ctgctgccca aactgaacaa tcacgactgt    540
cagatcagca atattgccac tgtgattgag ttccagcaga gaacaatcg cctgctggag    600 atcgcccggg agttcagcgt gaacgcaggc attaccacac cactgtccac ctacatgctg    660
acaaatagtg agctgctgtc actgattaac gacatgccca tcaccaatga tcagaagaaa    720
ctgatgagtt caaacgtgca gatcgtcagg cagcagagct attccattat gtgcgtggtc    780
aaggaggaag tgatggccta cgtggtccag ctgcctatct acggcgtgat cgatacacca    840
tgctggaagc tgcatacttc accctgtgt actaccgaca caaagagggg gagcaatatc    900
tgcctgacaa gaactgacag gggatggtac tgtgataacg ctggctctgt gagtttcttt    960
```

| | |
|---|---|
| cctcaggcag aaacctgcaa ggtgcagtct aaccgcgtct tctgtgatac aatgaatagt | 1020 |
| ctgaccctgc caacagacgt gaacctgtgc aatacagata tctttaatgc caagtacgac | 1080 |
| tgtaagatta tgacttccaa gaccgacatc agctcctctg tgatcacttc tattggggcc | 1140 |
| atcgtcagtt gctacggaaa gacaaaatgt actgctagca acaagaatcg gggcatcatc | 1200 |
| aagacattca gtaacgggtg tgattatgtg tcaaatagag gcgtggacac tgtgagcgtc | 1260 |
| gggaacaccc tgtactgtgt gaataagctg gagggaaaag ctctgtacat caagggcgaa | 1320 |
| cctatcatta actactatga tccactggtg ttcccctcag acgagtttga tgcaagcatt | 1380 |
| gcccaggtga acgccaaaat caatcagtct ctggctttta ttaggcgcag cgacgagctg | 1440 |
| ctgtccgcaa ttggcgggta catccccgaa gcccctaggg atggacaggc ttatgtgcgc | 1500 |
| aaggacggcg agtgggtcct gctgtccacc ttcctgggag gcctggtgcc cagaggctct | 1560 |
| caccatcacc atcaccattc agcctggagc acccctcagt tgaaaaaa | 1608 |

<210> SEQ ID NO 60
<211> LENGTH: 1611
<212> TYPE: DNA
<213> ORGANISM: Artificial Sequence
<220> FEATURE:
<223> OTHER INFORMATION: RB94 sc9 DS-Cav1 N183GC-N428C_nuc

<400> SEQUENCE: 60

| | |
|---|---|
| atggattcta agggttccag ccagaaaggt tccaggctgc tgctgctgct ggtggtgagc | 60 |
| aatctgctgc tgcctcaggg agtggtggga cagaacatca ccgaggagtt ctaccagtca | 120 |
| acctgcagcg ccgtgagccg gggctacctg agcgcactga gaccggatg gtatacatcc | 180 |
| gtggtcacta ttgagctgtc taagatccag aaaaacgtgt gtaattctac agatagtaac | 240 |
| gtcaagctga tcaaacagga gctggaaagg tataacaatg ctgtggtcga gctgcagtcc | 300 |
| ctgatgcaga acgaacctgc cagcagcagc ggcagcggca gcgccatcgc ttctggggtg | 360 |
| gcagtctgca aggtgctgca tctggaggga aagtcaaca agatcaaaaa tgcactgctg | 420 |
| agtactaaca agccgtggt cagtctgtca ggttgtgggg tgagcgtcct gaccctttaag | 480 |
| gtgctggacc tgaaaaacta catcgataag gagctgctgc ccaaactgaa caatcacgac | 540 |
| tgtcagatca gcaatattgc cactgtgatt gagttccagc agaagaacaa tcgcctgctg | 600 |
| gagatcgccc gggagttcag cgtgaacgca ggcattacca ccactgtc cacctacatg | 660 |
| ctgacaaata gtgagctgct gtcactgatt aacgacatgc ccatcaccaa tgatcagaag | 720 |
| aaactgatga gttcaaacgt gcagatcgtc aggcagcaga gctattccat tatgtgcgtg | 780 |
| gtcaaggagg aagtgatggc ctacgtggtc cagctgccta tctacggcgt gatcgataca | 840 |
| ccatgctgga agctgcatac ttcacccctg tgtactaccg acaacaaaga ggggagcaat | 900 |
| atctgcctga caagaactga cagggatgg tactgtgata acgctggctc tgtgagtttc | 960 |
| tttcctcagg cagaaacctg caaggtgcag tctaaccgcg tcttctgtga tacaatgaat | 1020 |
| agtctgaccc tgccaacaga cgtgaacctg tgcaatacag atatctttaa tgccaagtac | 1080 |
| gactgtaaga ttatgacttc caagaccgac atcagctcct ctgtgatcac ttctattggg | 1140 |
| gccatcgtca gttgctacgg aaagacaaaa tgtactgcta gcaacaagtg tcggggcatc | 1200 |
| atcaagacat tcagtaacgg gtgtgattat gtgtcaaata gaggcgtgga cactgtgagc | 1260 |
| gtcgggaaca ccctgtacta tgtgaataag ctggagggaa aagctctgta catcaagggc | 1320 |
| gaacctatca ttaactacta tgatccactg gtgttcccct cagacgagtt tgatgcaagc | 1380 |
| attgcccagg tgaacgccaa aatcaatcag tctctggctt ttattaggcg cagcgacgag | 1440 |

```
ctgctgtccg caattggcgg gtacatcccc gaagccccta gggatggaca ggcttatgtg   1500
cgcaaggacg gcgagtgggt cctgctgtcc accttcctgg gaggcctggt gcccagaggc   1560
tctcaccatc accatcacca ttcagcctgg agccaccctc agtttgaaaa a            1611
```

<210> SEQ ID NO 61
<211> LENGTH: 1593
<212> TYPE: DNA
<213> ORGANISM: Artificial Sequence
<220> FEATURE:
<223> OTHER INFORMATION: bRSV 391-2 sc9 DS-Cav1 A149C-Y458C_nuc

<400> SEQUENCE: 61

```
atggctgcta ctgctatgcg gatgattatc tcaattattt ttatttcaac ctacatgact     60
cacattaccc tgtgtcagaa cattaccgag gaattctacc agagcacttg ctccgccgtg    120
tctagaggat acctgtctgc tctgaggacc ggctggtata caagcgtggt cactattgag    180
ctgtccaaga tccagaaaaa cgtgtgtaag agtaccgatt caaaggtcaa actgatcaaa    240
caggagctgg aaaggtataa caatgccgtg attgagctgc agagcctgat gcagaatgaa    300
cctgctagct ctccgggtc tggaagtgcc atctgttccg gagtggccgt ctgcaaggtg    360
ctgcacctgg agggcgaagt caacaagatc aagaatgccc tgctgtctac aaacaaagct    420
gtggtctcac tgagcaatgg cgtgagtgtc ctgacttta aggtgctgga cctgaaaaac    480
tacatcgata aggagctgct gccaaaactg aacaatcatg actgtcggat cagcaatatt    540
gagacagtga ttgaattcca gcagaagaac aatcgactgc tggagatcgc aagagaattt    600
tcagtgaacg ccggcattac cacccctg agcacctaca tgctgacaaa ttctgagctg    660
ctgagtctga ttaacgacat gcctataccc aatgatcaga gaaactgat gagctccaac    720 gtgcagatcg tcagacagca gtcctattct attatgtgcg tggtcaagga ggaagtgatc    780
gcctacgtgg tccagctgcc tatctacggc gtgatcgata ccccatgctg gaagctgcac    840
acaagtcccc tgtgtactac cgacaacaaa gagggctcaa atatctgcct gacaaggact    900
gaccgcggct ggtactgtga taacgcaggg agtgtgtcat tctttccaca ggccgaaact    960
tgcaaggtgc agtccaacag ggtcttctgt gataccatga ttctctgac cctgcccaca   1020 gacgtgaacc tgtgcaacac tgatatcttt aataccaagt acgactgtaa gattatgact   1080
agcaagaccg acatctctag ttcagtgatc acctccattg gagctatcgt ctcttgctac   1140
ggcaagacaa aatgtactgc atctaacaag aatcgcggga tcatcaagac attctctaac   1200
ggatgtgatt atgtcagtaa tagggggtc gacacagtga gcgtcggaaa cactctgtac   1260
tgtgtgaata gctggagggg caaagccctg tacatcaaag gggaacctat cattaactac   1320
tatgatccac tggtgttccc cagtgacgag tttgatgcat caattgccca ggtgaacgct   1380
aagatcaatc agtccctggc cttcatccgg agatcagacg agctgctgag cgcaattggc   1440
gggtacatcc ccgaagctcc tcgcgatggc aggcatatg tgcgaaaaga cggggagtgg   1500
gtcctgctga gcaccttcct gggaggactg gtgcctcgag gatcccacca tcaccatcac   1560
catagcgctt ggtcccatcc acagtttgaa aag                                 1593
```

<210> SEQ ID NO 62
<211> LENGTH: 1605
<212> TYPE: DNA
<213> ORGANISM: Artificial Sequence
<220> FEATURE:
<223> OTHER INFORMATION: bRSV ATue51908 sc9-10 DS-Cav1 N183GC-N428C_nuc

<400> SEQUENCE: 62

```
atggattcca aggggagctc ccagaaagga tctaggctgc tgctgctgct ggtggtctcc      60
aacctgctgc tgccacaggg agtggtcgga cagaatatca cagaggaatt ctaccagagc     120
acttgctccg cagtgtctcg gggatacctg tctgccctga aactggctg gtatacctct      180
gtggtcacaa ttgagctgag taagatccag aagaacgtgt gcaaaagtac cgactcaaag     240
gtcaaactga tcaagcagga gctggaacgg tataacaatg ccgtggtcga gctgcagagc     300
ctgatgcaga acgaacctgc ttctggcagc ggatctgccg tggctagtgg agtggccgtc     360
tgcaaagtgc tgcatctgga gggcgaagtc aacaagatca gaatgcact gctgtctact      420
aacaaggccg tggtctcact gagcggctgc ggcgtgagtg tcctgacctt taaggtgctg     480
gacctgaaaa actacatcga taaggagctg ctgcctcagc tgaacaatca cgattgtagg     540
atctccaata ttgagacagt gattgaattc agcagaaga caatcgcct gctggagatc       600
gctcgagagt tcagcgtgaa cgcaggcatt accacaccac tgtcaacata catgctgact     660
aattcagagc tgctgagcct gattaacgac atgcccatca ccaatgatca agagaaactg     720
atgtctagta acgtgcagat cgtccgccag cagtcctatt ctattatgtg cgtggtcaag     780
gaggaagtga tcgcatacgt ggtccagctg cctatctacg cgtgatcga taccccatgc      840
tggaaactgc atacatctcc cctgtgcact accgacaaca aggaaggaag taatatttgc     900
ctgacaagaa ctgacagggg ctggtactgt gataacgctg cagcgtgag cttcttccct      960
cagaccgaaa catgcaaggt gcagagcaac cgggtcttct gtgatacaat gaattccctg    1020
actctgccaa ccgacgtgaa cctgtgcaac accgatatct taatacaaa gtacgactgt     1080
aagatcatga caagcaagac tgacatctca agctccgtga tcacaagtat tggagctatc    1140
gtgtcatgct acggcaagac caaatgtaca gcatctaaca aatgcagagg gatcattaag    1200
actttctcaa acggatgtga ttatgtgagc aacaagggg tcgacactgt gagcgtcgga      1260
aacacccctgt actatgtgaa taagctggag ggcaaagccc tgtacatcaa gggggaaccc    1320
atcattaact actatgatcc actggtgttc cccagcgacg agtttgatgc atccattgcc    1380
caggtgaacg ccaaaatcaa tcagtccctg gctttatta ggcgctccga cgagctgctg     1440
tctgccattg gcgggtacat ccccgaagcc cctagggatg ccaggcttga tgtgcgcaag    1500
gacgggagt gggtcctgct gtcaaccttc ctgggaggac tggtgccaag aggctcccac     1560
catcaccatc accatagcgc ctggtcccac cctcagtttg aaaag                   1605
```

<210> SEQ ID NO 63
<211> LENGTH: 531
<212> TYPE: PRT
<213> ORGANISM: Artificial Sequence
<220> FEATURE:
<223> OTHER INFORMATION: 391-2 sc9 DS-Cav1 N88C N254C

<400> SEQUENCE: 63

```
Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Gl

```
                65                  70                  75                  80

Gln Glu Leu Glu Arg Tyr Asn Cys Ala Val Ile Glu Leu Gln Ser Leu
                            85                  90                  95

Met Gln Asn Glu Pro Ala Ser Phe Ser Gly Ser Gly Ser Ala Ile Ala
                        100                 105                 110

Ser Gly Val Ala Val Cys Lys Val Leu His Leu Glu Gly Glu Val Asn
                    115                 120                 125

Lys Ile Lys Asn Ala Leu Leu Ser Thr Asn Lys Ala Val Val Ser Leu
                130                 135                 140

Ser Asn Gly Val Ser Val Leu Thr Phe Lys Val Leu Asp Leu Lys Asn
        145                 150                 155                 160

Tyr Ile Asp Lys Glu Leu Leu Pro Lys Leu Asn Asn His Asp Cys Arg
                        165                 170                 175

Ile Ser Asn Ile Glu Thr Val Ile Glu Phe Gln Gln Lys Asn Asn Arg
                        180                 185                 190

Leu Leu Glu Ile Ala Arg Glu Phe Ser Val Asn Ala Gly Ile Thr Thr
                    195                 200                 205

Pro Leu Ser Thr Tyr Met Leu Thr Cys Ser Glu Leu Leu Ser Leu Ile
                210                 215                 220

Asn Asp Met Pro Ile Thr Asn Asp Gln Lys Lys Leu Met Ser Ser Asn
        225                 230                 235                 240

Val Gln Ile Val Arg Gln Gln Ser Tyr Ser Ile Met Cys Val Val Lys
                        245                 250                 255

Glu Glu Val Ile Ala Tyr Val Val Gln Leu Pro Ile Tyr Gly Val Ile
                        260                 265                 270

Asp Thr Pro Cys Trp Lys Leu His Thr Ser Pro Leu Cys Thr Thr Asp
                    275                 280                 285

Asn Lys Glu Gly Ser Asn Ile Cys Leu Thr Arg Thr Asp Arg Gly Trp
                290                 295                 300

Tyr Cys Asp Asn Ala Gly Ser Val Ser Phe Phe Pro Gln Ala Glu Thr
        305                 310                 315                 320

Cys Lys Val Gln Ser Asn Arg Val Phe Cys Asp Thr Met Asn Ser Leu
                        325                 330                 335

Thr Leu Pro Thr Asp Val Asn Leu Cys Asn Thr Asp Ile Phe Asn Thr
                    340                 345                 350

Lys Tyr Asp Cys Lys Ile Met Thr Ser Lys Thr Asp Ile Ser Ser Ser
                355                 360                 365

Val Ile Thr Ser Ile Gly Ala Ile Val Ser Cys Tyr Gly Lys Thr Lys
                370                 375                 380

Cys Thr Ala Ser Asn Lys Asn Arg Gly Ile Ile Lys Thr Phe Ser Asn
        385                 390                 395                 400

Gly Cys Asp Tyr Val Ser Asn Lys Gly Val Asp Thr Val Ser Val Gly
                        405                 410                 415

Asn Thr Leu Tyr Tyr Val Asn Lys Leu Glu Gly Lys Ala Leu Tyr Ile
                        420                 425                 430

Lys Gly Glu Pro Ile Ile Asn Tyr Tyr Asp Pro Leu Val Phe Pro Ser
                    435                 440                 445

Asp Glu Phe Asp Ala Ser Ile Ala Gln Val Asn Ala Lys Ile Asn Gln
                450                 455                 460

Ser Leu Ala Phe Ile Arg Arg Ser Asp Glu Leu Leu Ser Ala Ile Gly
        465                 470                 475                 480

Gly Tyr Ile Pro Glu Ala Pro Arg Asp Gly Gln Ala Tyr Val Arg Lys
                        485                 490                 495
```

Asp Gly Glu Trp Val Leu Leu Ser Thr Phe Leu Gly Leu Val Pro
            500                 505                 510

Arg Gly Ser His His His His His Ser Ala Trp Ser His Pro Gln
            515                 520                 525

Phe Glu Lys
    530

<210> SEQ ID NO 64
<211> LENGTH: 531
<212> TYPE: PRT
<213> ORGANISM: Artificial Sequence
<220> FEATURE:
<223> OTHER INFORMATION: 391-2 sc9 DS-Cav1 sc9 E92C N254C

<400> SEQUENCE: 64

Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Cys Leu Gln Ser Leu
                85                  90                  95

Met Gln Asn Glu Pro Ala Ser Phe Ser Gly Ser Gly Ser Ala Ile Ala
            100                 105                 110

Ser Gly Val Ala Val Cys Lys Val Leu His Leu Glu Gly Glu Val Asn
        115                 120                 125

Lys Ile Lys Asn Ala Leu Leu Ser Thr Asn Lys Ala Val Val Ser Leu
    130                 135                 140

Ser Asn Gly Val Ser Val Leu Thr Phe Lys Val Leu Asp Leu Lys Asn
145                 150                 155                 160

Tyr Ile Asp Lys Glu Leu Leu Pro Lys Leu Asn Asn His Asp Cys Arg
                165                 170                 175

Ile Ser Asn Ile Glu Thr Val Ile Glu Phe Gln Gln Lys Asn Asn Arg
            180                 185                 190

Leu Leu Glu Ile Ala Arg Glu Phe Ser Val Asn Ala Gly Ile Thr Thr
        195                 200                 205

Pro Leu Ser Thr Tyr Met Leu Thr Cys Ser Glu Leu Leu Ser Leu Ile
    210                 215                 220

Asn Asp Met Pro Ile Thr Asn Asp Gln Lys Lys Leu Met Ser Ser Asn
225                 230                 235                 240

Val Gln Ile Val Arg Gln Gln Ser Tyr Ser Ile Met Cys Val Val Lys
                245                 250                 255

Glu Glu Val Ile Ala Tyr Val Val Gln Leu Pro Ile Tyr Gly Val Ile
            260                 265                 270

Asp Thr Pro Cys Trp Lys Leu His Thr Ser Pro Leu Cys Thr Thr Asp
        275                 280                 285

Asn Lys Glu Gly Ser Asn Ile Cys Leu Thr Arg Thr Asp Arg Gly Trp
    290                 295                 300

Tyr Cys Asp Asn Ala Gly Ser Val Ser Phe Phe Pro Gln Ala Glu Thr
305                 310                 315                 320

```
Cys Lys Val Gln Ser Asn Arg Val Phe Cys Asp Thr Met Asn Ser Leu
            325                 330                 335

Thr Leu Pro Thr Asp Val Asn Leu Cys Asn Thr Asp Ile Phe Asn Thr
            340                 345                 350

Lys Tyr Asp Cys Lys Ile Met Thr Ser Lys Thr Asp Ile Ser Ser Ser
            355                 360                 365

Val Ile Thr Ser Ile Gly Ala Ile Val Ser Cys Tyr Gly Lys Thr Lys
            370                 375                 380

Cys Thr Ala Ser Asn Lys Asn Arg Gly Ile Ile Lys Thr Phe Ser Asn
385                 390                 395                 400

Gly Cys Asp Tyr Val Ser Asn Lys Gly Val Asp Thr Val Ser Val Gly
                405                 410                 415

Asn Thr Leu Tyr Tyr Val Asn Lys Leu Glu Gly Lys Ala Leu Tyr Ile
            420                 425                 430

Lys Gly Glu Pro Ile Ile Asn Tyr Tyr Asp Pro Leu Val Phe Pro Ser
            435                 440                 445

Asp Glu Phe Asp Ala Ser Ile Ala Gln Val Asn Ala Lys Ile Asn Gln
            450                 455                 460

Ser Leu Ala Phe Ile Arg Arg Ser Asp Glu Leu Leu Ser Ala Ile Gly
465                 470                 475                 480

Gly Tyr Ile Pro Glu Ala Pro Arg Asp Gly Gln Ala Tyr Val Arg Lys
                485                 490                 495

Asp Gly Glu Trp Val Leu Leu Ser Thr Phe Leu Gly Gly Leu Val Pro
            500                 505                 510

Arg Gly Ser His His His His His His Ser Ala Trp Ser His Pro Gln
            515                 520                 525

Phe Glu Lys
    530

<210> SEQ ID NO 65
<211> LENGTH: 531
<212> TYPE: PRT
<213> ORGANISM: Artificial Sequence
<220> FEATURE:
<223> OTHER INFORMATION: 391-2 sc9 DS-Cav1 sc9 S238C Q279C

<400> SEQUENCE: 65

Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Val Thr Ile Glu Leu Ser Lys Ile
        50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Gln Asn Glu Pro Ala Ser Phe Ser Gly Ser Gly Ser Ala Ile Ala
            100                 105                 110

Ser Gly Val Ala Val Cys Lys Val Leu His Leu Glu Gly Glu Val Asn
            115                 120                 125

Lys Ile Lys Asn Ala Leu Leu Ser Thr Asn Lys Ala Val Val Ser Leu
            130                 135                 140
```

```
Ser Asn Gly Val Ser Val Leu Thr Phe Lys Val Leu Asp Leu Lys Asn
145                 150                 155                 160

Tyr Ile Asp Lys Glu Leu Leu Pro Lys Leu Asn Asn His Asp Cys Arg
            165                 170                 175

Ile Ser Asn Ile Glu Thr Val Ile Glu Phe Gln Gln Lys Asn Asn Arg
            180                 185                 190

Leu Leu Glu Ile Ala Arg Glu Phe Cys Val Asn Ala Gly Ile Thr Thr
            195                 200                 205

Pro Leu Ser Thr Tyr Met Leu Thr Asn Ser Glu Leu Leu Ser Leu Ile
            210                 215                 220

Asn Asp Met Pro Ile Thr Asn Asp Gln Lys Lys Leu Met Ser Ser Asn
225                 230                 235                 240

Val Cys Ile Val Arg Gln Gln Ser Tyr Ser Ile Met Cys Val Val Lys
            245                 250                 255

Glu Glu Val Ile Ala Tyr Val Val Gln Leu Pro Ile Tyr Gly Val Ile
            260                 265                 270

Asp Thr Pro Cys Trp Lys Leu His Thr Ser Pro Leu Cys Thr Thr Asp
            275                 280                 285

Asn Lys Glu Gly Ser Asn Ile Cys Leu Thr Arg Thr Asp Arg Gly Trp
290                 295                 300

Tyr Cys Asp Asn Ala Gly Ser Val Ser Phe Phe Pro Gln Ala Glu Thr
305                 310                 315                 320

Cys Lys Val Gln Ser Asn Arg Val Phe Cys Asp Thr Met Asn Ser Leu
            325                 330                 335

Thr Leu Pro Thr Asp Val Asn Leu Cys Asn Thr Asp Ile Phe Asn Thr
            340                 345                 350

Lys Tyr Asp Cys Lys Ile Met Thr Ser Lys Thr Asp Ile Ser Ser Ser
            355                 360                 365

Val Ile Thr Ser Ile Gly Ala Ile Val Ser Cys Tyr Gly Lys Thr Lys
            370                 375                 380

Cys Thr Ala Ser Asn Lys Asn Arg Gly Ile Ile Lys Thr Phe Ser Asn
385                 390                 395                 400

Gly Cys Asp Tyr Val Ser Asn Lys Gly Val Asp Thr Val Ser Val Gly
            405                 410                 415

Asn Thr Leu Tyr Tyr Val Asn Lys Leu Glu Gly Lys Ala Leu Tyr Ile
            420                 425                 430

Lys Gly Glu Pro Ile Ile Asn Tyr Tyr Asp Pro Leu Val Phe Pro Ser
            435                 440                 445

Asp Glu Phe Asp Ala Ser Ile Ala Gln Val Asn Ala Lys Ile Asn Gln
            450                 455                 460

Ser Leu Ala Phe Ile Arg Arg Ser Asp Glu Leu Leu Ser Ala Ile Gly
465                 470                 475                 480

Gly Tyr Ile Pro Glu Ala Pro Arg Asp Gly Gln Ala Tyr Val Arg Lys
            485                 490                 495

Asp Gly Glu Trp Val Leu Leu Ser Thr Phe Leu Gly Gly Leu Val Pro
            500                 505                 510

Arg Gly Ser His His His His His His Ser Ala Trp Ser His Pro Gln
            515                 520                 525

Phe Glu Lys
530
```